United States Patent
Luo et al.

(10) Patent No.: US 10,662,189 B2
(45) Date of Patent: May 26, 2020

(54) PDE4 INHIBITOR

(71) Applicant: SHIJIAZHUANG SAGACITY NEW DRUG DEVELOPMENT CO., LTD., Shijiazhuang, Hebei (CN)

(72) Inventors: Yunfu Luo, Shanghai (CN); Chundao Yang, Shanghai (CN); Maoyi Lei, Shanghai (CN); Ling Liu, Shanghai (CN); Guoping Hu, Shanghai (CN); Jian Li, Shanghai (CN); Shuhui Chen, Shanghai (CN)

(73) Assignee: SHIJIAZHUANG SAGACITY NEW DRUG DEVELOPMENT CO., LTD., Shijiazhuang (CN)

(*) Notice: Subject to any disclaimer, the term of this patent is extended or adjusted under 35 U.S.C. 154(b) by 0 days.

(21) Appl. No.: 16/326,976

(22) PCT Filed: Aug. 22, 2017

(86) PCT No.: PCT/CN2017/098461
§ 371 (c)(1),
(2) Date: Feb. 21, 2019

(87) PCT Pub. No.: WO2018/036469
PCT Pub. Date: Mar. 1, 2018

(65) Prior Publication Data
US 2019/0177318 A1 Jun. 13, 2019

(30) Foreign Application Priority Data
Aug. 22, 2016 (CN) .......................... 2016 1 0700714

(51) Int. Cl.
| | |
|---|---|
| *C07D 471/04* | (2006.01) |
| *C07D 498/04* | (2006.01) |
| *A61P 29/00* | (2006.01) |
| *A61P 37/00* | (2006.01) |
| *A61K 31/519* | (2006.01) |
| *A61P 19/02* | (2006.01) |

(52) U.S. Cl.
CPC .......... *C07D 471/04* (2013.01); *A61K 31/519* (2013.01); *A61P 19/02* (2018.01); *A61P 29/00* (2018.01); *A61P 37/00* (2018.01); *C07D 498/04* (2013.01)

(58) Field of Classification Search
CPC ..... C07D 471/04; C07D 498/04; A61P 19/02; A61P 37/00; A61P 29/00; A61K 31/519
See application file for complete search history.

(56) References Cited

FOREIGN PATENT DOCUMENTS

| | | |
|---|---|---|
| CN | 101119996 A | 2/2008 |
| CN | 101573360 A | 11/2009 |
| WO | 2006087538 A1 | 8/2006 |
| WO | 2008051493 A2 | 5/2008 |
| WO | 2010030500 A1 | 3/2010 |
| WO | 2011021678 A1 | 2/2011 |

OTHER PUBLICATIONS

Poole, R. M., "Apremilast: first global approval." Drugs 74.7 (2014): 825-837.*
Wendling, D., "An overview of investigational new drugs for treating ankylosing spondylitis." Expert opinion on investigational drugs 25.1 (2016): 95-104.*
Schafer, P., "Apremilast mechanism of action and application to psoriasis and psoriatic arthritis." Biochemical pharmacology 83.12 (2012): 1583-1590.*
Berge et al., "Pharmaceutical Salts", Journal of Pharmaceutical Sciences, 1977, vol. 66, No. 1, pp. 1-19.
International Search Report and Written Opinion of PCT/CN2017/098461 dated Nov. 22, 2017.

* cited by examiner

*Primary Examiner* — John M Mauro
(74) *Attorney, Agent, or Firm* — SZDC Law P.C.

(57) ABSTRACT

Provided are a PDE4 inhibitor and a use thereof in the preparation of a medicament for treating PDE4 related diseases. Specifically disclosed are the compound as shown in formula (I) and a pharmaceutically acceptable salt thereof.

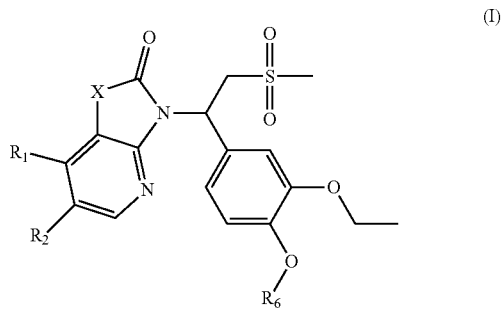

31 Claims, No Drawings

PDE4 INHIBITOR

RELATED APPLICATION REFERENCE

The present application is the National Stage Application of PCT/CN2017/098461, filed on Aug. 22, 2017, which claims priority of the Chinese Patent Application No. CN201610700714.2 filed to National Intellectual Property Administration, PRC on Aug. 22, 2016, the contents of which are incorporated herein by reference for all purposes as if fully set forth herein.

FIELD OF INVENTION

The present invention relates to a class of phosphodiesterase-4 (PDE4) inhibitor and a use thereof in manufacturing of a medicament for treating a disease related to PDE4. Specifically, related is a compound as shown in formula (I) and a pharmaceutically acceptable salt thereof.

PRIOR ARTS

Tumor necrosis factor alpha (TNF-α) is a cytokine released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. However, excessive release of TNF-α also causes diseases, when administered to mammals or humans, TNF-α causes or aggravates inflammation, fever, cardiovascular effects, hemorrhage, coagulation, and acute phase responses similar to those seen during acute infections and shock states. Enhanced or uncontrolled TNF-α production in animals or humans often indicates a number of diseases, for example, endotoxemia and/or toxic shock syndrome, cachexia, adult respiratory distress, syndrome, cancers (such as solid tumors and hematological tumors), heart disease (such as congestive heart failure), viral infection, and genetic, inflammatory, allergic, or autoimmune diseases.

Cancer is a particularly devastating disease, and the increase in TNF-α levels in blood indicates cancer or a risk of cancer spreading. Normally, in healthy subjects, cancer cells fail to survive in the circulatory system, one of the reasons is that the inner wall of blood vessels acts as a barrier to tumor-cell extravasation. ELAM-1 on endothelial cells was shown to mediate the increased adhesion of colon cancer cells to endothelium treated with cytokines.

Cyclic adenosine monophosphate (cAMP) also plays a role in many diseases and symptoms. It has been shown that the elevation of cAMP in inflammatory leukocytes inhibits their activation and then release inflammatory mediators, including TNF-α and nuclear factor κB (NF-κB). The increase in cAMP levels also lead to the relaxation of airway smooth muscle.

It is believed that primary cellular mechanism for the inactivation of cAMP is the breakdown of cAMP by a family of isoenzymes referred to as cyclic nucleotide phosphodiesterases (PDE). There are eleven known members of the family of PDEs. So far it has been recognized that the inhibition of PDE type IV (PDE4) is particularly effective both in inhibition of inflammatory mediators release and in relaxation of airway smooth muscle. Therefore, PDE4 has become one of the most popular drug targets. The family of PDE-4 can be divided into four subtypes (PDE-4A, B, C, D) based on different genetic codes, wherein PDE-4A, PDE-4B and PDE-4D are more widely expressed in inflammatory cells (such as B cells, T cells and neutrophils) than PDE-4C. The inhibition of PDE4 leads to an increase in cAMP levels, thereby regulating TNFα levels for therapeutic purposes.

CONTENT OF THE PRESENT INVENTION

The present invention provides a compound as shown in formula (I) and a pharmaceutically acceptable salt thereof,

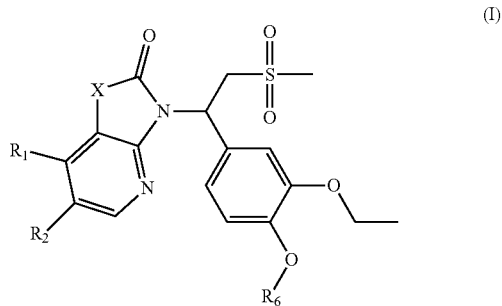

wherein,
X is selected from O, N($R_3$), —CH($R_3$)—;
$R_3$ is selected from H, F, Cl, Br, I, OH, CN, $NH_2$, COOH, $R_4$-$L_1$-, or selected from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, each of which is optionally substituted by 1, 2 or 3 R;
$R_4$ is selected from the group consisting of $C_{3-6}$ cycloalkyl, 3-6 membered heterocycloalkyl, phenyl and 5-6 membered heteroaryl, each of which is optionally substituted by 1, 2 or 3 R;
$L_1$ is selected from —$CH_2$—, —$CH_2CH_2$—, O, S, NH, —C(=O)—;
$R_1$ and $R_2$ are each independently selected from H, F, Cl, Br, I, OH, CN, $NH_2$, $R_5$-$L_2$-, or selected from the group consisting of $C_{1-6}$ alkyl, $C_{1-6}$ alkoxy, $C_{1-6}$ alkylthio, $C_{1-6}$ alkylamino, $C_{2-6}$ alkenyl, $C_{3-6}$ cycloalkenyl, 3-6 membered heterocycloalkenyl, $C_{3-6}$ cycloalkyl, 3-6 membered heterocycloalkyl, phenyl and 5-6 membered heteroaryl, each of which is optionally substituted by 1, 2 or 3 R;
$R_5$ is selected from the group consisting of $C_{3-6}$ cycloalkyl, 3-6 membered heterocycloalkyl, 3-6 membered heterocycloalkenyl, phenyl and 5-6 membered heteroaryl, each of which is optionally substituted by 1, 2 or 3 R;
$L_2$ is selected from —$CH_2$—, —$CH_2CH_2$—, O, S, NH;
$R_6$ is selected from $C_{1-3}$ alkyl, which is optionally substituted by 1, 2 or 3 R;
R is selected from H, halogen, OH, $NH_2$, CN, or selected from the group consisting of $C_{1-6}$ alkyl and $C_{1-6}$ heteroalkyl, each of which is optionally substituted by 1, 2 or 3 R';
R' is selected from H, F, Cl, Br, I, OH, $NH_2$, Me, Et, $CF_3$, $CHF_2$, $CH_2F$, $NHCH_3$, $N(CH_3)_2$;
the "hetero" in the $C_{1-6}$ heteroalkyl, 3-6 membered heterocycloalkyl, 5-6 membered heteroaryl and 3-6 membered heterocycloalkenyl is selected from —C(=O)NH—, —NH—, —C(=NH)—, —S(=O)$_2$NH—, —S(=O)NH—, —O—, —S—, =O, =S, —O—N=, —C(=O)O—, —C(=O)—, —C(=S)—, —S(=O)—, —S(=O)$_2$— and —NHC(=O)NH—;
in any of the above cases, the number of the heteroatom or the heteroatom group is independently selected from 1, 2 or 3.

In some embodiments of the present invention, R is selected from H, F, Cl, Br, I, OH, $NH_2$, CN, or selected from the group consisting of $C_{1-3}$ alkyl, $C_{1-3}$ alkoxy, $C_{1-3}$ alkyl-thio, $C_{1-3}$ alkylamino, $C_{1-4}$-alkyl-OC(=O)— and N,N'-di($C_{1-3}$ alkyl)amino, each of which is optionally substituted by 1, 2 or 3 R'.

In some embodiments of the present invention, R is selected from H, F, Cl, Br, I, OH, $NH_2$, CN, Me, $CF_3$, $CHF_2$, $CH_2F$, Et,

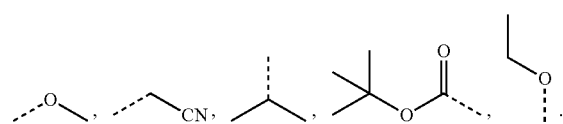

In some embodiments of the present invention, $R_4$ is selected from the group consisting of: phenyl, pyridyl, pyrimidinyl, pyrazinyl, thienyl, imidazolyl, pyrazolyl, oxazolyl, thiazolyl, isoxazolyl and isothiazolyl, each of which is optionally substituted by 1, 2 or 3 R.

In some embodiments of the present invention, $R_4$ is selected from the group consisting of

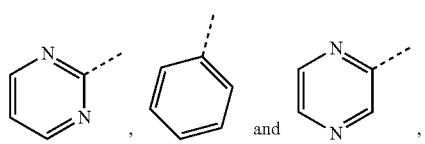

each of which is optionally substituted by 1, 2 or 3 R.

In some embodiments of the present invention, $R_4$ is selected from

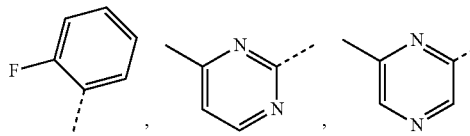

In some embodiments of the present invention, $R_4$-$L_1$- is selected from

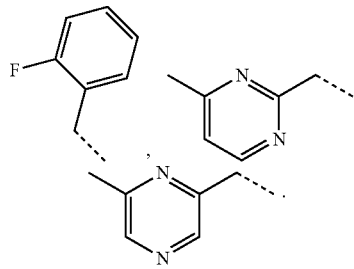

In some embodiments of the present invention, $R_3$ is selected from H, F, Cl, Br, I, OH, $NH_2$, $R_4$-$L_1$-, or selected from the group consisting of $C_{1-3}$ alkyl, $C_{3-6}$ cycloalkyl, —$C_{1-3}$-alkyl-C(=O)O—$C_{1-3}$ alkyl-, $C_{1-3}$-alkyl-S(=O)$_2$—$C_{1-3}$ alkyl-, phenyl, pyridyl, pyrimidinyl and pyrazinyl, each of which is optionally substituted by 1, 2 or 3 R.

In some embodiments of the present invention, $R_3$ is selected from H, F, Cl, Br, I, OH, $NH_2$, $R_4$-$L_1$-, or selected from the group consisting of Me, Et,

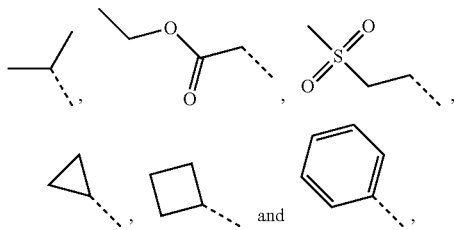

each of which is optionally substituted by 1, 2 or 3 R.

In some embodiments of the present invention, $R_3$ is selected from H, F, Cl, Br, I, OH, $NH_2$, Me, Et,

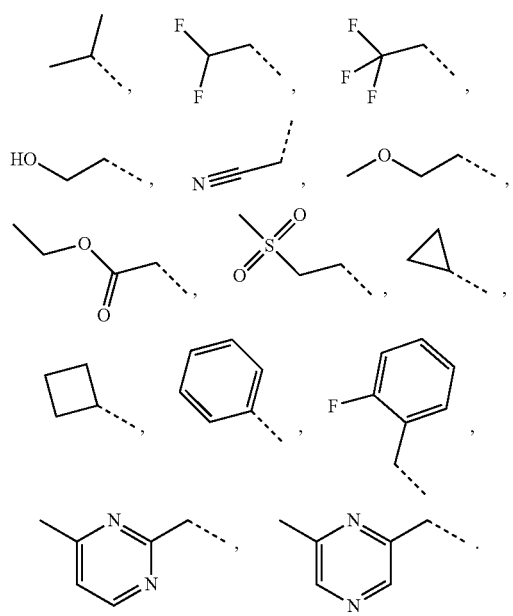

In some embodiments of the present invention, X is selected from

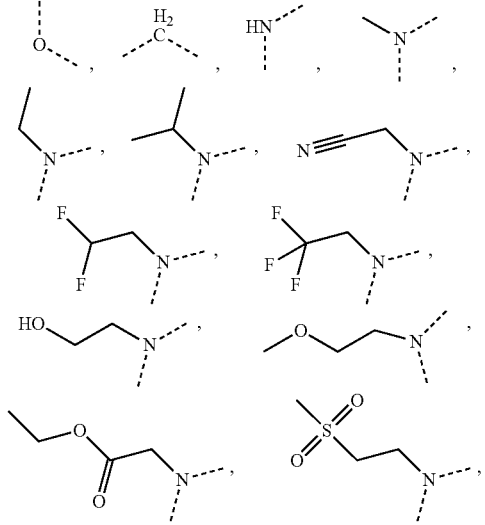

-continued

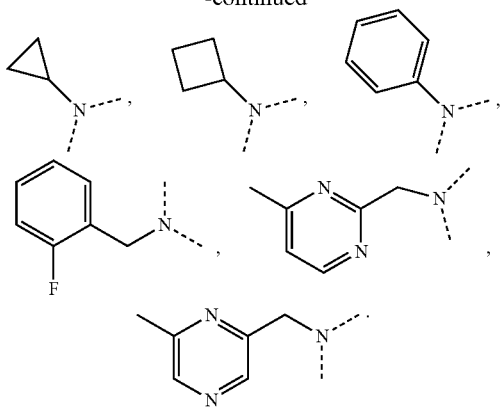

In some embodiments of the present invention, R$_5$ is selected from the group consisting of phenyl, pyridyl, pyrimidinyl, pyrazinyl, pyridazinyl, thienyl, imidazolyl, pyrazolyl, oxazolyl, thiazolyl, isoxazolyl and isothiazolyl, each of which is optionally substituted by 1, 2 or 3 R.

In some embodiments of the present invention, R$_5$ is selected from the group consisting of

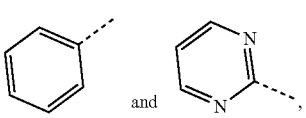

each of which is optionally substituted by 1, 2 or 3 R.

In some embodiments of the present invention, R$_5$ is selected from

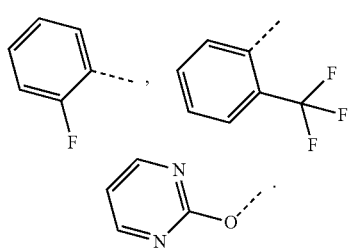

In some embodiments of the present invention, R$_5$-L$_2$- is selected from

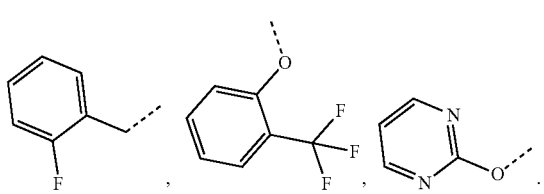

In some embodiments of the present invention, R$_1$ and R$_2$ are each independently selected from H, F, Cl, Br, I, OH, NH$_2$, CN, R$_5$-L$_2$-, or selected from the group consisting of C$_{1-3}$ alkyl, C$_{1-3}$ alkoxy, C$_{1-3}$ alkylthio, C$_{1-3}$ alkylamino, C$_{2-4}$ alkenyl, 1,2,3,6-tetrahydropyridyl, pyridin-2(1H)-one-yl, phenyl, pyridyl, pyrimidinyl, pyrazinyl, pyridazinyl, pyrazolyl, imidazolyl, thiazolyl, isothiazolyl and thienyl, each of which is optionally substituted by 1, 2 or 3 R.

In some embodiments of the present invention, R$_1$ and R$_2$ are each independently selected from H, F, Cl, Br, I, OH, NH$_2$, CN, R$_5$-L$_2$-, or selected from the group consisting of Me,

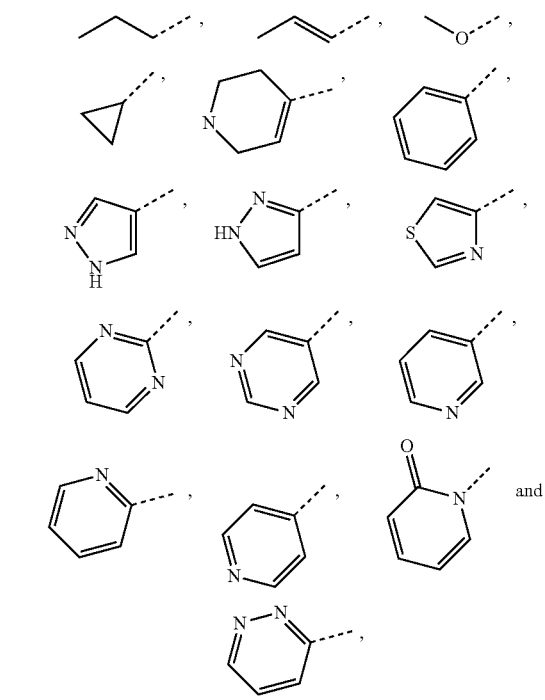

each of which is optionally substituted by 1, 2 or 3 R.

In some embodiments of the present invention, R$_1$ and R$_2$ are each independently selected from H, F, Cl, Br, I, OH, NH$_2$, CN, Me,

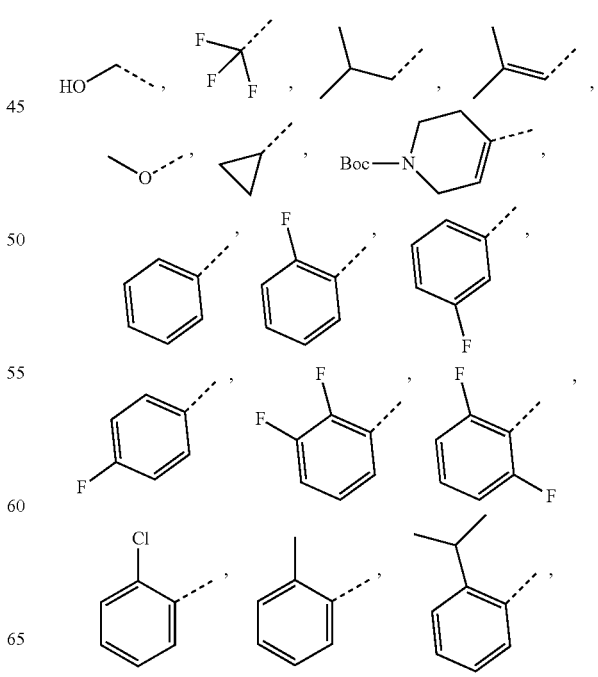

-continued

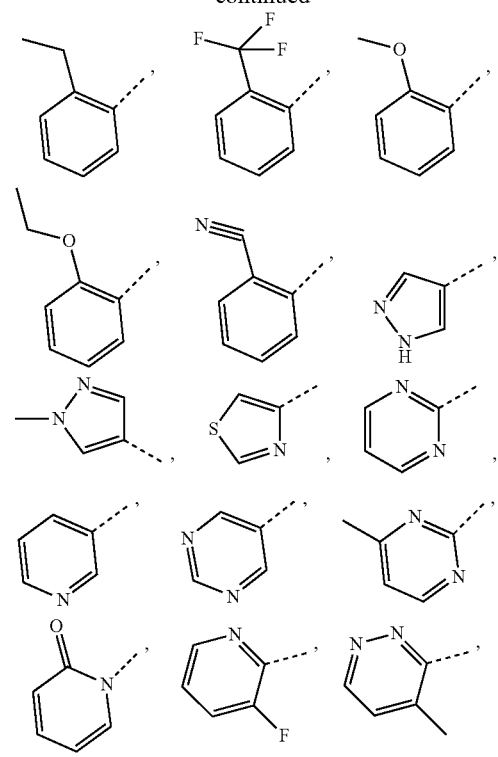

In some embodiments of the present invention, R$_6$ is selected from the group consisting of Me and Et, each of which is optionally substituted by 1, 2 or 3 R.

In some embodiments of the present invention, R$_6$ is selected from Me, CH$_2$F, CHF$_2$.

In some embodiments of the present invention, R is selected from H, F, Cl, Br, I, OH, NH$_2$, CN, or selected from the group consisting of C$_{1-3}$ alkyl, C$_{1-3}$ alkoxy, C$_{1-3}$ alkyl-thio, C$_{1-3}$ alkylamino, C$_{1-4}$-alkyl-OC(=O)— and N,N'-di (C$_{1-3}$ alkyl)amino, each of which is optionally substituted by 1, 2 or 3 R', and other variables are as defined above.

In some embodiments of the present invention, R is selected from H, F, Cl, Br, I, OH, NH$_2$, CN, Me, CF$_3$, CHF$_2$, CH$_2$F, Et,

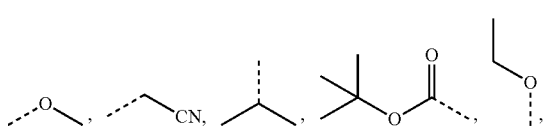

and other variables are as defined above.

In some embodiments of the present invention, R$_4$ is selected from the group consisting of phenyl, pyridyl, pyrimidinyl, pyrazinyl, thienyl, imidazolyl, pyrazolyl, oxazolyl, thiazolyl, isoxazolyl and isothiazolyl, each of which is optionally substituted by 1, 2 or 3 R, and other variables are as defined above.

In some embodiments of the present invention, R$_4$ is selected from the group consisting of

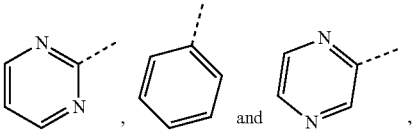

each of which is optionally substituted by 1, 2 or 3 R, and other variables are as defined above.

In some embodiments of the present invention, R$_4$ is selected from

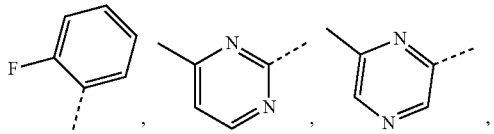

each of which is optionally substituted by 1, 2 or 3 R, and other variables are as defined above.

In some embodiments of the present invention, R$_4$-L$_1$- is selected from

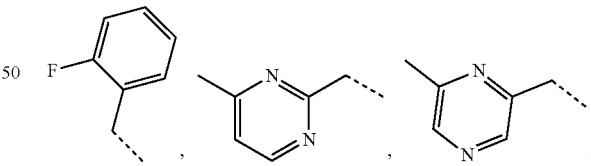

and other variables are as defined above.

In some embodiments of the present invention, R$_3$ is selected from H, F, Cl, Br, I, OH, NH$_2$, R$_4$-L$_1$-, or selected from the group consisting of C$_{1-3}$ alkyl, C$_{3-6}$ cycloalkyl, —C$_{1-3}$-alkyl-C(=O)O—C$_{1-3}$ alkyl-, C$_{1-3}$-alkyl-S(=O)$_2$—C$_{1-3}$ alkyl-, phenyl, pyridyl, pyrimidinyl and pyrazinyl, each of which is optionally substituted by 1, 2 or 3 R, and other variables are as defined above.

In some embodiments of the present invention, R$_3$ is selected from H, F, Cl, Br, I, OH, NH$_2$, R$_4$-L$_1$-, or selected from the group consisting of Me, Et,

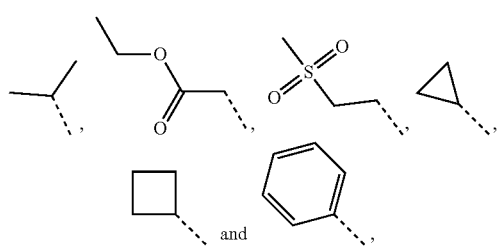

and other variables are as defined above.

each of which is optionally substituted by 1, 2 or 3 R, and other variables are as defined above.

In some embodiments of the present invention, $R_3$ is selected from H, F, Cl, Br, I, OH, $NH_2$, Me, Et,

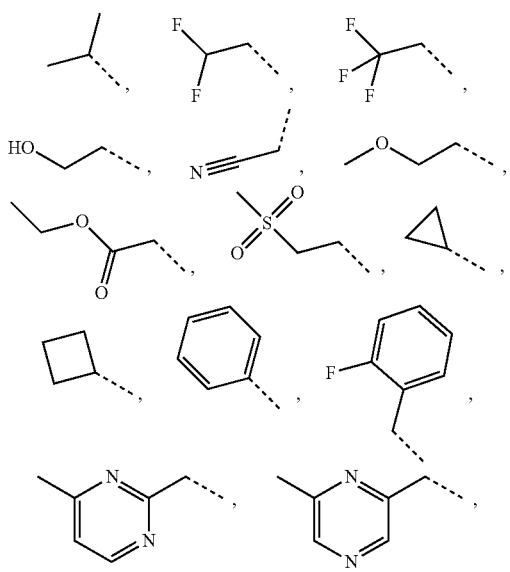

and other variables are as defined above.

In some embodiments of the present invention, X is selected from

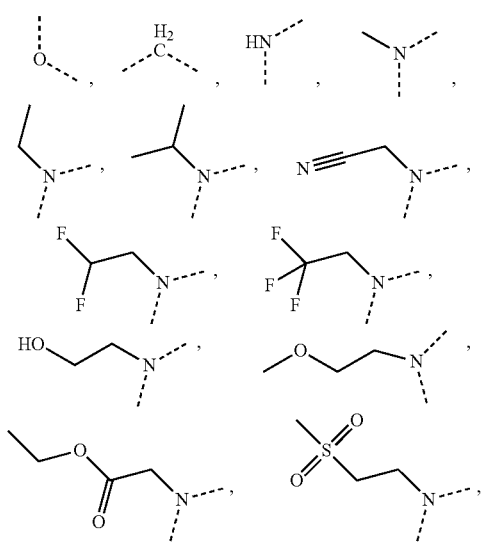

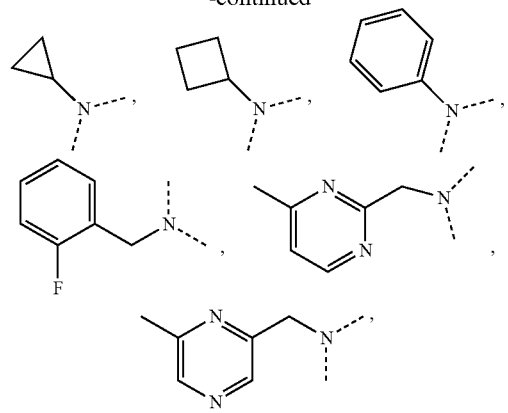

and other variables are as defined above.

In some embodiments of the present invention, $R_5$ is selected from the group consisting of phenyl, pyridyl, pyrimidinyl, pyrazinyl, pyridazinyl, thienyl, imidazolyl, pyrazolyl, oxazolyl, thiazolyl, isoxazolyl and isothiazolyl, each of which is optionally substituted by 1, 2 or 3 R, and other variables are as defined above.

In some embodiments of the present invention, $R_5$ is selected from the group consisting of

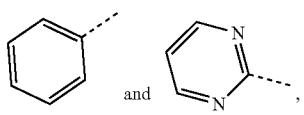

each of which is optionally substituted by 1, 2 or 3 R, and other variables are as defined above.

In some embodiments of the present invention, $R_5$ is selected from

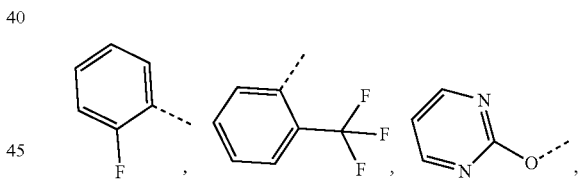

and other variables are as defined above.

In some embodiments of the present invention, $R_5\text{-}L_2\text{-}$ is selected from

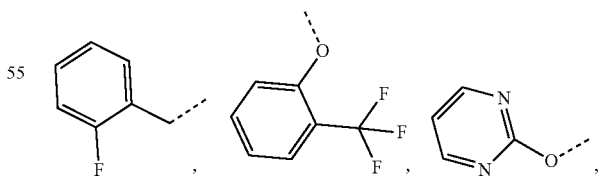

and other variables are as defined above.

In some embodiments of the present invention, $R_1$ and $R_2$ are each independently selected from H, F, Cl, Br, I, OH, $NH_2$, CN, $R_5\text{-}L_2\text{-}$, or the group consisting of $C_{1-3}$ alkyl, $C_{1-3}$ alkoxy, $C_{1-3}$ alkylthio, $C_{1-3}$ alkylamino, $C_{2-4}$ alkenyl, 1,2,3, 6-tetrahydropyridyl, pyridin-2(1H)-one-yl, phenyl, pyridyl, pyrimidinyl, pyrazinyl, pyridazinyl, pyrazolyl, imidazolyl, thiazolyl, isothiazolyl and thienyl, each of which is optionally substituted by 1, 2 or 3 R, and other variables are as defined above.

In some embodiments of the present invention, $R_1$ and $R_2$ are each independently selected from H, F, Cl, Br, I, OH, $NH_2$, CN, $R_5$-$L_2$-, or selected from the group consisting of Me,

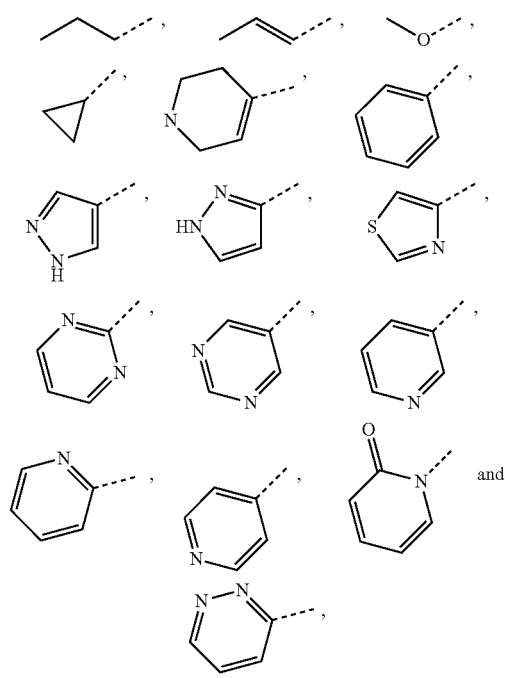

each of which is optionally substituted by 1, 2 or 3 R, and other variables are as defined above.

In some embodiments of the present invention, $R_1$ and $R_2$ are each independently selected from H, F, Cl, Br, I, OH, $NH_2$, CN, Me,

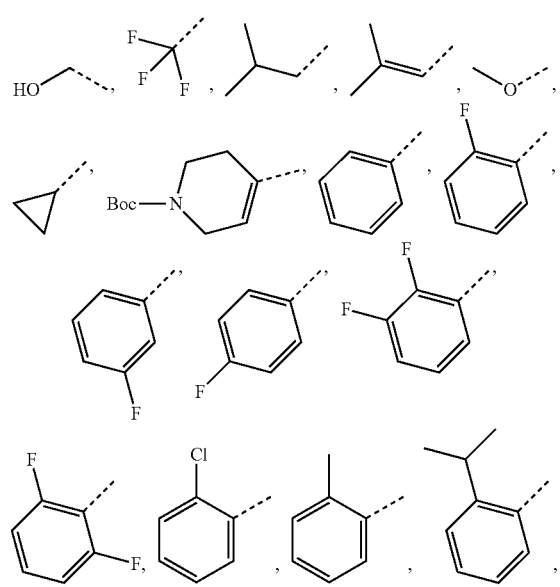

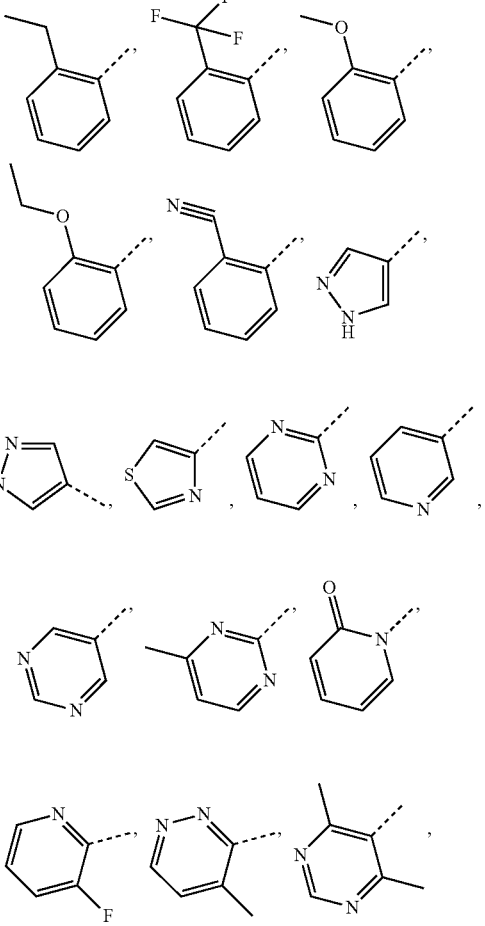

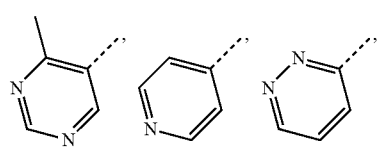

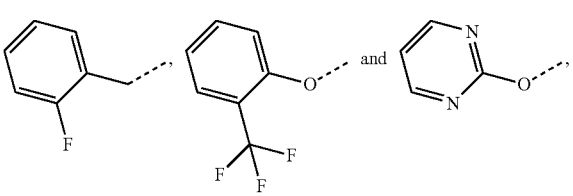

and other variables are as defined above.

In some embodiments of the present invention, $R_6$ is selected from the group consisting of Me and Et, each of which is optionally substituted by 1, 2 or 3 R, and other variables are as defined above.

In some embodiments of the present invention, $R_6$ is selected from Me, $CH_2F$ and $CHF_2$, and other variables are as defined above.

In some embodiments of the present invention, the compound or the pharmaceutically acceptable salt thereof is selected from

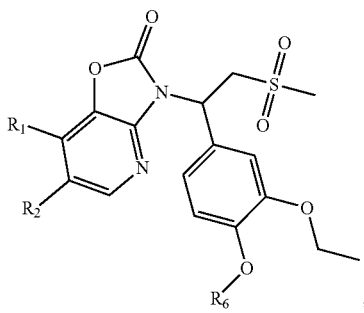
(I-1)
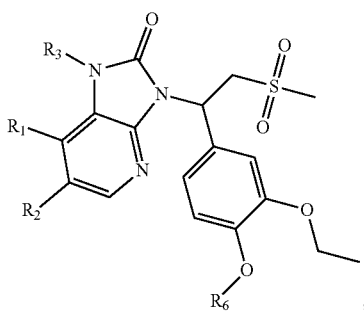
(I-2)
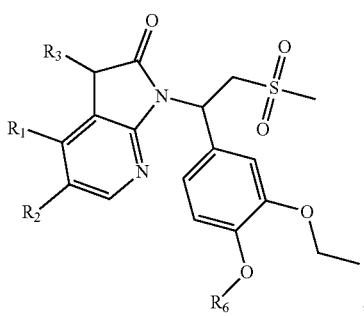
(I-3)
wherein $R_1$, $R_2$, $R_3$ and $R_6$ are defined as above.
In some embodiments of the present invention, the compound or the pharmaceutically acceptable salt thereof is selected from
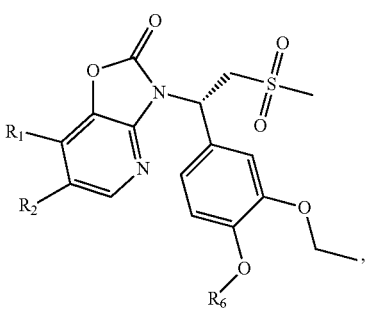
(I-1A)
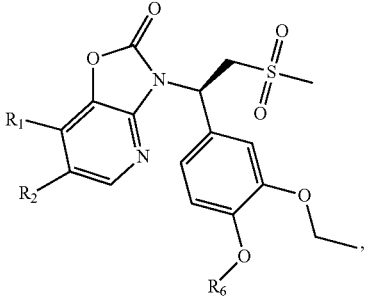
(I-1B)
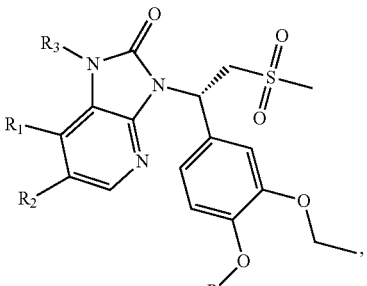
(I-2A)
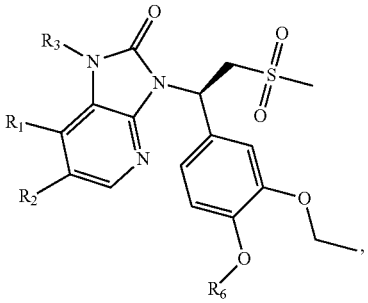
(I-2B)
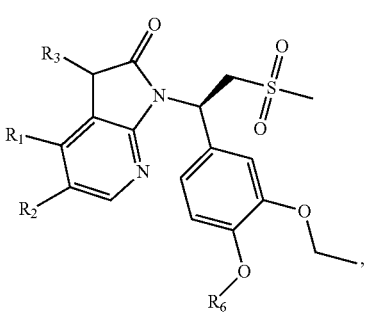
(I-3A)
(I-3B)
wherein $R_1$, $R_2$, $R_3$ and $R_6$ are defined as above.
The above variables can be arbitrarily combined, then other embodiments of the present invention are obtained.

The present invention also provides a compound as shown in formula below or a pharmaceutically acceptable salt thereof, which is selected from the group consisting of
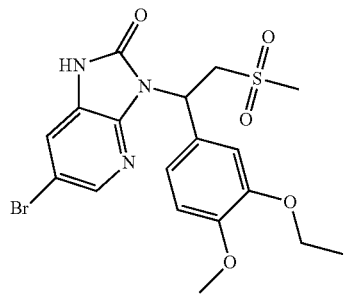
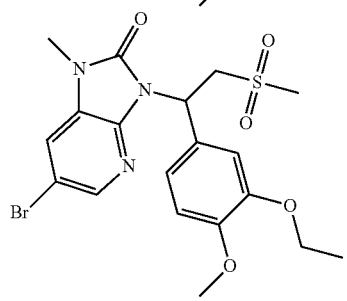
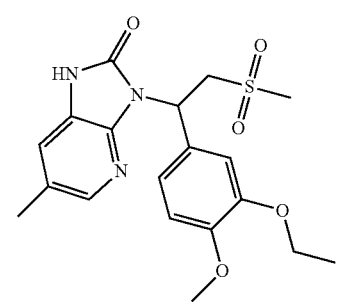
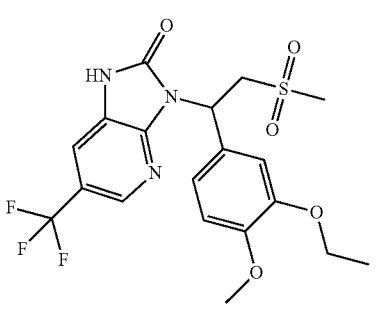
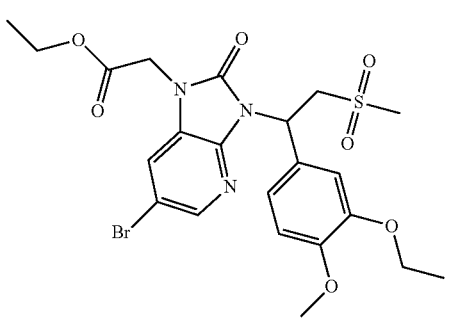
-continued
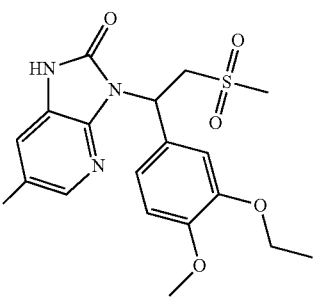
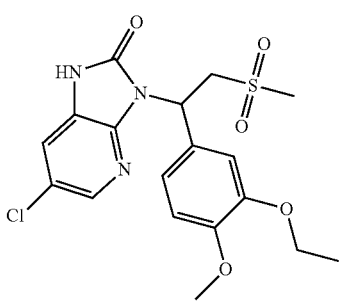
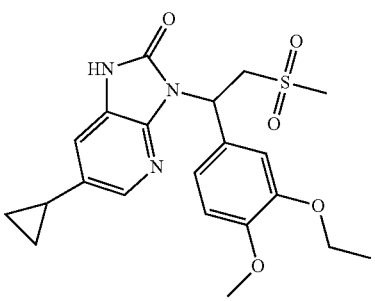
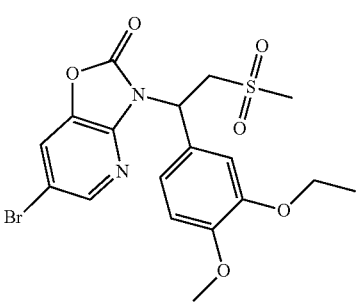
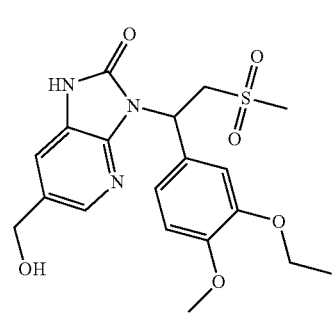

-continued
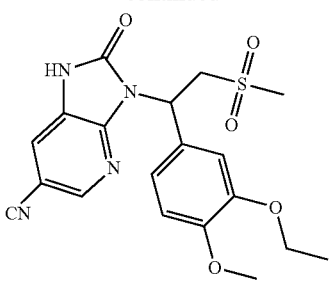
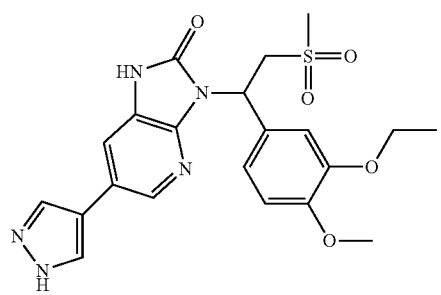
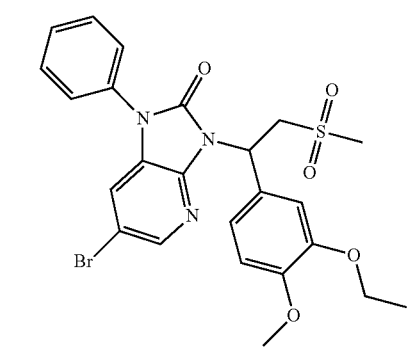
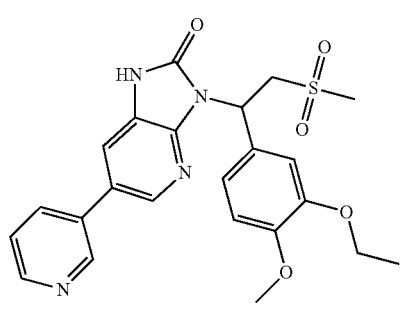
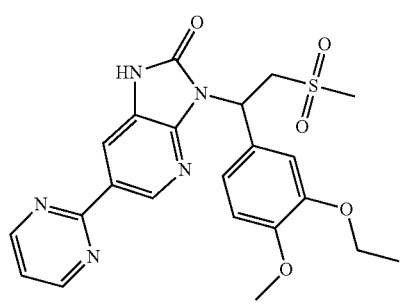
-continued
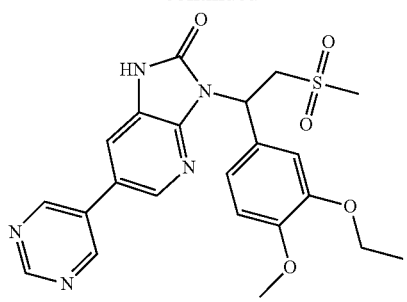
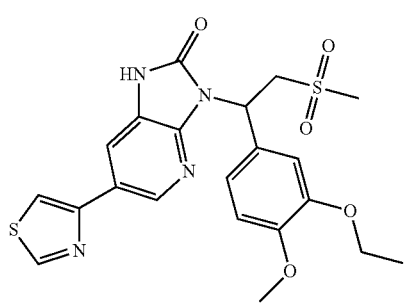
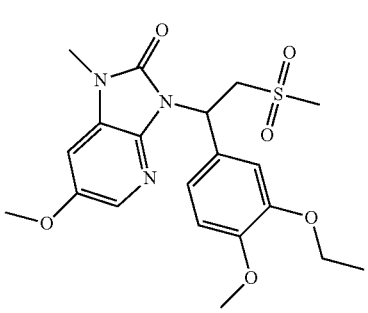
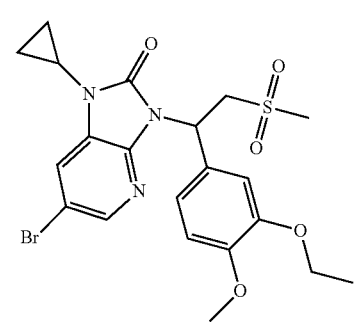
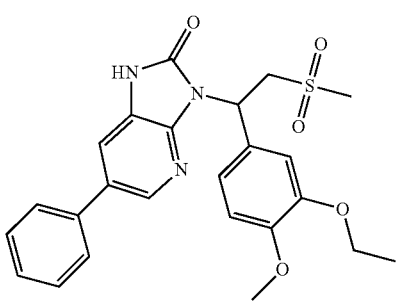

-continued

-continued
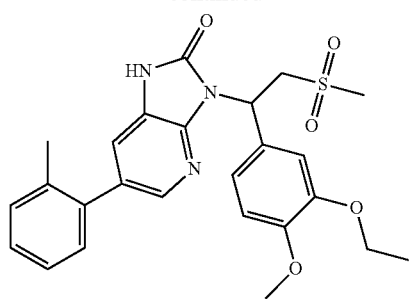
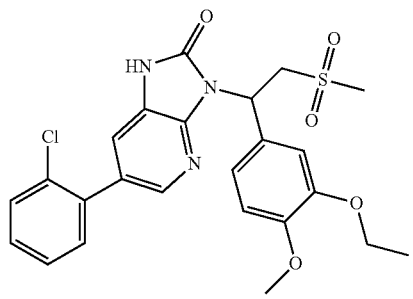
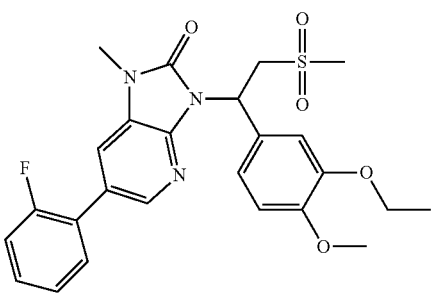
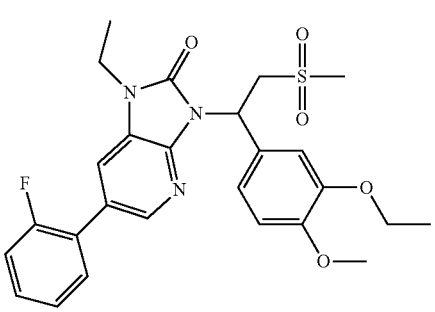
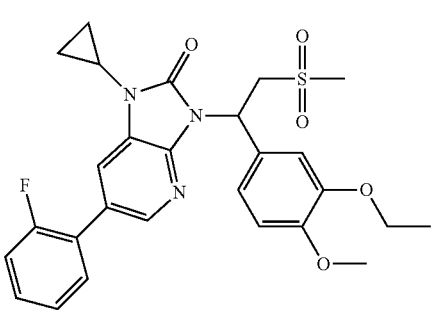
-continued
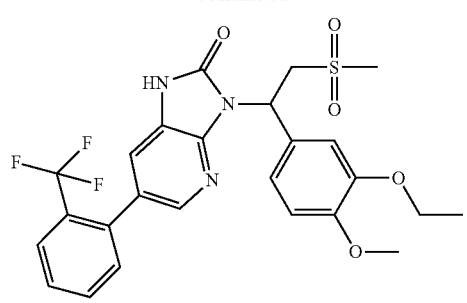
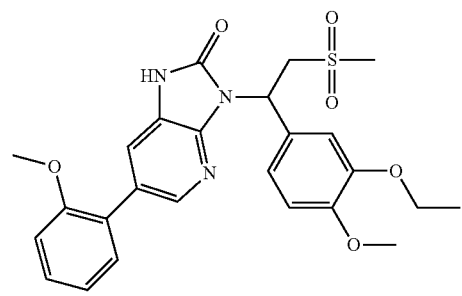
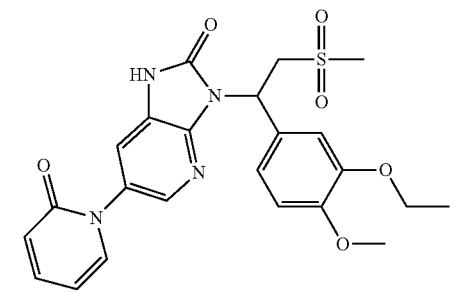
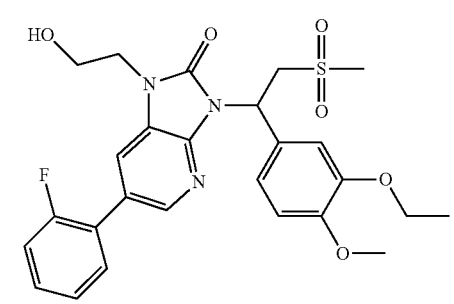
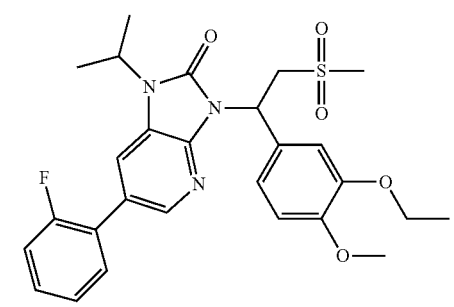

23
-continued
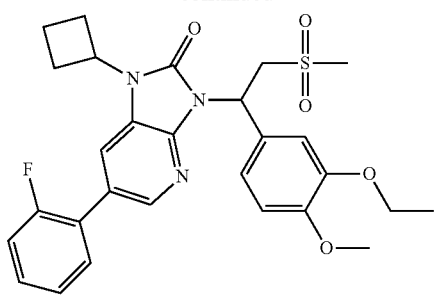
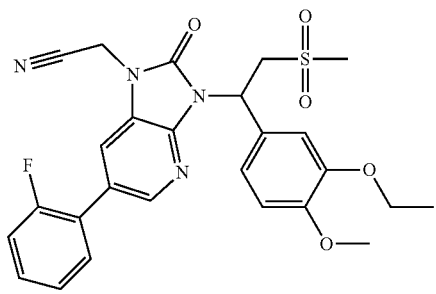
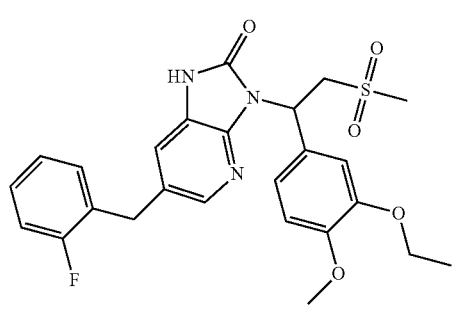
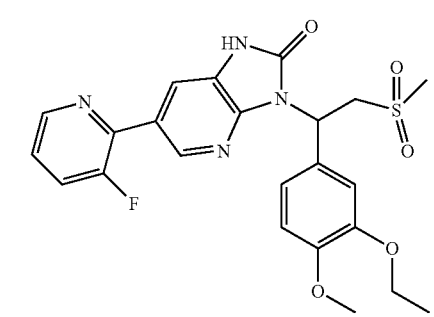
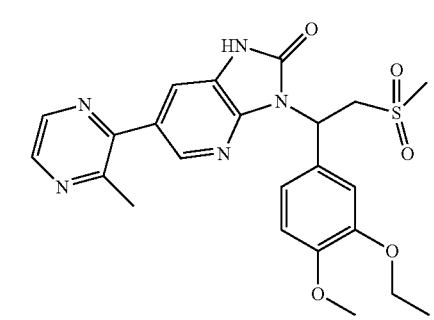
24
-continued
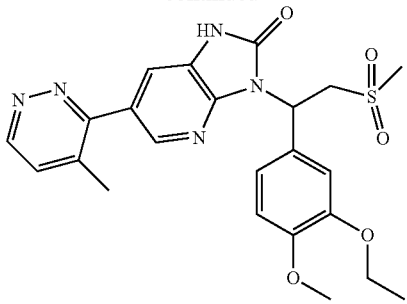
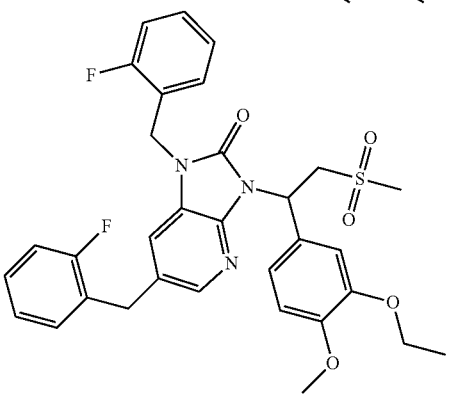
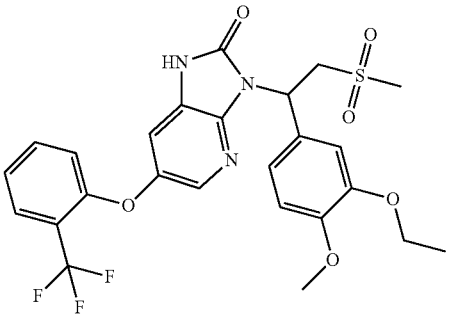
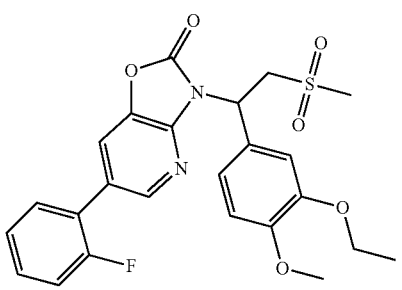
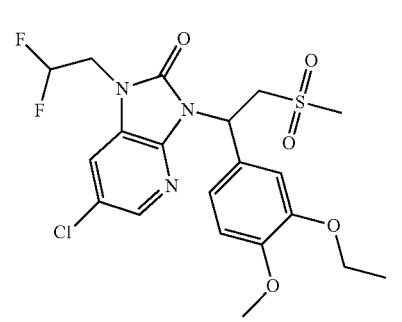

25
-continued
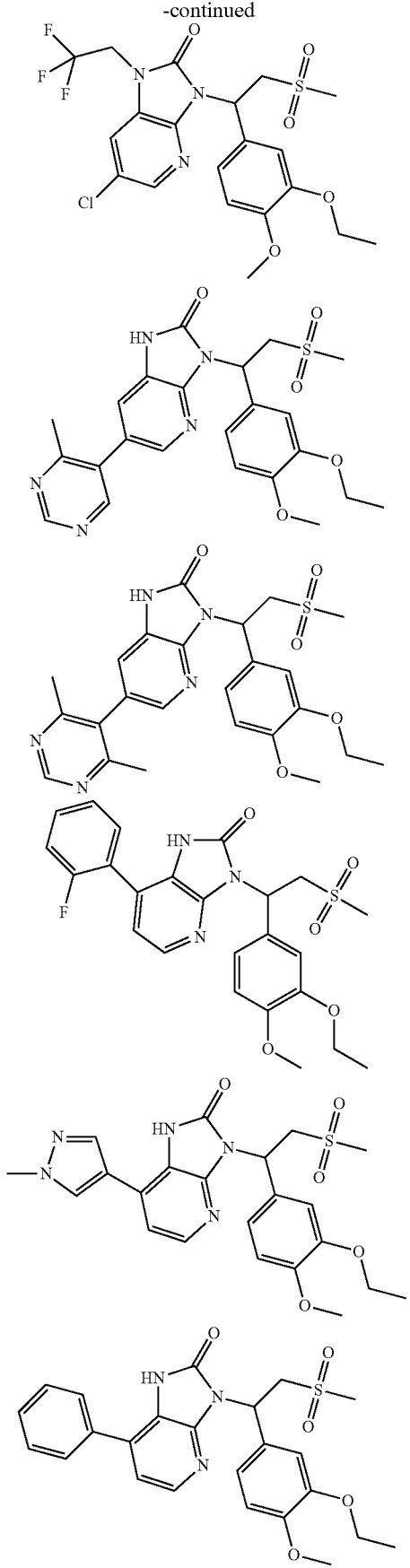
26
-continued
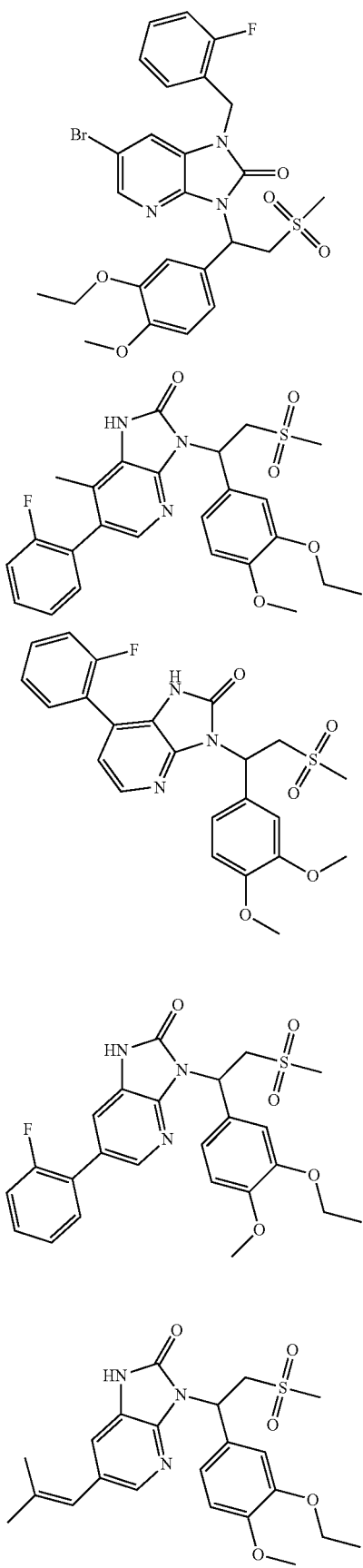

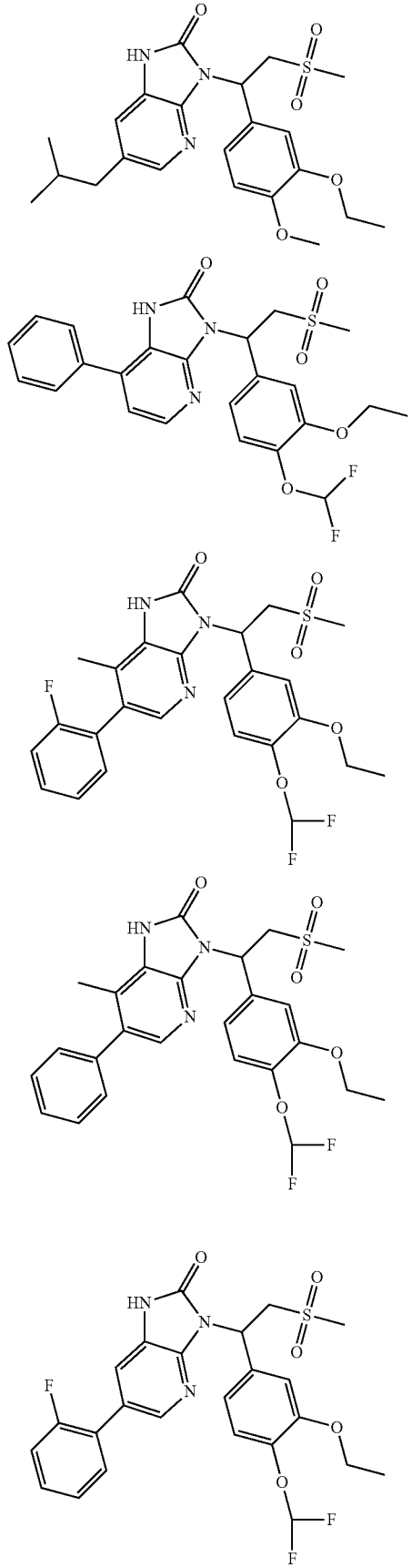
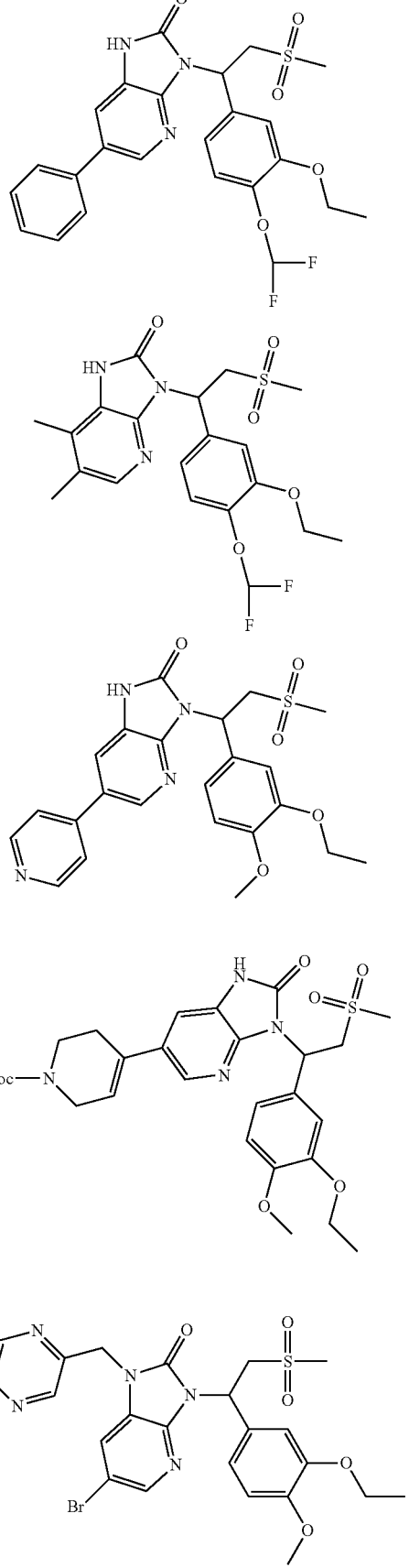

-continued
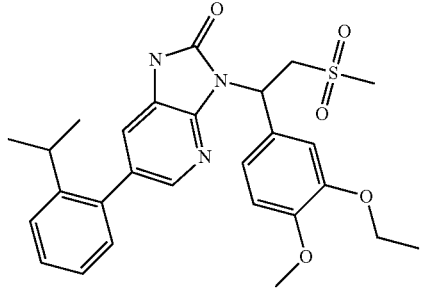
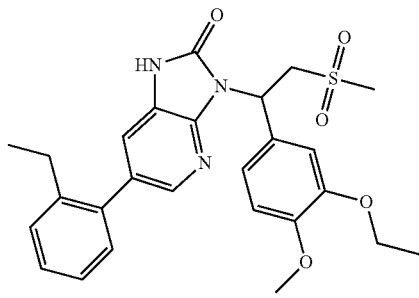
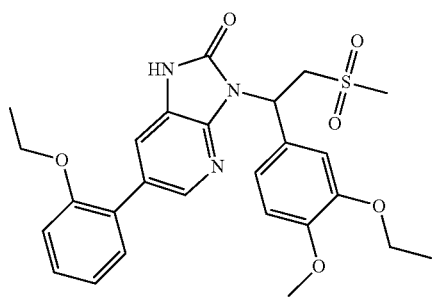
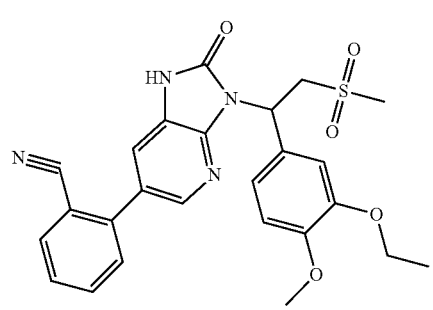
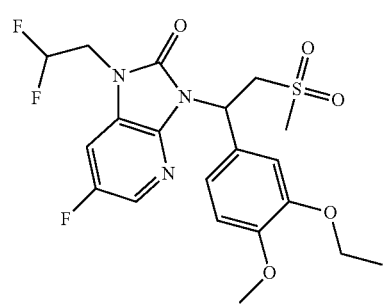
-continued
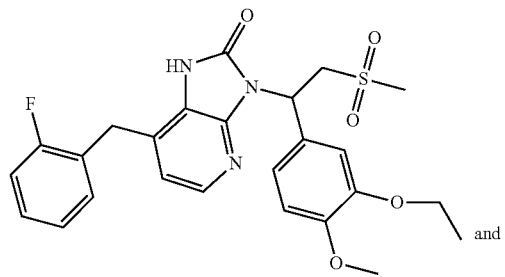
and
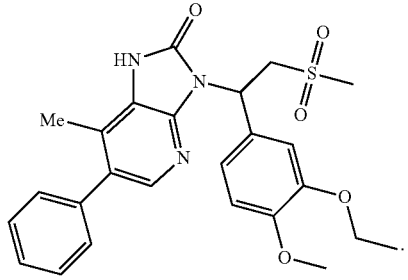
In some embodiments of the present invention, the compound or the pharmaceutically acceptable salt thereof is selected from the group consisting of
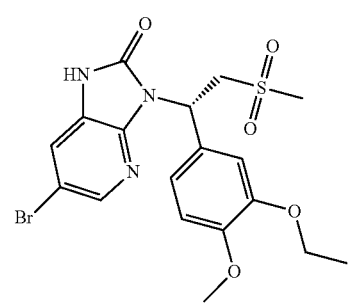
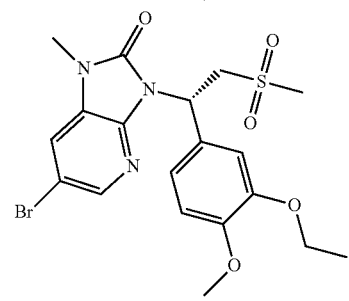
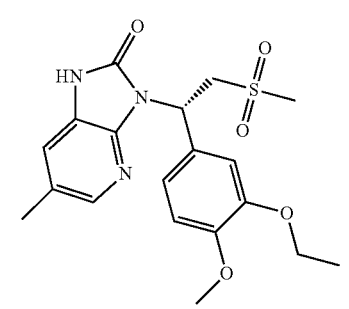

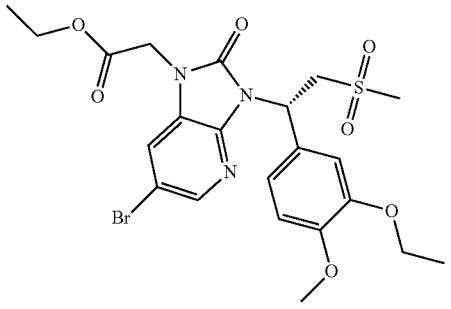
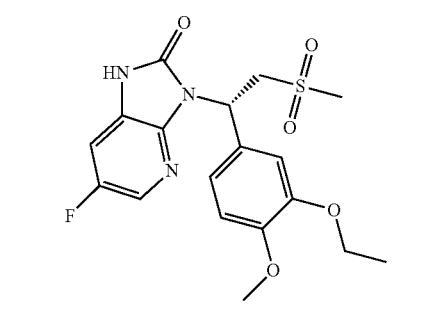
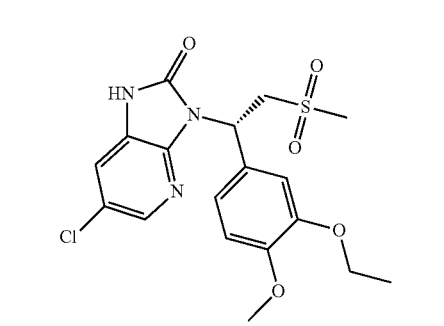
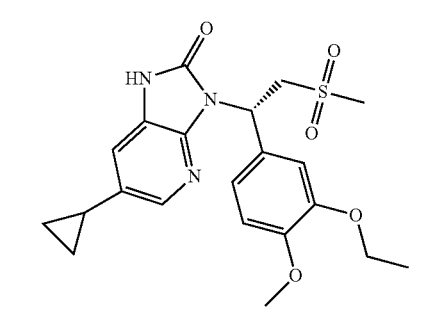
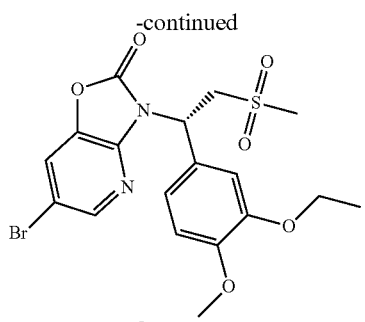
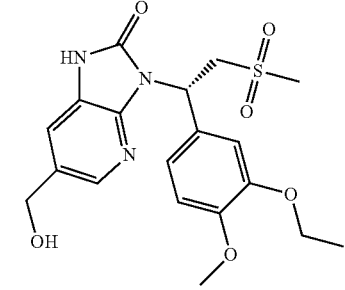
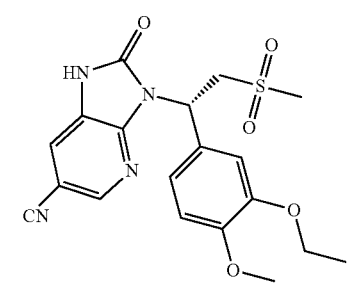
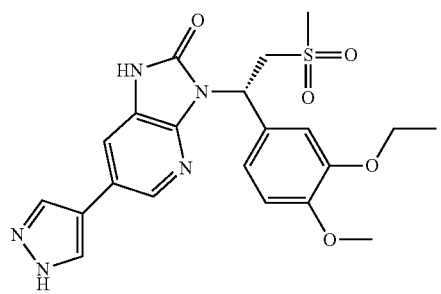
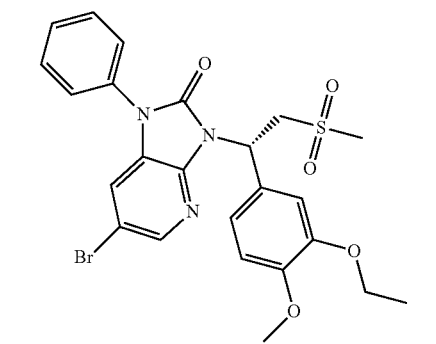

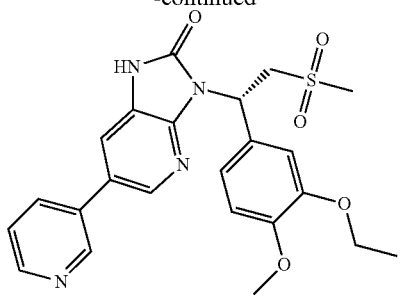
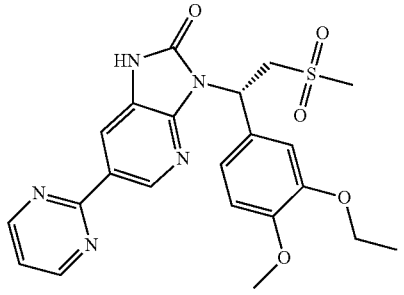
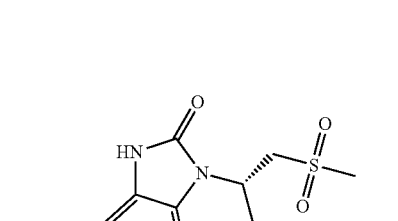
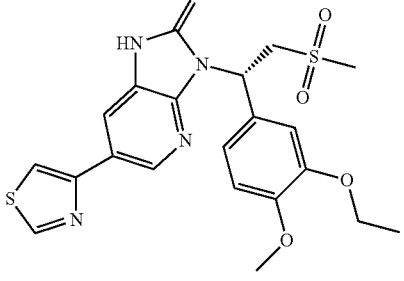
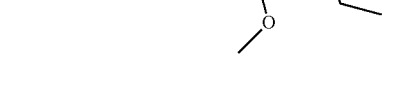
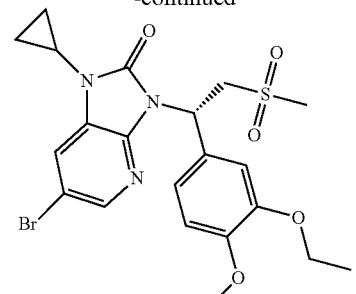
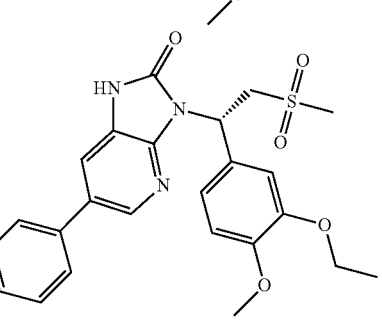
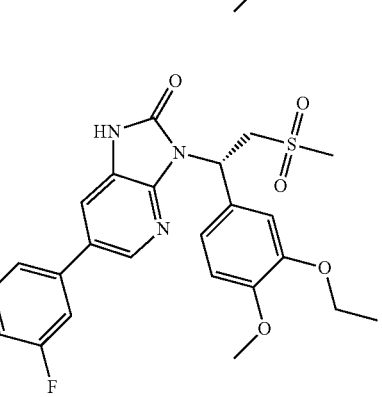
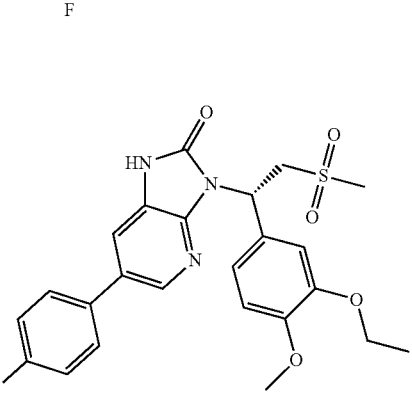
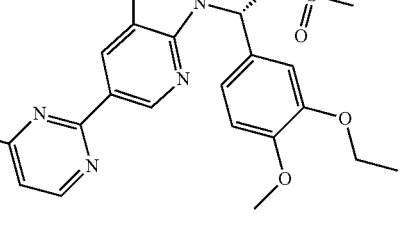

-continued
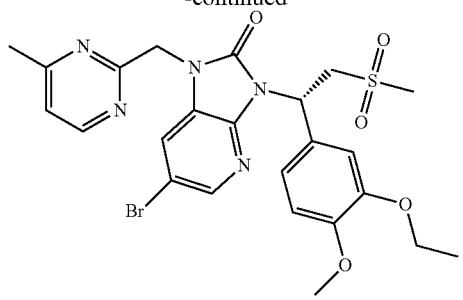
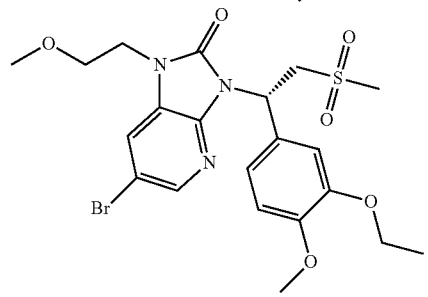
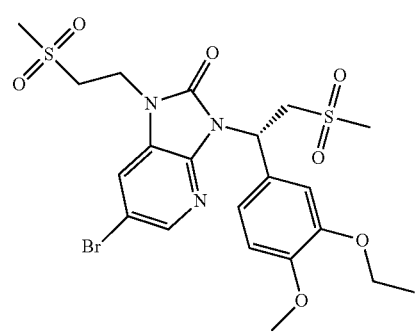
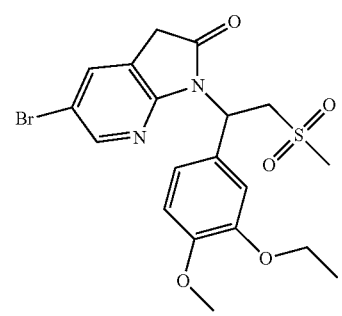
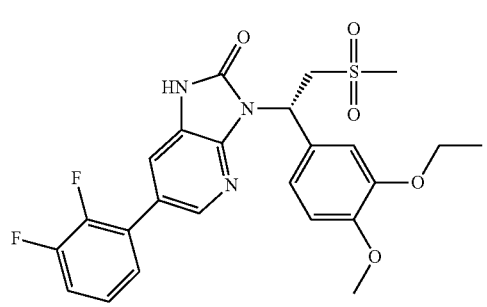
-continued
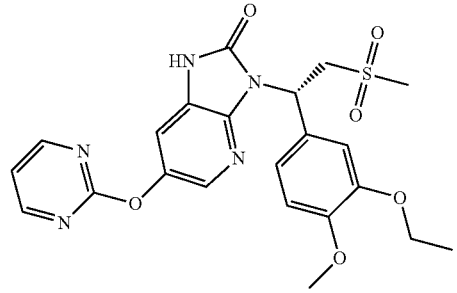
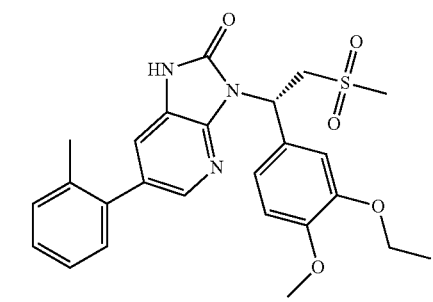
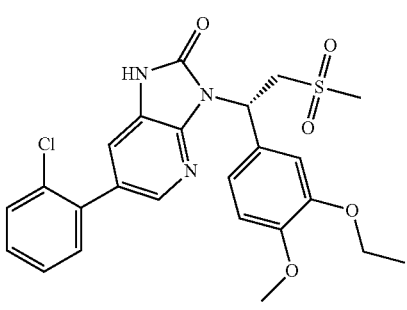
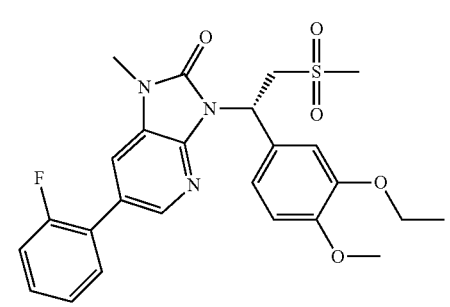

-continued
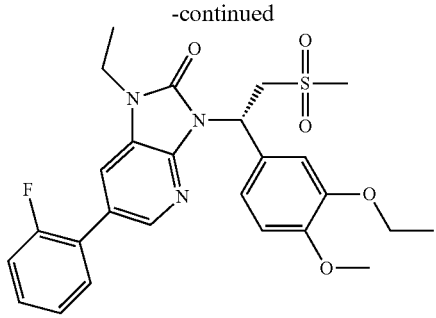
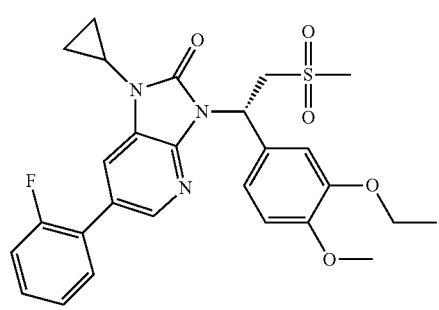
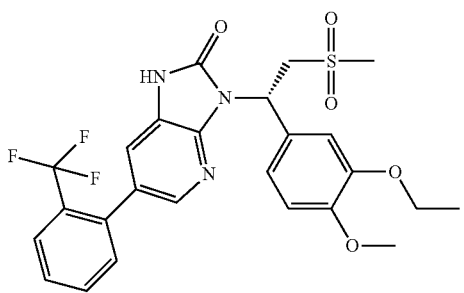
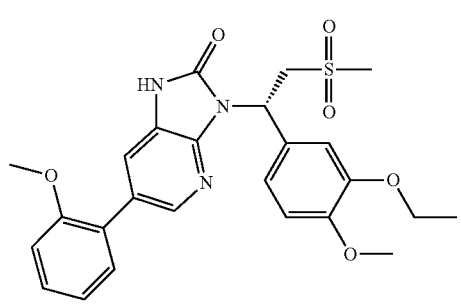
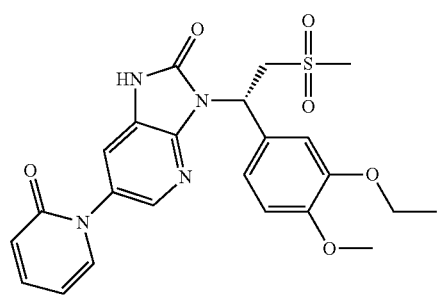
-continued
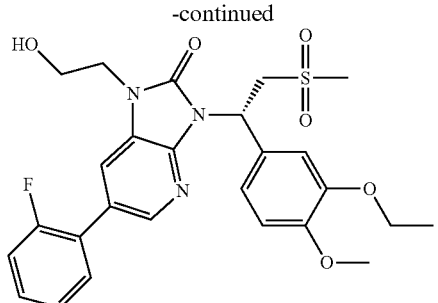
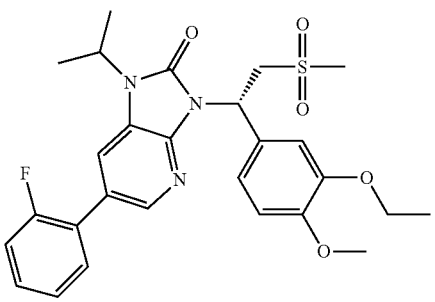
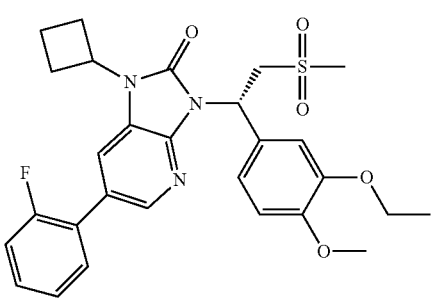
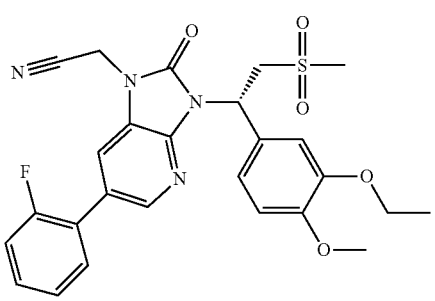
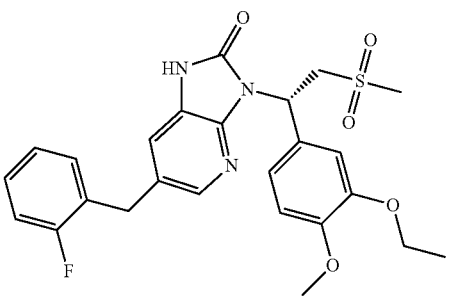

-continued
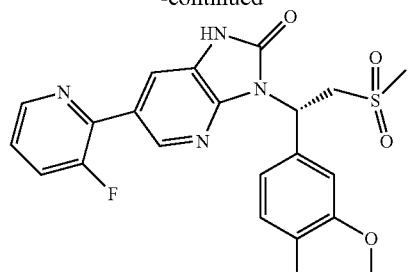
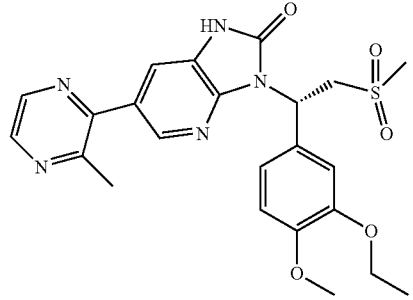
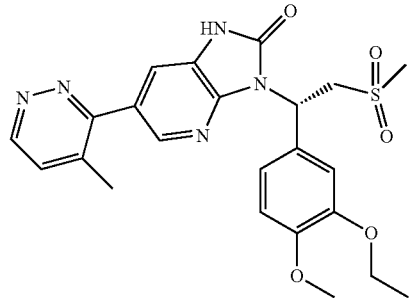
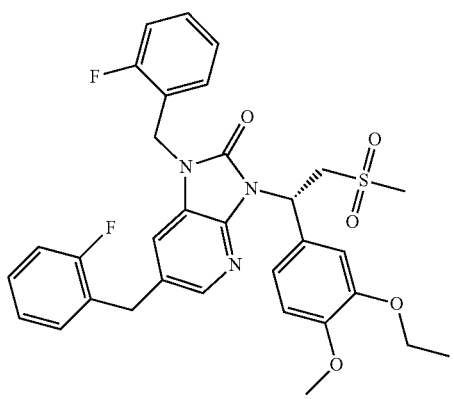
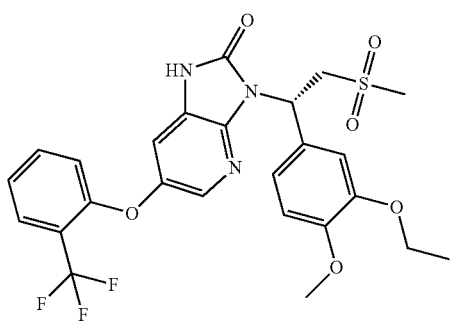
-continued
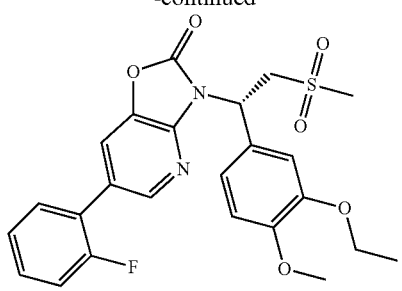
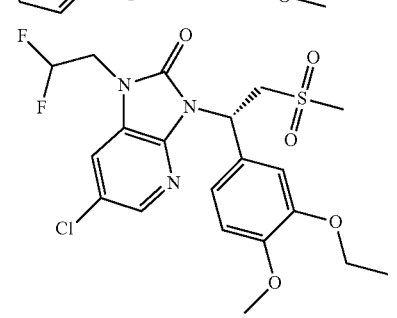
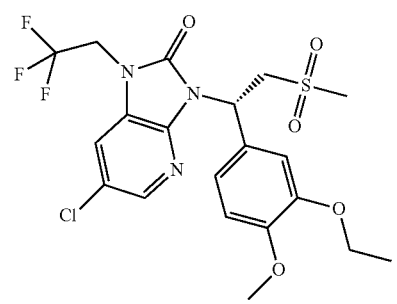
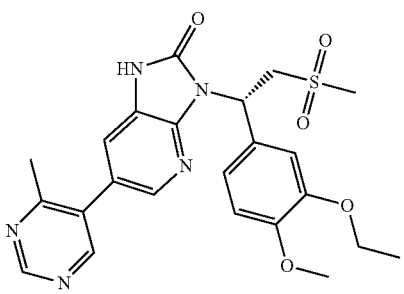
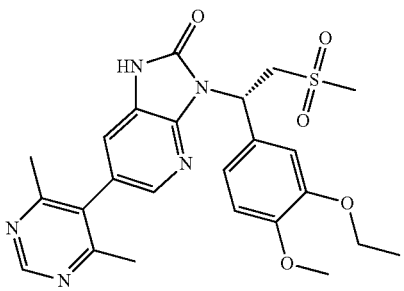

41
-continued
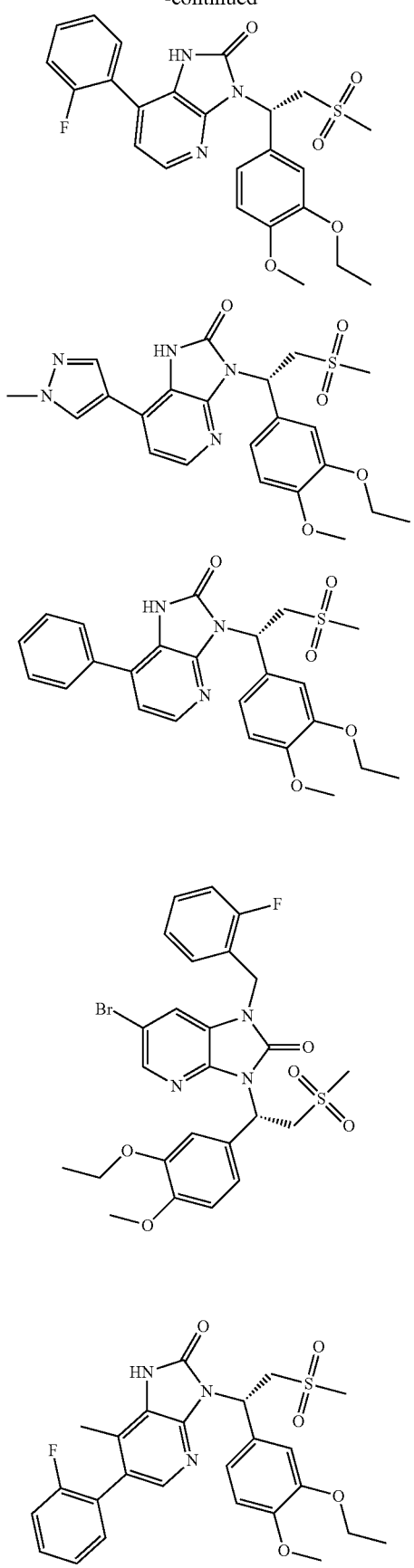
42
-continued
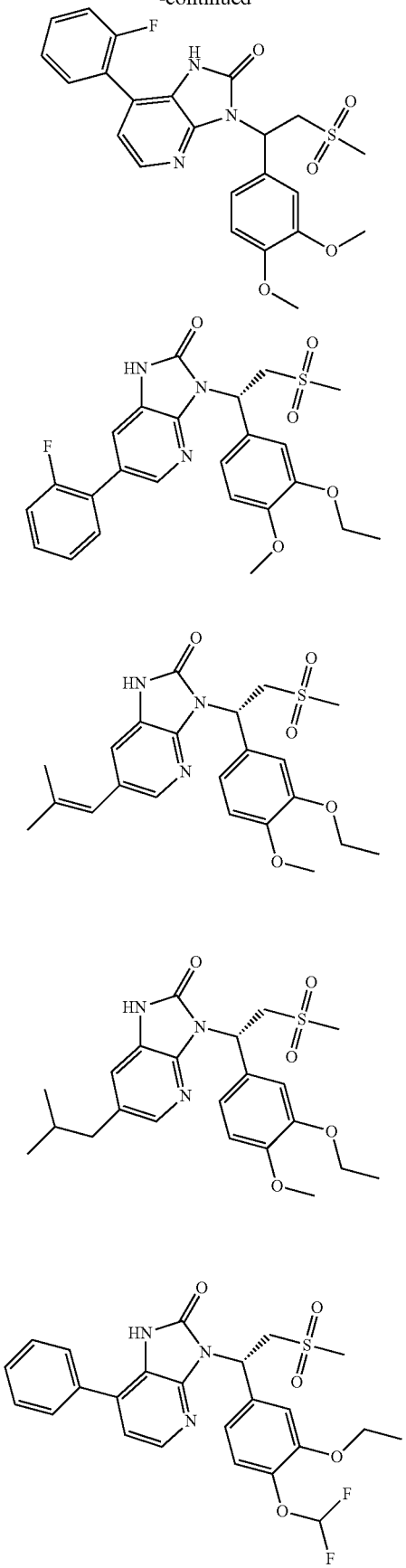

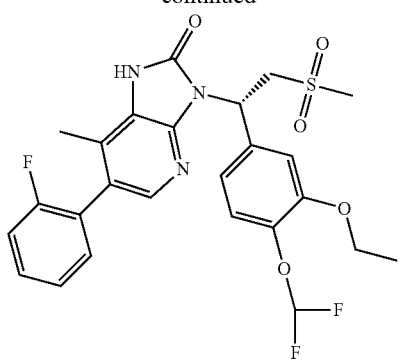
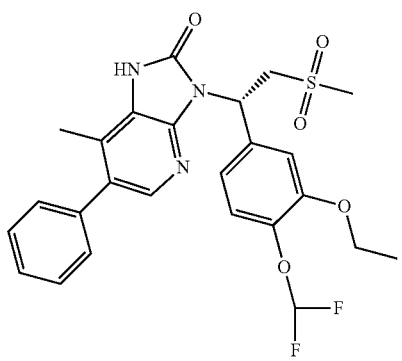
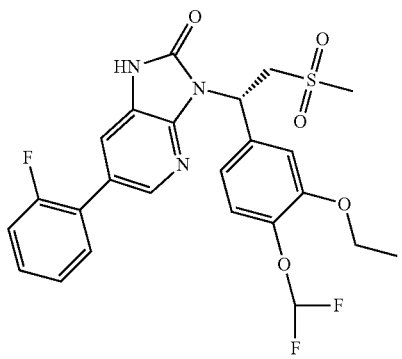
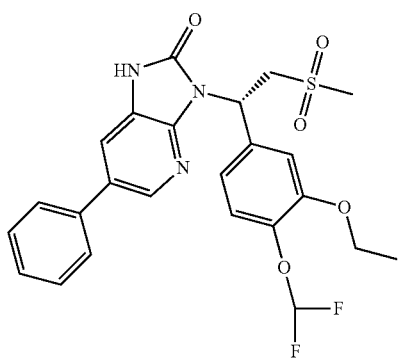
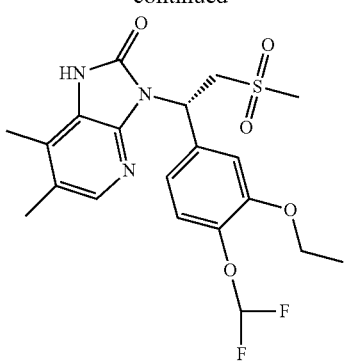
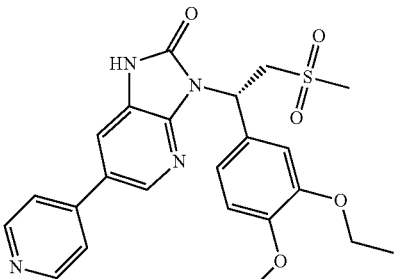
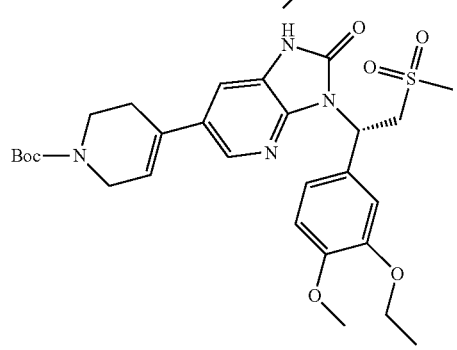
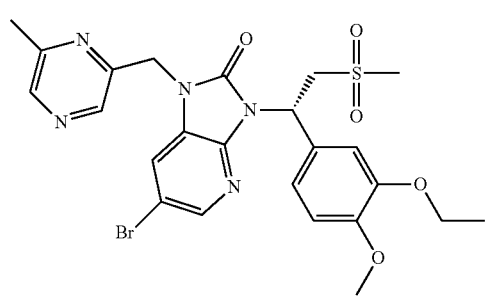
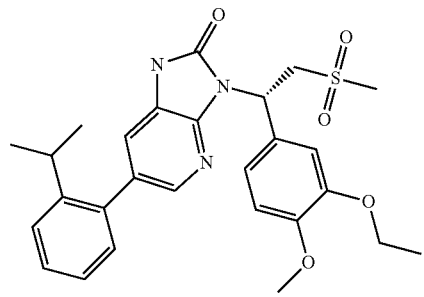

45
-continued
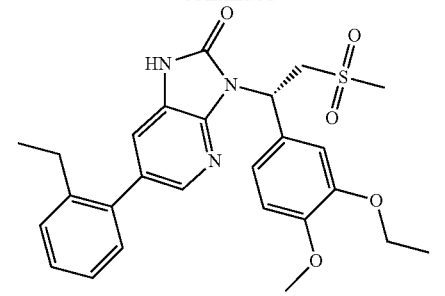
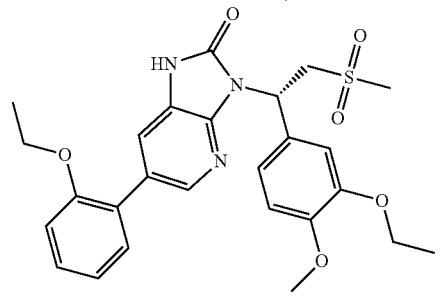
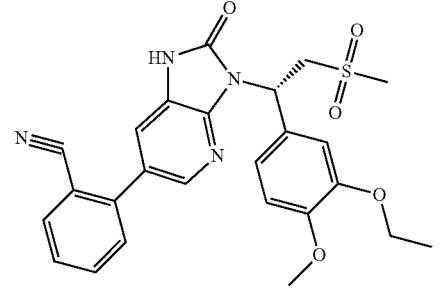
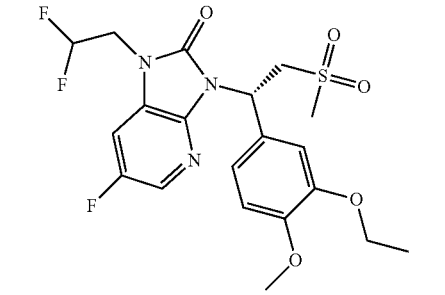
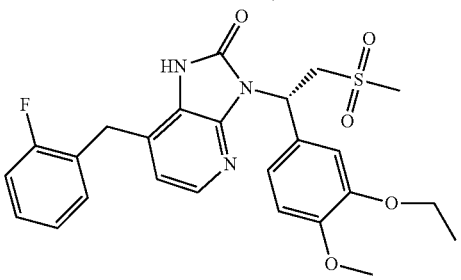
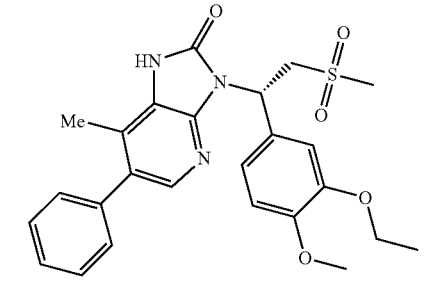
46
-continued
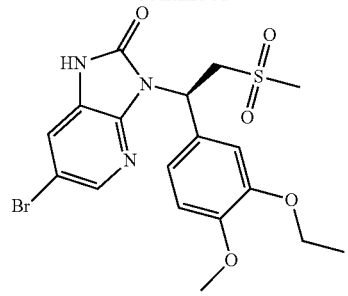
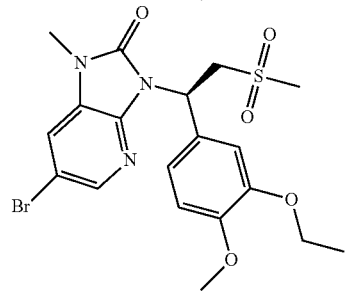
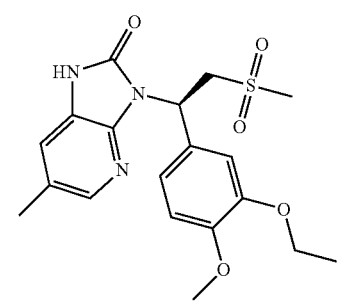
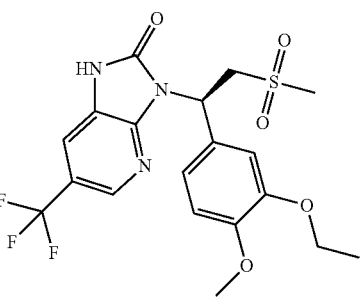
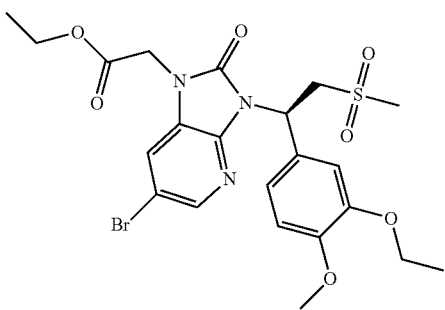

-continued
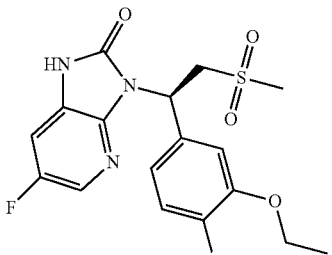
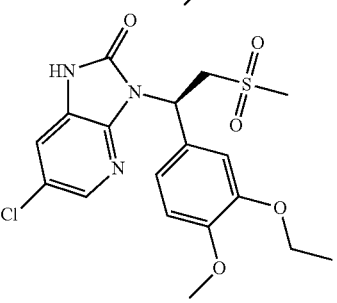
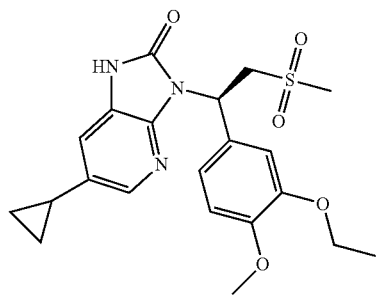
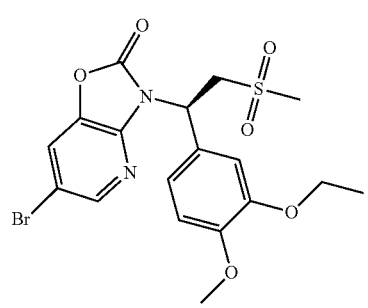
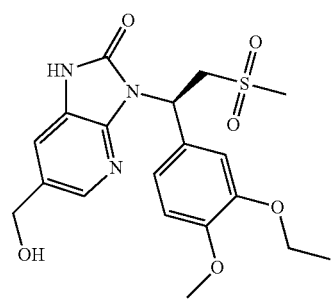
-continued
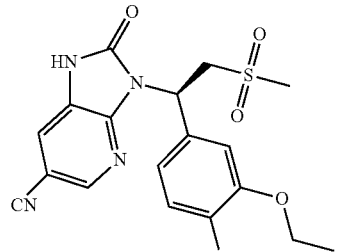
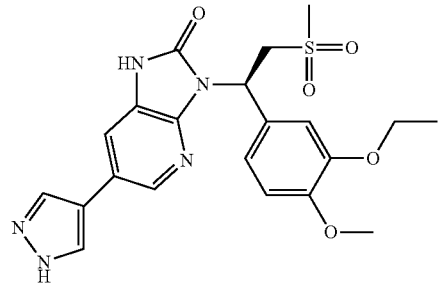
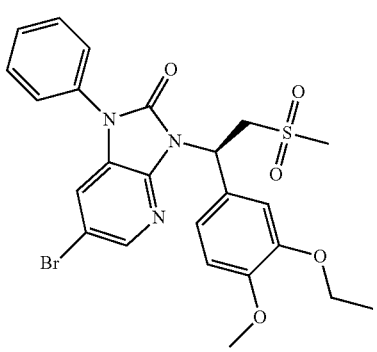
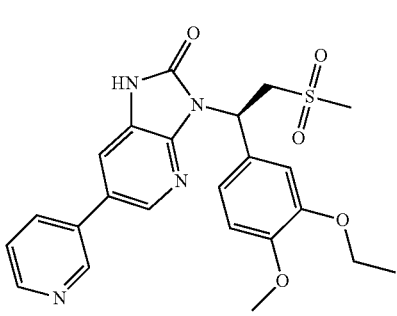
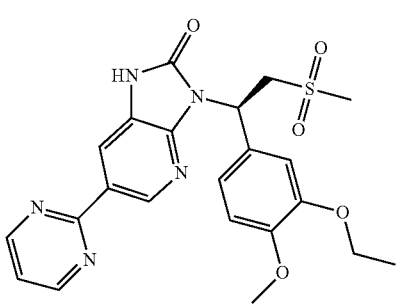

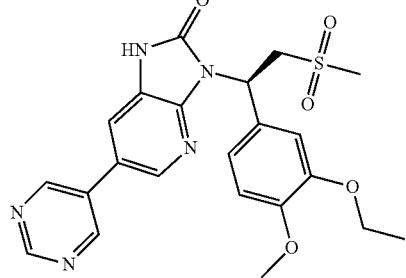
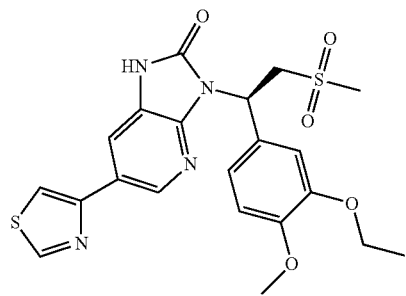
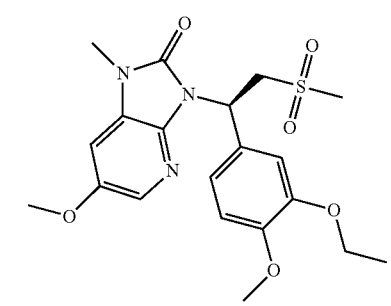
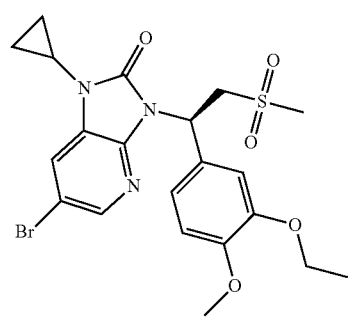
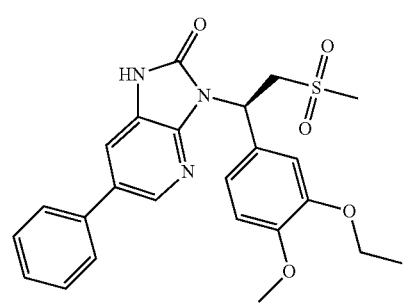
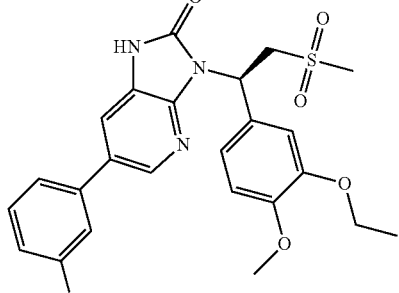
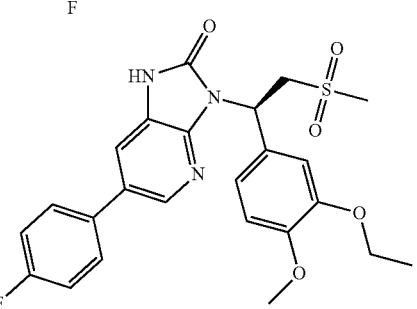
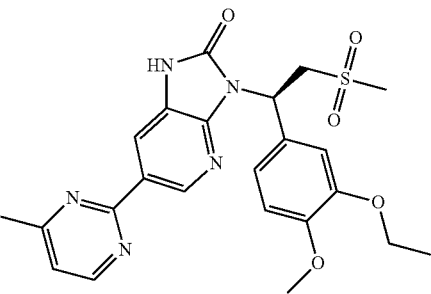
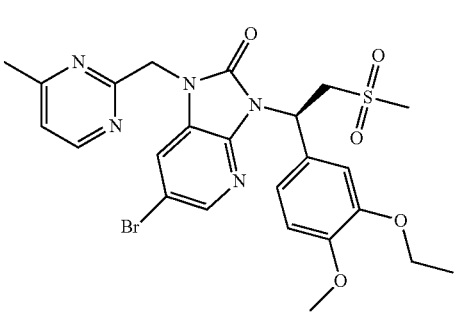
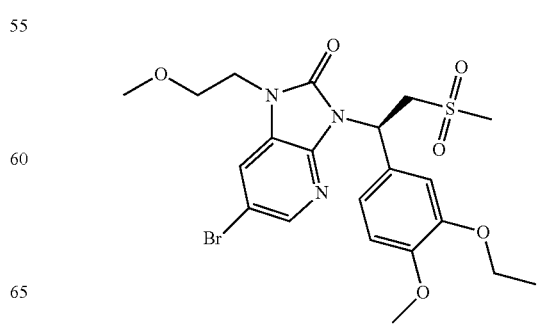

51
-continued
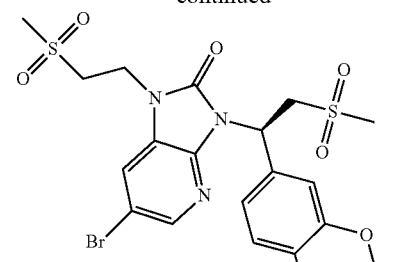
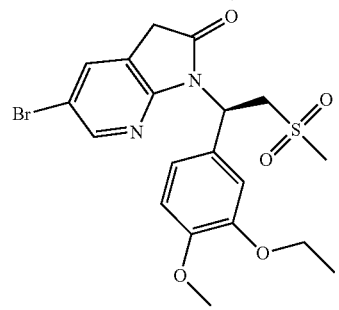
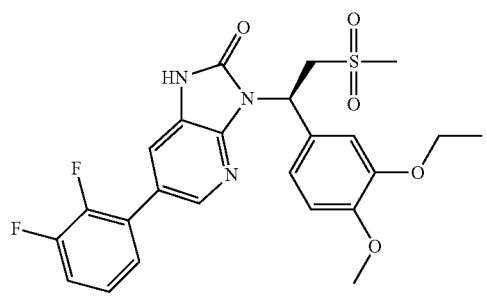
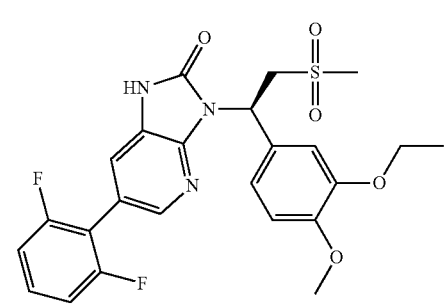
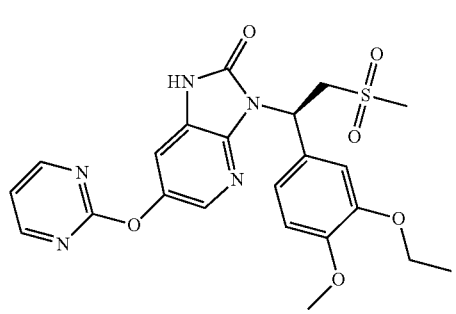
52
-continued
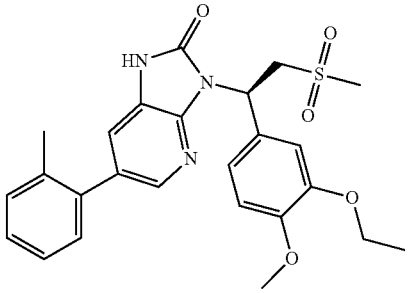
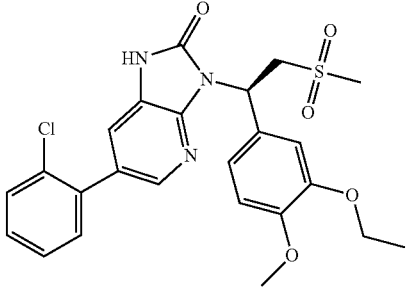
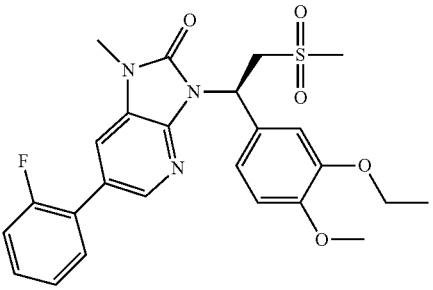
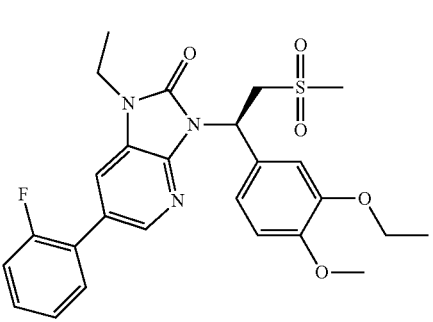
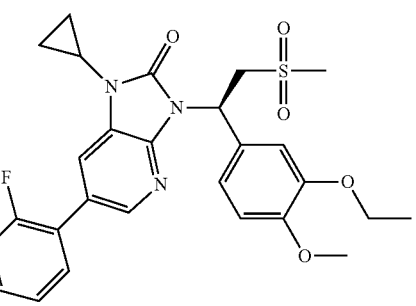

53
-continued
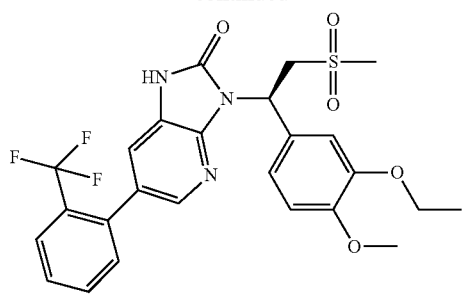
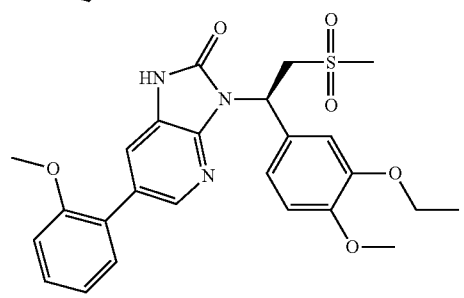
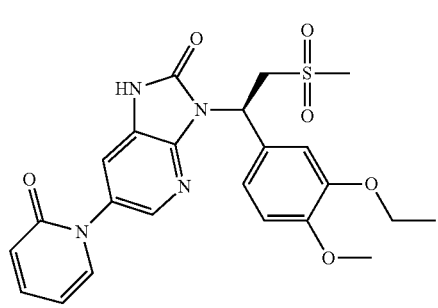
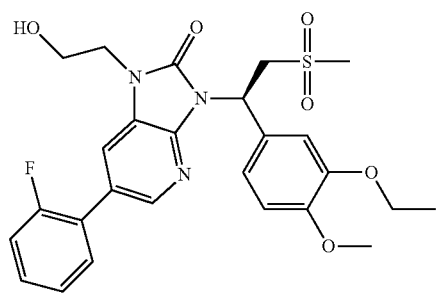
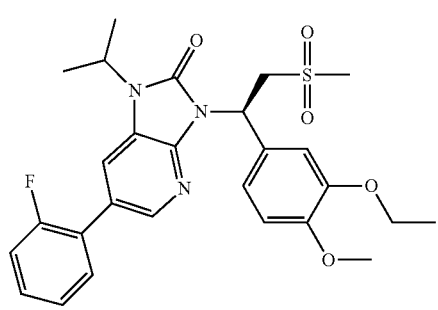
54
-continued
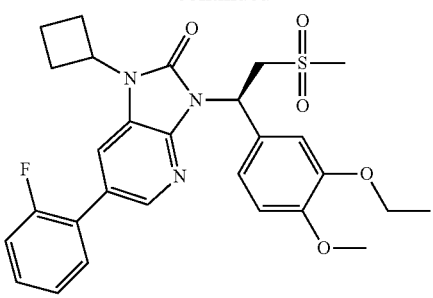
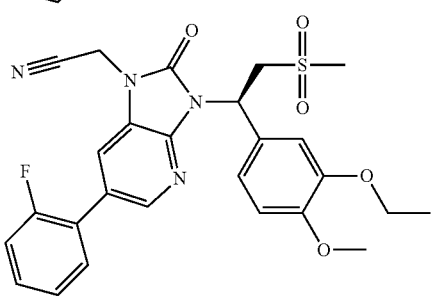
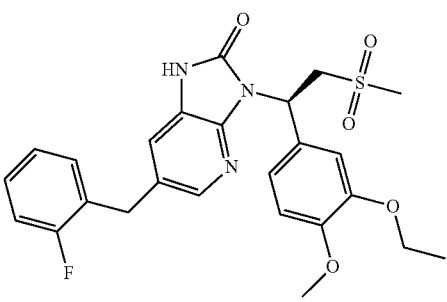
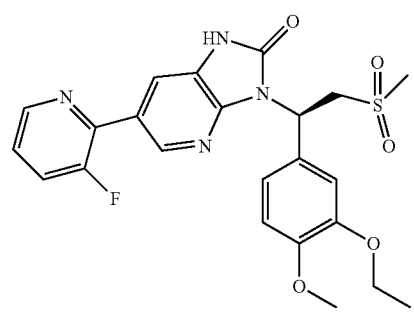
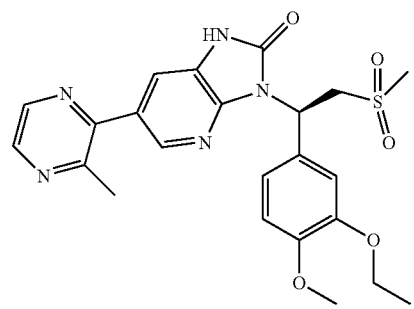

55
-continued
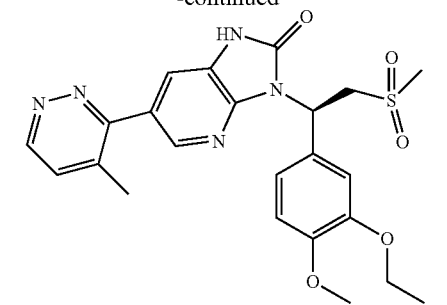
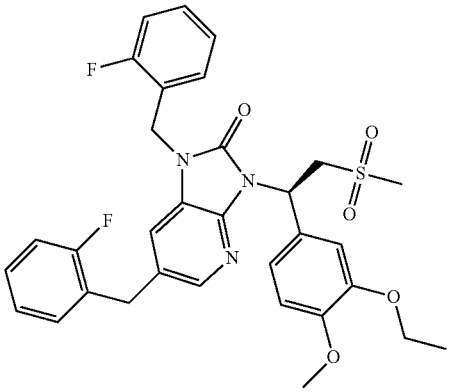
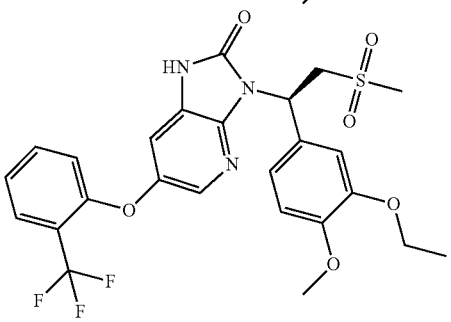
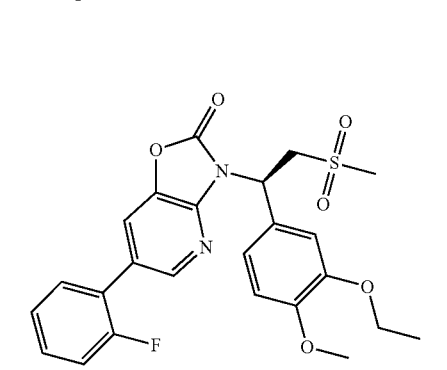
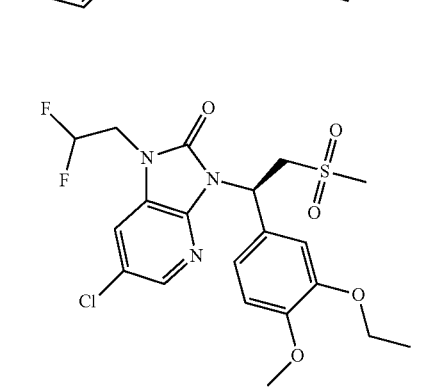
56
-continued
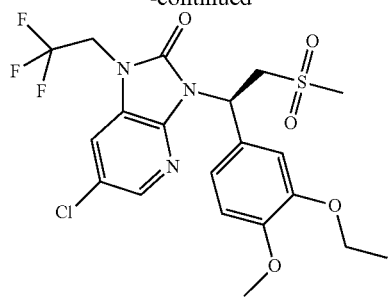
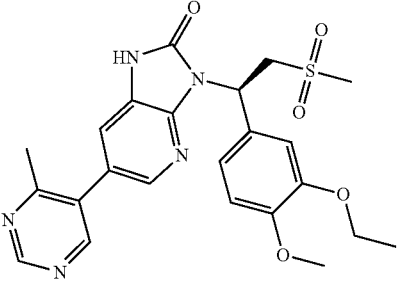
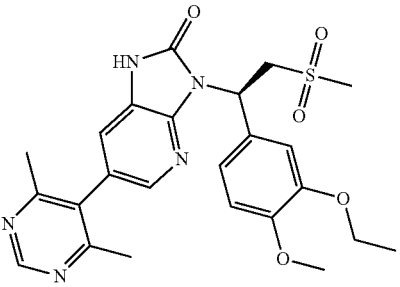
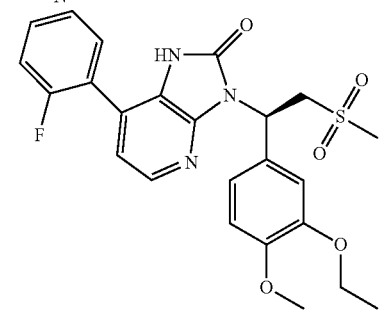
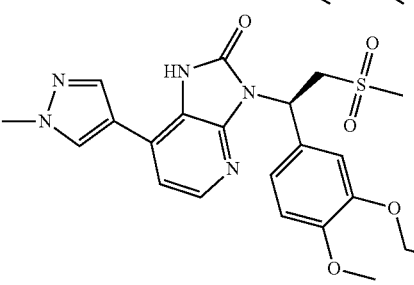
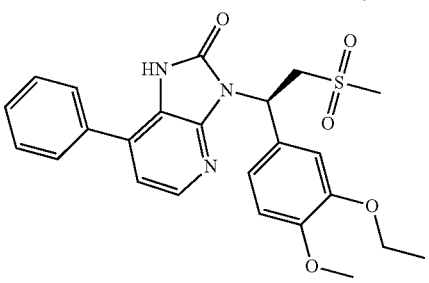

57
-continued
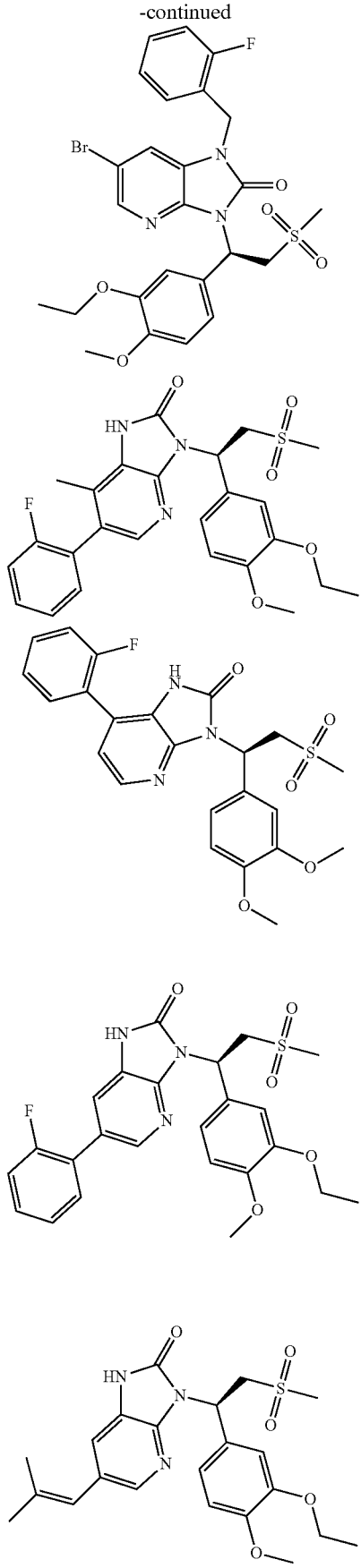
58
-continued
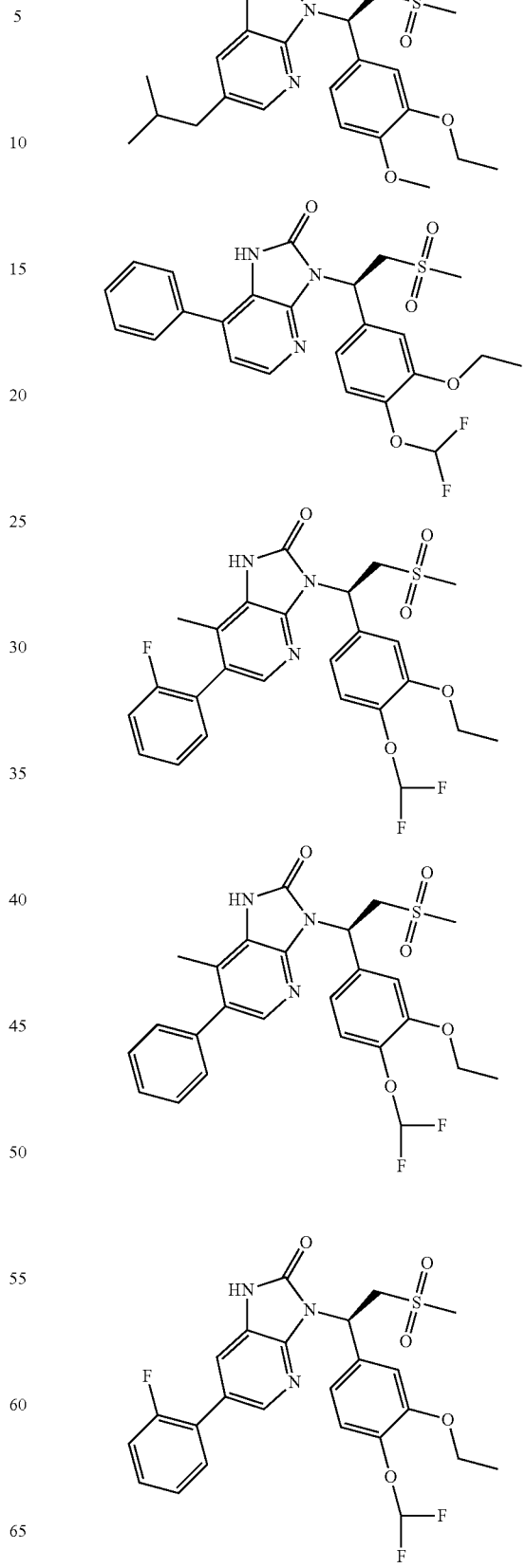

-continued
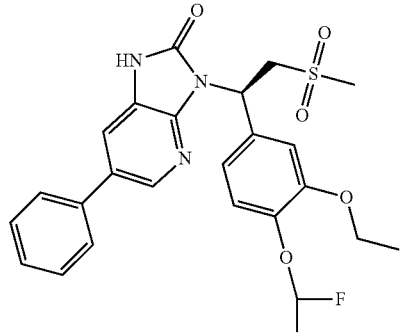
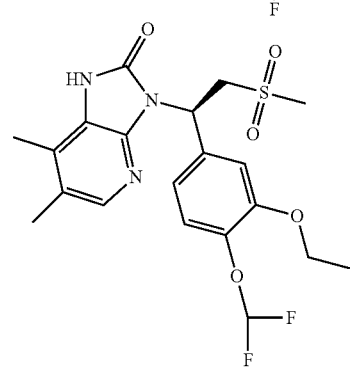
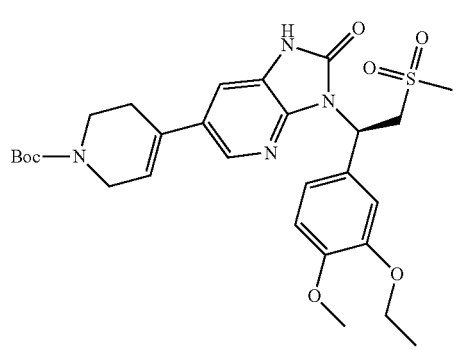
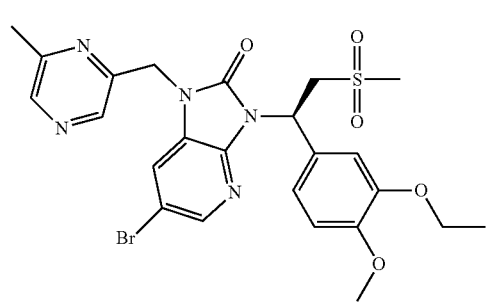
-continued
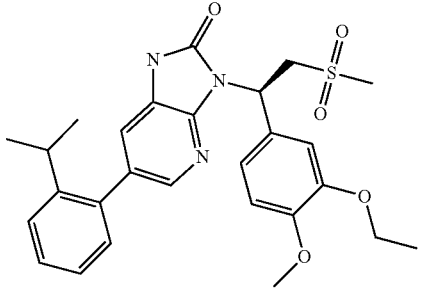
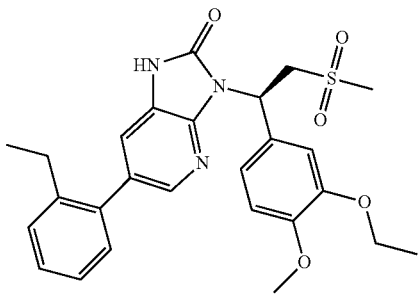
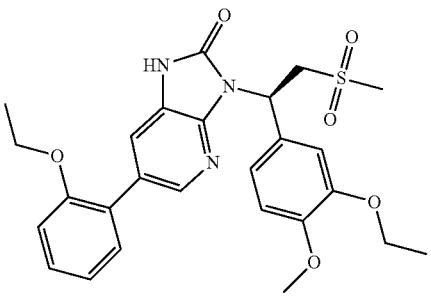
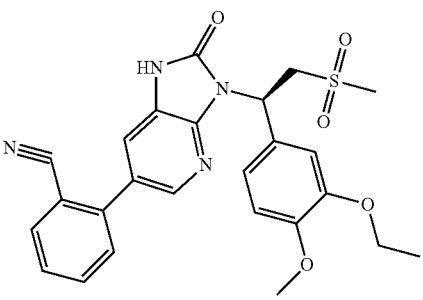
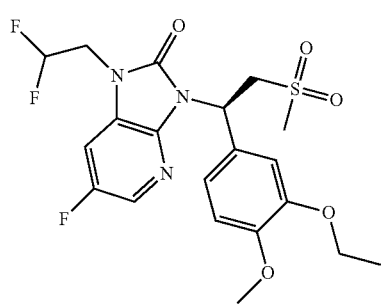

-continued

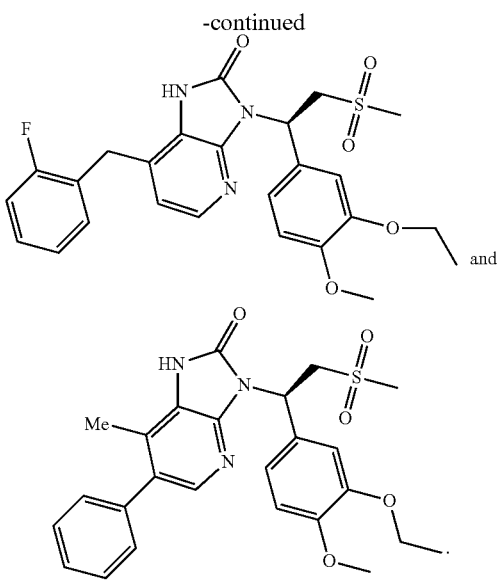

The present invention also provides a use of the compound or the pharmaceutically acceptable salt thereof in manufacturing a medicament for treating a disease related to PDE4.

In some embodiments of the present invention, the disease related to PDE4 is psoriasis, psoriatic arthritis, chronic obstructive pneumonia, ankylosing spondylitis, inflammatory bowel disease.

Technical Effect

Compared with Apremilast, the compound of the present invention reduces the distribution in the brain, potentially reducing vomiting and side effects associated with the brain.

It significantly increases the inhibitory effect of the compound of the present invention on TNFα in hPBMC and reduces the therapeutically effective dose in animal experiments, thereby reducing the therapeutically effective dose for human and increasing the safety factor therefor. It has improved the characteristics of pharmacokinetics and is expected to be administered to a human once a day.

Definition and Description

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "Pharmaceutical Salts", Journal of Pharmaceutical Science 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in a nonsolvated form or a solvated form, including hydrated form. Generally, the solvated form is equivalent to the nonsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, the absolute configuration of a stereogenic center is represented by a wedged solid bond () and a wedged dashed bond (), and the relative configuration of a stereogenic center is represented by a straight solid bond () and a straight dashed bond (). When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is a ketone (i.e. =O), it means two hydrogen atoms are substituted. Positions on an aromatic ring can not be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

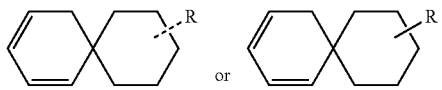

or means that the substituent R can be located at any position on cyclohexyl or cyclohexadiene.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one.

The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkyene" or "alkenylalkyl" refers to an alkyl substituted by an alkenyl.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy. Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butyloxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. This present invention adopts the abbreviating words as followed: aq refers to aqueous; "HATU" refers to 2-(7-Azabenzotriazol-1-yl)-N,N,N',N'-tetramethyluroniumhexafluorophosphate; "EDC" refers to N-(3-Dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodiformate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to carbobenzyloxy, a kind of protecting group for amine; "BOC" refers to t-butyloxy carbonyl; "HOAc" refers to acetic acid; "NaCNBH$_3$" refers to sodium cyanoborohydride; r.t. refers to room temperature; O/N refers to overnight; "THF" refers to tetrahydrofuran; "Boc$_2$O" refers to di-tert-butyl dicarbonate; "TFA" refers to trifluoroacetic acid; "DIPEA" refers to ethyldiisopropylamine; "SOCl$_2$" refers to thionyl chloride; "CS$_2$" refers to carbon disulfide; TsOH refers to p-toluenesulfonic acid; "NFSI" refers to N-Fluorobenzenesulfonimide; "NCS" refers to 1-chloropyrrolidine-2,5-diketone; "n-Bu4NF" refers to tetrabutylammonium fluoride; "iPrOH" refers to 2-propanol; "mp" refers to melting point; "LDA" refers to lithium diisopropylamide.

Compounds are named manually or by ChemDraw® software, the commercially available compounds use their vendor directory names.

DETAILED DESCRIPTION OF THE PREFERRED EMBODIMENT

The following examples further illustrate the present invention, but the present invention is not limited thereto. The present invention has been described in detail herein, and the specific embodiments thereof are also disclosed. For one skilled in the art, it is obvious to modify and improve the embodiments of the present invention within the spirit and scope of the present invention.

Embodiment 1: WX001

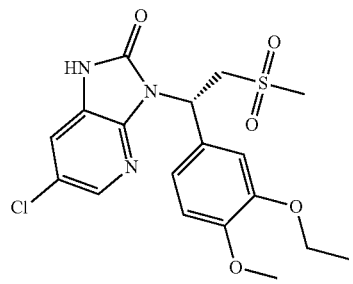 [SMILES: CCOc1cc([C@@H](CS(C)(=O)=O)n2c(=O)[nH]c3cc(Cl)cnc32)ccc1OC]

Synthetic Route:

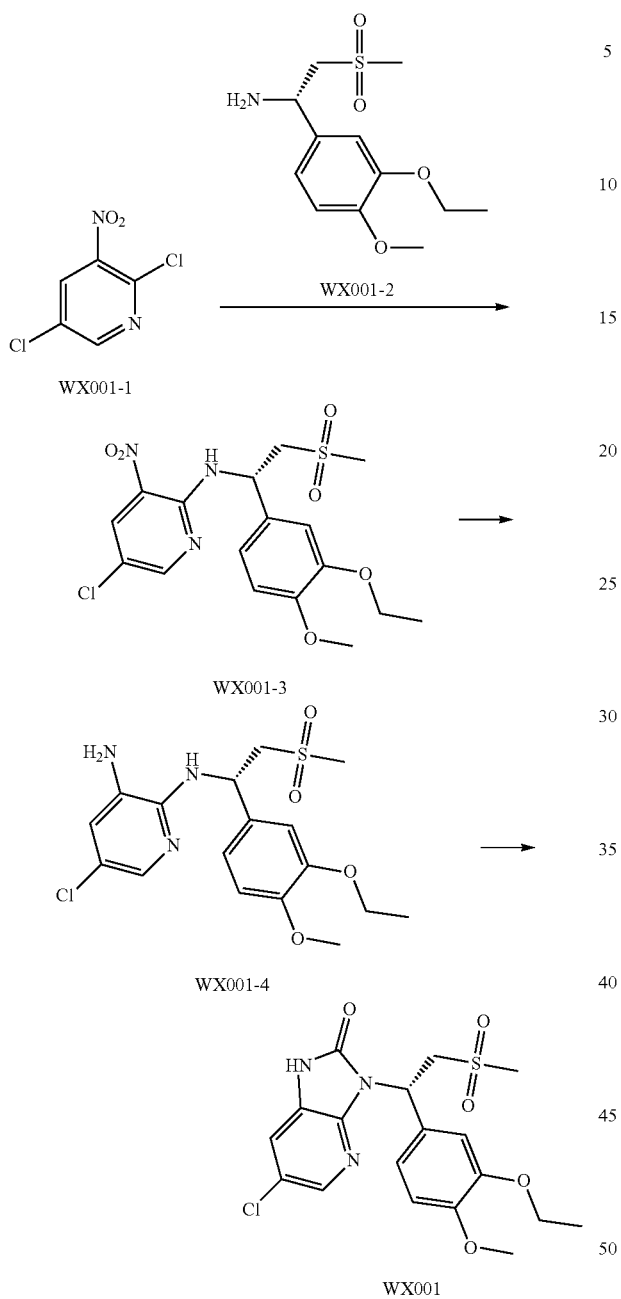

Step 1: Preparation of Compound WX001-3

2,5-Dichloro-3-nitropyridine (WX001-1) (464.42 mg, 1.04 mmol) and compound WX001-2 (569.40 mg, 2.08 mmol) were dissolved in acetonitrile (3.00 mL) at room temperature, followed by the addition of potassium carbonate (287.48 mg, 2.08 mmol). The reaction mixture was heated to 80° C. and stirred for 2 hours. After the reaction, the mixture was cooled to room temperature, diluted with water (10 mL) and extracted with ethyl acetate (5 mL×2). The organic phases were combined and dried over anhydrous sodium sulfate, followed by filtration. The filtrate was concentrated under reduced pressure to remove the solvent. The obtained residue was purified by column chromatography (eluent: petroleum ether/ethyl acetate=10/1-2/1, volume ratio) to obtain the target product WX001-3. MS-ESI m/z: 430.0 [M+H]$^+$.

Step 2: Preparation of Compound WX001-4

Compound WX001-3 (180.00 mg, 418.73 μmol) and ammonium chloride (179.18 mg, 3.35 mmol) was dissolved in ethanol (5.00 mL) and water (500.00 μL) at room temperature, followed by the addition of iron powder (116.93 mg, 2.09 mmol). The reaction mixture was stirred at 80° C. for 3 hours. After the reaction, ethyl acetate (5 mL) was added, followed by filtration, the filtrate was concentrated under reduced pressure. Water (8 mL) was added to the obtained residue and extracted with ethyl acetate (5 mL×2). The organic phases were combined and dried over anhydrous sodium sulfate, followed by filtration. The filtrate was concentrated under reduced pressure to remove the solvent to obtain the crude product WX001-4. MS-ESI m/z: 400.0 [M+H]$^+$.

Step 3: Preparation of Compound WX001

Compound WX001-4 (100.00 mg, 250.07 μmol) and triethylamine (50.6 mg, 500.14 μmol) were dissolved in tetrahydrofuran (2 mL) at room temperature. The solution was cooled to 0° C. in ice bath and triethyl orthoformate (89.05 mg, 300.08 μmol) was added thereto. The reaction mixture was stirred at 0° C. for 0.5 hour. After the reaction, the mixture was quenched with water (8 mL) and extracted with ethyl acetate (5 mL×2). The organic phases were combined and dried over anhydrous sodium sulfate, followed by filtration. The filtrate was concentrated under reduced pressure. The obtained residue was isolated by preparative HPLC to obtain the target product WX001. MS-ESI m/z: 426.0 [M+H]$^+$. $^1$H NMR (400 MHz, CD$_3$OD) δ: 8.03 (d, J=2.0 Hz, 1H), 7.36 (dd, J=1.9, 19.4 Hz, 2H), 7.17 (dd, J=1.8, 8.3 Hz, 1H), 6.93 (d, J=8.3 Hz, 1H), 6.15 (dd, J=3.9, 10.7 Hz, 1H), 4.87-4.77 (m, 1H), 4.09-3.99 (m, 3H), 3.82 (s, 3H), 2.95 (s, 3H), 1.40 (t, J=7.0 Hz, 3H).

Embodiment 2: WX002

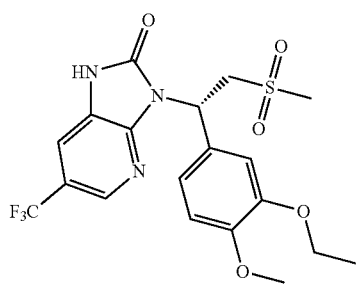 [SMILES: CCOc1cc([C@@H](CS(C)(=O)=O)n2c(=O)[nH]c3cc(C(F)(F)F)cnc32)ccc1OC]

Synthetic Route:

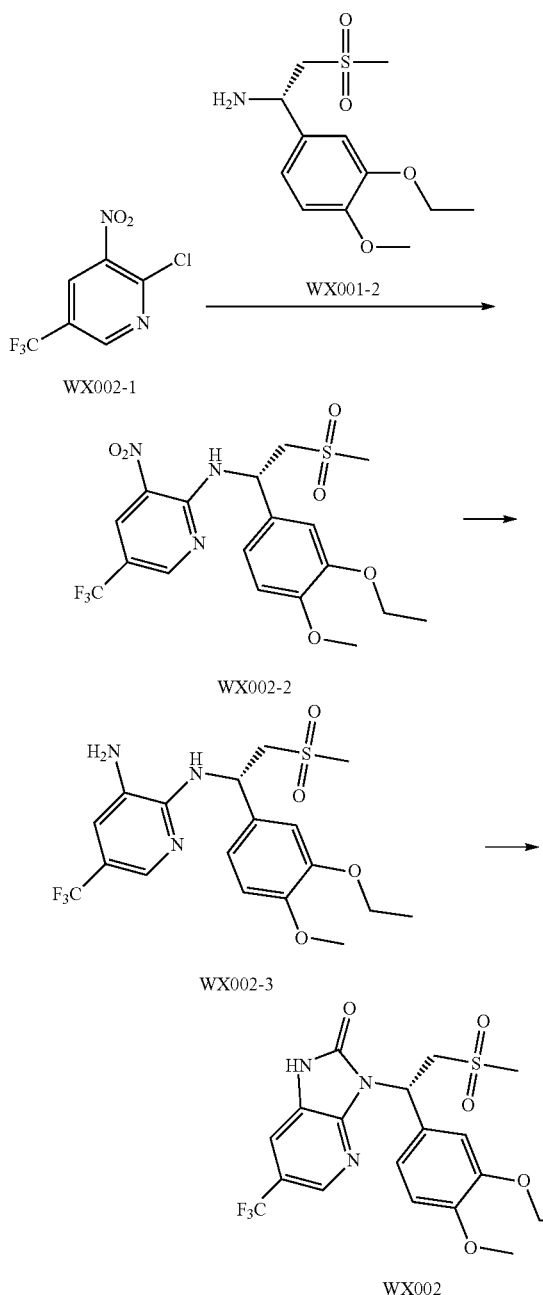

Step 1: Preparation of Compound WX002-2

Compound WX002-1 (295.68 mg, 662.13 μmol) and compound WX001-2 (354.9 mg, 1.30 mmol) were dissolved in acetonitrile (3.00 mL) at room temperature, followed by the addition of potassium carbonate (183.03 mg, 1.32 mmol). The reaction mixture was heated at room temperature and stirred for 2 hours. After the reaction, the mixture was diluted with water (10 mL) and extracted with ethyl acetate (5 mL×2). The organic phases were combined and dried over anhydrous sodium sulfate, followed by filtration. The filtrate was concentrated under reduced pressure to remove the solvent. The obtained residue was isolated by column chromatography (eluent: petroleum ether/ethyl acetate=10/1-2/1, volume ratio) to obtain the target product WX002-2. MS-ESI m/z: 464.0 [M+H]$^+$.

Step 2: Preparation of Compound WX002-3

Compound WX002-2 (200.00 mg, 431.56 μmol) and ammonium chloride (184.67 mg, 3.45 mmol) were added to ethanol (5.00 mL) and water (500.00 μL) at room temperature, followed by the addition of iron powder (120.51 mg, 2.16 mmol). The reaction mixture was stirred at 90° C. for 3 hours. After the reaction, ethyl acetate (8 mL) was added, and the insolubles was removed by filtration. The filtrate was concentrated under reduced pressure. The water (10 mL) was added to the residue, extracted with ethyl acetate (8 mL×2). The organic phases were combined and dried over anhydrous sodium sulfate, followed by filtration. The filtrate was concentrated under reduced pressure to obtain the crude product WX002-3. MS-ESI m/z: 434.0 [M+Na]$^+$.

Step 3: Preparation of Compound WX002

Compound WX002-3 (30.00 mg, 69.21 μmol) and triethylamine (14.12 mg, 0.14 mmol) were dissolved in tetrahydrofuran (2.00 mL) at room temperature. The solution was cooled to 0° C. in ice bath and triethyl orthoformate (24.65 mg, 83.05 μmol) was added thereto. The reaction mixture was stirred at 0° C. for 30 minutes. After the reaction, water (8 mL) was added and extracted with ethyl acetate (5 mL×2). The organic phases were combined and dried over anhydrous sodium sulfate, followed by filtration. The filtrate was concentrated under reduced pressure to remove the solvent. The obtained residue was isolated by preparative HPLC to obtain the target product WX002. MS-ESI m/z: 460.0 [M+H]$^+$. $^1$H NMR (400 MHz, CDCl$_3$) δ: 9.97 (br s, 1H), 8.39 (s, 1H), 7.50 (s, 1H), 7.33 (s, 1H), 7.25 (d, J=8.3 Hz, 1H), 6.86 (d, J=8.3 Hz, 1H), 6.26 (dd, J=4.0, 10.0 Hz, 1H), 4.93 (dd, J=10.4, 14.2 Hz, 1H), 4.20-4.06 (m, 2H), 3.97-3.78 (m, 4H), 2.86 (s, 3H), 1.47 (t, J=6.9 Hz, 3H).

Embodiment 3: WX003

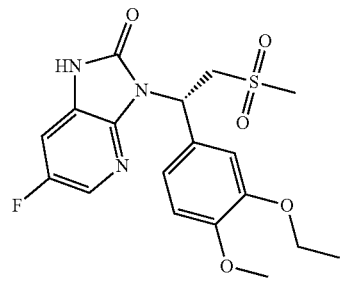 [SMILES: CCOc1cc([C@@H](CS(C)(=O)=O)n2c(=O)[nH]c3cc(F)cnc32)ccc1OC]

Synthetic Route:

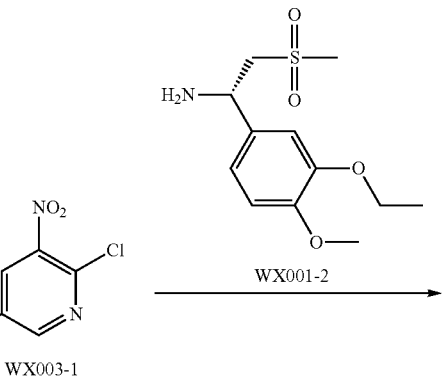

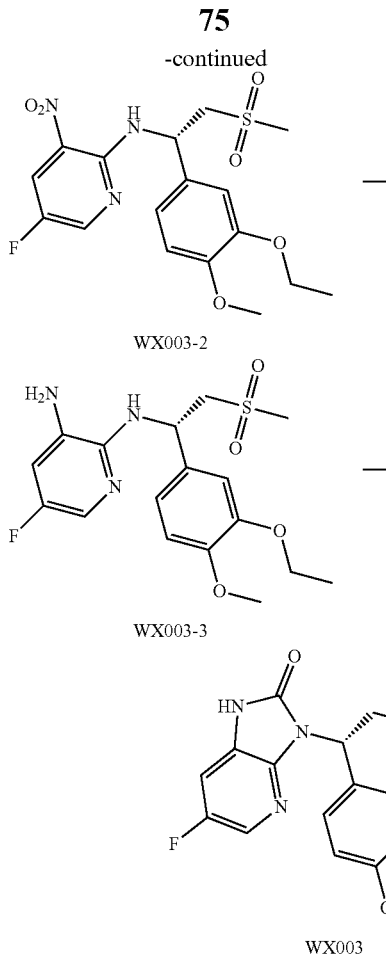

WX003-2

WX003-3

WX003

Step 1: Preparation of Compound WX003-2

Compound WX003-1 (505.93 mg, 1.13 mmol) and compound WX001-2 (671.00 mg, 2.26 mmol) were dissolved in acetonitrile (3.00 mL) at room temperature, followed by the addition of potassium carbonate (313.17 mg, 2.27 mmol). The reaction mixture was heated to 80° C. and stirred for 16 hours. After the reaction, water (10 mL) was added and extracted with ethyl acetate (5 mL×2). The organic phases were combined and dried over anhydrous sodium sulfate, followed by filtration. The filtrate was concentrated under reduced pressure to remove the solvent. The obtained residue was isolated by column chromatography (eluent: petroleum ether/ethyl acetate=10/1-2/1, volume ratio) to obtain the target product WX003-2. MS-ESI m/z: 435.9 [M+Na]⁺.

Step 2: Preparation of Compound WX003-3

Compound WX003-2 (150.00 mg, 362.83 µmol) and ammonium chloride (155.26 mg, 2.90 mmol) were dissolved in ethanol (5.00 mL) and water (500.00 µL) at room temperature, followed by the addition of iron powder (101.32 mg, 1.81 mmol). The reaction mixture was heated to 80° C. and stirred for 3 hours. After the reaction, the mixture was diluted with ethyl acetate (5 mL), followed by filtration, and the filtrate was concentrated under reduced pressure. Water (5 mL) was added to the obtained residue and extracted with ethyl acetate (5 mL×2). The organic phases were combined, wash with water (10 mL) and dried over anhydrous sodium sulfate, followed by filtration. The filtrate was concentrated under reduced pressure to remove the solvent to obtain the crude product WX003-3. MS-ESI m/z: 384.0 [M+Na]⁺.

Step 3: Preparation of Compound WX003

Compound WX003-3 (70.00 mg, 182.56 mmol) and triethylamine (36.42 mg, 0.36 mmol) were dissolved in tetrahydrofuran (2.00 mL) at room temperature. The solution was cooled to 0° C. in ice bath and triethyl orthoformate (65.01 mg, 219.07 µmol) was added thereto. The reaction mixture was stirred at 0° C. for 0.5 hour. After the reaction, water (8 mL) was added and extracted with ethyl acetate (5×2 mL). The organic phases were combined and dried over anhydrous sodium sulfate, followed by filtration. The filtrate was concentrated under reduced pressure to remove the solvent. The obtained residue was isolated by preparative HPLC to obtain the target product WX003. MS-ESI m/z: 410.1 [M+H]⁺. ¹H NMR (400 MHz, CD₃OD) δ: 7.95 (t, J=2.0 Hz, 1H), 7.33 (d, J=1.8 Hz, 1H), 7.24 (dd, J=2.4, 8.4 Hz, 1H), 7.17 (dd, J=1.8, 8.3 Hz, 1H), 6.93 (d, J=8.3 Hz, 1H), 6.15 (dd, J=3.8, 10.8 Hz, 1H), 4.88-4.82 (m, 1H), 4.13-3.99 (m, 3H), 3.81 (s, 3H), 2.98-2.90 (m, 3H), 1.39 (t, J=7.0 Hz, 3H).

Embodiment 4: WX004

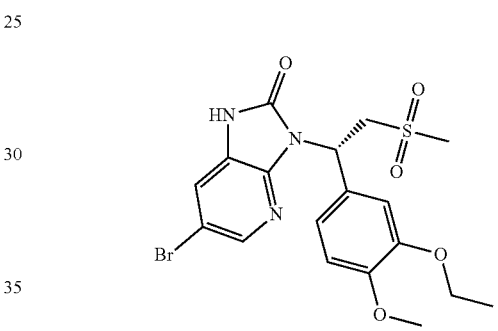

Synthetic Route:

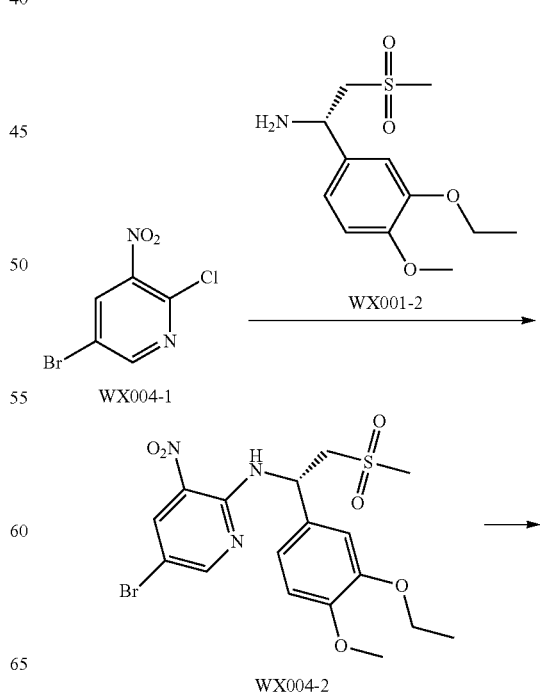

WX004-1

WX004-2

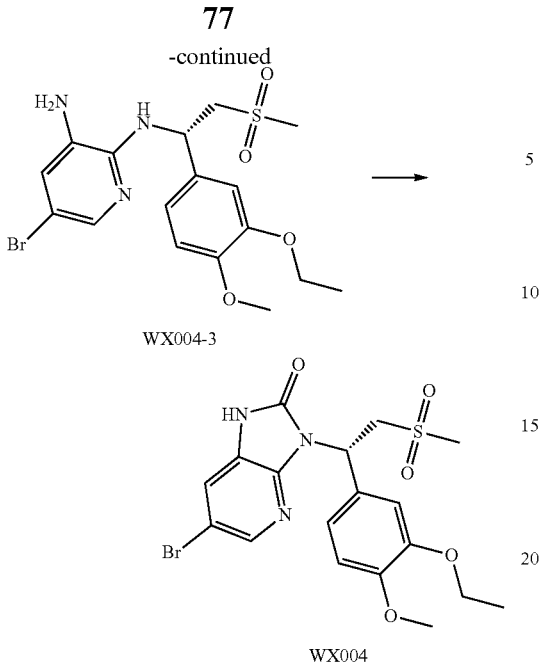

WX004-3

WX004

Step 1: Preparation of Compound WX004-2

Compound WX001-2 (10.00 g, 36.58 mmol) was dissolved in N,N-dimethylformamide (100.00 mL) at room temperature, followed by the stepwise addition of N,N-diisopropylethylamine (14.18 g, 109.74 mmol, 19.16 mL) and compound WX004-1 (17.37 g, 73.16 mmol). The reaction mixture was heated to 100° C. and stirred for 12 hours under nitrogen atmosphere. After the reaction, the mixture was cooled to room temperature and concentrated under reduced pressure to remove the solvent. Methanol (30 mL) was added to the residue and stirred at room temperature for 10 minutes, followed by filtration. The filtrate was concentrated under reduced pressure to remove the solvent to obtain the target product WX004-2. MS (ESI) m/z: 473.7 $[M+H]^+$, 475.7 $[M+H+2]^+$.

Step 2: Preparation of Compound WX004-3

Compound WX004-2 (5.00 g, 10.54 mmol) and ammonium chloride (5.64 g, 105.40 mmol) were dissolved in methanol (50.00 mL) at room temperature, followed by the portionwise addition of zinc powder (3.45 g, 52.70 mmol). The reaction mixture was stirred at room temperature for 1 hour under nitrogen atmosphere. After the reaction, the mixture was filtered by diatomite. The filtrate was concentrated under reduced pressure to remove the solvent. Water (50 mL) and ethyl acetate (50 mL) was added to the obtained residue. The aqueous phase was extracted with ethyl acetate (30 mL×3). The organic phases were combined, washed with saturated brine (50 mL) and dried over anhydrous sodium sulfate, followed by filtration. The filtrate was concentrated under reduced pressure to obtain the crude product WX004-3. MS (ESI) m/z: 443.7 $[M+H]^+$, 445.7 $[M+H+2]^+$.

Step 3: Preparation of Compound WX004

Compound WX004-3 (4.20 g, 9.45 mmol) and triethylamine (5.26 g, 51.99 mmol, 7.21 mL) were dissolved in tetrahydrofuran (50.00 mL) at room temperature. The solution was cooled to 0° C. in ice bath and triethyl orthoformate (981.73 mg, 3.31 mmol) was added thereto in 4 batches. The reaction mixture was warmed to room temperature and stirred for 12 hours. After the reaction, the mixture was quenched with saturated brine (15 mL), diluted with water (15 mL) and extracted with ethyl acetate (10×3 mL). The organic phases were combined, washed with water (25×2 mL) and dried over anhydrous sodium sulfate, followed by filtration. The filtrate was concentrated under reduced pressure to remove the solvent. The obtained residue was isolated by column chromatography (eluent: petroleum ether/ethyl acetate=4/1-2/3, volume ratio) to obtain the target product WX004. (3.5 g, yield: 77.17%). MS (ESI) m/z: 470.0 $[M+H]^+$, 472.0 $[M+H+2]^+$. $^1$H NMR (400 MHz, CDCl$_3$) δ: 9.09 (s, 1H), 8.14 (d, J=2.0 Hz, 1H), 7.41 (d, J=2.0 Hz, 1H), 7.31 (d, J=2.0 Hz, 1H), 7.22 (dd, J=2.0, 8.3 Hz, 1H), 6.84 (d, J=8.3 Hz, 1H), 6.17 (dd, J=4.5, 10.0 Hz, 1H), 4.86 (dd, J=10.3, 14.6 Hz, 1H), 4.98-4.78 (m, 1H), 4.13-4.08 (m, 2H), 3.88 (d, J=4.5 Hz, 1H), 3.85 (s, 4H), 2.81 (s, 3H), 1.46 (t, J=6.9 Hz, 3H).

Embodiment 5: WX005

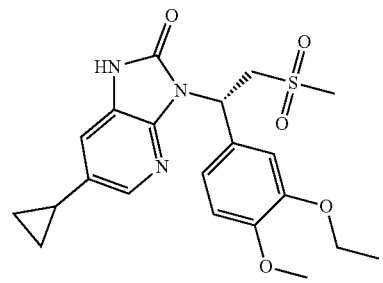 [SMILES: CCOc1cc([C@@H](CS(C)(=O)=O)n2c(=O)[nH]c3cc(C4CC4)cnc32)ccc1OC]

Synthetic Route:

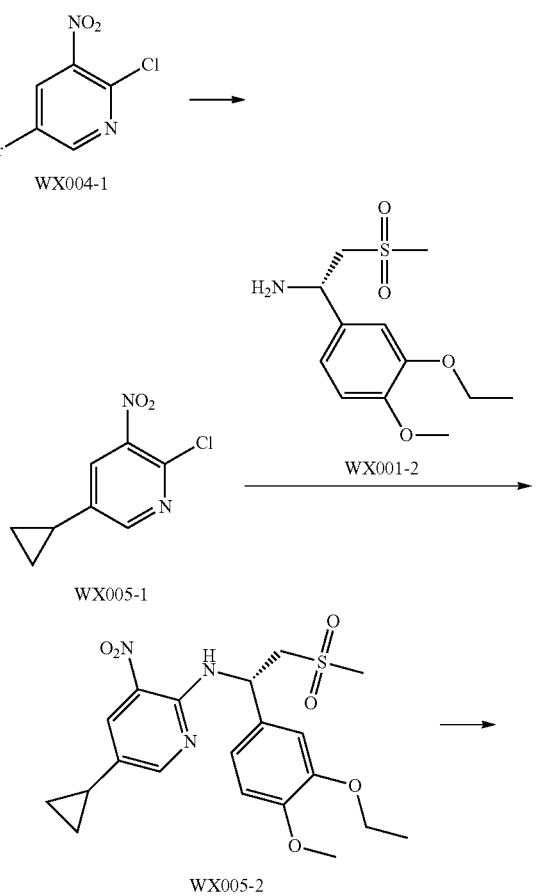

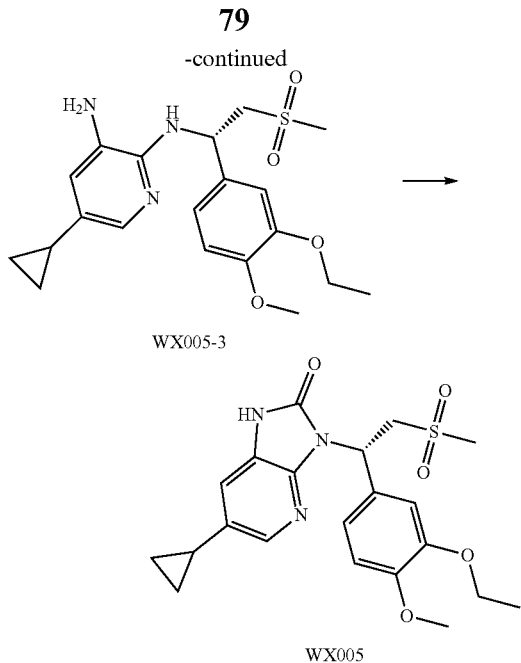

WX005-3

WX005

Step 1: Preparation of Compound WX005-1

Compound WX004-1 (2.17 g, 25.26 mmol) were dissolved in dioxane (30.00 mL) at room temperature, followed by the stepwise addition of potassium phosphate (5.36 g, 25.26 mmol), tricyclohexylphosphine (3.54 g, 12.63 mmol) and tetrakis(triphenylphosphine) palladium (1.46 g, 1.26 mmol). The reaction mixture was heated to 100° C. and stirred for 12 hours under nitrogen atmosphere. After the reaction, the mixture was cooled to room temperature and diluted with water (30 mL) and ethyl acetate (30 mL). The aqueous phase was extracted with ethyl acetate (30 mL×3). The organic phases were combined, washed with saturated brine (20 mL×2) and dried over anhydrous sodium sulfate, followed by filtration. The filtrate was concentrated under reduced pressure to remove the solvent. The obtained residue was isolated by column chromatography (eluent: petroleum ether/ethyl acetate=40/1-10/1, volume ratio) to obtain the target product WX005-1. MS-ESI m/z: 199.0 [M+H]⁺.

Step 2: Preparation of Compound WX005-2

Compound WX005-1 (200.00 mg, 1.01 mmol) was dissolved in acetonitrile (4.00 mL) at room temperature, followed by the addition of potassium carbonate (279.18 mg, 2.02 mmol). The reaction mixture was heated to 90° C. and stirred for 0.2 hour, followed by the addition of compound WX001-2 (276.08 mg, 1.01 mmol). And the reaction mixture was stirred for further 11.8 hours. After the reaction, the mixture was cooled to room temperature and diluted with water (10 mL) and ethyl acetate (10 mL), partioned. The aqueous phase was extracted with ethyl acetate (10 mL×3). The organic phases were combined, washed with saturated brine (10 mL×2) and dried over anhydrous sodium sulfate, followed by filtration. The filtrate was concentrated under reduced pressure to remove the solvent. The obtained residue was isolated by column chromatography (eluent: petroleum ether/ethyl acetate=10/1-1/2, volume ratio) to obtain the target product WX005-2. MS-ESI m/z: 436.0 [M+Na]⁺.

Step 3: Preparation of Compound WX005-3

Compound WX005-2 (100.00 mg, 229.63 μmol), iron powder (76.95 mg, 1.38 mmol) and ammonium chloride (122.83 mg, 2.30 mmol) were dissolved in water (300.00 μL) and ethanol (3.00 mL) at room temperature. The reaction mixture was heated to 90° C. and stirred for 2 hours under nitrogen atmosphere. After the reaction, the mixture was cooled to room temperature, followed by filtration. The filtrate was concentrated under reduced pressure and the obtained residue was diluted with water (10 mL) and ethyl acetate (10 mL). The aqueous phase was extracted with ethyl acetate (10 mL×3). The organic phases were combined, washed with water (10 mL×2) and dried over anhydrous sodium sulfate, followed by filtration. The filtrate was concentrated under reduced pressure to obtain the crude product WX005-3. MS-ESI m/z: 406.1 [M+Na]+.

Step 4: Preparation of Compound WX005

Compound WX005-3 (100.00 mg, 246.60 μmol) and triethylamine (124.89 mg, 1.23 mmol, 172.02 μL) were dissolved in tetrahydrofuran (4.00 mL) at room temperature. The reaction mixture was cooled to 0° C. in ice bath and stirred for 10 minutes, followed by the addition of triethyl orthoformate (87.81 mg, 295.92 μmol). The reaction was carried out at 0° C. with stirring for 80 minutes. After the reaction, the mixture was diluted with water (10 mL) and ethyl acetate (10 mL). The aqueous phase was extracted with ethyl acetate (10 mL×3). The organic phases were combined, washed with water (10 mL×2) and dried over anhydrous sodium sulfate, followed by filtration. The filtrate was concentrated under reduced pressure to remove the solvent. The obtained residue was isolated by preparative HPLC to obtain the target product WX005. MS-ESI m/z: 432.1 [M+H]⁺. ¹H NMR (400 MHz, CD₃OD) δ: 7.92 (d, J=1.5 Hz, 1H), 7.34 (d, J=2.0 Hz, 1H), 7.20-7.15 (m, 1H), 7.14-7.10 (m, 1H), 6.93 (d, J=8.3 Hz, 1H), 6.27-5.86 (m, 1H), 4.88-4.82 (m, 1H), 4.07 (d, J=7.0 Hz, 3H), 3.82 (s, 3H), 2.95 (s, 3H), 2.16-1.80 (m, 1H), 1.39 (t, J=6.9 Hz, 3H), 1.03 (dd, J=1.5, 8.3 Hz, 2H), 0.83-0.65 (m, 2H).

Embodiment 6: WX006

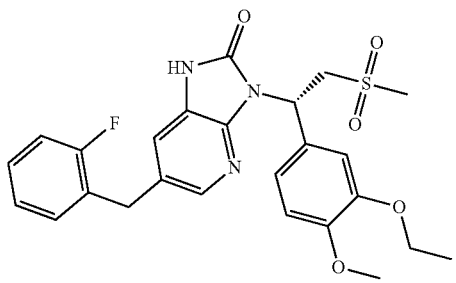 [SMILES: CCOc1cc([C@@H](CS(C)(=O)=O)n2c(=O)[nH]c3cc(Cc4ccccc4F)cnc32)ccc1OC]

Synthetic Route:

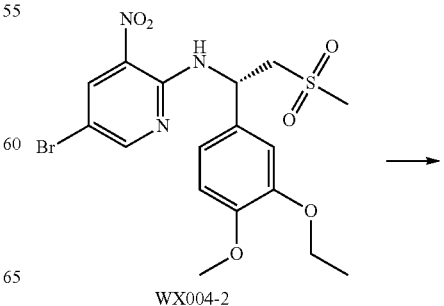

WX004-2

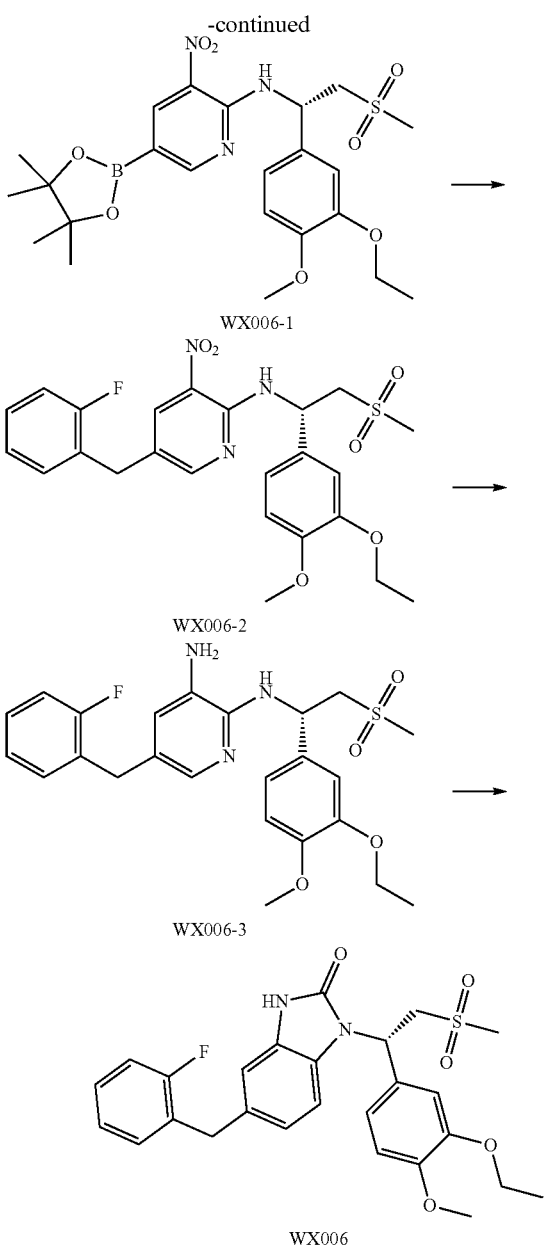

WX006-1

WX006-2

WX006-3

WX006

Step 1: Preparation of Compound WX006-1

Compound WX004-2 (200.00 mg, 421.65 µmol), bis(pinacolato)diboron (214.15 mg, 843.30 µmol), potassium acetate (124.14 mg, 1.26 mmol) and [1,1'-bis(diphenylphosphino)ferrocene] palladium dichloride dichloromethane complex (34.43 mg, 42.17 µmol) were dissolved in dimethyl sulfoxide (5.00 mL) at room temperature. The reaction mixture was heated to 90° C. and stirred for 3 hours under nitrogen atmosphere. After the reaction, the mixture was cooled to room temperature, quenched with water (8 mL) and extracted with ethyl acetate (10 mL×2). The organic phases were combined and dried over anhydrous sodium sulfate, followed by filtration. The filtrate was concentrated under reduced pressure to remove the solvent. The obtained residue was isolated by silica gel column chromatography (eluent: petroleum ether/ethyl acetate=1/1, volume ratio) to obtain the target product WX006-1. MS-ESI m/z: 522.2 [M+H]$^+$.

Step 2: Preparation of compound WX006-2

Compound WX006-1 (80.00 mg, 153.44 µmol), 2-fluorobenzyl bromide (58.01 mg, 306.88 µmol), potassium phosphate (65.14 mg, 306.87 µmol) and tetrakis(triphenylphosphine) palladium (177.30 mg, 153.44 µmol) dissolved in ethylene glycol dimethyl ether (2.00 mL), ethanol (500.00 µL) and water (500.00 µL) at room temperature. The reaction mixture was heated to 90° C. and stirred for 2 hours under nitrogen atmosphere. After the reaction, the mixture was cooled to room temperature, quenched with water (8 mL) and extracted with ethyl acetate (10 mL×2). The organic phases were combined and dried over anhydrous sodium sulfate, followed by filtration. The filtrate was concentrated under reduced pressure to remove the solvent. The obtained residue was isolated by silica gel column chromatography (eluent: petroleum ether/ethyl acetate=2/1, volume ratio) to obtain the target product WX006-2. MS-ESI m/z: 504.2 [M+H]$^+$.

Step 3: Preparation of Compound WX006-3

Compound WX006-2 (80.00 mg, 158.88 µmol), zinc powder (83.11 mg, 1.27 mmol) and ammonium chloride (84.98 mg, 1.59 mmol) were dissolved in methanol (3.00 mL) at room temperature. The reaction mixture was stirred at room temperature for 2 hours. After the reaction, ethyl acetate (8 mL) was added, followed by filtration. Water (8 mL) was added to the obtained residue and extracted with ethyl acetate (10 mL×2). The organic phases were combined and dried over anhydrous sodium sulfate, followed by filtration. The filtrate was concentrated under reduced pressure to remove the solvent to obtain the crude product WX006-3. MS-ESI m/z: 474.2 [M+H]$^+$.

Step 4: Preparation of Compound WX006

Compound WX006-3 (30.00 mg, 63.35 µmol) and triethylamine (19.23 mg, 190.05 µmol, 26.34 µL) were dissolved in tetrahydrofuran (2.00 mL) at room temperature. The reaction mixture was cooled to 0° C. in ice bath and triethyl orthoformate (7.52 mg, 25.34 µmol) was added thereto. The reaction was carried out at 0° C. with stirring for 0.5 hour. After the reaction, the mixture was quenched with water (5 mL) and extracted with ethyl acetate (8 mL×2). The organic phases were combined and dried over anhydrous sodium sulfate, followed by filtration. The filtrate was concentrated under reduced pressure. The obtained residue was isolated by preparative HPLC to obtain the target product WX006. MS-ESI m/z: 500.2 [M+H]$^+$. $^1$H NMR (400 MHz, CD$_3$OD) δ: 7.95 (s, 1H), 7.37-7.01 (m, 7H), 6.91 (d, J=8.3 Hz, 1H), 6.12 (dd, J=4.0, 10.5 Hz, 1H), 4.86-4.85 (m, 1H), 4.09-3.98 (m, 5H), 3.79 (s, 3H), 2.91 (s, 3H), 1.35 (t, J=6.9 Hz, 3H).

Embodiment 7: WX007

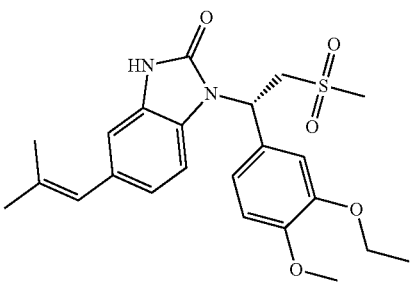 [SMILES: CCOc1cc([C@@H](CS(C)(=O)=O)n2c(=O)[nH]c3cc(C=C(C)C)ccc32)ccc1OC]

Synthetic Route:

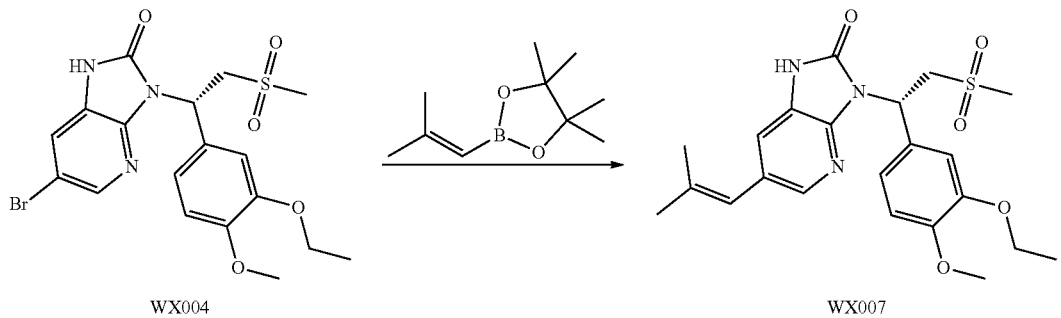

Compound WX004 (150.00 mg, 318.92 μmol) and 4,4,5,5-tetramethyl-2(2-methylpropan-1-alkenyl)-1,3,2-dioxaborolane (69.68 mg, 382.70 μmol) were dissolved in dioxane (20.00 mL) at room temperature, followed by the addition of potassium carbonate (132.23 mg, 956.75 μmol) and water (2.00 mL). The reaction mixture was stirred at room temperature for 30 minutes under nitrogen atmosphere, followed by the addition of [1,1'-bis(diphenylphosphino)ferrocene] palladium dichloride (70.01 mg, 95.68 μmol). The reaction mixture was heated to 80° C. and stirred for 16 hours. After the reaction, the mixture was cooled to room temperature and concentrated under reduced pressure to remove the solvent. Water (30 mL) was added to the obtained residue and extracted with ethyl acetate (20 mL×3). The organic phases were combined and dried over anhydrous sodium sulfate, followed by filtration. The filtrate was concentrated under reduced pressure. The obtained residue was isolated by preparative HPLC to obtain the target product WX007. MS-ESI m/z: 446.2 [M+H]$^+$. $^1$H NMR (400 MHz, CDCl$_3$) δ: 8.70 (s, 1H), 7.85 (s, 1H), 7.39 (s, 1H), 7.24 (d, J=7.6 Hz, 1H), 7.16 (s, 1H), 6.76 (d, J=8.0 Hz, 1H), 6.31 (s, 1H), 6.11 (s, 1H), 4.86 (dd, J=14.2, 10.2 Hz, 1H), 4.05 (dd, J=7.0, 3.4 Hz, 2H), 0.3.81 (d, J=3.2 Hz, 1H), 3.77 (s, 3H), 2.81 (s, 3H), 1.86 (s, 3H), 1.78 (s, 3H), 1.37 (t, J=6.8 Hz, 3H).

Embodiment 8: WX008

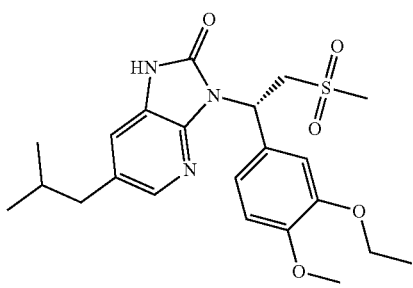 [SMILES: CCOc1cc([C@@H](CS(C)(=O)=O)n2c(=O)[nH]c3cc(CC(C)C)cnc32)ccc1OC]

Synthetic Route:

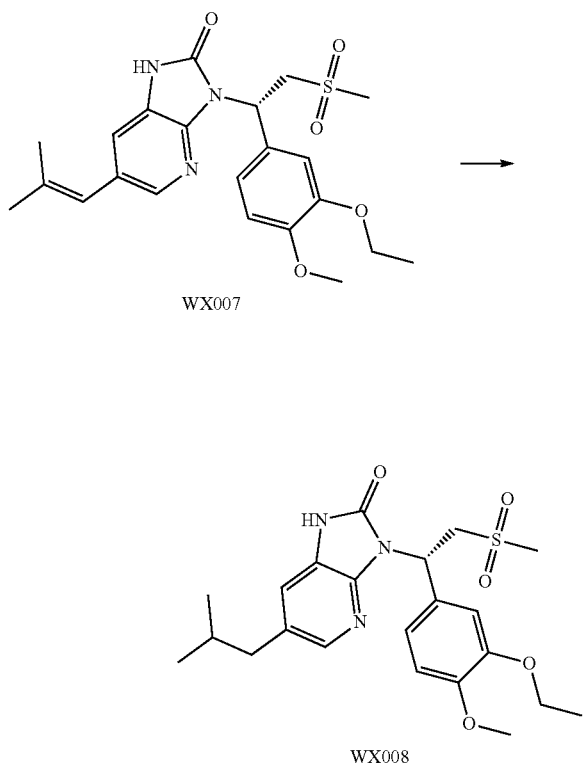

Compound WX007 (100.00 mg, 224.45 μmol) was dissolved in methanol (10.00 mL) at room temperature, followed by the addition of palladium hydroxide (31.52 mg, 224.45 μmol). The reaction mixture was stirred at room temperature for 16 hours under hydrogen atmosphere (40 psi). After the reaction, the insoluble catalysts were removed by filtration. The filtrate was isolated by preparative HPLC to obtain the target product WX008. MS-ESI m/z: 448.2 [M+H]$^+$. $^1$H NMR (400 MHz, CDCl$_3$) δ: 9.83 (s, 1H), 7.78 (s, 1H), 7.32 (s, 1H), 7.17 (d, J=8.4 Hz, 1H), 7.07 (s, 1H), 6.74 (d, J=8.0 Hz, 1H), 6.13 (dd, J=9.0, 4.6 Hz, 1H), 4.82 (dd, J=14.6, 9.4 Hz, 1H), 4.09-3.95 (m, 2H), 3.88 (dd, J=14.4, 4.4 Hz, 1H), 3.75 (s, 3H), 2.65 (s, 3H), 2.40 (d, J=6.8 Hz, 2H), 1.83-1.70 (m, 1H), 1.35 (t, J=7.0 Hz, 3H), 0.84 (d, J=6.4 Hz, 6H).

Embodiment 9: WX009

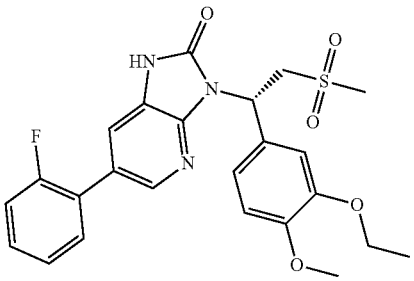 [SMILES: CCOc1cc([C@@H](CS(C)(=O)=O)n2c(=O)[nH]c3cc(-c4ccccc4F)cnc32)ccc1OC]

Synthetic Route:

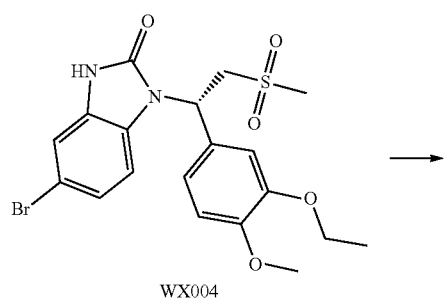

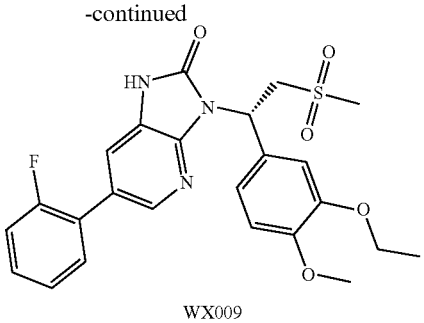

Compound WX004 (1.00 g, 2.13 mmol), 2-fluorophenylboronic acid (357.6 mg, 2.56 mmol) and potassium carbonate (441.58 mg, 3.20 mmol) were dissolved in dioxane (10.00 mL) at room temperature, followed by the addition of [1,1'-bis(diphenylphosphino)ferrocene]palladium dichloride dichloromethane complex (173.94 mg, 213.00 μmol). The reaction mixture was heated to 80° C. and stirred for 12 hours under nitrogen atmosphere. After the reaction, the mixture was cooled to room temperature, filtered by diatomite and concentrated under reduced pressure to remove the solvent. The obtained residue was diluted with water (50 mL) and ethyl acetate (50 mL), partioned. The aqueous phase was extracted with ethyl acetate (30 mL×3). The organic phases were combined, washed with saturated brine (50 mL) and dried over anhydrous sodium sulfate, followed by filtration. The filtrate was concentrated under reduced pressure. The obtained residue was isolated by preparative HPLC to obtain the target product WX009. MS-ESI m/z: 486.1 [M+H]$^+$. $^1$H NMR (400 MHz, CDCl$_3$) δ: 10.24 (br s, 1H), 8.24 (br s, 1H), 7.73-7.03 (m, 7H), 6.98-6.08 (m, 2H), 4.94 (br s, 1H), 4.36-3.50 (m, 6H), 2.78 (br s, 3H), 1.94 (br s, 1H), 1.42 (br s, 3H).

The compounds of each embodiment in the following table were prepared according to the method of embodiment 9.

TABLE 1

| Embodiment | Fragment 1 | Fragment 2 | Structure | Compound |
|---|---|---|---|---|
| 10 | WX004 | phenylboronic acid | 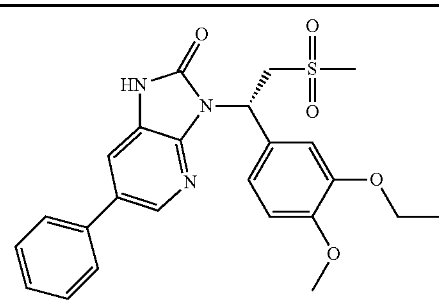 | WX010 |
| 11 | WX004 | 3-fluorophenylboronic acid | 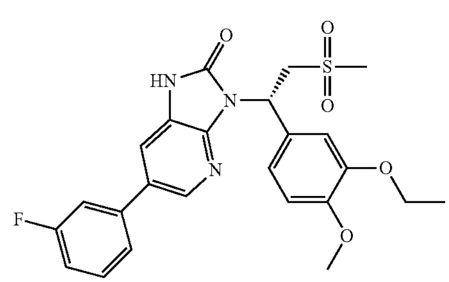 [SMILES: CCOc1cc([C@@H](CS(C)(=O)=O)n2c(=O)[nH]c3cc(-c4cccc(F)c4)cnc32)ccc1OC] | WX011 |

TABLE 1-continued

| Embodiment | Fragment 1 | Fragment 2 | Structure | Compound |
|---|---|---|---|---|
| 12 | WX004 | 4-fluorophenylboronic acid | 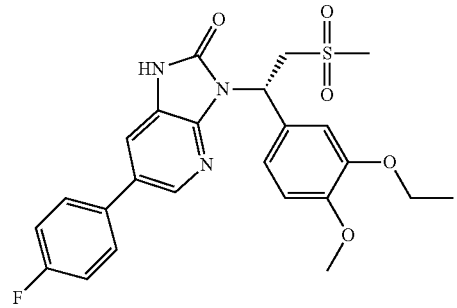 [SMILES: CCOc1cc([C@@H](CS(C)(=O)=O)n2c(=O)[nH]c3cc(-c4ccc(F)cc4)cnc32)ccc1OC] | WX012 |
| 13 | WX004 | 2,3-difluorophenylboronic acid | 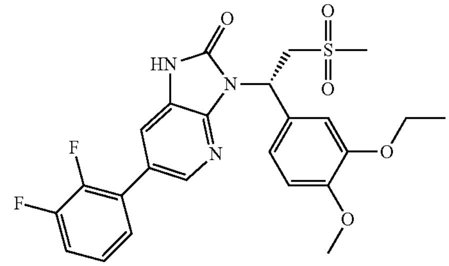 [SMILES: CCOc1cc([C@@H](CS(C)(=O)=O)n2c(=O)[nH]c3cc(-c4cccc(F)c4F)cnc32)ccc1OC] | WX013 |
| 14 | WX004 | 2-methylphenylboronic acid | 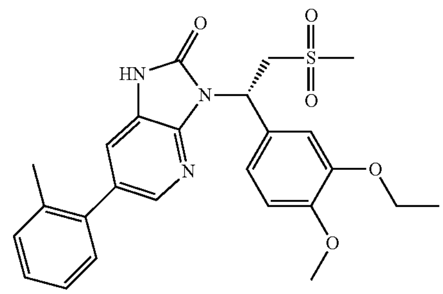 [SMILES: CCOc1cc([C@@H](CS(C)(=O)=O)n2c(=O)[nH]c3cc(-c4ccccc4C)cnc32)ccc1OC] | WX014 |
| 15 | WX004 | 2-isopropylphenylboronic acid | 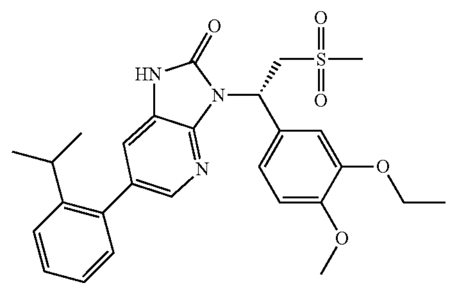 [SMILES: CCOc1cc([C@@H](CS(C)(=O)=O)n2c(=O)[nH]c3cc(-c4ccccc4C(C)C)cnc32)ccc1OC] | WX015 |
| 16 | WX004 | 2-chlorophenylboronic acid | 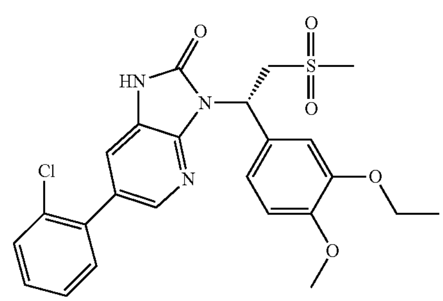 [SMILES: CCOc1cc([C@@H](CS(C)(=O)=O)n2c(=O)[nH]c3cc(-c4ccccc4Cl)cnc32)ccc1OC] | WX016 |

TABLE 1-continued

| Embodiment | Fragment 1 | Fragment 2 | Structure | Compound |
|---|---|---|---|---|
| 17 | WX004 | OMe, OH, B, OH | 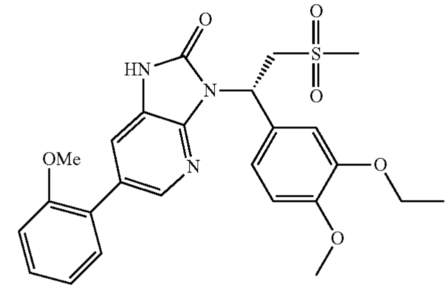 [SMILES: CCOc1cc([C@@H](CS(C)(=O)=O)n2c(=O)[nH]c3cc(-c4ccccc4OC)cnc32)ccc1OC] | WX017 |
| 18 | WX004 | CF₃, OH, B, OH | 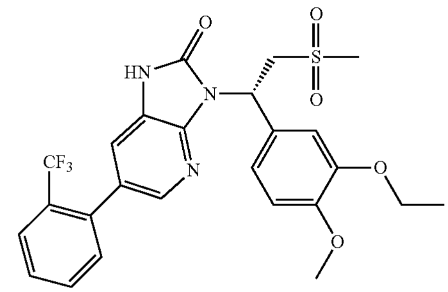 [SMILES: CCOc1cc([C@@H](CS(C)(=O)=O)n2c(=O)[nH]c3cc(-c4ccccc4C(F)(F)F)cnc32)ccc1OC] | WX018 |
| 19 | WX004 | pyrazole pinacol boronate | 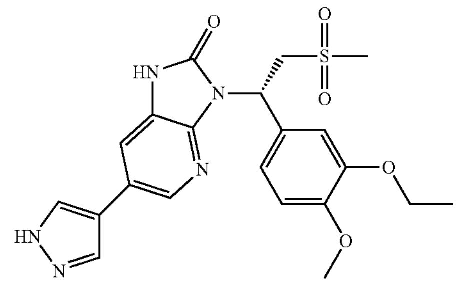 [SMILES: CCOc1cc([C@@H](CS(C)(=O)=O)n2c(=O)[nH]c3cc(-c4cn[nH]c4)cnc32)ccc1OC] | WX019 |
| 20 | WX004 | trimethylboroxine | 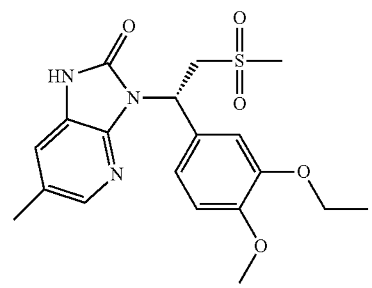 [SMILES: CCOc1cc([C@@H](CS(C)(=O)=O)n2c(=O)[nH]c3cc(C)cnc32)ccc1OC] | WX020 |

LCMS and ¹HNMR data of each embodiment

TABLE 2

| Embodiment | Compound | HNMR | LCMS |
|---|---|---|---|
| 10 | WX010 | $^1$H NMR (400 MHz, DMSO-$d_6$) δ: 11.36 (s, 1H), 8.26 (s, 1H), 7.67 (d, J = 7.5 Hz, 2H), 7.53 (s, 1H), 7.48 (t, J = 7.4 Hz, 2H), 7.41-7.35 (m, 1H), 7.27 (s, 1H), 7.05-6.99 (m, 1H), 6.93 (d, J = 8.3 Hz, 1H), 6.06 (dd, J = 3.4, 9.9 Hz, 1H), 4.71 (dd, J = 10.7, 13.9 Hz, 1H), 4.16 (dd, J = 3.5, 14.3 Hz, 1H), 4.01 (q, J = 6.8 Hz, 2H), 3.72 (s, 3H), 3.00 (s, 3H), 1.32 (t, J = 6.9 Hz, 3H). | MS-ESI m/z: 468.1 [M + H]⁺. |
| 11 | WX011 | $^1$H NMR (400 MHz, CDCl₃) δ: 9.73 (br s, 1H), 8.27 (s, 1H), 7.46-7.18 (m, 6H), 7.07-6.81 (m, 2H), 6.26-6.24 (m, | MS-ESI m/z: 486.1 |

TABLE 2-continued

| Embodiment | Compound | HNMR | LCMS |
|---|---|---|---|
| | | 1H), 5.00-4.94 (m, 1H), 4.11-3.83 (m, 6H), 2.84 (s, 3H), 1.44 (t, J = 7.2 Hz, 3H). | [M + H]+ |
| 12 | WX012 | ¹H NMR (400 MHz, CD₃OD) δ: 8.24 (d, J = 1.3 Hz, 1H), 7.60-7.58 (m, 2H), 7.51 (d, J = 1.3 Hz, 1H), 7.36 (d, J = 1.6 Hz, 1H), 7.21-7.18 (m, 3H), 6.92 (d, J = 8.4 Hz, 1H), 6.18 (dd, J = 3.6, 10.8 Hz, 1H), 4.96-4.93 (m, 1H), 4.08-4.01 (m, 3H), 3.80 (s, 3H), 2.94 (s, 3H), 1.37 (t, J = 6.8 Hz, 3H). | MS-ESI m/z: 486.1 [M + H]+ |
| 13 | WX013 | ¹H NMR (400 MHz, CDCl₃) δ: 9.81 (br s, 1H), 8.24 (br s, 1H), 7.50 (br s, 1H), 7.40 (br s, 1H), 7.33-7.12 (m, 4H), 6.85 (d, J = 8.3 Hz, 1H), 6.26 (d, J = 4.8 Hz, 1H), 5.02-4.89 (m, 1H), 4.13 (d, J = 5.5 Hz, 2H), 3.96 (d, J = 11.0 Hz, 1H), 3.85 (s, 3H), 2.82 (br s, 3H), 1.45 (t, J = 6.7 Hz, 3H). | MS-ESI m/z: 504.1 [M + H]+ |
| 14 | WX014 | ¹H NMR (400 MHz, CDCl₃) δ: 8.94 (br s, 1H), 8.02 (d, J = 1.8 Hz, 1H), 7.42 (d, J = 1.8 Hz, 1H), 7.32-7.26 (m, 4H), 7.24 (d, J = 1.5 Hz, 1H), 7.21-7.17 (m, 1H), 6.84 (d, J = 8.3 Hz, 1H), 6.22 (dd, J = 5.0, 9.3 Hz, 1H), 4.89 (dd, J = 9.5, 14.6 Hz, 1H), 4.20-4.06 (m, 2H), 3.98 (dd, J = 4.9, 14.7 Hz, 1H), 3.84 (s, 3H), 2.77 (s, 3H), 2.27 (s, 3H), 1.43 (t, J = 7.0 Hz, 3H). | MS-ESI m/z: 482.1 [M + H]+ |
| 15 | WX015 | ¹H NMR (400 MHz, CDCl₃) δ: 8.02 (d, J = 1.8 Hz, 1H), 7.48-7.38 (m, 3H), 7.31 (d, J = 2.0 Hz, 1H), 7.28-7.22 (m, 2H), 7.18-7.15 (m, 1H), 6.87 (d, J = 8.3 Hz, 1H), 6.25 (dd, J = 5.0, 9.3 Hz, 1H), 4.90 (dd, J = 9.5, 14.6 Hz, 1H), 4.20-4.09 (m, 2H), 4.01 (dd, J = 5.0, 14.8 Hz, 1H), 3.87 (s, 3H), 3.00 (quin, J = 6.8 Hz, 1H), 2.80 (s, 3H), 1.46 (t, J = 7.0 Hz, 3H), 1.20 (s, 3H), 1.18 (s, 3H). | MS-ESI m/z: 510.1 [M + H]+. |
| 16 | WX016 | ¹H NMR (400 MHz, CDCl₃) δ: 9.03 (br s, 1H), 8.11 (d, J = 1.8 Hz, 1H), 7.53-7.47 (m, 1H), 7.43-7.39 (m, 2H), 7.37-7.27 (m, 4H), 6.84 (d, J = 8.5 Hz, 1H), 6.23 (dd, J = 4.8, 9.5 Hz, 1H), 4.89 (dd, J = 9.5, 14.8 Hz, 1H), 4.15-4.06 (m, 2H), 3.97 (dd, J = 4.9, 14.7 Hz, 1H),3.84 (s, 3H), 2.78 (s, 3H), 1.43 (t, J = 7.0 Hz, 3H). | MS-ESI m/z: 502.0 [M + H]+ |
| 17 | WX017 | ¹H NMR (400 MHz, CDCl₃) δ: 9.62 (br s, 1H), 8.02 (br s, 1H), 7.78 (d, J = 7.3 Hz, 1H), 7.65-7.49 (m, 2H), 7.47-7.24 (m, 4H), 6.83 (d, J = 8.0 Hz, 1H), 6.21 (br s, 1H), 4.87 (dd, J = 9.8, 14.1 Hz, 1H), 4.17-3.94 (m, 3H), 3.84 (s, 3H), 2.73 (s, 3H), 1.41 (t, J = 6.5 Hz, 3H). | MS-ESI m/z: 498.1 [M + H]+ |
| 18 | WX018 | ¹H NMR (400 MHz, CDCl₃) δ: 9.62 (br s, 1H), 8.02 (br s, 1H), 7.78 (d, J = 7.3 Hz, 1H), 7.65-7.49 (m, 2H), 7.47-7.24 (m, 4H), 6.83 (d, J = 8.0 Hz, 1H), 6.21 (br s, 1H), 4.87 (dd, J = 9.8, 14.1 Hz, 1H), 4.17-3.94 (m, 3H), 3.84 (s, 3H), 2.73 (s, 3H), 1.41 (t, J = 6.5 Hz, 3H). | MS-ESI m/z: 536.1 [M + H]+ |
| 19 | WX019 | ¹H NMR (400 MHz, CD₃OD) δ: 8.28 (d, J = 1.3 Hz, 1H), 8.01 (s, 2H), 7.51 (d, J = 1.3 Hz, 1H), 7.34 (d, J = 1.8 Hz, 1H), 7.17 (dd, J = 1.9, 8.4 Hz, 1H), 6.91 (d, J = 8.5 Hz, 1H), 6.16 (dd, J = 3.6, 10.7 Hz, 1H), 4.10-3.96 (m, 3H), 3.79 (s, 3H), 2.93 (s, 3H), 1.37 (t, J = 7.0 Hz, 3H). | MS-ESI m/z: 458.1 [M + H]+ |
| 20 | WX020 | ¹H NMR (400 MHz, CD₃OD) δ: 7.89 (s, 1H), 7.36 (d, J = 1.5 Hz, 1H), 7.21 (s, 1H), 7.16 (s, 1H), 6.93 (d, J = 8.0 Hz, 1H), 6.24-5.99 (m, 1H), 5.10-4.92 (m, 1H), 4.17-3.95 (m, 3H), 3.82 (s, 3H), 2.92 (s, 3H), 2.36 (s, 3H), 1.39 (t, J = 7.0 Hz, 3H). | MS-ESI m/z: 406.1 [M + H]+ |

Embodiment 21: WX021

Synthetic Route:

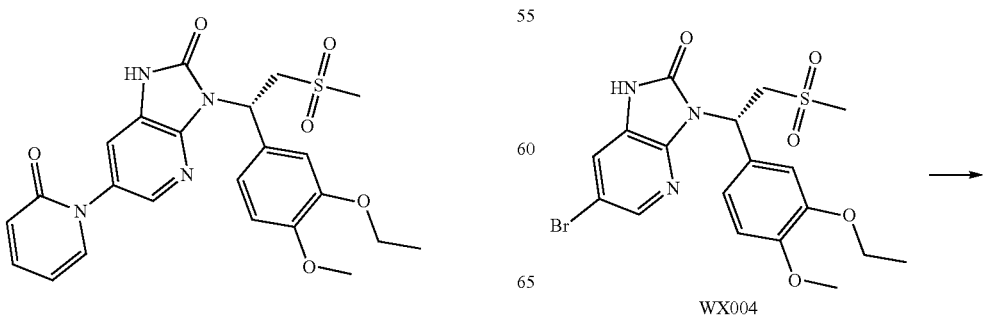

WX004

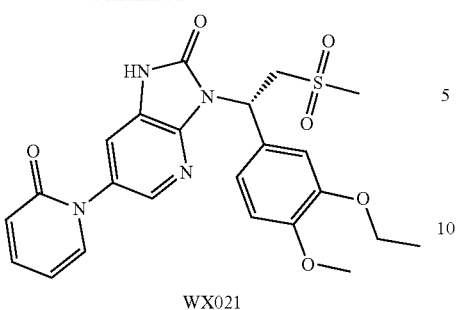

WX021

1H-pyridine-2-ketone (24.26 mg, 255.14 μmol), compound WX004 (60.00 mg, 127.57 μmol), $N^1,N^2$-dimethylethylenediamine (4.50 mg, 51.03 μmol), potassium carbonate (35.26 mg, 255.154 μmol) and cuprous iodide (4.86 mg, 25.51 μmol) were dissolved in N,N-dimethylformamide (2.00 mL) at room temperature. The reaction mixture was heated to 120° C. for 15 hours under nitrogen atmosphere. After the reaction, the mixture was cooled to room temperature, followed by filtration. The filtrate was concentrated under reduced pressure. The obtained residue was isolated by preparative HPLC to obtain the target product WX021. MS-ESI m/z: 485.3 [M+H]$^+$. $^1$H NMR (400 MHz, CDCl$_3$) δ: 9.54 (br s, 1H), 7.99 (s, 1H), 7.53-7.42 (m, 2H), 7.38 (d, J=6.5 Hz, 1H), 7.30 (s, 1H), 7.22 (d, J=8.3 Hz, 1H), 6.81 (d, J=8.3 Hz, 1H), 6.75 (d, J=8.3 Hz, 1H), 6.35 (t, J=6.8 Hz, 1H), 6.20 (dd, J=4.6, 9.2 Hz, 1H), 4.91-4.79 (m, 1H), 4.18-4.04 (m, 2H), 3.96-3.86 (m, 1H), 3.83 (s, 3H), 2.82 (s, 3H), 1.44 (t, J=6.9 Hz, 3H).

Embodiment 22: WX022

Synthetic Route:

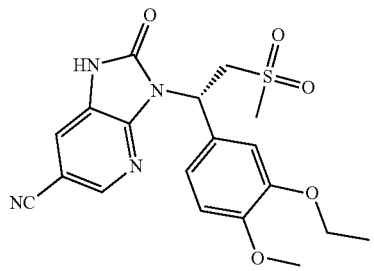 [SMILES: CCOc1cc([C@@H](CS(C)(=O)=O)n2c(=O)[nH]c3cc(C#N)cnc32)ccc1OC]

WX004

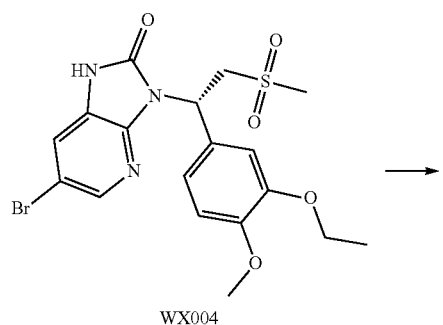

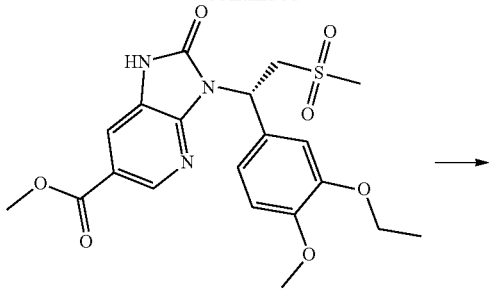

WX022-1

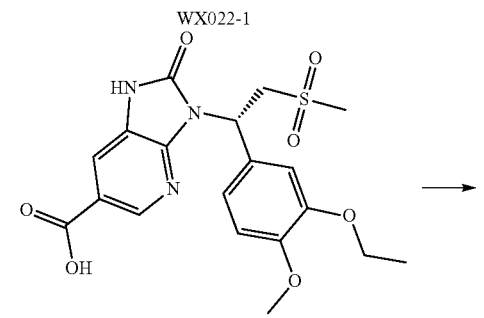

WX022-2

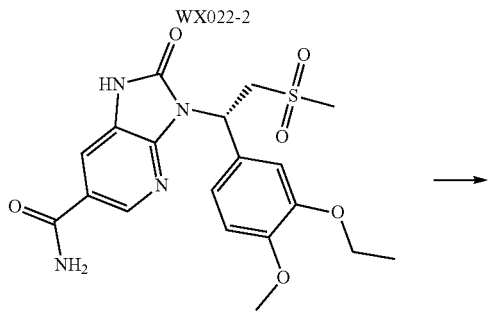

WX022-3

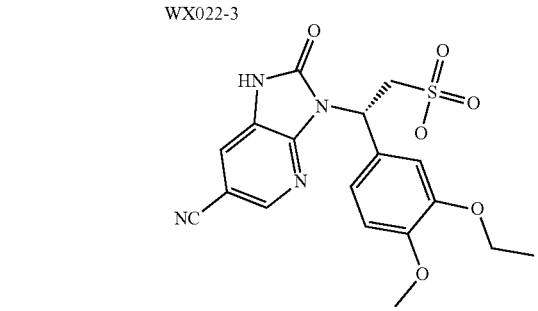

WX022

Step 1: Preparation of Compound WX022-1

Compound WX004 (100.00 mg, 212.61 mol) was dissolved in methanol (5.00 mL) at room temperature, followed by the stepwise addition of triethylamine (43.03 mg, 425.22 mol) and [1,1'-bis(diphenylphosphino)ferrocene] palladium dichloride (155.57 mg, 212.61 mol). The reaction mixture was heated to 60° C. and stirred for 12 hours under carbon monoxide atmosphere (50 psi). After the reaction, the mixture was cooled to room temperature, diluted with water (10 mL) and ethyl acetate (10 mL), partioned. The aqueous phase was extracted with ethyl acetate (10 mL×3). The organic phases were combined, washed with saturated brine (10 mL×2) and dried over anhydrous sodium sulfate, followed by filtration. The filtrate was concentrated under reduced pressure to remove the solvent. The obtained residue was isolated by preparative HPLC to obtain the target product WX022-1. MS-ESI m/z: 450.1 [M+H]$^+$. $^1$HNMR (400 MHz, CDCl₃) δ: 8.95 (br s, 1H), 8.79 (s, 1H), 7.86 (br s, 1H), 7.37 (br s, 1H), 6.84 (d, J=7.5 Hz, 1H), 6.27 (br s, 1H), 4.90 (br s, 1H), 4.11 (br s, 2H), 3.99-3.82 (m, 8H), 2.84 (br s, 3H), 1.46 (t, J=6.5 Hz, 3H).

Step 2: Preparation of Compound WX022-2

Compound WX022-1 (30.00 mg, 66.74 μmol) was dissolved in methanol (1.00 mL) and tetrahydrofuran (500.00 μL) at the room temperature, followed by the addition of lithium hydroxide monohydrate (5.60 mg, 133.49 mol) and water (300.00 μL). The reaction mixture was heated to 50° C. and stirred for 3 hours. After the reaction, the mixture was cooled to room temperature, dilute hydrochloric acid (2M, 0.1 mL) was added thereto and extracted with ethyl acetate (8 mL×3). The organic phases were combined and dried over anhydrous sodium sulfate, followed by filtration. The filtrate was concentrated under reduced pressure to remove the solvent. The obtained residue was isolated by preparative HPLC to obtain the target product WX022-2. MS-ESI m/z: 436.1 [M+H]⁺. ¹H NMR (400 MHz, CD₃OD) δ: 8.75 (s, 1H), 7.85 (s, 1H), 7.37 (s, 1H), 7.20 (d, J=8.0 Hz, 1H), 6.95 (d, J=8.3 Hz, 1H), 6.22 (dd, J=3.8, 10.5 Hz, 1H), 4.95 (br s, 1H), 4.14-3.99 (m, 3H), 3.82 (s, 3H), 2.96 (s, 3H), 1.40 (t, J=7.0 Hz, 3H).

Step 3: Preparation of Compound WX022-3

Compound WX022-2 (40.00 mg, 91.86 μmol), ammonium chloride (19.65 mg, 367.44 mmol) and tetramethyluronium hexafluorphosphate (10.48 mg, 27.56 μmol) dissolved in ethyldiisopropylamine (47.49 mg, 367.44 μmol) and N,N-dimethylformamide (2.00 mL) at room temperature. The reaction mixture was stirred at room temperature for 3 hours. After the reaction, the mixture was diluted with water (5 mL) and extracted with ethyl acetate (8 mL×3). The organic phases were combined, washed with saturated brine (5 mL) and dried over anhydrous sodium sulfate, followed by filtration. The filtrate was concentrated under reduced pressure to remove the solvent. The obtained residue was isolated by preparative HPLC to obtain the target product WX022-3. MS-ESI m/z: 435.1 [M+H]⁺. ¹H NMR (400 MHz, CD₃OD) δ: 8.61 (s, 1H), 7.79 (s, 1H), 7.36 (d, J 1.5 Hz, 1H), 7.23-7.12 (m, 1H), 6.93 (d, J=8.3 Hz, 1H), 6.21 (dd, J=3.8, 10.5 Hz, 1H), 4.94 (br s, 1H), 4.14-3.98 (m, 3H), 3.81 (s, 3H), 2.96 (s, 3H).

Step 4: Preparation of Compound WX022

Compound WX022-3 (30.00 mg, 69.05 μmol) and triethylamine (20.96 mg, 207.15 μmol) were dissolved in dichloromethane (1.00 mL), followed by the dropwise addition of trifluoroacetic anhydride (29.00 mg, 138.10 μmol) at 0° C. The reaction mixture was stirred at 0° C. for 1 hour. After the reaction, the mixture was diluted with water (3 mL) and extracted with ethyl acetate (5 mL×3). The organic phases were combined, wash with saturated brine (5 mL) and dried over anhydrous sodium sulfate, followed by filtration. The filtrate was concentrated under reduced pressure to remove the solvent. The obtained residue was isolated by preparative HPLC to obtain the target product WX022. MS-ESI m/z: 417.1 [M+H]⁺. ¹H NMR (400 MHz, CD₃OD) δ: 8.43 (d, J=1.8 Hz, 1H), 7.61 (d, J=1.6 Hz, 1H), 7.33 (d, J=2.0 Hz, 1H), 7.18 (dd, J=2.0, 8.2 Hz, 1H), 6.94 (d, J=8.6 Hz, 1H), 6.21 (dd, J=3.8, 10.8 Hz, 1H), 4.83 (br s, 1H), 4.13-3.99 (m, 3H), 3.82 (s, 3H), 2.98 (s, 3H), 1.40 (t, J=7.0 Hz, 3H).

Embodiment 23: WX023

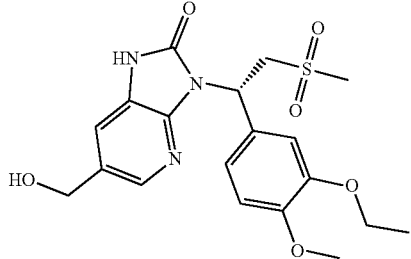 [SMILES: CCOc1cc([C@@H](CS(C)(=O)=O)n2c(=O)[nH]c3cc(CO)cnc32)ccc1OC]

Synthetic Route:

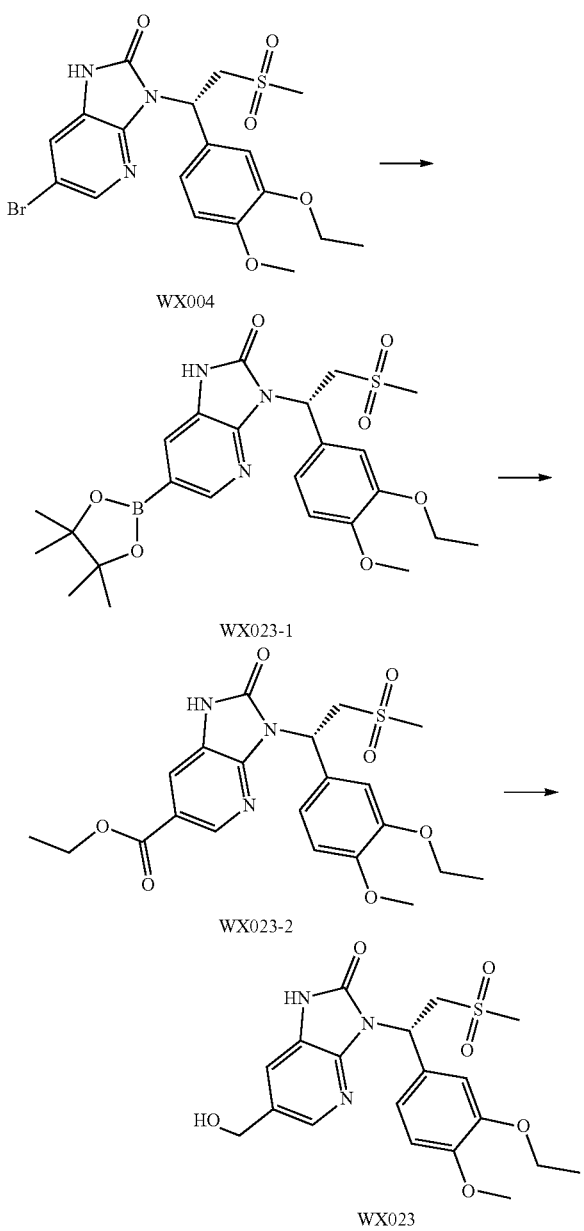

Step 1: Preparation of Compound WX023-1

[1,1'-bis(diphenylphosphino)ferrocene] palladium dichloride (46.67 mg, 63.78 μmol) was added to the solution of bis(pinacolato)diboron (388.73 mg, 1.53 mmol), compound WX004 (300.00 mg, 637.84 μmol) and potassium acetate (375.58 mg, 3.83 mmol) in dioxane (5.00 mL) at room temperature. The reaction mixture was heated to 100° C. and stirred for 3 hours under nitrogen atmosphere. After the reaction, the mixture was cooled to room temperature, quenched with water (10 mL) and extracted with ethyl acetate (10 mL×3). The organic phases were combined, washed with saturated brine (15 mL) and dried over anhydrous sodium sulfate, followed by filtration. The filtrate was concentrated under reduced pressure to remove the solvent. The obtained residue was isolated by column chromatography (eluent: petroleum ether/ethyl acetate=3/1-1/2, volume ratio) to obtain the target product WX023-1. MS-ESI m/z: 518.1 [M+H]$^+$.

Step 2: Preparation of Compound WX023-2

Palladium acetate (5.42 mg, 24.16 μmol) was added to and the solution of compound WX023-1 (250.00 mg, 483.19 μmol) and benzophenone (88.05 mg, 483.19 μmol) in ethanol (1.00 mL) at room temperature. The reaction mixture was stirred at room temperature for 12 hours under carbon monoxide atmosphere (15 psi). After the reaction, the mixture was diluted with water (10 mL) and extracted with ethyl acetate (10 mL×3). The organic phases were combined, washed with saturated brine (15 mL) and dried over anhydrous sodium sulfate, followed by filtration. The filtrate was concentrated under reduced pressure to remove the solvent. The obtained residue was isolated column chromatography (eluent: petroleum ether/ethyl acetate=3/1-1/2, volume ratio) to obtain the target product WX023-2. MS-ESI m/z: 464.1 [M+H]$^+$. $^1$HNMR (400 MHz, CDCl$_3$) δ: 9.60 (s, 1H), 8.79 (d, J=1.5 Hz, 1H), 7.86 (d, J=1.8 Hz, 1H), 7.34 (d, J=2.0 Hz, 1H), 7.23 (dd, J=1.9, 8.4 Hz, 1H), 6.83 (d, J=8.3 Hz, 1H), 6.23 (dd, J=4.5, 10.0 Hz, 1H), 4.90 (dd, J=10.2, 14.7 Hz, 1H), 4.40 (q, J=7.0 Hz, 2H), 4.09 (dquin, J=2.5, 7.0 Hz, 2H), 3.96-3.78 (m, 4H), 2.80 (s, 3H), 1.49-1.35 (m, 6H).

Step 3: Preparation of Compound WX023

LiBH$_4$ (3.38 mg, 155.34 μmol) was added to the solution of compound WX023-2 (60.00 mg, 129.45 μmol) in tetrahydrofuran (4.00 mL) at room temperature. The reaction mixture was heated to 50° C. and stirred for 2 hours. After the reaction, the mixture was cooled to room temperature, quenched with water (8 mL) and extracted with ethyl acetate (10 mL×2). The organic phases were combined and dried over anhydrous sodium sulfate, followed by filtration. The filtrate was concentrated under reduced pressure to remove the solvent. The obtained residue was isolated by preparative HPLC to obtain the target product WX023. MS-ESI m/z: 422.1 [M+H]$^+$. $^1$H NMR (400 MHz, DMSO_d$_6$) δ: 8.06 (s, 1H), 7.53 (s, 1H), 7.36 (d, J=2.0 Hz, 1H), 7.19 (dd, J=2.0, 8.2 Hz, 1H), 6.95 (d, J=8.6 Hz, 1H), 6.19 (dd, J=3.6, 10.8 Hz, 1H), 4.87 (d, J=11.0 Hz, 1H), 4.67 (s, 2H), 4.13-4.01 (m, 3H), 3.82 (s, 3H), 2.97 (s, 3H), 1.40 (t, J=7.0 Hz, 3H).

Embodiment 24: WX024

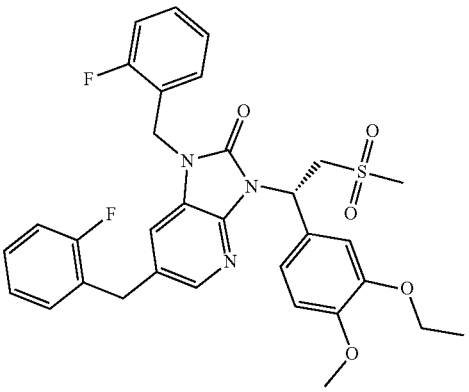 [SMILES: CCOc1cc([C@@H](CS(C)(=O)=O)n2c(=O)n(Cc3ccccc3F)c3cc(Cc4ccccc4F)cnc32)ccc1OC]

Synthetic Route:

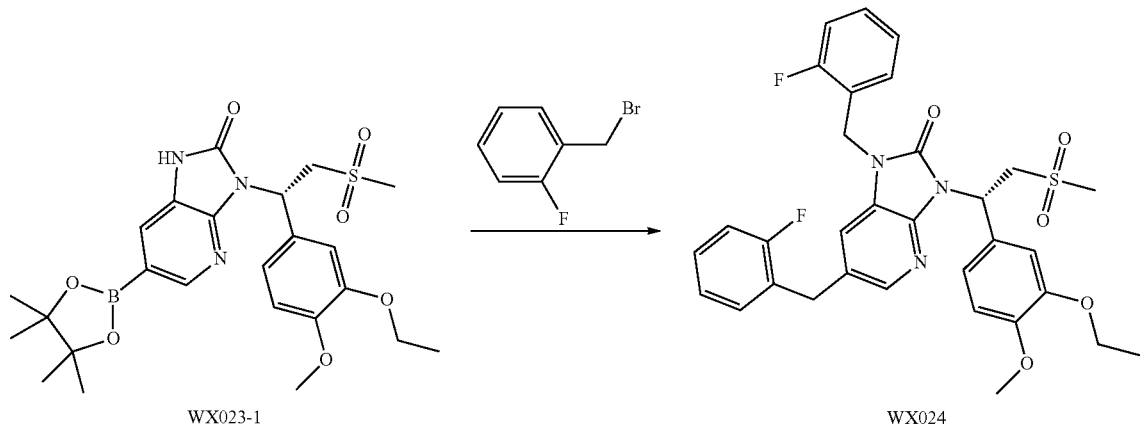

Compound WX023-1 (50.00 mg, 96.64 μmol), 2-fluorobenzyl bromide (36.53 mg, 193.28 μmol), tetrakis(triphenylphosphine) palladium (11.17 mg, 9.66 μmol) and potassium phosphate (41.03 mg, 193.28 μmol) were dissolved in dimethyl ether (2.00 mL), ethanol (500.00 μL) and water (500.00 μL) at room temperature. The reaction mixture was heated to 90° C. and stirred for 3 hours under nitrogen atmosphere. After the reaction, the mixture was cooled to room temperature and concentrated under reduced pressure to remove the solvent. Water (5 mL) was added to the obtained residue and extracted with ethyl acetate (5 mL×3). The organic phases were combined and dried over anhydrous sodium sulfate, followed by filtration. The filtrate was concentrated under reduced pressure. The obtained residue was isolated by preparative HPLC to obtain the target product WX024. MS-ESI m/z: 608.2 [M+H]$^+$. $^1$H NMR (400 MHz, CDCl$_3$) δ: 7.86 (s, 1H), 7.29 (s, 1H), 7.19-7.12 (m, 4H), 7.05-6.87 (m, 6H), 6.74 (d, J=8.5 Hz, 1H), 6.18 (dd, J=4.5, 10.0 Hz, 1H), 4.97 (s, 2H), 4.79 (dd, J=10.0, 14.6 Hz, 1H), 4.05-3.94 (m, 2H), 3.88-3.74 (m, 6H), 2.69 (s, 3H), 1.36 (t, J=7.0 Hz, 3H).

Embodiment 25: WX025

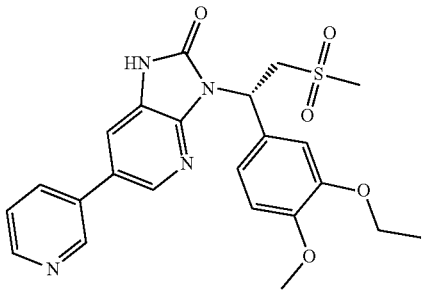 [SMILES: CCOc1cc([C@@H](CS(C)(=O)=O)n2c(=O)[nH]c3cc(-c4cccnc4)cnc32)ccc1OC]

Synthetic Route:

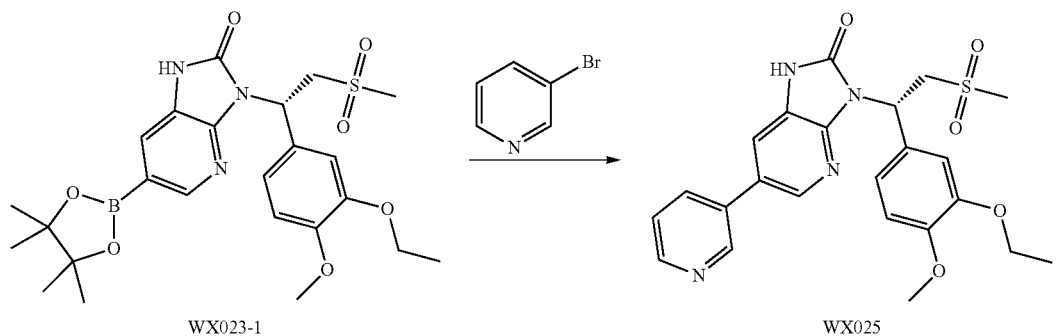

[1,1'-bis(diphenylphosphino)ferrocene] palladium dichloride dichloromethane complex (3.95 mg, 4.83 μmol) was added to the solution of 3-bromopyridine (15.27 mg, 96.64 μmol), compound WX023-1 (50.00 mg, 96.64 μmol) and potassium carbonate (40.07 mg, 289.92 μmol) in dioxane (3.00 mL) and water (1.00 mL) at room temperature. The reaction mixture was heated to 70-80° C. and stirred for 12 hours under nitrogen atmosphere. After the reaction, the mixture was cooled to room temperature and water (3 mL) and ethyl acetate (3 mL) were added thereto, followed by filtration. The filtrate was extracted with ethyl acetate (10 mL×3). The organic phases were combined, washed with saturated brine (10 mL) and dried over anhydrous sodium sulfate, followed by filtration. The filtrate was concentrated under reduced pressure. The obtained residue was isolated by preparative HPLC to obtain the target product WX025. MS-ESI m/z: 469.1 [M+H]$^+$. $^1$H NMR (400 MHz, CDCl$_3$) δ: 9.18 (br s, 1H), 8.78 (br s, 1H), 8.40 (d, J=6.8 Hz, 1H), 8.31 (br s, 1H), 7.87 (br s, 1H), 7.62 (br s, 1H), 7.33 (br s, 1H), 7.28 (s, 1H), 7.25 (d, J=8.3 Hz, 1H), 6.84 (d, J=8.5 Hz, 1H), 6.29 (d, J=10.5 Hz, 1H), 5.05 (t, J=12.4 Hz, 1H), 4.11 (d, J=7.0 Hz, 2H), 3.85 (s, 4H), 2.93 (s, 3H), 1.46 (t, J=6.8 Hz, 3H).

The compounds of each embodiment in the following table were prepared according to the method of embodiment 25.

TABLE 3

| Embodiment- | Fragment 1 | Fragment 2 | Structure | Compound |
|---|---|---|---|---|
| 26 | WX023-1 | | 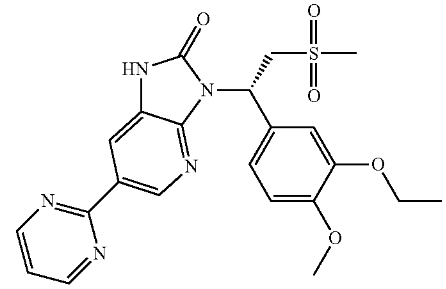 [SMILES: CCOc1cc([C@@H](CS(C)(=O)=O)n2c(=O)[nH]c3cc(-c4ncccn4)cnc32)ccc1OC] | WX026 |
| 27 | WX023-1 | | 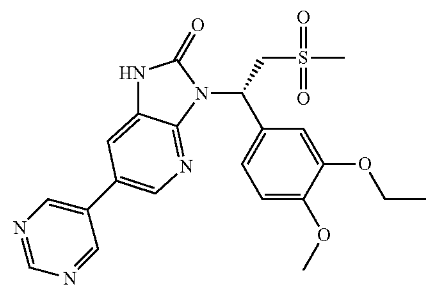 [SMILES: CCOc1cc([C@@H](CS(C)(=O)=O)n2c(=O)[nH]c3cc(-c4cncnc4)cnc32)ccc1OC] | WX027 |
| 28 | WX023-1 | | 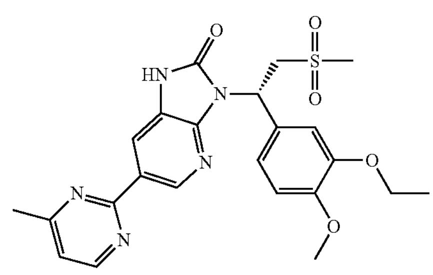 [SMILES: CCOc1cc([C@@H](CS(C)(=O)=O)n2c(=O)[nH]c3cc(-c4nccc(C)n4)cnc32)ccc1OC] | WX028 |

TABLE 3-continued

| Embodiment- | Fragment 1 | Fragment 2 | Structure | Compound |
|---|---|---|---|---|
| 29 | WX023-1 | | 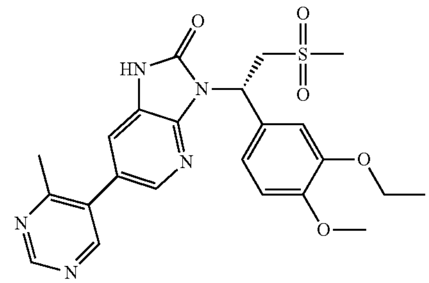 [SMILES: CCOc1cc([C@@H](CS(C)(=O)=O)n2c(=O)[nH]c3cc(-c4cncnc4C)cnc32)ccc1OC] | WX029 |
| 30 | WX023-1 | | 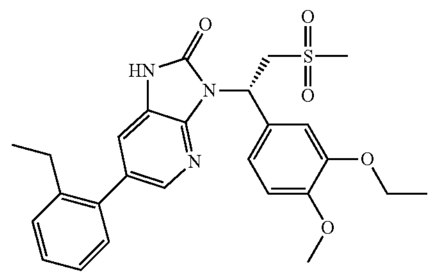 [SMILES: CCOc1cc([C@@H](CS(C)(=O)=O)n2c(=O)[nH]c3cc(-c4ccccc4CC)cnc32)ccc1OC] | WX030 |
| 31 | WX023-1 | | 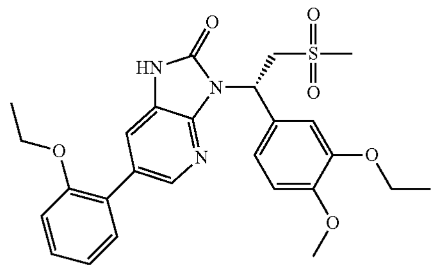 [SMILES: CCOc1cc([C@@H](CS(C)(=O)=O)n2c(=O)[nH]c3cc(-c4ccccc4OCC)cnc32)ccc1OC] | WX031 |
| 32 | WX023-1 | | 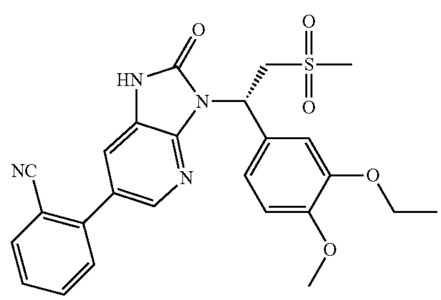 [SMILES: CCOc1cc([C@@H](CS(C)(=O)=O)n2c(=O)[nH]c3cc(-c4ccccc4C#N)cnc32)ccc1OC] | WX032 |

TABLE 3-continued
| Embodiment | Fragment 1 | Fragment 2 | Structure | Compound |
|---|---|---|---|---|
| 33 | 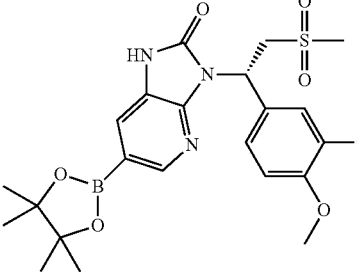<br>WX023-1 | 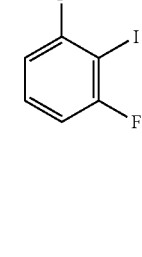 | 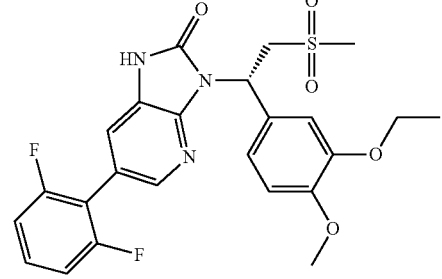 | WX033 |
| 34 | 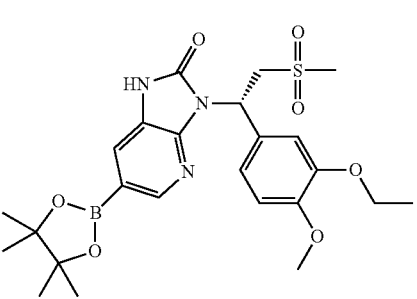<br>WX023-1 | 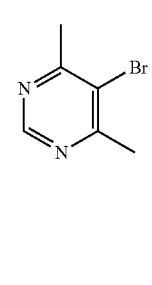 | 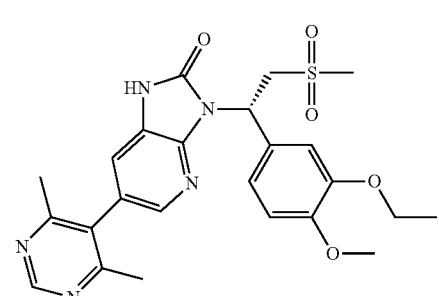 | WX034 |
| 35 | 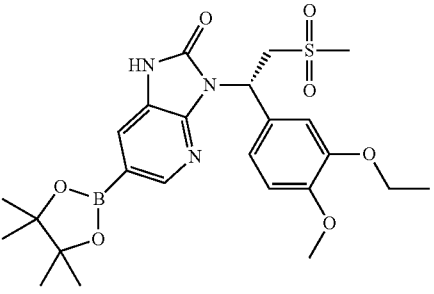<br>WX023-1 | 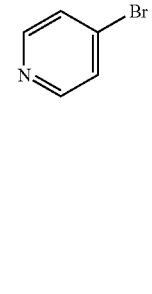 | 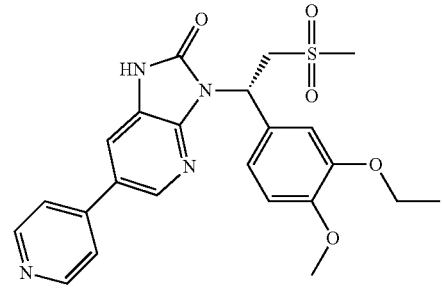 [SMILES: CCOc1cc([C@@H](CS(C)(=O)=O)n2c(=O)[nH]c3cc(-c4ccncc4)cnc32)ccc1OC] | WX035 |
| 36 | 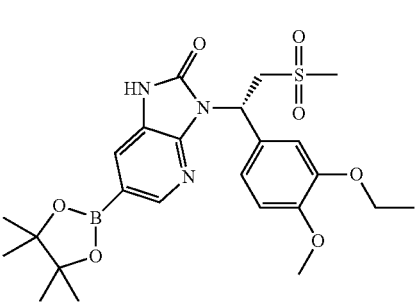<br>WX023-1 | 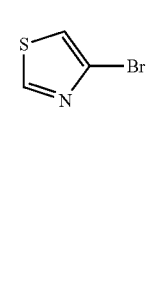 | 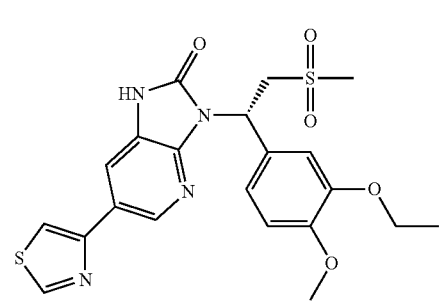 [SMILES: CCOc1cc([C@@H](CS(C)(=O)=O)n2c(=O)[nH]c3cc(-c4cscn4)cnc32)ccc1OC] | WX036 |

TABLE 3-continued
| Embodiment | Fragment 1 | Fragment 2 | Structure | Compound |
|---|---|---|---|---|
| 37 | 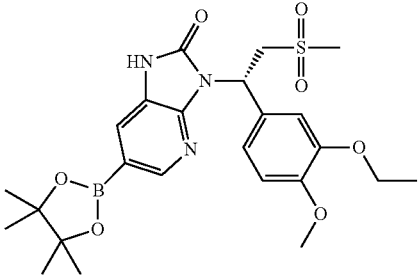 WX023-1 | 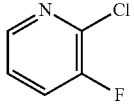 | 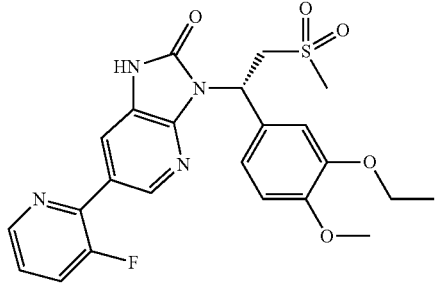 [SMILES: CCOc1cc([C@@H](CS(C)(=O)=O)n2c(=O)[nH]c3cc(-c4ncccc4F)cnc32)ccc1OC] | WX037 |
| 38 | 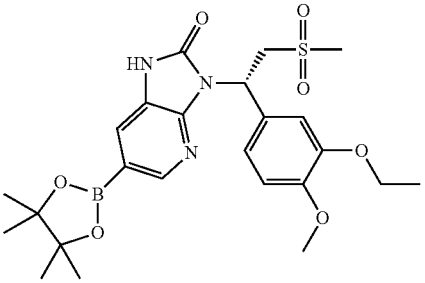 WX023-1 | 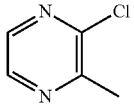 | 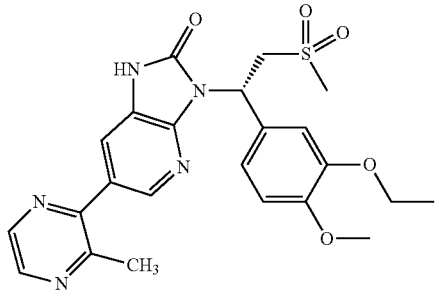 [SMILES: CCOc1cc([C@@H](CS(C)(=O)=O)n2c(=O)[nH]c3cc(-c4nccnc4C)cnc32)ccc1OC] | WX038 |
| 39 | 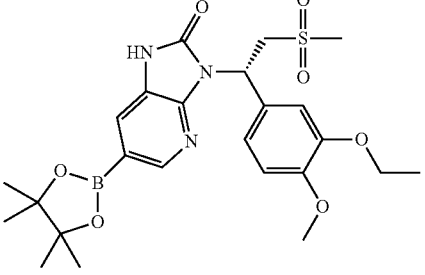 WX023-1 | 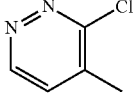 | 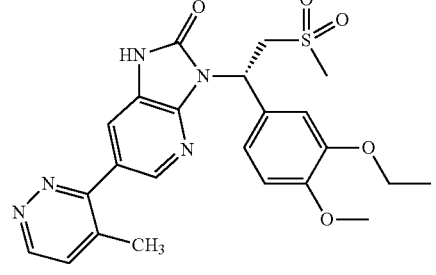 | WX039 |
| 40 | 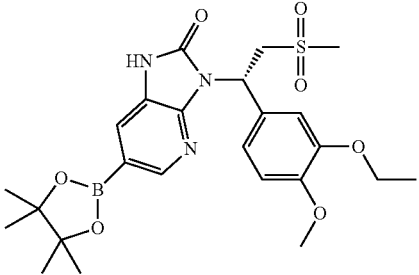 WX023-1 | 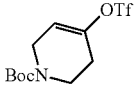 | 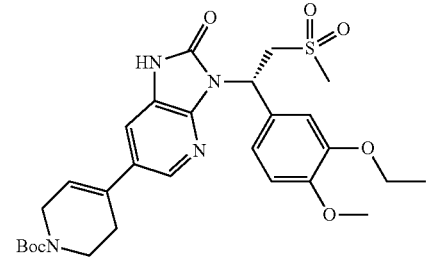 [SMILES: CCOc1cc([C@@H](CS(C)(=O)=O)n2c(=O)[nH]c3cc(C4=CCN(C(=O)OC(C)(C)C)CC4)cnc32)ccc1OC] | WX040 |

LCMS and $^1$HNMR Results of Each Embodiment

TABLE 4

| Embodiment | Compound | HNMR | LCMS |
|---|---|---|---|
| 26 | WX026 | $^1$H NMR (400 MHz, CDCl$_3$) δ: 10.12 (br s, 1H), 9.21 (d, J = 1.5 Hz, 1H), 8.81 (d, J = 5.0 Hz, 2H), 8.35-8.29 (m, 1H), 7.41 (d, J = 1.5 Hz, 1H), 7.29 (d, J = 1.5 Hz, 1H), 7.22 (t, J = 5.0 Hz, 1H), 6.82 (d, J = 8.5 Hz, 1H), 6.26 (dd, J = 4.5, 9.5 Hz, 1H), 4.96 (dd, J = 10.0, 14.6 Hz, 1H), 4.18-4.05 (m, 2H), 3.98 (dd, J = 4.5, 14.6 Hz, 1H), 3.82 (s, 3H), 2.79 (s, 3H), 1.44 (t, J = 7.0 Hz, 3H). | MS-ESI m/z: 470.1 [M + H]$^+$ |
| 27 | WX027 | $^1$H NMR (400 MHz, CDCl$_3$) δ: 9.65 (br s, 1H), 9.25 (s, 1H), 8.95 (s, 2H), 8.27 (br s, 1H), 7.50 (br s, 1H), 7.36 (br s, 1H), 7.30-7.22 (m, 1H), 6.85 (d, J = 8.3 Hz, 1H), 6.41-6.20 (m, 1H), 5.13-4.94 (m, 1H), 4.12 (dd, J = 3.3, 6.8 Hz, 2H), 3.92-3.82 (m, 4H), 2.90 (s, 3H), 1.46 (td, J = 3.5, 6.8 Hz, 3H). | MS-ESI m/z: 470.1 [M + H]$^+$ |
| 28 | WX028 | $^1$H NMR (400 MHz, CDCl$_3$) δ: 10.09 (br s, 1H), 9.21 (s, 1H), 8.65 (d, J = 5.3 Hz, 1H), 8.34 (s, 1H), 7.40 (s, 1H), 7.29 (d, J = 8.3 Hz, 1H), 7.07 (d, J = 5.3 Hz, 1H), 6.83 (d, J = 8.3 Hz, 1H), 6.25 (dd, J = 4.8, 9.5 Hz, 1H), 4.95 (dd, J = 9.8, 14.8 Hz, 1H), 4.18-4.05 (m, 2H), 3.99 (dd, J = 4.8, 14.8 Hz, 1H), 3.82 (s, 3H), 2.75 (s, 3H), 2.59 (s, 3H), 1.44 (t, J = 7.0 Hz, 3H). | MS-ESI m/z: 484.1 [M + H]$^+$ |
| 29 | WX029 | $^1$H NMR (400 MHz, CDCl$_3$) δ: 9.11 (s, 1H), 8.53 (s, 1H), 8.02 (d, J = 1.8 Hz, 1H), 7.37 (d, J = 2.0 Hz, 1H), 7.29-7.24 (m, 3H), 6.85 (d, J = 8.3 Hz, 1H), 6.24 (dd, J = 4.5, 10.0 Hz, 1H), 4.91 (dd, J = 10.0, 14.6 Hz, 1H), 4.11 (dquin, J = 2.5, 6.8 Hz, 2H), 3.91 (dd, J = 4.5, 14.6 Hz, 1H), 3.84 (s, 3H), 2.84 (s, 3H), 2.53 (s, 3H), 1.45 (t, J = 7.0 Hz, 3H). | MS-ESI m/z: 484.1 [M + H]$^+$ |
| 30 | WX030 | $^1$H NMR (400 MHz, CDCl$_3$) δ: 9.77 (br s, 1H), 8.01 (d, J = 1.8 Hz, 1H), 7.43 (d, J = 1.8 Hz, 1H), 7.39-7.31 (m, 2H), 7.29-7.26 (m, 2H), 7.26-7.23 (m, 1H), 7.17 (d, J = 7.3 Hz, 1H), 6.83 (d, J = 8.3 Hz, 1H), 6.22 (dd, J = 5.0, 9.5 Hz, 1H), 4.89 (dd, J = 9.4, 14.7 Hz, 1H), 4.18-4.03 (m, 2H), 3.99 (dd, J = 5.1, 14.7 Hz, 1H), 3.83 (s, 3H), 2.76 (s, 3H), 2.58 (q, J = 7.5 Hz, 2H), 1.41 (t, J = 7.0 Hz, 3H), 1.11 (t, J = 7.5 Hz, 3H). | MS-ESI m/z: 496.1 [M + H]$^+$. |
| 31 | WX031 | $^1$H NMR (400 MHz, CDCl$_3$) δ: 9.72 (br s, 1H), 8.23 (d, J = 1.8 Hz, 1H), 7.57-7.52 (m, 1H), 7.43 (d, J = 2.0 Hz, 1H), 7.36-7.28 (m, 2H), 7.27-7.24 (m, 1H), 7.06-6.95 (m, 2H), 6.81 (d, J = 8.3 Hz, 1H), 6.22 (dd, J = 5.0, 9.3 Hz, 1H), 4.90 (dd, J = 9.4, 14.7 Hz, 1H), 4.16-3.97 (m, 5H), 3.82 (s, 3H), 2.73 (s, 3H), 1.42 (t, J = 7.0 Hz, 3H), 1.35 (t, J = 7.0 Hz, 3H). | MS-ESI m/z: 512.2 [M + H]$^+$. |
| 32 | WX032 | $^1$H NMR (400 MHz, CDCl$_3$) δ: 8.23 (d, J = 1.8 Hz, 1H), 7.82-7.76 (m, 1H), 7.69 (dt, J = 1.4, 7.7 Hz, 1H), 7.53-7.47 (m, 3H), 7.39 (d, J = 2.0 Hz, 1H), 7.27-7.25 (m, 1H), 6.84 (d, J = 8.3 Hz, 1H), 6.24 (dd, J = 4.9, 9.7 Hz, 1H), 4.89 (dd, J = 9.7, 14.7 Hz, 1H), 4.18-4.04 (m, 2H), 3.97 (dd, J = 5.0, 14.6 Hz, 1H), 3.90-3.77 (m, 3H), 2.79 (s, 3H), 1.44 (t, J = 6.9 Hz, 3H). | MS-ESI m/z: 493.1 [M + H]$^+$. |
| 33 | WX033 | $^1$H NMR (400 MHz, CDCl$_3$) δ: 9.95 (br s, 1H), 8.18 (s, 1H), 7.46-7.38 (m, 2H), 7.37-7.29 (m, 1H), 7.28-7.23 (m, 1H), 7.02 (t, J = 7.8 Hz, 2H), 6.83 (d, J = 8.5 Hz, 1H), 6.23 (dd, J = 4.9, 9.4 Hz, 1H), 4.89 (dd, J = 9.4, 14.7 Hz, 1H), 4.15-4.05 (m, 2H), 4.00 (dd, J = 5.0, 14.8 Hz, 1H), 3.83 (s, 3H), 2.76 (s, 3H), 1.42 (t, J = 6.9 Hz, 3H). | MS-ESI m/z: 504.1 [M + H]$^+$ |
| 34 | WX034 | $^1$H NMR (400 MHz, CDCl$_3$) δ: 9.46 (br s, 1H), 9.09 (s, 1H), 7.90 (s, 1H), 7.38 (s, 1H), 7.18 (s, 1H), 6.86 (d, J = 8.3 Hz, 1H), 6.23 (dd, J = 4.3, 9.8 Hz, 1H), 4.87 (dd, J = 9.9, 14.2 Hz, 1H), 4.18-4.04 (m, 2H), 3.98-3.78 (m, 4H), 2.84 (s, 3H), 2.38 (s, 6H), 1.44 (t, J = 6.9 Hz, 3H). | MS-ESI m/z: 498.2 [M + H]$^+$ |
| 35 | WX035 | $^1$H NMR (400 MHz, DMSO_d$_6$) δ: 11.66 (d, J = 9.5 Hz, 1H), 8.81 (br s, 2H), 8.58 (br s, 1H), 8.14 (d, J = 3.8 Hz, 2H), 7.82 (br s, 1H), 7.29-7.23 (m, 1H), 7.04-6.99 (m, 1H), 6.93 (d, J = 8.3 Hz, 1H), 6.12-6.04 (m, 1H), 4.70 (dd, J = 11.2, 13.9 Hz, 1H), 4.23-4.14 (m, 1H), 4.01 (q, J = 6.8 Hz, 2H), 3.02 (s, 3H), 2.03 (s, 3H), 1.31 (t, J = 6.9 Hz, 3H). | MS-ESI m/z: 469.1 [M + H]$^+$ |
| 36 | WX036 | $^1$H NMR (400 MHz, CD$_3$OD) δ: 9.46 (br s, 1H), 8.39 (br s, 2H), 7.65 (s, 1H), 7.35 (d, J = 1.5 Hz, 1H), 7.20 (d, J = 8.3 Hz, 1H), 6.94 (d, J = 8.3 Hz, 1H), 6.20 (dd, J = 3.5, 11.0 Hz, 1H), 4.12-4.01 (m, 4H), 3.82 (s, 3H), 3.03-2.94 (m, 3H), 1.40 (t, J = 7.0 Hz, 3H). | MS-ESI m/z: 475.0 [M + H]$^+$ |
| 37 | WX037 | $^1$H NMR (400 MHz, CDCl$_3$) δ: 9.46 (br s, 1H), 8.77 (s, 1H), 8.55 (d, J = 4.3 Hz, 1H), 7.99 (s, 1H), 7.60-7.50 (m, 1H), 7.41 (d, J = 1.5 Hz, 1H), 7.37-7.29 (m, 2H), 6.86 (d, J = 8.5 Hz, 1H), 6.26 (dd, J = 4.9, 9.7 Hz, 1H), 4.95 (dd, J = 9.8, 14.8 Hz, 1H), 4.18-4.09 (m, 2H), 3.98 (dd, J = 4.6, 14.7 Hz, 1H), 3.86 (s, 3H), 2.79 (s, 3H), 1.46 (t, J = 7.0 Hz, 3H). | MS-ESI m/z: 487.1 [M + H]$^+$ |

TABLE 4-continued

| Embodiment | Compound | HNMR | LCMS |
|---|---|---|---|
| 38 | WX038 | $^1$H NMR (400 MHz, CDCl$_3$) δ: 9.25 (br s, 1H), 8.56-8.43 (m, 2H), 8.33 (d, J = 1.5 Hz, 1H), 7.57 (d, J = 1.5 Hz, 1H), 7.37 (s, 1H), 7.31-7.26 (m, 2H), 6.84 (d, J = 8.3 Hz, 1H), 6.25 (dd, J = 4.8, 9.8 Hz, 1H), 4.91 (dd, J = 9.8, 14.6 Hz, 1H), 4.12 (dd, J = 3.9, 6.9 Hz, 2H), 3.96 (dd, J = 4.8, 14.6 Hz, 1H), 3.85 (s, 3H), 2.80 (s, 3H), 2.71 (s, 3H), 1.45 (t, J = 6.9 Hz, 3H). | MS-ESI m/z: 484.1 [M + H]$^+$ |
| 39 | WX039 | $^1$H NMR (400 MHz, CDCl$_3$) δ: 10.34 (br s, 1H), 9.09 (d, J = 5.0 Hz, 1H), 8.28 (s, 1H), 7.83 (s, 1H), 7.47 (d, J = 5.0 Hz, 1H), 7.38 (s, 1H), 7.27 (br s, 1H), 6.85 (d, J = 8.3 Hz, 1H), 6.27 (dd, J = 4.8, 9.5 Hz, 1H), 4.94 (dd, J = 9.9, 14.7 Hz, 1H), 4.12 (dd, J = 2.5, 7.0 Hz, 2H), 3.97 (dd, J = 4.6, 14.4 Hz, 1H), 3.86 (s, 3H), 2.81 (s, 3H), 2.51 (s, 3H), 1.46 (t, J = 6.9 Hz, 3H). | MS-ESI m/z: 484.1 [M + H]$^+$ |
| 40 | WX040 | $^1$H NMR (400 MHz, MeOD) δ: 8.09 (s, 1H), 7.35 (d, J = 14.8 Hz, 2H), 7.16 (d, J = 7.8 Hz, 1H), 6.91 (d, J = 8.3 Hz, 1H), 6.14 (dd, J = 3.4, 10.4 Hz, 1H), 6.07 (br s, 1H), 4.14-3.95 (m, 5H), 3.79 (s, 3H), 3.64 (br s, 2H), 2.92 (s, 3H), 2.53 (br s, 2H), 1.49 (s, 9H), 1.37 (t, J = 6.9 Hz, 3H). | MS-ESI m/z: 573.2 [M + H]$^+$. |

Embodiment 41: WX041

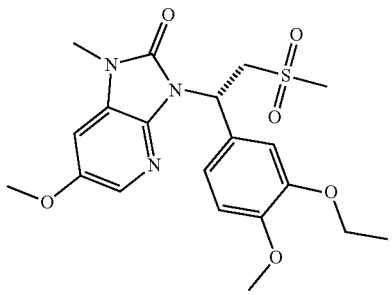 [SMILES: CCOc1cc([C@@H](CS(C)(=O)=O)n2c(=O)n(C)c3cc(OC)cnc32)ccc1OC]

Synthetic Route:

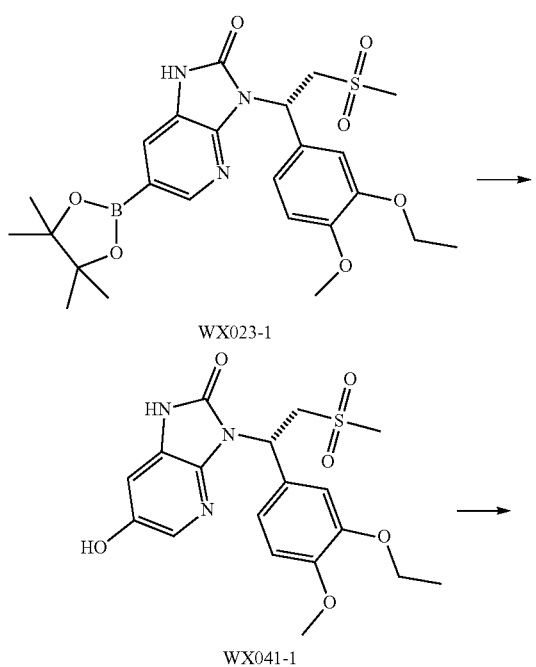

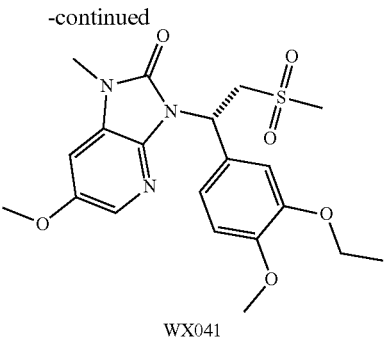

WX041

Step 1: Preparation of WX041-1

H$_2$O$_2$ (21.91 mg, 193.28 μmol, 30%) and potassium carbonate (26.71 mg, 193.28 μmol) were added to the solution of compound WX023-1 (50.00 mg, 96.64 μmol) in dichloromethane (1.00 mL) at 0° C. The reaction mixture was warmed to room temperature and stirred for 10 hours. After the reaction, the mixture was concentrated under reduced pressure to remove the dichloromethane. The obtained residue was diluted with water (5 mL), acidified with saturated citric acid solution to pH 3-4 and extracted with dichloromethane/methanol=4/1 (5 mL×5). The organic phases were combined and dried over anhydrous sodium sulfate, followed by filtration. The filtrate was concentrated under reduced pressure. The residue was isolated by preparative HPLC to obtain the target product WX041-1. $^1$H NMR (400 MHz, CD$_3$OD) δ: 7.65 (d, J=2.3 Hz, 1H), 7.34 (d, J=1.5 Hz, 1H), 7.23-7.11 (m, 1H), 6.98-6.85 (m, 2H), 6.09 (dd, J=3.9, 10.4 Hz, 1H), 4.86-4.79 (m, 1H), 4.14-3.95 (m, 3H), 3.82 (s, 3H), 2.91 (s, 3H), 1.39 (t, J=7.0 Hz, 3H).

Step 2: Preparation of WX041-1

Compound WX041-1 (30.00 mg, 73.63 μmol), 2-iodopyrimidine (104.51 mg, 736.30 μmol), and potassium carbonate (10.18 mg, 73.63 μmol) were dissolved in N,N-dimethylformamide (1.00 mL) at room temperature. The reaction mixture was stirred at room temperature for 2 hours under nitrogen atmosphere. After the reaction, water (8 mL) and ethyl acetate (10 mL) were added into the reaction mixture, partioned. The organic phase was washed with saturated brine (5 mL×2), dried over anhydrous sodium sulfate, followed by filtration. The filtrate was concentrated under reduced pressure. The obtained residue was isolated by preparative HPLC to obtain the target product WX041. MS-ESI m/z: 436.1 [M+H]$^+$. $^1$H NMR (400 MHz, CDCl$_3$) δ: 7.76 (d, J=1.5 Hz, 1H), 7.34 (s, 1H), 7.23 (d, J=8.0 Hz, 1H), 6.84-6.78 (m, 2H), 6.15 (dd, J=5.0, 9.5 Hz, 1H), 4.85 (dd, J=10.0, 14.6 Hz, 1H), 4.10 (dd, J=3.5, 7.0 Hz, 2H), 3.94-3.80 (m, 7H), 3.37 (s, 3H), 2.74 (s, 3H), 1.45 (t, J=7.0 Hz, 3H).

Embodiment 42: WX042

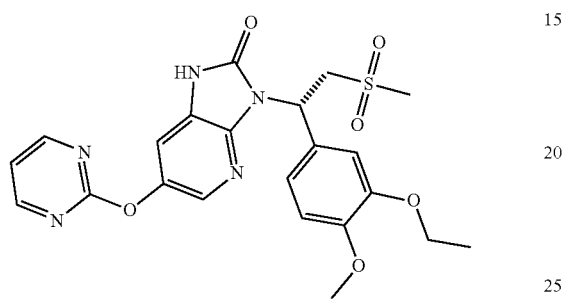

Synthetic Route:

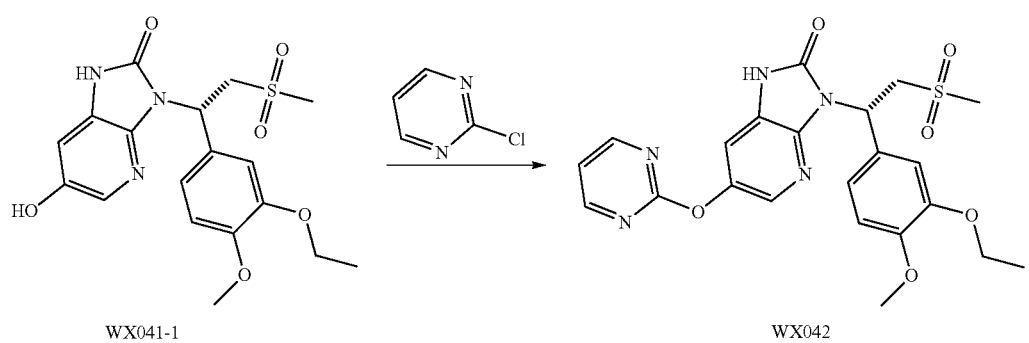

Potassium carbonate (67.84 mg, 490.86 mol) was added to the solution of compound WX041-1 (100.00 mg) and 2-chloropyrimidine (28.11 mg, 245.43 mol) in N,N-dimethylformamide (3.00 mL) at room temperature. The reaction mixture was heated to 50° C. and stirred for 10 hours. After the reaction, the mixture was cooled to room temperature and concentrated under reduced pressure to remove the solvent, followed by filtration. The obtained residue was isolated by preparative HPLC to obtain the target product WX042. MS-ESI m/z: 486.1 [M+H]$^+$. $^1$H NMR (400 MHz, CD$_3$OD) δ: 8.61 (d, J=4.8 Hz, 1H), 7.97 (d, J=2.3 Hz, 1H), 7.37 (d, J=1.8 Hz, 1H), 7.30 (d, J=2.3 Hz, 1H), 7.27-7.18 (m, 2H), 6.96 (d, J=8.3 Hz, 1H), 6.19 (dd, J=4.0, 10.5 Hz, 1H), 4.95 (br s, 1H), 4.15-4.01 (m, 3H), 3.83 (s, 3H), 2.96 (s, 3H), 1.40 (t, J=7.0 Hz, 3H).

Embodiment 43: WX043

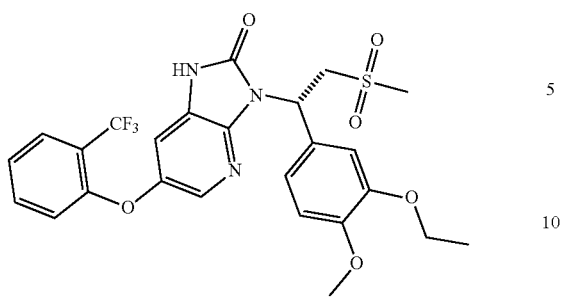

Synthetic Route:

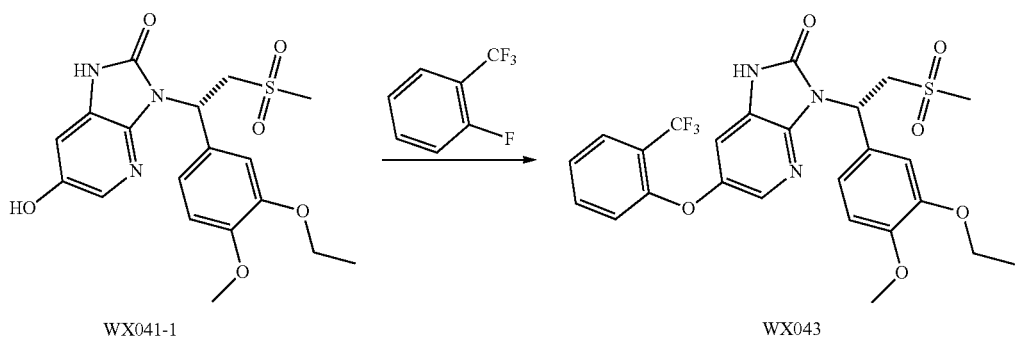

Compound WX041-1 (90.00 mg, 220.89 μmol), 1-fluoro-2-trifluoromethylbenzene (54.37 mg, 331.34 μmol) and potassium carbonate (91.59 mg, 662.67 μmol) were dissolved in methylpyrrolidone (2.00 mL) at room temperature. The reaction mixture was heated to 160° C. by microwave irradiation and stirred for 50 minutes. After the reaction, the mixture was cooled to room temperature. Water (8 mL) was added to the mixture and extracted with ethyl acetate (10 mL×2). The organic phases were combined and dried over anhydrous sodium sulfate, followed by filtration. The filtrate was concentrated under reduced pressure. The obtained residue was isolated by preparative HPLC to obtain the target product WX043. MS-ESI m/z: 552.1 [M+H]$^+$. $^1$H NMR (400 MHz, CD$_3$OD) δ: 7.87 (d, J=2.3 Hz, 1H), 7.74 (d, J=7.5 Hz, 1H), 7.63-7.51 (m, 1H), 7.37 (s, 1H), 7.30-7.17 (m, 2H), 7.13 (d, J=2.3 Hz, 1H), 6.97 (dd, J=8.5, 13.8 Hz, 2H), 6.18 (dd, J=3.8, 10.5 Hz, 1H), 4.83-4.81 (m, 1H), 4.12-3.99 (m, 3H), 3.83 (s, 3H), 2.97 (s, 3H), 1.40 (t, J=7.0 Hz, 3H).

Embodiment 44: WX044

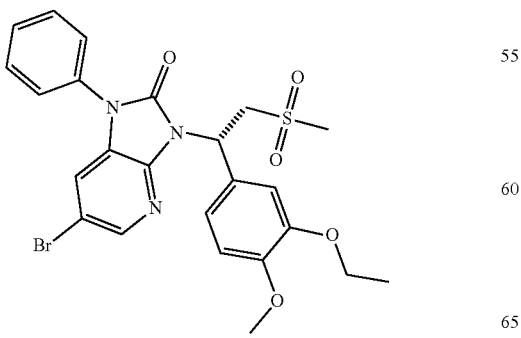

Synthetic Route:

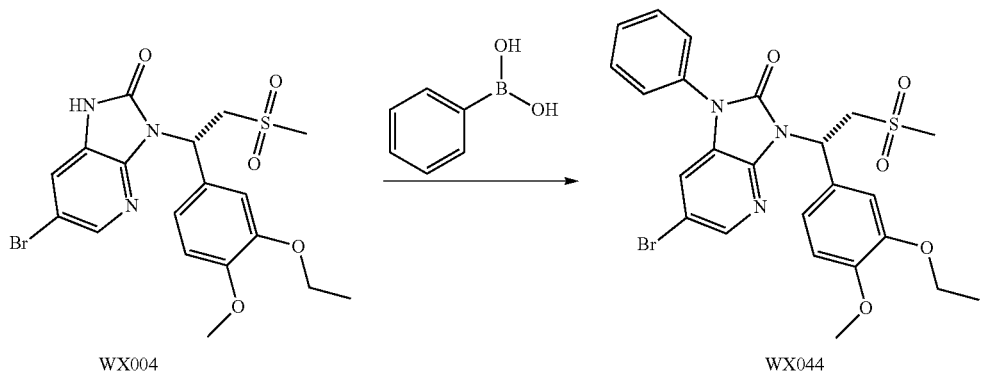

Copper acetate (19.31 mg, 106.31 µmol) and 2-(2-pyridyl)pyridine (16.60 mg, 106.31 µmol) were added to the solution of compound WX004 (50.00 mg, 106.31 µmol) and phenylboronic acid (19.44 mg, 159.47 µmol) in dichloromethane (2.00 mL) at room temperature. The reaction mixture was stirred at room temperature for 24 hours under nitrogen atmosphere. After the reaction, the mixture was filtered and concentrated under reduced pressure. The obtained residue was isolated by preparative HPLC to obtain the target product WX044. MS-ESI m/z: 546.0 [M+H]$^+$, 548.0 [M+H+2]$^+$. $^1$H NMR (400 MHz, CD$_3$OD) δ: 8.23 (d, J=2.0 Hz, 1H), 7.65-7.58 (m, 2H), 7.56-7.46 (m, 4H), 7.40 (d, J=2.0 Hz, 1H), 7.24 (dd, J=2.1, 8.4 Hz, 1H), 6.97 (d, J=8.5 Hz, 1H), 6.27 (dd, J=4.0, 10.8 Hz, 1H), 4.17-4.02 (m, 3H), 3.84 (s, 3H), 3.27-3.22 (m, 1H), 3.00 (s, 3H), 1.41 (t, J=6.9 Hz, 3H).

Embodiment 45: WX045

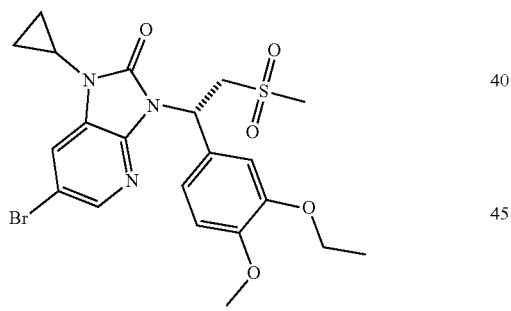

Synthetic Route:

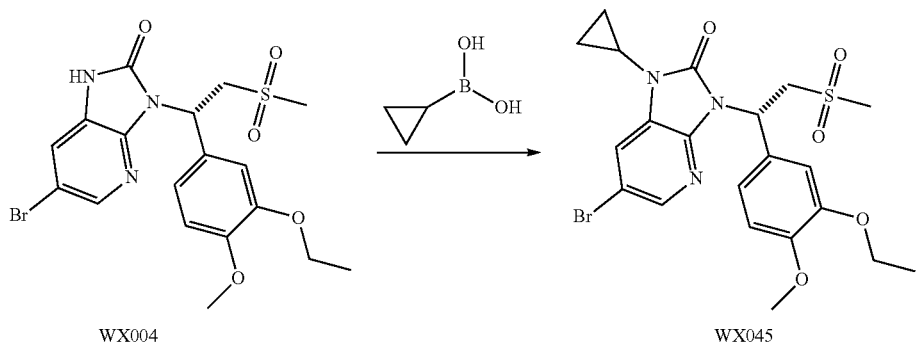

Copper acetate (19.31 mg, 106.31 µmol) and 2-(2-pyridyl)pyridine (16.60 mg, 106.31 µmol) were added to the solution of compound WX004 (50.00 mg, 106.31 µmol) and cyclopropylboronic acid (9.13 mg, 106.31 µmol) in dichloromethane (2.00 mL) at room temperature. The reaction mixture was stirred at room temperature for 10 hours under nitrogen atmosphere. After the reaction, the mixture was filtered and concentrated under reduced pressure. The obtained residue was isolated by preparative HPLC to obtain the target product WX045. MS-ESI m/z: 510.0 [M+H]+, 512.0 [M+H+2]+. 1H NMR (400 MHz, CDCl3) δ: 8.12 (s, 1H), 7.48 (s, 1H), 7.34 (s, 1H), 7.24 (d, J=8.3 Hz, 1H), 6.84 (d, J=8.5 Hz, 1H), 6.14 (dd, J=4.6, 9.9 Hz, 1H), 4.79 (dd, J=10.0, 14.3 Hz, 1H), 4.19-4.05 (m, 2H), 3.93-3.83 (m, 4H), 2.88 (d, J=3.3 Hz, 1H), 2.80 (s, 3H), 2.20 (s, 1H), 1.48 (t, J=6.9 Hz, 3H), 1.13 (d, J=6.8 Hz, 2H), 0.99 (br s, 2H).

Embodiment 46: WX046 pressure to remove the solvent. The obtained residue was isolated by preparative HPLC to obtain the target product WX046. MS-ESI m/z: 526.1 [M+H]+. 1H NMR (400 MHz, CDCl3) δ: 8.19 (s, 1H), 7.52 (t, J=1.8 Hz, 1H), 7.46-7.32 (m, 3H), 7.29-7.26 (m, 1H), 7.26-7.15 (m, 2H), 6.83 (d, J=8.3 Hz, 1H), 6.19 (dd, J=5.0, 9.8 Hz, 1H), 4.83 (dd, J=9.5, 14.6 Hz, 1H), 4.17-4.07 (m, 2H), 3.95 (dd, J=5.0, 14.8 Hz, 1H), 3.84 (s, 3H), 2.94-2.86 (m, 1H), 2.77 (s, 3H), 1.45 (t, J=7.0 Hz, 3H), 1.14-0.97 (m, 4H).

Embodiment 47: WX047

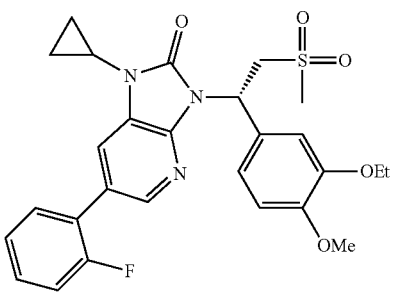 [SMILES: CCOc1cc([C@@H](CS(C)(=O)=O)n2c(=O)n(C3CC3)c3cc(-c4ccccc4F)cnc32)ccc1OC]

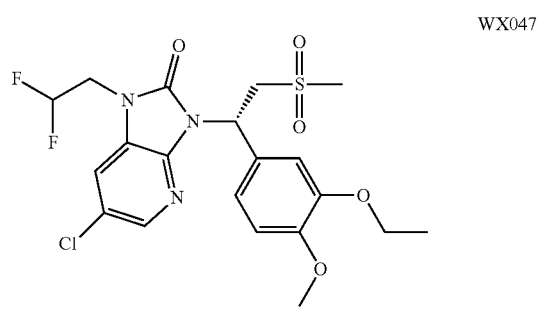

Synthetic Route:

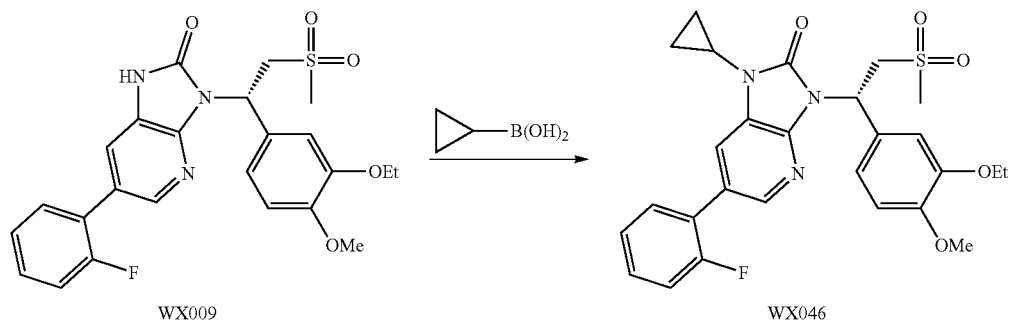

Copper acetate (18.70 mg, 102.98 µmol) and 2-(2-pyridyl)pyridine (16.08 mg, 102.98 µmol) were added to the solution of cyclopropylboronic acid (13.27 mg, 154.47 µmol) and compound WX009 (50.00 mg, 102.98 µmol) in dichloromethane (2.00 mL) at room temperature. The reaction mixture was stirred at 20-40° C. for 85 hours under nitrogen atmosphere. After the reaction, the mixture was cooled to room temperature, quenched with water (10 mL) and extracted with dichloromethane (10 mL×3). The organic phases were combined, washed with saturated brine (10 mL×2) and dried over anhydrous sodium sulfate, followed by filtration. The filtrate was concentrated under reduced Synthetic Route:

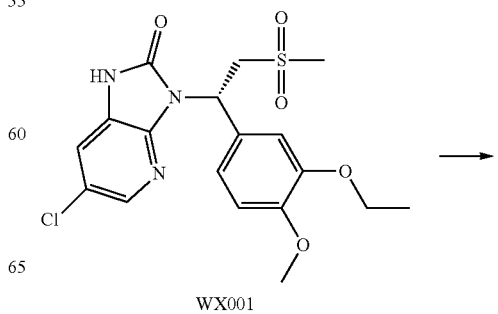

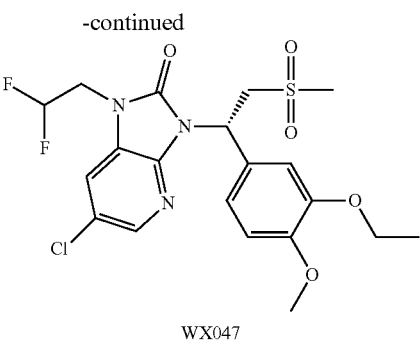
WX047

Compound WX001 (300.00 mg, 704.41 μmol), 2,2-difluoroethyl 4-methylbenzenesulfonate (498.72 mg, 2.11 mmol) and potassium carbonate (292.07 mg, 2.11 mmol) were dissolved in N,N-dimethylformamide (10.00 mL) at room temperature. The reaction mixture was heated to 30° C. and stirred for 12 hours under nitrogen atmosphere. After the reaction, ethyl acetate (100 mL) and water (30 mL) were added to the mixture. The organic phases were separated, washed with saturated brine and dried over anhydrous sodium sulfate, followed by filtration. The filtrate was concentrated under reduced pressure to remove the solvent. The obtained residue was purified by column chromatography (eluent: petroleum ether/ethyl acetate=5/1-1/1, volume ratio) to obtain the target product WX047. MS (ESI) m/z 490.0 [M+H]$^+$. $^1$H NMR (400 MHz, CDCl$_3$) δ: 8.06 (d, J=2.0 Hz, 1H), 7.31-7.20 (m, 3H) 6.84 (d, J=8.4 Hz, 1H), 6.19-6.15 (m, 2H), 4.82 (m, 1H), 4.20-4.09 (m, 4H), 3.86-3.81 (m, 4H), 2.80 (s, 3H), 1.46 (t, J=6.8 Hz, 3H).

The compounds of each embodiment in the following table were prepared according to the method of embodiment 47.

TABLE 5

| Embodiment | Fragment 1 | Fragment 2 | Structure | Compound |
|---|---|---|---|---|
| 48 | WX001 | F₃C-CH₂-OTf | 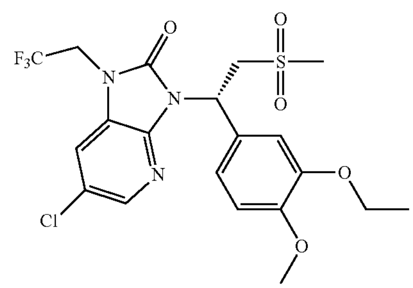 [SMILES: CCOc1cc([C@@H](CS(C)(=O)=O)n2c(=O)n(CC(F)(F)F)c3cc(Cl)cnc32)ccc1OC] | WX048 |
| 49 | WX003 | F₂CH-CH₂-OTs | 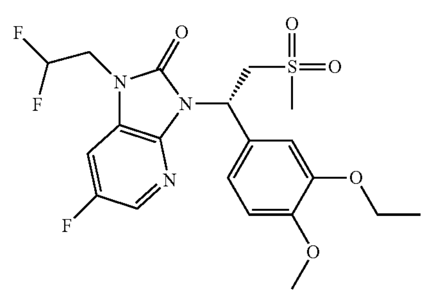 [SMILES: CCOc1cc([C@@H](CS(C)(=O)=O)n2c(=O)n(CC(F)F)c3cc(F)cnc32)ccc1OC] | WX049 |
| 50 | WX004 | Me—I | 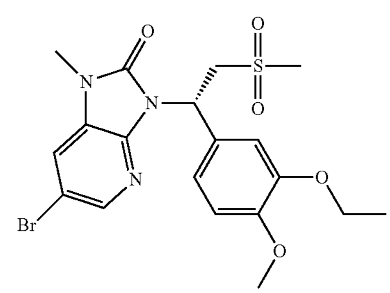 [SMILES: CCOc1cc([C@@H](CS(C)(=O)=O)n2c(=O)n(C)c3cc(Br)cnc32)ccc1OC] | WX050 |

TABLE 5-continued

| Embodiment | Fragment 1 | Fragment 2 | Structure | Compound |
|---|---|---|---|---|
| 51 | WX004 | | 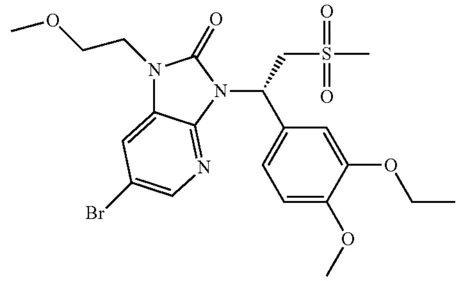 [SMILES: CCOc1cc([C@@H](CS(C)(=O)=O)n2c(=O)n(CCOC)c3cc(Br)cnc32)ccc1OC] | WX051 |
| 52 | WX004 | | 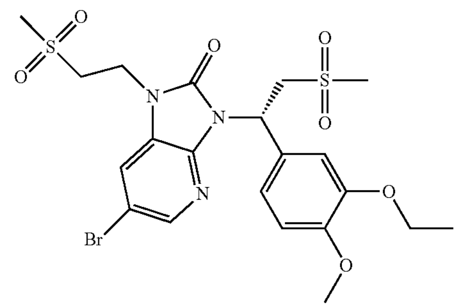 [SMILES: CCOc1cc([C@@H](CS(C)(=O)=O)n2c(=O)n(CCS(C)(=O)=O)c3cc(Br)cnc32)ccc1OC] | WX052 |
| 53 | WX004 | | 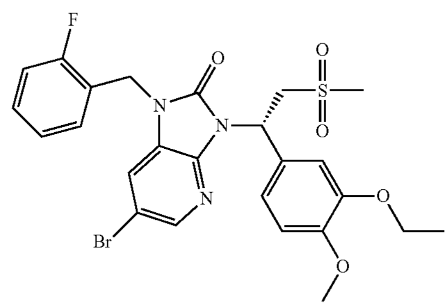 [SMILES: CCOc1cc([C@@H](CS(C)(=O)=O)n2c(=O)n(Cc3ccccc3F)c3cc(Br)cnc32)ccc1OC] | WX053 |
| 54 | WX004 | | 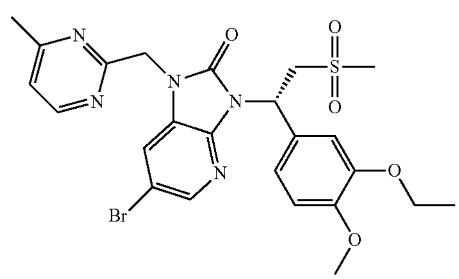 [SMILES: CCOc1cc([C@@H](CS(C)(=O)=O)n2c(=O)n(Cc3nccc(C)n3)c3cc(Br)cnc32)ccc1OC] | WX054 |
| 55 | WX004 | | 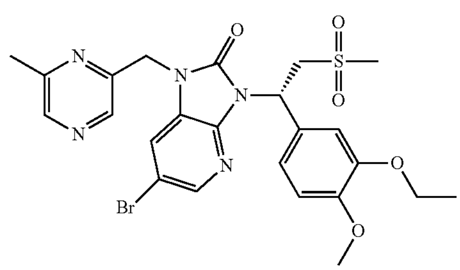 [SMILES: CCOc1cc([C@@H](CS(C)(=O)=O)n2c(=O)n(Cc3cncc(C)n3)c3cc(Br)cnc32)ccc1OC] | WX055 |

TABLE 5-continued

| Embodiment | Fragment 1 | Fragment 2 | Structure | Compound |
|---|---|---|---|---|
| 56 | WX004 | EtO-CH2-C(=O)-Br | 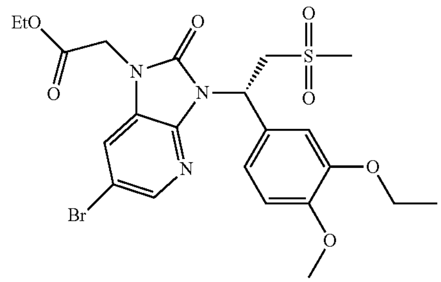 [SMILES: CCOC(=O)Cn1c(=O)n([C@H](CS(C)(=O)=O)c2ccc(OC)c(OCC)c2)c2ncc(Br)cc21] | WX056 |
| 57 | WX009 | Me—I | 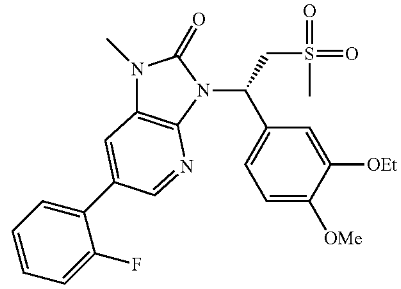 [SMILES: CCOc1cc([C@@H](CS(C)(=O)=O)n2c(=O)n(C)c3cc(-c4ccccc4F)cnc32)ccc1OC] | WX057 |
| 58 | WX009 | Et-Br | 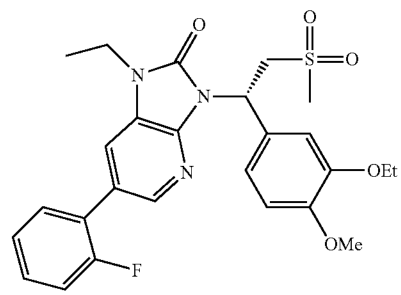 [SMILES: CCOc1cc([C@@H](CS(C)(=O)=O)n2c(=O)n(CC)c3cc(-c4ccccc4F)cnc32)ccc1OC] | WX058 |
| 59 | WX009 | HO-CH2CH2-Br | 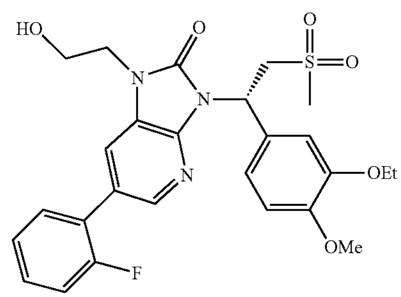 [SMILES: CCOc1cc([C@@H](CS(C)(=O)=O)n2c(=O)n(CCO)c3cc(-c4ccccc4F)cnc32)ccc1OC] | WX059 |
| 60 | WX009 | iPr-I | 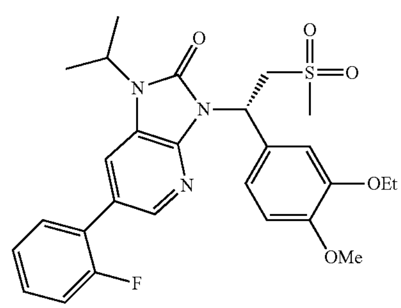 [SMILES: CCOc1cc([C@@H](CS(C)(=O)=O)n2c(=O)n(C(C)C)c3cc(-c4ccccc4F)cnc32)ccc1OC] | WX060 |

TABLE 5-continued

| Embodiment | Fragment 1 | Fragment 2 | Structure | Compound |
|---|---|---|---|---|
| 61 | 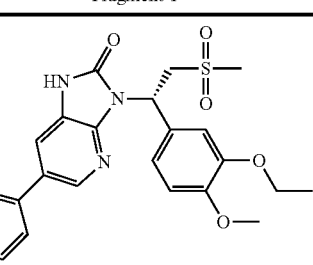 WX009 | NC-CH₂-Br | 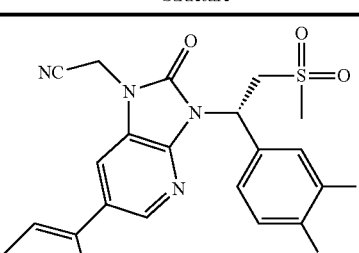 | WX061 |
| 62 | 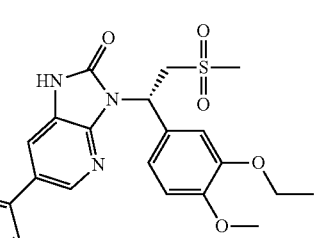 WX009 | cyclobutyl-Br | 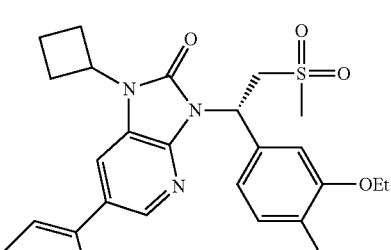 | WX062 |

LCMS and ¹HNMR Data of Each Embodiment

TABLE 6

| Embodiment | Compound | HNMR | LCMS |
|---|---|---|---|
| 48 | WX048 | ¹H NMR (400 MHz, CDCl₃) δ: 8.08 (d, J =1.6 Hz, 1H), 7.29-7.18 (m, 3H) 6.83 (d, J = 8 Hz, 1H), 6.19(dd, J = 4.4,10 Hz, 1H), 4.80 (dd, J = 10.8,14.8 Hz, 1H), 4.45-4.40 (m, 2H), 4.10-4.08 (q, J = 3.6 Hz, 2H), 3.86-3.82 (m, 4H), 2.99 (s, 3H),1.45 (t, J = 6.8 Hz, 3H). | MS (ESI) m/z: 508.0 [M + H]⁺. |
| 49 | WX049 | ¹H NMR (400 MHz, CD₃OD) δ: 8.02 (s, 1H), 7.55-7.43 (m, 1H), 7.33 (d, J = 2.0 Hz, 1H), 7.18 (dd, J = 1.8, 8.3 Hz, 1H), 6.94 (d, J = 8.5 Hz, 1H), 6.35-5.95 (m, 2H), 4.83 (d, J = 11.0 Hz, 1H), 4.34 (dt, J = 3.5, 15.1 Hz, 2H), 4.11-4.00 (m, 3H), 3.82 (s, 3H), 2.94 (s, 3H), 1.39 (t, J = 7.0 Hz, 3H). | MS (ESI) m/z: 474.1 [M + H]⁺. |
| 50 | WX050 | ¹H NMR (400 MHz, CD₃OD) δ: 8.15 (s, 1H), 7.69 (s, 1H), 7.34 (s, 1H), 7.17 (d, J = 8.5 Hz, 1H), 6.93 (d, J = 8.5 Hz, 1H), 6.17 (dd, J = 4.0, 10.5 Hz, 1H), 4.86 (d, J = 4.0 Hz, 1H), 4.24-3.97 (m, 3H), 3.82 (s, 3H), 3.41 (s, 3H), 2.95 (s, 3H), 1.40 (t, J = 6.8 Hz, 3H). | MS-ESI m/z: 484.0 [M + H]⁺, 486.0 [M + H + 2]⁺. |
| 51 | WX051 | ¹H NMR (400 MHz, CDCl₃) δ: 8.09 (br s, 1H), 7.46 (br s, 1H), 7.31 (br s, 1H), 7.21 (d, J = 7.5 Hz, 1H), 6.81 (d, J = 7.8 Hz, 1H), 6.15 (d, J = 4.8 Hz, 1H), 4.85-4.72 (m, 1H), 4.16-3.94 (m, 4H), 3.92-3.79 (m, 4H), 3.61 (br s, 2H), 3.28 (br s, 3H), 2.74 (br s, 3H), 1.44 (t, J = 6.1 Hz, 3H). | MS-ESI m/z: 528.0 [M + H]⁺, 530.0 [M + H + 2]⁺. |
| 52 | WX052 | ¹H NMR (400 MHz, CDCl₃) δ: 8.14 (br s, 1H), 7.50 (br s, 1H), 7.26 (br s, 1H), 7.17 (d, J = 7.8 Hz, 1H), 6.82 (d, J = 8.0 Hz, 1H), 6.16 (d, J = 7.8 Hz, 1H), 4.98-4.83 (m, 1H), 4.31 (br s, 2H), 4.08 (d, J = 5.8 Hz, 2H), 3.84 (s, 3H), 3.70 (d, J = 13.8 Hz, 1H), 3.49 (d, J = 7.5 Hz, 2H), 2.85 (t, J = 7.5 Hz, 6H), 1.45 (t, J = 6.5 Hz, 3H). | MS-ESI m/z: 575.9 [M + H]⁺, 578.0 [M + H + 2]⁺. |
| 53 | WX053 | ¹H NMR (400 MHz, CDCl₃) δ: 8.09 (d, J = 2.0 Hz, 1 H), 7.32-7.30 (m, 2 H), 7.29 (s, 1 H), 7.25-7.18 (m, 2 H), 7.13-7.05 (m, 2 H), 6.83 (d, J = 8.4 Hz, 1 H), 6.20 (dd, J = 10.4, 4.4 Hz, 1 H), 5.07 (s, 2 H), 4.84 (dd, J = 14.6, 10.2 Hz, 1 H), 4.14-4.05 (m, 2 H), 3.88-3.81 (m, 1 H), 3.84 (s, 3 H), 2.78 (s, 3 H), 1.45 (t, J = 7.2 Hz, 3 H). | MS-ESI m/z: 578.0 [M + H]⁺, 580.0 [M + H + 2]⁺. |
| 54 | WX054 | ¹H NMR (400 MHz, CDCl₃) δ: 8.41 (d, J = 5.0 Hz, 1H), 8.11 (d, J = 1.3 Hz, 1H), 7.29 (s, 1H), 7.24-7.16 (m, 2H), 7.05 (d, J = 5.0 Hz, 1H), 6.82 (d, J = 8.3 Hz, 1H), 6.22 (dd, J = 4.5, 9.8 Hz, 1H), 5.18 (q, J = 17.1 Hz, 2H), 4.91 (dd, | MS-ESI m/z: 576.0 [M + H]⁺, 578.0 |

TABLE 6-continued

| Embodiment | Compound | HNMR | LCMS |
|---|---|---|---|
| | | J = 9.9, 14.9 Hz, 1H), 4.15-4.01 (m, 2H), 3.90-3.85 (m, 1H), 3.83 (s, 3H), 2.75 (s, 3H), 2.44 (s, 3H), 1.44 (t, J = 6.9 Hz, 3H). | [M + H + 2]⁺. |
| 55 | WX055 | ¹H NMR (400 MHz, CDCl₃) δ: 8.40 (br s, 2H), 8.12 (s, 1H), 7.38 (s, 1H), 7.30 (d, J = 1.8 Hz, 1H), 7.22 (d, J = 8.0 Hz, 1H), 6.83 (d, J = 8.3 Hz, 1H), 6.20 (dd, J = 4.3, 10.3 Hz, 1H), 5.20-5.07 (m, 2H), 4.86 (dd, J = 10.4, 14.4 Hz, 1H), 4.16-4.00 (m, 2H), 3.87-3.77 (m, 4H), 2.81 (s, 3H), 2.53 (s, 3H), 1.45 (t, J = 6.9 Hz, 3H). | MS-ESI m/z: 576.1 [M + H]⁺, 578.1 [M + H+2]⁺. |
| 56 | WX056 | ¹H NMR (400 MHz, CDCl₃) δ: 8.17 (d, J = 1.8 Hz, 1H), 7.29-7.26 (m, 1H), 7.25 (d, J = 1.8 Hz, 1H), 7.20 (dd, J = 1.9, 8.4 Hz, 1H), 6.84 (d, J = 8.3 Hz, 1H), 6.21 (dd, J = 4.5, 10.0 Hz, 1H), 4.86 (dd, J = 10.0, 14.8 Hz, 1H),4.63-4.54 (m, 2H), 4.25 (q, J = 7.0 Hz, 2H), 4.11 (dq, J = 1.9, 7.0 Hz, 2H), 3.90-3.82 (m, 4H), 2.77 (s, 3H), 1.47 (t, J = 6.9 Hz, 3H), 1.34-1.25 (m, 3H). | MS-ESI m/z: 556.0 [M + H]⁺, 558.0 [M + H + 2]⁺. |
| 57 | WX057 | ¹H NMR (400 MHz, CDCl₃) δ: 8.21 (s, 1H), 7.45-7.33 (m, 4H), 7.28 (d, J = 2.0 Hz, 1H), 7.25-7.14 (m, 2H), 6.83 (d, J = 8.5 Hz, 1H), 6.23 (dd, J = 4.9, 9.7 Hz, 1H), 4.89 (dd, J = 9.7, 14.7 Hz, 1H), 4.16-4.06 (m, 2H), 3.96 (dd, J = 4.9, 14.7 Hz, 1H), 3.84 (s, 3H), 3.43 (s, 3H), 2.78 (s, 3H), 1.45 (t, J = 6.9 Hz, 3H). | MS-ESI m/z: 500.1 [M + H]⁺. |
| 58 | WX058 | ¹H NMR (400 MHz, CDCl₃) δ: 8.20 (s, 1H), 7.46-7.33 (m, 4H), 7.29-7.26 (m, 1H), 7.25-7.15 (m, 2H), 6.84 (d, J = 8.3 Hz, 1H), 6.23 (dd, J = 5.0, 9.5 Hz, 1H), 4.87 (dd, J = 9.5, 14.8 Hz, 1H), 4.12 (dquin, J = 2.8, 6.8 Hz, 2H), 3.99-3.90 (m, 3H), 3.84 (s, 3H), 2.76 (s, 3H), 1.45 (t, J = 7.0 Hz, 3H), 1.34 (t, J = 7.3 Hz, 3H). | MS-ESI m/z: 514.2 [M + H]⁺. |
| 59 | WX059 | ¹H NMR (400 MHz, CDCl₃) δ: 8.21 (s, 1H), 7.47 (t, J = 1.6 Hz, 1H), 7.45-7.32 (m, 3H), 7.27 (d, J = 2.0 Hz, 1H), 7.26-7.14 (m, 2H), 6.85 (d, J = 8.5 Hz, 1H), 6.25 (dd, J = 4.3, 10.5 Hz, 1H), 4.92 (dd, J = 10.5, 14.6 Hz, 1H), 4.17-3.92 (m, 6H), 3.87-3.79 (m, 4H), 2.84 (s, 3H), 2.47 (s, 5.6 Hz, 1H), 1.46 (t, J = 7.0 Hz, 3H). | MS-ESI m/z: 530.2 [M + H]⁺. |
| 60 | WX060 | ¹H NMR (400 MHz, CDCl₃) δ: 8.21-8.15 (m, 1H), 7.48 (t, J = 1.8 Hz, 1H), 7.44-7.31 (m, 3H), 7.28 (d, J = 2.0 Hz, 1H), 7.25-7.11 (m, 2H), 6.83 (d, J = 8.3 Hz, 1H), 6.23 (dd, J = 5.0, 9.5 Hz, 1H), 4.84 (dd, J = 9.5, 14.6 Hz, 1H), 4.74 (quin, J = 7.0 Hz, 1H), 4.16-4.07 (m, 2H), 3.94 (dd, J = 5.0, 14.8 Hz, 1H), 3.84-3.83 (m, 3H), 2.75 (s, 3H), 1.51 (dd, J = 3.0, 6.8 Hz, 6H), 1.47-1.42 (m, 3H). | MS-ESI m/z: 528.2 [M + H]⁺. |
| 61 | WX061 | ¹H NMR (400 MHz, CDCl₃) δ: 8.30 (s, 1H), 7.53 (d, J = 1.5 Hz, 1H), 7.46-7.33 (m, 3H), 7.29-7.26 (m, 1H), 7.26-7.16 (m, 2H), 6.85 (d, J = 8.3 Hz, 1H), 6.22 (dd, J = 4.6, 9.9 Hz, 1H), 4.92-4.76 (m, 3H), 4.16-4.07 (m, 2H), 3.93 (dd, J = 4.8, 14.6 Hz, 1H), 3.87-3.81 (m, 3H), 2.81 (s, 3H), 1.46 (t, J = 6.9 Hz, 3H). | MS-ESI m/z: 525.1 [M + H]⁺. |
| 62 | WX062 | ¹H NMR (400 MHz, CDCl₃) δ: 8.19 (s, 1H), 7.57 (s, 1H), 7.46-7.34 (m, 3H), 7.29-7.26 (m, 1H), 7.26-7.15 (m, 2H), 6.83 (d, J = 8.3 Hz, 1H), 6.21 (dd, J = 5.3, 9.3 Hz, 1H), 4.93-4.77 (m, 2H), 4.18-4.06 (m, 2H), 3.99 (dd, J = 5.0, 14.8 Hz, 1H), 3.84 (s, 3H), 2.84-2.77 (m, 2H), 2.75 (s, 3H), 2.47-2.36 (m, 2H), 2.02-1.78 (m, 2H), 1.45 (t, J = 7.0 Hz, 3H). | MS-ESI m/z: 540.2 [M + H]⁺. |

Embodiment 63: WX063

Synthetic Route:

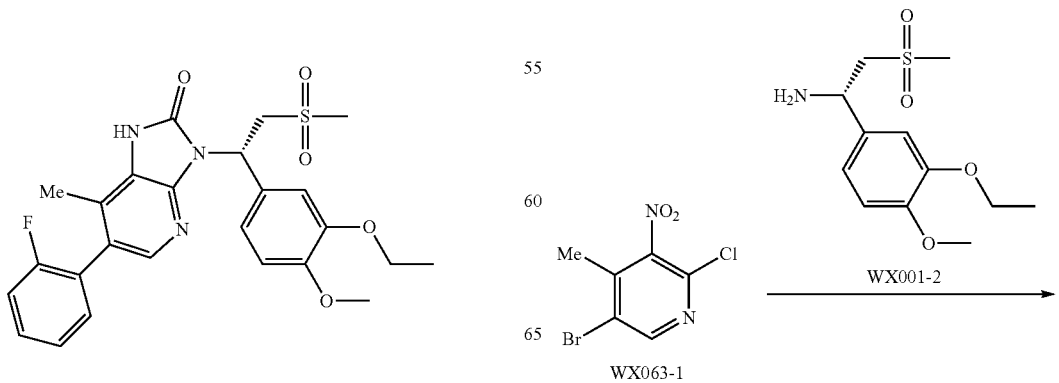

131

-continued

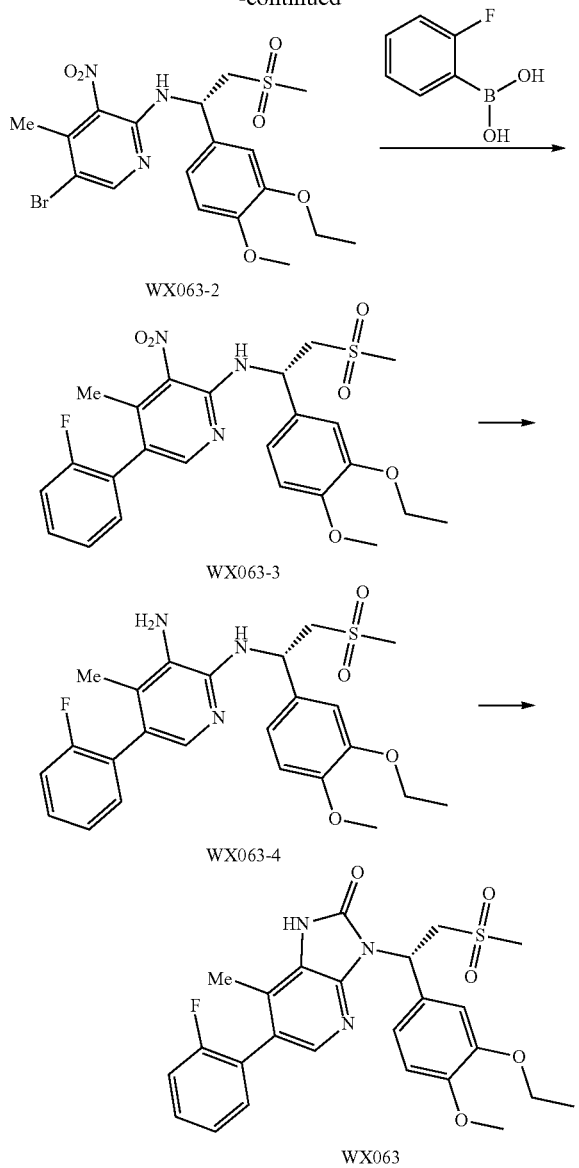

Step 1: Preparation of Compound WX063-2

Compound WX063-1 (500.00 mg, 1.99 mmol), compound WX001-2 (489.15 mg, 1.79 mmol) and diisopropylamine (513.94 mg, 3.98 mmol) were dissolved in N,N-dimethylformamide (10.00 mL) at room temperature. The reaction mixture was heated to 120° C. and stirred for 12 hours under nitrogen atmosphere. After the reaction, the mixture was cooled to room temperature, diluted with water (50 mL) and extracted with ethyl acetate (50 mL×2). The organic phases were combined, washed with saturated brine (50 mL×3) and dried over anhydrous sodium sulfate, followed by filtration. The filtrate was concentrated under reduced pressure to remove the solvent. The obtained residue was isolated by column chromatography (eluent: petroleum ether/ethyl acetate=1/0-1/1, volume ratio) to obtain the target product WX063-2. $^1$H NMR (400 MHz, CDCl$_3$) δ: 8.34 (s, 1H), 7.33 (d, J=6.8 Hz, 1H), 6.99-6.94 (m, 1H), 6.92 (d, J=2.0 Hz, 1H), 6.90-6.86 (m, 1H), 5.78 (q, J=6.7 Hz, 1H), 4.15-4.06 (m, 2H), 3.86 (s, 3H), 3.75 (dd, J=6.5, 14.6 Hz, 1H), 3.46 (dd, J=6.4, 14.7 Hz, 1H), 2.59 (s, 3H), 2.52 (s, 3H), 1.47 (t, J=7.0 Hz, 3H).

132

Step 2: Preparation of Compound WX063-3

Compound WX063-2 (200.00 mg, 409.54 μmol), 2-fluorophenylboronic acid (85.95 mg, 614.31 μmol), [1,1'-bis(diphenylphosphino)ferrocene] palladium dichloride dichloromethane complex (33.44 mg, 40.95 μmol) and potassium carbonate (113.21 mg, 819.08 μmol) were dissolved in dioxane (3.00 mL) and water (1.00 mL) at room temperature. The reaction mixture was heated to 80° C. and stirred for 12 hours under nitrogen atmosphere. After the reaction, the mixture was cooled to room temperature, diluted with water (30 mL) and extracted with ethyl acetate (30 mL×2). The organic phases were combined, washed with saturated brine (30 mL×3) and dried over anhydrous sodium sulfate, followed by filtration. The filtrate was concentrated under reduced pressure to obtain the crude product WX063-3.

Step 3: Preparation of Compound WX063-4

Compound WX063-3 (220.00 mg, 436.91 μmol), zinc powder (285.69 mg, 4.37 mmol) and ammonium chloride (233.70 mg, 4.37 mmol) were dissolved in methanol (5.00 mL) at room temperature. The reaction mixture was stirred at room temperature for 2 hours under nitrogen atmosphere. After the reaction, the mixture was filtered and concentrated under reduced pressure. Dichloromethane (30 mL) was added to the obtained residue with stirring for 0.5 hour at room temperature, followed by filtration. The filtrate was concentrated under reduced pressure to obtain the crude product WX063-4. $^1$H NMR (400 MHz, CDCl$_3$) δ: 7.51-7.29 (m, 3H), 7.24-6.94 (m, 7H), 6.82 (d, J=7.8 Hz, 1H), 4.10 (dd, J=6.8, 11.5 Hz, 2H), 3.99-3.89 (m, 1H), 3.86-3.78 (m, 4H), 3.55 (d, J=11.5 Hz, 1H), 2.87 (br s, 3H), 2.02 (s, 3H), 1.44-1.40 (m, 3H).

Step 4: Preparation of Compound WX063

Compound WX063-4 (200.00 mg, 422.33 μmol), triethylamine (213.68 mg, 2.11 mmol) and triphosgene (50.13 mg, 168.93 μmol) were dissolved in tetrahydrofuran (10.00 mL) at room temperature. The reaction mixture was stirred at 0-5° C. for 2 hours under nitrogen atmosphere. After the reaction, the mixture was warmed to room temperature, quenched with water (50 mL) and extracted with ethyl acetate (50 mL×2). The organic phases were combined, washed with saturated brine (50 mL×3) and dried over anhydrous sodium sulfate, followed by filtration. The filtrate was concentrated under reduced pressure to remove the solvent. The obtained residue was isolated by preparative HPLC to obtain the target product WX063. MS-ESI m/z: 500.1 [M+H]$^+$. $^1$H NMR (400 MHz, CDCl$_3$) δ: 10.12 (br s, 1H), 7.87 (br s, 1H), 7.32 (br s, 1H), 7.15 (br s, 4H), 7.10-7.01 (m, 1H), 6.71 (d, J=7.8 Hz, 1H), 6.13 (d, J=5.0 Hz, 1H), 4.92-4.75 (m, 1H), 3.98 (d, J=4.5 Hz, 2H), 3.82 (d, J=11.5 Hz, 1H), 3.72 (br s, 3H), 2.70 (br s, 3H), 2.11 (br s, 3H), 1.39-1.25 (m, 3H).

Embodiment 64: WX064

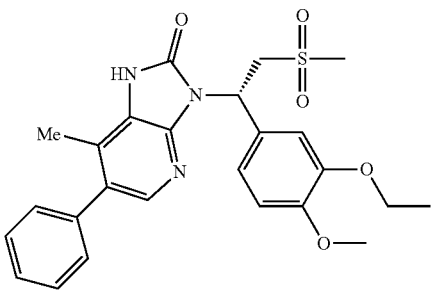 [SMILES: CCOc1cc([C@@H](CS(C)(=O)=O)n2c(=O)[nH]c3c(C)c(-c4ccccc4)cnc32)ccc1OC]

Synthetic Route:

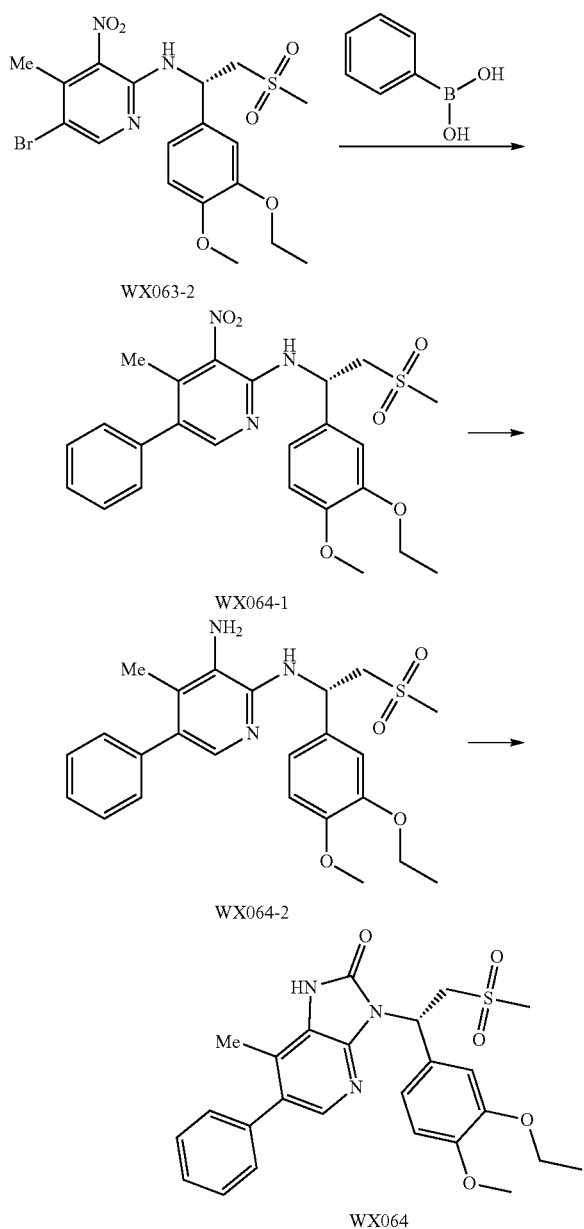

Step 1: Preparation of Compound WX064-1

Compound WX063-2 (1.00 g, 2.05 mmol), phenylboronic acid (374.93 mg, 3.08 mmol), [1,1'-bis(diphenylphosphino)ferrocene] palladium dichloride dichloromethane complex (167.41 mg, 205.00 µmol) and potassium carbonate (849.99 mg, 6.15 mmol) were dissolved in dioxane (40.00 mL) and water (10.00 mL) at room temperature. The reaction mixture was heated to 80-90° C. and stirred for 12 hours under nitrogen atmosphere. After the reaction, the mixture was cooled to room temperature, diluted with water (30 mL) and ethyl acetate (100 mL). The organic phases were separated and dried over anhydrous sodium sulfate, followed by filtration. The filtrate was concentrated under reduced pressure to remove the solvent. The obtained residue was isolated by column chromatography (eluent: petroleum ether/ethyl acetate=5/1-1/2, volume ratio) to obtain the target product WX064-1. MS-ESI m/z: 486.1 [M+H]$^+$. $^1$H NMR (400 MHz, CDCl$_3$) δ: 8.16 (s, 1H), 7.48-7.35 (m, 3H), 7.29-7.21 (m, 3H), 7.05-6.96 (m, 2H), 6.90 (d, J=8.3 Hz, 1H), 5.90 (q, J=6.5 Hz, 1H), 4.13 (q, J=7.0 Hz, 2H), 3.91-3.79 (m, 4H), 3.50 (dd, J=6.5, 14.8 Hz, 1H), 2.63 (s, 3H), 2.34 (s, 3H), 1.48 (t, J=7.0 Hz, 3H).

Step 2: Preparation of Compound WX064-2

Compound WX064-1 (800.00 mg, 1.65 mmol) was dissolved in methanol (50.00 mL) at room temperature followed by the addition of zinc powder (1.08 g, 16.50 mmol) and ammonium chloride (1.08 g, 16.50 mmol). The reaction mixture was stirred at 0-5° C. for 1.5 hours under nitrogen atmosphere. After the reaction, the mixture was filtered by diatomite and the filtrate was concentrated under reduced pressure to remove the solvent. Dichloromethane (100 mL) and water (30 mL) were added to the obtained residue. The organic phases were separated and dried over anhydrous sodium sulfate, followed by filtration. The filtrate was concentrated under reduced pressure to obtain the crude product WX064-2. MS-ESI m/z: 456.1 [M+H]$^+$.

Step 3: Preparation of Compound WX064

Compound WX064-2 (700.00 mg, 1.54 mmol), triphosgene (274.20 mg, 924.00 µmol) and triethylamine (935.00 mg, 9.24 mmol, 1.28 mL) were dissolved in tetrahydrofuran (30.00 mL) at room temperature. The reaction mixture was stirred at 0-5° C. for 2 hours under nitrogen atmosphere. After the reaction, the mixture was diluted with water (20 mL) and ethyl acetate (100 mL). The organic phases were separated, wash with saturated brine (30 mL×2) and dried over anhydrous sodium sulfate, followed by filtration. The filtrate was concentrated under reduced pressure to remove the solvent. The obtained residue was isolated by column chromatography (eluent: petroleum ether/ethyl acetate=10/1-1/2, volume ratio) to obtain the target product WX064. MS-ESI m/z: 482.1 [M+H]$^+$. $^1$H NMR (400 MHz, CDCl$_3$) δ: 10.16 (br s, 1H), 7.89 (s, 1H), 7.43-7.29 (m, 3H), 7.28-7.13 (m, 4H), 6.74 (d, J=8.3 Hz, 1H), 6.15 (dd, J=4.4, 9.7 Hz, 1H), 4.89 (dd, J=9.8, 14.6 Hz, 1H), 4.10-3.96 (m, 2H), 3.86 (dd, J=4.4, 14.7 Hz, 1H), 3.75 (s, 3H), 2.70 (s, 3H), 2.22 (s, 3H), 1.35 (t, J=6.9 Hz, 3H).

Embodiment 65: WX065

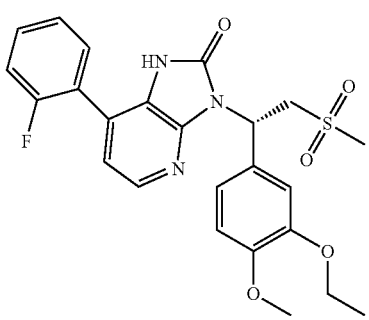 [SMILES: CCOc1cc([C@@H](CS(C)(=O)=O)n2c(=O)[nH]c3c(-c4ccccc4F)ccnc32)ccc1OC]

Synthetic Route:

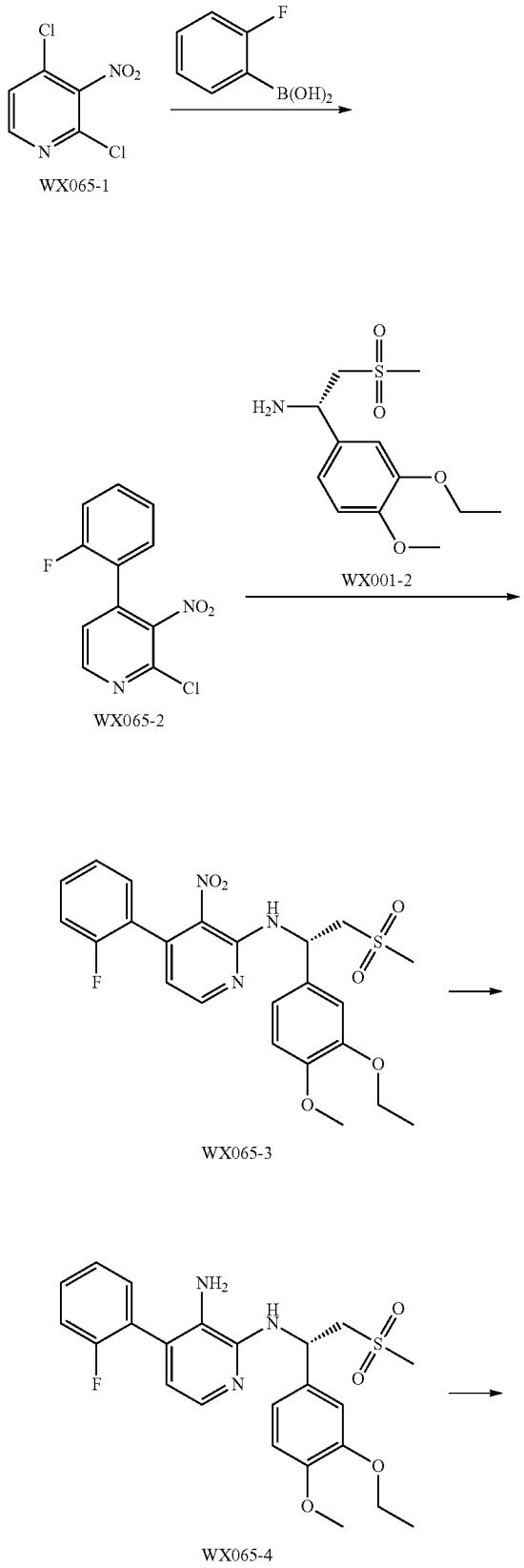

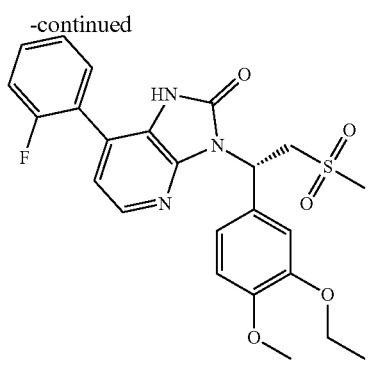

Step 1: Preparation of Compound WX065-2

Compound WX065-1 (2.00 g, 10.36 mmol), 2-fluorophenylboronic acid (1.45 g, 10.36 mmol), [1,1'-bis(diphenylphosphino)ferrocene]palladium dichloride dichloromethane complex (846.30 mg, 1.04 mmol) and potassium carbonate (2.15 g, 15.54 mmol) were dissolved in dioxane (20.00 mL) and water (7.00 mL) at room temperature. The reaction mixture was heated to 60° C. and stirred for 4 hours under nitrogen atmosphere. After the reaction, the mixture was cooled to room temperature, quenched with saturated brine (25 mL), diluted with water (25 mL) and extracted with ethyl acetate (10 mL×3). The organic phases were combined, washed with water (30 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=1/0-10/1, volume ratio) to obtain the target product WX065-2. $^1$H NMR (400 MHz, CDCl$_3$) δ: 8.58 (d, J=5.0 Hz, 1H), 7.54-7.45 (m, 1H), 7.41 (d, J=4.8 Hz, 1H), 7.34-7.17 (m, 3H).

Step 2: Preparation of Compound WX065-3

Compound WX065-2 (997.38 mg, 3.95 mmol) and compound WX001-2 (900.00 mg, 3.29 mmol) were dissolved in N,N-dimethylformamide (20.00 mL) at room temperature, followed by the addition of diisopropylethylamine (851.04 mg, 6.58 mmol, 1.15 mL). The reaction mixture was heated to 80° C. and stirred for 3 hours under nitrogen atmosphere. After the reaction, the mixture was cooled to room temperature, quenched with saturated brine (20 mL), diluted with water (60 mL) and extracted with ethyl acetate (30 mL×3). The organic phases were combined, washed with water (100 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=1/0-2/1, volume ratio) to obtain the target product WX065-3. $^1$H NMR (400 MHz, CDCl$_3$) δ: 8.40 (d, J=4.8 Hz, 1H), 7.86 (d, J=7.0 Hz, 1H), 7.49-7.39 (m, 1H), 7.38-7.30 (m, 1H), 7.19-7.10 (m, 1H), 7.09-6.98 (m, 2H), 6.94 (d, J=8.3 Hz, 1H), 6.68 (d, J=4.8 Hz, 1H), 5.92 (q, J=6.8 Hz, 1H), 4.16 (q, J=7.0 Hz, 2H), 4.01-3.85 (m, 4H), 3.53 (dd, J=7.0, 14.6 Hz, 1H), 2.62 (s, 3H), 1.50 (t, J=7.0 Hz, 3H).

Step 3: Preparation of Compound WX065-4

Compound WX065-3 (350.00 mg, 714.99 μmol) and ammonium chloride (573.67 mg, 10.72 mmol, 374.95 μL) were dissolved in methanol (10.00 mL) at room temperature, followed by the addition of zinc powder (467.53 mg, 7.15 mmol) in 5 batches. The reaction mixture was stirred at room temperature for 4 hours under nitrogen atmosphere. After the reaction, the mixture was filtered by diatomite. The filtrate was concentrated under reduced pressure to remove the solvent. Dichloromethane (20 mL) was added to the obtained residue with stirring for 5 minutes, followed by filtration. The filtrate was concentrated under reduced pressure to obtain the crude product WX065-4.

Step 4: Preparation of Compound WX065

Compound WX065-4 (300.00 mg, 652.84 μmol) and triethylamine (264.24 mg, 2.61 mmol, 361.97 μL) were dissolved in tetrahydrofuran (30.00 mL) at room temperature. The solution was then cooled to 0° C., followed by the addition of triphosgene (67.81 mg, 228.49 μmol). The reaction mixture was warmed to room temperature and stirred for 5 hours. After the reaction, insolubles was removed by filtration and the filtrate was concentrated under reduced pressure. The obtained residue was isolated by preparative HPLC to obtain the target product WX065. MS-ESI m/z: 486.1 [M+H]$^+$. $^1$HNMR (400 MHz, CDCl$_3$) δ: 8.16 (d, J=5.3 Hz, 1H), 7.61-7.47 (m, 2H), 7.44 (s, 1H), 7.40-7.28 (m, 3H), 7.16 (d, J=5.0 Hz, 1H), 6.82 (d, J=8.3 Hz, 1H), 6.39 (d, J=4.8 Hz, 1H), 4.92-4.79 (m, 1H), 4.09 (q, J=6.8 Hz, 2H), 3.90 (d, J=11.8 Hz, 1H), 3.84 (s, 3H), 2.85 (s, 3H), 1.44 (t, J=6.9 Hz, 3H).

Embodiment 66: WX066

Synthetic Route:

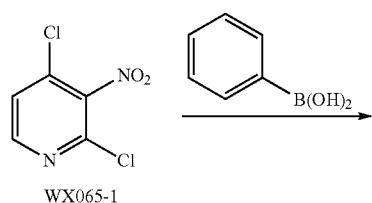

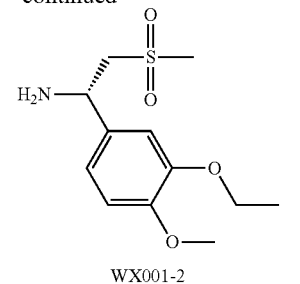

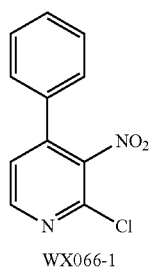

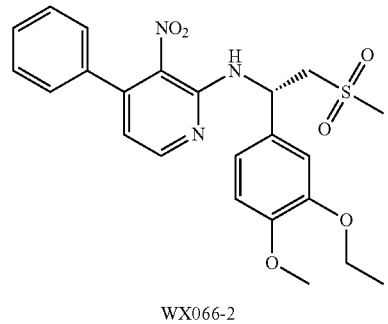

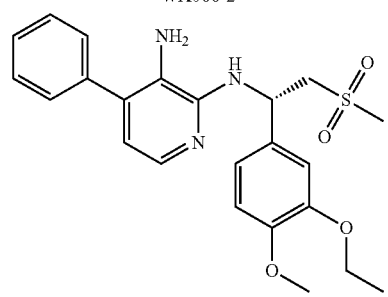

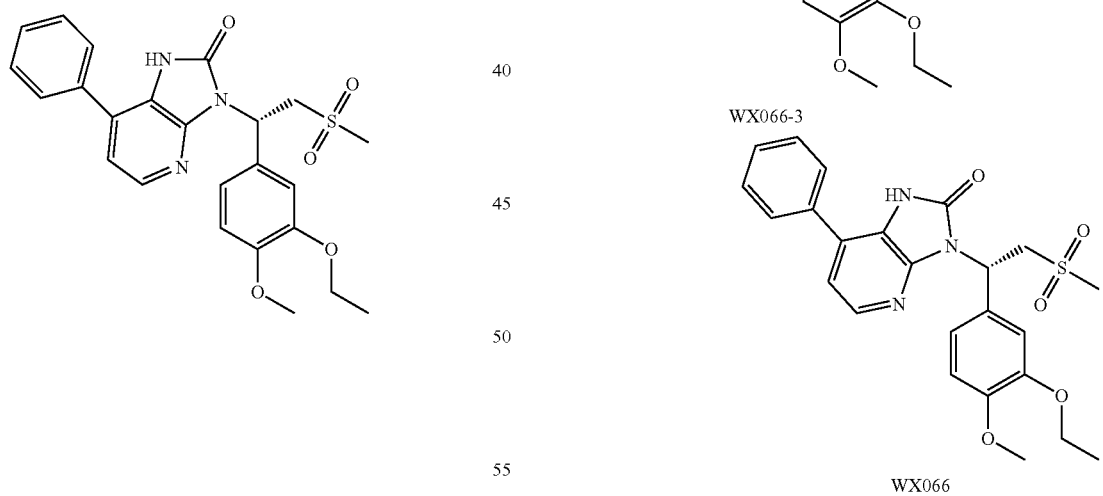

Step 1: Preparation of Compound WX066-1

Compound WX065-1 (1.00 g, 5.18 mmol), phenylboronic acid (758.15 mg, 6.22 mmol), [1,1'-bis(diphenylphosphino)ferrocene] palladium dichloride dichloromethane complex (189.51 mg, 259.00 μmol) and potassium carbonate (2.15 g, 15.54 mmol) were dissolved in dioxane (18.00 mL) and water (6.00 mL) at room temperature. The reaction mixture was heated to 80° C. and stirred for 2 hours under nitrogen atmosphere. After the reaction, the mixture was cooled to room temperature, diluted with water (20 mL) and extracted with ethyl acetate (30 mL×3). The organic phases were combined, washed with saturated brine (30 mL×2) and dried over anhydrous sodium sulfate, followed by filtration. The filtrate was concentrated under reduced pressure to remove the solvent. The obtained residue was isolated by column chromatography (eluent: petroleum ether/ethyl acetate=40/1-20/1, volume ratio) to obtain the target product WX066-1. $^1$H NMR (400 MHz, DMSO_$d_6$) δ: 8.75 (d, J=5.0 Hz, 1H), 7.80 (d, J=5.0 Hz, 1H), 7.58-7.55 (m, 3H), 7.50-7.39 (m, 2H).

Step 2: Preparation of Compound WX066-2

Compound WX066-1 (300.00 mg, 1.28 mmol) was dissolved in acetonitrile (20.00 mL) at room temperature followed by the addition of compound WX001-2 (291.57 mg, 1.07 mmol) and potassium carbonate (442.27 mg, 3.20 mmol). The reaction mixture was heated to 90° C. and stirred for 72 hours under nitrogen atmosphere. After the reaction, the mixture was cooled to room temperature, diluted with water (20 mL) and extracted with ethyl acetate (20 mL×3). The organic phases were combined, washed with saturated brine (20 mL×2) and dried over anhydrous sodium sulfate, followed by filtration. The filtrate was concentrated under reduced pressure to remove the solvent. The obtained residue was isolated by preparative layer chromatography (eluent: petroleum ether/ethyl acetate=1/1, volume ratio) to obtain the target product WX066-2. $^1$H NMR (400 MHz, CDCl$_3$) δ: 8.30 (d, J=5.0 Hz, 1H), 7.46-7.40 (m, 3H), 7.37 (d, J=6.8 Hz, 1H), 7.31-7.27 (m, 2H), 7.05-6.97 (m, 2H), 6.92-6.87 (m, 1H), 6.67 (d, J=4.8 Hz, 1H), 5.88 (d, J=6.8 Hz, 1H), 4.14-4.11 (m, 2H), 3.90-3.82 (m, 4H), 3.50 (dd, J=14.6, 6.8 Hz, 1H), 2.61 (s, 3H), 1.51-1.45 (m, 3H).

Step 3: Preparation of Compound WX066-3

Compound WX066-2 (110.00 mg, 233.28 μmol) and ammonium chloride (124.78 mg, 2.33 mmol, 81.56 μL) were dissolved in methanol (10.00 mL) at room temperature, followed by the addition of zinc powder (152.54 mg, 2.33 mmol). The reaction mixture was stirred at room temperature for 0.1 hour under nitrogen atmosphere. After the reaction, the mixture was filtered by diatomite. The filter cake was washed with dichloromethane (20 mL×2). The filtrate was combined and concentrated under reduced pressure to remove the solvent. Dichloromethane (20 mL) was added to the obtained residue with stirring for 5 minutes, followed by filtration. The filtrate was concentrated under reduced pressure to obtain the product WX066-3. MS-ESI m/z: 442.1 [M+H]$^+$.

Step 4: Preparation of Compound WX066

Compound WX066-3 (100.00 mg, 226.48 μmol) and triethylamine (114.59 mg, 1.13 mmol, 156.97 μL) were dissolved in tetrahydrofuran (25.00 mL) at room temperature. The solution was then cooled to 0° C., followed by the addition of triphosgene (26.88 mg, 90.59 μmol). The reaction mixture was stirred at 0° C. for 5 hours. After the reaction, the mixture was diluted with water (10 mL) and extracted with ethyl acetate (10 mL×3). The organic phases were combined, washed with saturated brine (10 mL×2) and dried over anhydrous sodium sulfate, followed by filtration. The filtrate was concentrated under reduced pressure. The obtained residue was isolated by preparative HPLC to obtain the target product WX066. MS-ESI m/z: 468.1 [M+H]$^+$. $^1$H NMR (400 MHz, CDCl$_3$) δ: 10.13 (s, 1H), 8.15 (s, 1H), 7.68-7.42 (m, 6H), 7.30 (s, 1H), 7.20 (s, 1H), 6.80 (d, J=7.5 Hz, 1H), 6.49 (s, 1H), 4.91 (s, 1H), 4.18-3.98 (m, 2H), 3.93-3.70 (m, 4H), 2.92 (s, 3H), 1.41 (t, J=6.3 Hz, 3H).

Embodiment 67: WX067

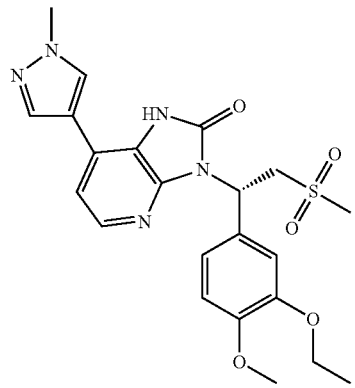 [SMILES: CCOc1cc([C@@H](CS(C)(=O)=O)n2c(=O)[nH]c3c(-c4cnn(C)c4)ccnc32)ccc1OC]

Synthetic Route:

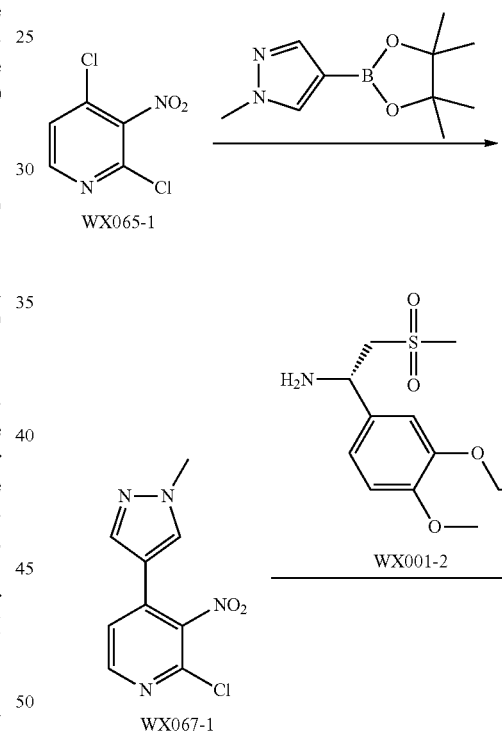

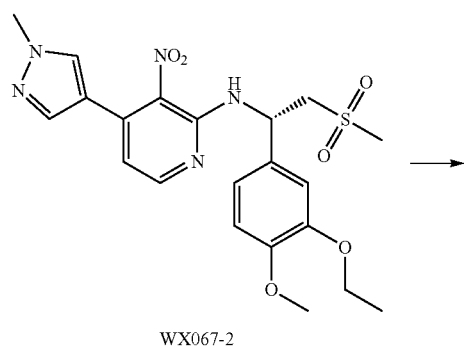

-continued

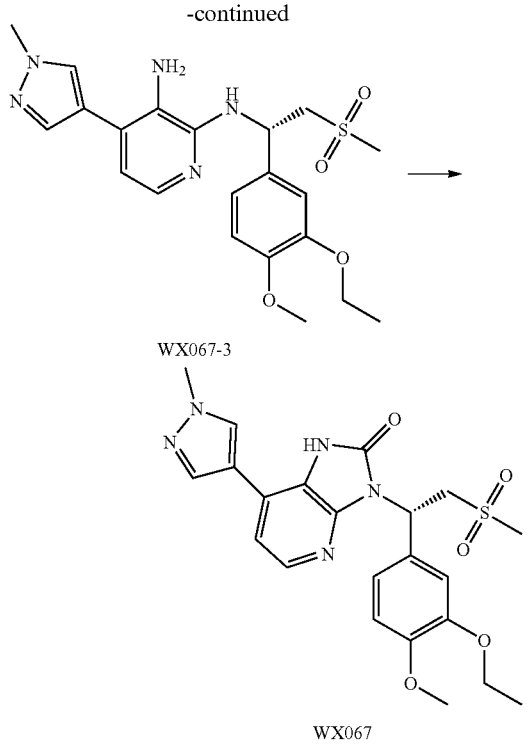

Step 3: Preparation of compound WX067-3

Compound WX067-2 (500.00 mg, 1.05 mmol), zinc powder (686.60 mg, 10.50 mmol) and ammonium chloride (561.65 mg, 10.50 mmol) were dissolved in methanol (20.00 mL) at room temperature. The reaction mixture was stirred at room temperature for 15 hours under nitrogen atmosphere. After the reaction, the mixture was filtered by diatomite. The filtrate was concentrated under reduced pressure to remove the solvent. Dichloromethane (20 mL) was added to the obtained residue with stirring for 20 minutes, followed by filtration. The filtrate was concentrated under reduced pressure to obtain the crude product WX067-3. MS-ESI m/z: 446.1 [M+H]$^+$.

Step 4: Preparation of Compound WX067

Compound WX067-3 (200.00 mg, 448.90 μmol), triphosgene (79.93 mg, 269.34 μmol) and triethylamine (136.27 mg, 1.35 mmol, 186.68 μL) were dissolved in tetrahydrofuran (20.00 mL) at room temperature. The reaction mixture was then cooled to 0-5° C. and stirred for 5 hours. After the reaction, the reaction solution was poured into iced water (20.00 mL), followed by the addition of ethyl acetate (50.00 mL). The organic phases were separated, washed with saturated brine (20 mL×2) and dried over anhydrous sodium sulfate, followed by filtration. The filtrate was concentrated under reduced pressure to remove the solvent. The obtained residue was isolated by preparative HPLC to obtain the target product WX067. MS-ESI m/z: 472.1[M+H]$^+$. $^1$H NMR (400 MHz, CDCl$_3$): δ: 11.18 (s, 1H), 8.45 (s, 1H), 8.10 (s, 1H), 7.95 (d, J=5.6 Hz, 1H), 7.28-7.25 (m, 2H), 7.02 (d, J=8.0 Hz, 1H), 6.92 (d, J=8.8 Hz, 1H), 6.07 (dd, J=3.6, 9.6 Hz, 1H), 4.73-4.69 (m, 1H), 4.18-4.14 (m, 1H), 4.03-3.97 (m, 2H), 3.90 (s, 3H), 3.72 (s, 3H), 2.98 (s, 3H), 1.32 (t, J=7.2 Hz, 3H).

Step 1: Preparation of Compound WX067-1

Compound WX065-1 (5.00 g, 25.91 mmol), 1-methyl-4-(4,4,5,5-tetramethyl-1,3,2-dioxaborolane-2-yl-pyrazole (5.39 g, 25.91 mmol), potassium carbonate (10.74 g, 77.73 mmol) and [1,1'-bis(diphenylphosphino)ferrocene] palladium dichloride dichloromethane complex (4.23 g, 5.18 mmol) dissolved in dioxane (50.00 mL) and water (10.00 mL) at room temperature. The reaction mixture was heated to 80-90° C. and stirred for 3 hours under nitrogen atmosphere. After the reaction, the mixture was cooled to room temperature and concentrated under reduced pressure to remove the solvent. The obtained residue was diluted with ethyl acetate (100 mL) and filtered by diatomite. Water (30 mL) was added to the filtrate and stirred for 10 minutes. The organic phases were separated, washed with saturated brine (30 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=5/1-1/1, volume ratio) to obtain the target product WX067-1. MS-ESI m/z: 239.0 [M+H]$^+$.

Step 2: Preparation of Compound WX067-2

Compound WX067-1 (2.00 g, 8.38 mmol), compound WX001-2 (2.29 g, 8.38 mmol) and potassium carbonate (3.47 g, 25.14 mmol) were dissolved in acetonitrile (50.00 mL) at room temperature. The reaction mixture was heated to 90-100° C. and stirred for 12 hours under nitrogen atmosphere. After the reaction, the mixture was cooled to room temperature, diluted with water (30 mL) and ethyl acetate (200 mL). The organic phases were separated, washed with saturated brine (30 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=3/1-1/2, volume ratio) to obtain the target product WX067-2. MS-ESI m/z: 476.1 [M+H]$^+$.

Embodiment 68: WX068

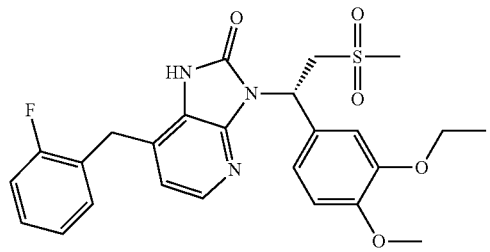 [SMILES: CCOc1cc([C@@H](CS(C)(=O)=O)n2c(=O)[nH]c3c(Cc4ccccc4F)ccnc32)ccc1OC]

Synthetic Route:

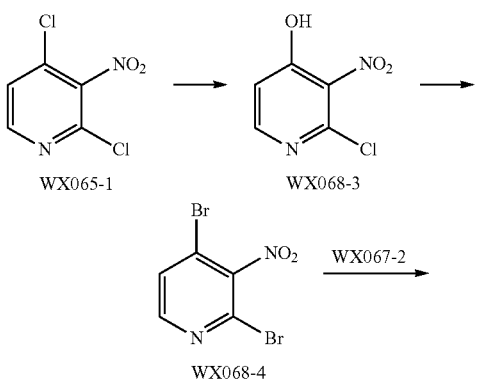

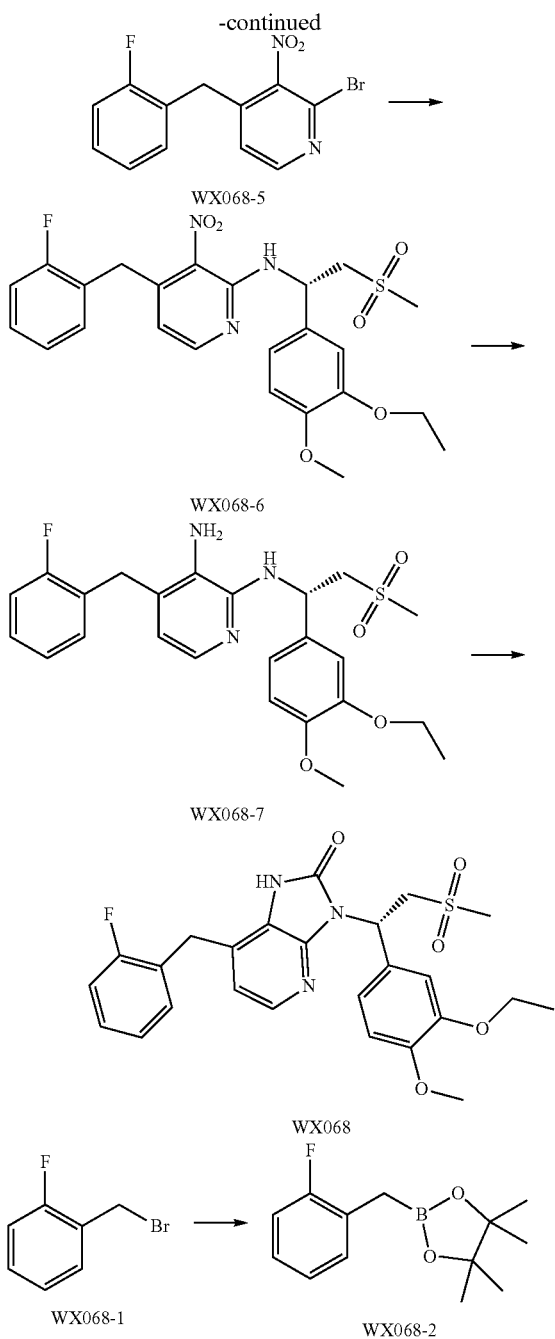

Step 1: Preparation of Compound WX068-2

Compound WX068-1 (5.00 g, 26.45 mmol, 3.18 mL), bis(pinacolato)diboron (10.08 g, 39.67 mmol), tetrakis(triphenylphosphine) palladium (3.06 g, 2.64 mmol) and potassium carbonate (10.97 g, 79.35 mmol) were dissolved in dioxane (100.00 mL) at room temperature. The reaction mixture was heated to 80-90° C. for 12 hours under nitrogen atmosphere. After the reaction, the mixture was cooled to room temperature, diluted with water (200 mL) and ethyl acetate (500 mL). The organic phases were separated, washed with saturated brine (100 mL×2) and dried over anhydrous sodium sulfate, followed by filtration. The filtrate was concentrated under reduced pressure to remove the solvent. The obtained residue was isolated by column chromatography (eluent: petroleum ether/ethyl acetate=100/1- 10/1, volume ratio) to obtain the target product WX068-2. $^{1}$H NMR (400 MHz, CDCl$_{3}$) δ: 7.28-6.93 (m, 4H), 2.26 (s, 2H), 1.25 (s, 12H).

Step 2: Preparation of Compound WX068-3

Compound WX065-1 (35.00 g, 181.36 mmol) and sodium acetate (44.63 g, 544.08 mmol) were dissolved in N,N-dimethylformamide (600.00 mL) at room temperature. The reaction mixture was heated to 120° C. and stirred for 3 hours under nitrogen atmosphere. After the reaction, the mixture was cooled to room temperature and concentrated under reduced pressure to remove the solvent. Ethyl acetate (500 mL) and water (200 mL) were added to the obtained residue. The organic phases were separated and the aqueous phases were extracted with ethyl acetate (200 mL×3). The organic phases were combined, washed with saturated brine (200 mL) and dried over anhydrous sodium sulfate, followed by filtration. The filtrate was concentrated under reduced pressure to remove the solvent to obtain the crude product. The obtained crude product was slurried for 30 minutes with the mixture of petroleum ether and ethyl acetate, followed by filtration. The filter cake was dried in vacuum for 30 minutes to obtain the target product WX068-3. $^{1}$H NMR (400 MHz, DMSO_d$_{6}$) δ: 8.19 (d, J=6.0 Hz, 1H), 7.03 (d, J=6.0 Hz, 1H).

Step 3: Preparation of Compound WX068-4

Compound WX068-3 (10.00 g, 57.29 mmol) and phosphorus oxybromide (49.28 g, 171.87 mmol) were dissolved in acetonitrile (600.00 mL) at room temperature. The reaction mixture was heated to 90-100° C. and stirred for 5 hours under nitrogen atmosphere. After the reaction, the mixture was cooled to room temperature and concentrated under reduced pressure to remove the solvent. The obtained residue was diluted with ethyl acetate (500 mL) and the pH of which was adjusted by saturated sodium bicarbonate solution to 7-8 at 0-5° C.

The organic phases were separated, washed with saturated brine (100 mL) and dried over anhydrous sodium sulfate, followed by filtration. The filtrate was concentrated under reduced pressure to remove the solvent. The obtained residue was isolated by column chromatography (eluent: petroleum ether/ethyl acetate=10/1-3/1, volume ratio) to obtain the target product WX068-4. $^{1}$H NMR (400 MHz, CDCl$_{3}$) δ: 8.33 (d, J=5.6 Hz, 1H), 7.64 (d, J=5.6 Hz, 1H).

Step 4: Preparation of Compound WX068-5

Compound WX068-4 (3.50 g, 12.42 mmol), [1,1'-bis(diphenylphosphino)ferrocene]palladium dichloride dichloromethane complex (1.38 g, 1.69 mmol) and potassium carbonate (4.68 g, 33.89 mmol) were dissolved in dioxane (100.00 mL) and water (30.00 mL) at room temperature. The reaction mixture was heated to 80° C. and stirred for 12 hours under nitrogen atmosphere. After the reaction, the mixture was cooled to room temperature, filtered by diatomite and diluted with ethyl acetate (500 mL) and water (100 mL). The organic phases were separated, wash with saturated brine (100 mL×2) and dried over anhydrous sodium sulfate, followed by filtration. The filtrate was concentrated under reduced pressure to remove the solvent. The obtained residue was isolated by preparative HPLC to obtain the target product WX068-5. MS-ESI m/z: 310.8 [M+H]$^{+}$, 312.8 [M+H+2]$^{+}$. $^{1}$H NMR (400 MHz, CDCl$_{3}$) δ: 8.28 (d, J=5.0 Hz, 1H), 7.28-7.17 (m, 1H), 7.11-6.97 (m, 4H), 3.92 (s, 2H).

Step 5: Preparation of Compound WX068-6

The trifluoroacetate salt of compound WX068-5 (800.00 mg, 1.88 mmol), compound WX001-2 (771.58 mg, 2.82 mmol) and diisopropylethylamine (729.60 mg, 5.65 mmol, 985.95 μL) were dissolved in N,N-dimethylformamide (30.00 mL) at room temperature. The reaction mixture was heated to 120-130° C. and stirred for 12 hours under nitrogen atmosphere. After the reaction, the mixture was cooled to room temperature and diluted with ethyl acetate (200 mL) and water (100 mL). The organic phases were separated, wash with saturated brine (100 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=10/1-1/2, volume ratio) to obtain the target product WX068-6. MS-ESI m/z: 504.1 [M+H]⁺.

Step 6: Preparation of Compound WX068-7

Compound WX068-6 (300.00 mg, 595.78 μmol), zinc powder (389.58 mg, 5.96 mmol) and ammonium chloride (318.68 mg, 5.96 mmol, 208.29 μL) were dissolved in methanol (30.00 mL) at room temperature. The reaction mixture was cooled to 0-5° C. and stirred for 1 hour under nitrogen atmosphere. After the reaction, the mixture was filtered by diatomite and the filter cake was wash with dichloromethane (20 mL×2). The combined filtrate was concentrated under reduced pressure to remove the solvent. Dichloromethane (50 mL) and water (20 mL) were added to the obtained residue. The organic phases were separated, wash with saturated brine (20 mL×2) and dried over anhydrous sodium sulfate, followed by filtration. The filtrate was concentrated under reduced pressure to remove the solvent to obtain the target product WX068-7. MS-ESI m/z: 474.2 [M+H]⁺.

Step 7: Preparation of Compound WX068

Compound WX068-7 (200.00 mg, 422.33 μmol), triphosgene (75.20 mg, 253.40 μmol) and triethylamine (256.41 mg, 2.53 mmol, 351.25 μL) were dissolved in tetrahydrofuran (30.00 mL) at room temperature. The reaction mixture was stirred at 0-5° C. for 2 hours under nitrogen atmosphere. After the reaction, the mixture was diluted with water (20 mL) and ethyl acetate (100 mL). The organic phases were separated, wash with saturated brine (20 mL×2) and dried over anhydrous sodium sulfate, followed by filtration. The filtrate was concentrated under reduced pressure to remove the solvent. The obtained residue was isolated by preparative HPLC to obtain the target product WX068. MS-ESI m/z: 500.0 [M+H]⁺. ¹H NMR (400 MHz, CDCl₃) δ: 10.32 (br s, 1H), 8.16 (d, J=5.2 Hz, 1H), 7.52 (d, J=1.6 Hz, 1H), 7.43-7.38 (m, 3H), 7.27-7.25 (m, 2H), 7.03 (d, J=5.2 Hz, 1H), 6.94 (d, J=8.4 Hz, 1H), 6.37 (br dd, J=4.8, 9.0 Hz, 1H), 5.01 (br dd, J=9.4, 14.7 Hz, 1H), 4.24-4.19 (m, 4H), 4.13-4.09 (m, 1H), 3.98 (s, 3H), 2.87 (s, 3H), 1.56 (t, J=6.8 Hz, 3H).

Embodiment 69: WX069

Synthetic Route:

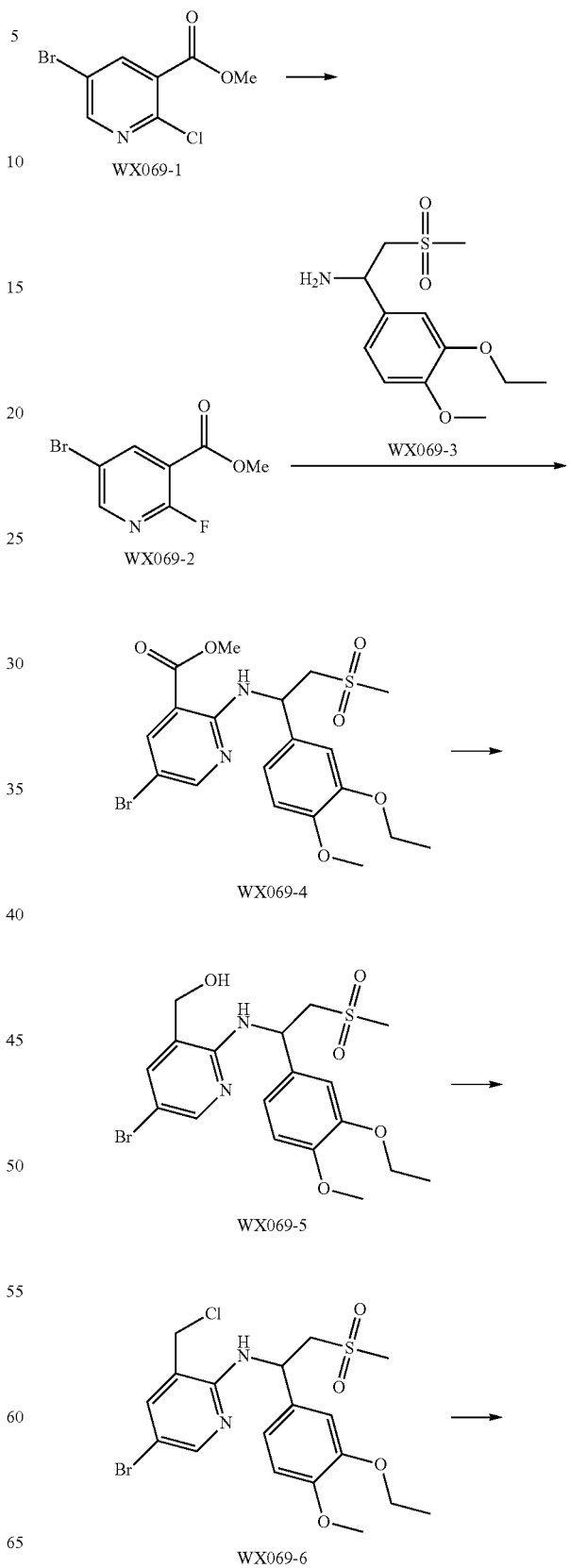

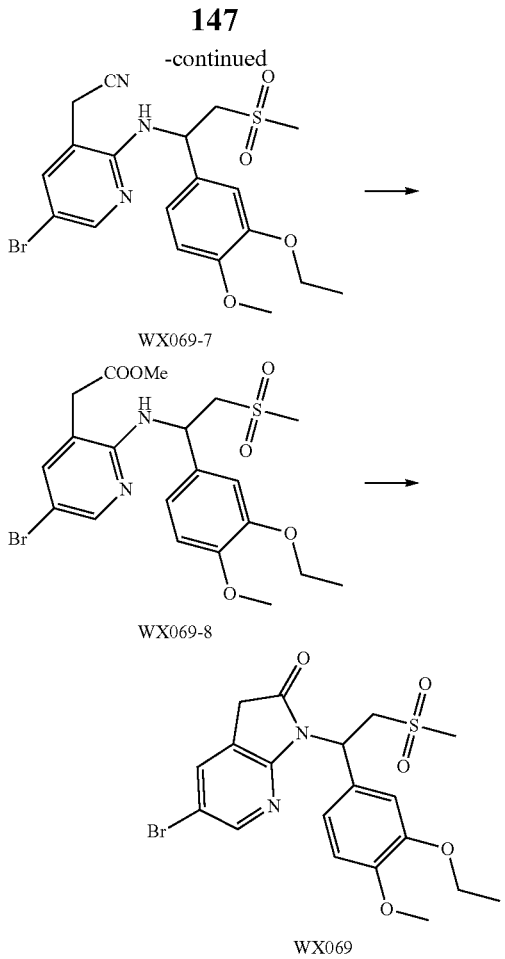

WX069-7

WX069-8

WX069

Step 1: Preparation of Compound WX069-2

Compound WX069-1 (7.00 g, 27.95 mmol) was dissolved in dimethyl sulfoxide solution (50.00 mL) at room temperature, followed by the addition of cesium fluoride (8.00 g, 52.67 mmol) at room temperature. The reaction mixture was heated to 55° C. and stirred for 14 hours. After the reaction, the mixture was cooled to room temperature, quenched with saturated brine (10 mL), diluted with water (50 mL) and extracted with ethyl acetate (20 mL×3). The organic phases were separated, washed with water (50 mL×2) and dried over anhydrous sodium sulfate, followed by filtration. The filtrate was concentrated under reduced pressure. The obtained residue was isolated by silica gel column chromatography (eluent: petroleum ether/ethyl acetate=100/1-100/15, volume ratio) to obtain the target product WX069-2. $^1$H NMR (400 MHz, CDCl$_3$) δ: 8.64-8.31 (m, 2H), 3.98 (s, 3H).

Step 2: Preparation of Compound WX069-4

Compound WX069-2 (2.70 g, 3.46 mmol) and compound WX069-3 (946.13 mg, 3.46 mmol) were dissolved in acetonitrile (20.00 mL) at room temperature followed by the addition of potassium carbonate (559.70 mg, 4.05 mmol). The reaction mixture was heated to 80° C. and stirred for 5 hours under nitrogen atmosphere. After the reaction, the mixture was cooled to room temperature, quenched with water (20 mL), diluted with water (40 mL) and extracted with ethyl acetate (20 mL×3). The organic phases were combined, washed with saturated brine (20 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=100/0-100/70, volume ratio) to obtain the target product WX069-4. $^1$H NMR (400 MHz, CDCl$_3$) δ: 8.57 (d, J=7.5 Hz, 1H), 8.32 (d, J=2.5 Hz, 1H), 8.24 (d, J=2.5 Hz, 1H), 7.06-6.95 (m, 2H), 6.89 (d, J=8.3 Hz, 1H), 5.82 (q, J=6.6 Hz, 1H), 4.13 (q, J=7.0 Hz, 2H), 3.89 (d, J=13.1 Hz, 6H), 3.81 (dd, J=6.5, 14.8 Hz, 1H), 3.47 (dd, J=6.4, 14.7 Hz, 1H), 2.64 (s, 3H), 1.48 (t, J=6.9 Hz, 3H).

Step 3: Preparation of Compound WX069-5

Compound WX069-4 (700.00 mg, 1.44 mmol) was dissolved in tetrahydrofuran (10.00 mL) at room temperature, followed by the addition of lithium borohydride (94.09 mg, 4.32 mmol) at 0° C. The reaction mixture was stirred at 0° C. for 0.5 hour and then warmed to 30° C. with stirring for another 2.5 hours under nitrogen atmosphere. After the reaction, the mixture was quenched with saturated ammonium chloride solution until no bubble was formed, diluted with water (40 mL) and extracted with dichloromethane (20 mL×3). The organic phases were combined, washed with water (50 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=1/1-1/3, volume ratio) to obtain the target product WX069-5. $^1$H NMR (400 MHz, CDCl$_3$) δ: 8.01 (br s, 1H), 7.34 (br s, 1H), 6.96 (br s, 2H), 6.82 (d, J=6.5 Hz, 1H), 6.26 (d, J=5.8 Hz, 1H), 5.72 (d, J=4.0 Hz, 1H), 4.55 (q, J=11.1 Hz, 2H), 4.07 (d, J=5.8 Hz, 2H), 3.94-3.60 (m, 4H), 3.44 (d, J=11.0 Hz, 1H), 2.63 (br s, 3H), 2.02 (br s, 1H), 1.42 (br s, 3H).

Step 4: Preparation of Compound WX069-6

Compound WX069-5 (491.50 mg, 1.07 mmol) and triethylamine (108.27 mg, 1.07 mmol) were dissolved in dichloromethane (5.00 mL) at room temperature. The solution was then cooled to 0° C., followed by the addition of MsCl (122.57 mg, 1.07 mmol). The reaction mixture was warmed to room temperature and stirred for 2 hours under nitrogen atmosphere. After the reaction, the mixture was quenched with saturated brine (20 mL), diluted with water (20 mL) and extracted with ethyl acetate (20 mL×3). The organic phases were combined, wash with water (70 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=1/0-1/1, volume ratio) to obtain the crude product WX069-6. $^1$H NMR (400 MHz, CDCl$_3$) δ: 8.13 (d, J=1.8 Hz, 1H), 7.52 (d, J=2.0 Hz, 1H), 7.05-6.94 (m, 2H), 6.89 (d, J=7.8 Hz, 1H), 5.92-5.74 (m, 2H), 4.63-4.43 (m, 2H), 4.18-4.03 (m, 2H), 3.87 (s, 3H), 3.79 (dd, J=5.9, 14.7 Hz, 1H), 3.53 (dd, J=5.1, 14.7 Hz, 1H), 2.58 (s, 3H), 1.45 (t, J=7.0 Hz, 3H).

Step 5: Preparation of Compound WX069-7

Compound WX069-6 (175 mg, crude product) was dissolved in N,N-dimethylformamide (3.00 mL) at room temperature, followed by the stepwise addition of sodium cyanide (17.95 mg, 366.26 μmol) and triethylamine (74.12 mg, 732.52 μmol). The reaction mixture was stirred at room temperature for 4 hours. After the reaction, the mixture was quenched with saturated brine (20 mL), diluted with water (40 mL) and extracted with ethyl acetate (15 mL×3). The organic phases were combined, wash with saturated brine (25 mL×2) and dried over anhydrous sodium sulfate, followed by filtration. The filtrate was concentrated under reduced pressure to remove the solvent. The obtained residue was isolated by flash silica gel column chromatography (eluent: petroleum ether/ethyl acetate=1/0-2/3, volume ratio) to obtain the target product WX069-7. $^1$H NMR (400

MHz, CDCl$_3$) δ: 8.13 (d, J=2.3 Hz, 1H), 7.62 (d, J=2.0 Hz, 1H), 7.06-6.94 (m, 2H), 6.93-6.82 (m, 1H), 5.82-5.71 (m, 1H), 5.61 (d, J=6.3 Hz, 1H), 4.11 (dq, J=4.3, 6.9 Hz, 2H), 3.87 (s, 3H), 3.71 (dd, J=6.9, 14.7 Hz, 1H), 3.59 (d, J=3.8 Hz, 2H), 3.51 (dd, J=4.9, 14.7 Hz, 1H), 2.62 (s, 3H), 1.46 (t, J=6.9 Hz, 3H).

Step 6: Preparation of Compound WX069-8

Compound WX069-7 (60.00 mg, 128.11 μmol) was dissolved in the solution of hydrochloric acid in methanol (4 M, 5 mL) at room temperature. The mixture was stirred at room temperature for 5 hours. After the reaction, the pH of the mixture was adjusted by saturated sodium carbonate solution to 7-8. The solution was diluted with saturated brine (30 mL) and extracted with ethyl acetate (10 mL×3). The organic phases were combined, wash with water (30 mL×2) and dried over anhydrous sodium sulfate, followed by filtration. The filtrate was concentrated under reduced pressure to remove the solvent. The obtained residue was isolated by flash column chromatography (eluent: petroleum ether/ethyl acetate=1/0-2/3, volume ratio) to obtain the target product WX069-8.

Step 7: Preparation of Compound WX069

Compound WX069-8 (60.00 mg, 119.67 μmol) was dissolved in acetic acid (2.00 mL) at room temperature. The reaction mixture was heated to 150° C. by microwave irradiation and stirred for 20 minutes. After the reaction, the mixture was cooled to room temperature, diluted with ethyl acetate (50 mL) and concentrated under reduced pressure to remove the solvent. The obtained residue was isolated by preparative HPLC to obtain the target product WX069. MS-ESI m/z: 469.2 [M+H]$^+$, 471.2 [M+H+2]$^+$. $^1$H NMR (400 MHz, CDCl$_3$) δ: 8.26 (d, J=1.8 Hz, 1H), 7.58 (s, 1H), 7.26 (d, J=2.0 Hz, 1H), 7.19 (dd, J=1.9, 8.2 Hz, 1H), 6.83 (d, J=8.3 Hz, 1H), 6.11 (dd, J=4.5, 10.3 Hz, 1H), 4.78 (dd, J=10.3, 14.3 Hz, 1H), 4.10 (q, J=7.1 Hz, 2H), 3.85 (s, 3H), 3.79 (dd, J=4.3, 14.6 Hz, 1H), 3.55 (s, 2H), 2.84 (s, 3H), 1.47 (t, J=6.9 Hz, 3H).

Embodiment 70: WX070

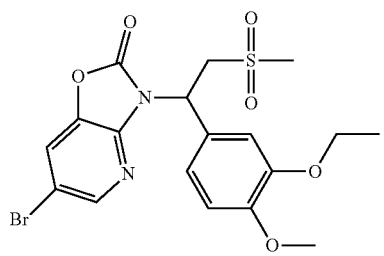 [SMILES: CCOc1cc(C(CS(C)(=O)=O)n2c(=O)oc3cc(Br)cnc32)ccc1OC]

Synthetic Route:

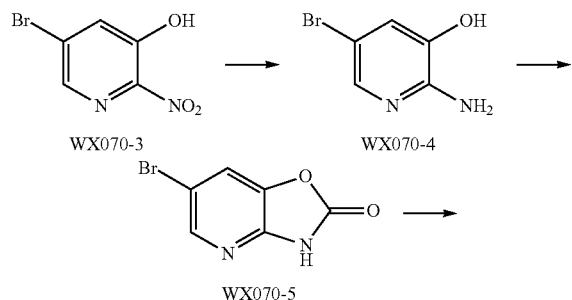

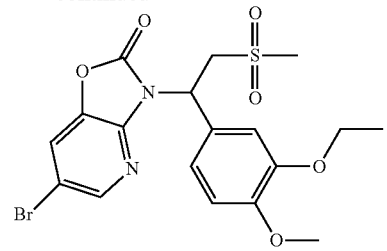

WX070

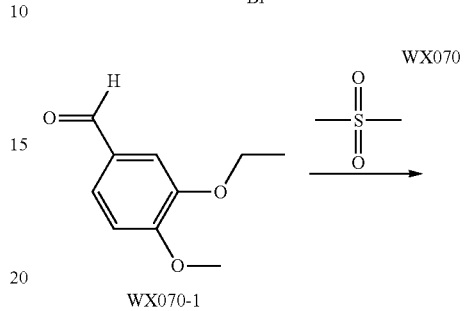

WX070-1

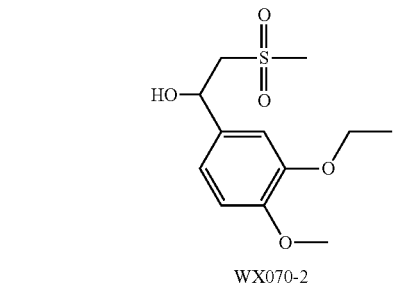

WX070-2

Step 1: Preparation of Compound WX070-2

Dimethyl sulfone (5.22 g, 55.50 mmol) was dissolved in tetrahydrofuran (50.00 mL), and n-butyllithium (2.5 M, 22.20 mL) was added dropwise at 0° C. The reaction mixture was stirred at 0° C. for 1 hour under nitrogen atmosphere, followed by the dropwise addition of the solution of the compound WX070-1 (5.00 g, 27.75 mmol) in tetrahydrofuran (20.00 mL) at 0° C. The reaction mixture was stirred at 0° C. for another 1.5 hours under nitrogen atmosphere. After the reaction, the mixture was warmed to room temperature, quenched with saturated ammonium chloride solution (50 mL), diluted with water (150 mL) and extracted with ethyl acetate (50 mL×3). The organic phases were combined, washed with water (100 mL×2) and dried over anhydrous sodium sulfate, followed by filtration. The filtrate was concentrated under reduced pressure to remove the solvent. The obtained residue was recrystallized with ethyl acetate (20 mL) to obtain the target product WX070-2. $^1$H NMR (400 MHz, DMSO_d$_6$) δ: 6.99 (s, 1H), 6.91 (s, 2H), 5.83 (d, J=4.0 Hz, 1H), 4.96 (ddd, J=2.8, 4.3, 10.0 Hz, 1H), 4.02 (q, J=7.0 Hz, 2H), 3.73 (s, 3H), 3.57 (dd, J=10.0, 14.6 Hz, 1H), 3.15 (d, J=14.6 Hz, 1H), 3.01 (s, 3H), 1.33 (t, J=7.0 Hz, 3H).

Step 2: Preparation of Compound WX070-4

Compound WX070-3 (200.00 mg, 913.28 μmol) was dissolved in acetic acid (5.00 mL) and methanol (5.00 mL), followed by the addition of iron powder (153.02 mg, 2.74 mmol) in one time. The reaction mixture was stirred at 0-5° C. for 1.5 hours under nitrogen atmosphere. After the reaction, the mixture was diluted with water (50 mL) and ethyl acetate (50 mL) and the pH of which was adjusted to 9-10 with aqueous sodium hydroxide solution (1 M). The separated aqueous phase was extracted with ethyl acetate (20 mL×3). The organic phases were combined, washed with saturated brine (20 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=5/1-1/4, volume ratio) to obtain the target product WX070-4. $^1$H NMR (400 MHz, MeOD) δ: 7.46 (d, J=2.0 Hz, 1H), 6.99 (d, J=2.0 Hz, 1H).

Step 3: Preparation of Compound WX070-5

Compound WX070-4 (300.00 mg, 1.59 mmol) was dissolved in dichloromethane (20.00 mL) and pyridine (10.00 mL), followed by the addition of triphosgene (471.83 mg, 1.59 mmol) at 0° C. The reaction mixture was heated to 40° C. and stirred for 3 hours under nitrogen atmosphere. After the reaction, the mixture was diluted with water (20 mL). The separated aqueous phase was extracted with dichloromethane (20 mL×3). The organic phases were combined, washed with saturated brine (20 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=10/1-1/1, volume ratio) to obtain the target product WX070-5. $^1$H NMR (400 MHz, MeOD) δ: 8.14 (d, J=2.0 Hz, 1H), 7.77 (d, J=2.0 Hz, 1H).

Step 4: Preparation of Compound WX070

Compound WX070-5 (230.00 mg, 1.07 mmol), triphenylphosphine (336.78 mg, 1.28 mmol) and compound WX070-2 (293.53 mg, 1.07 mmol) were dissolved in tetrahydrofuran (4.00 mL) at room temperature, followed by the addition of diisopropyl azodicarboxylate (259.64 mg, 1.28 mmol) at 0° C. The reaction mixture was stirred at 0-20° C. for 12 hours under nitrogen atmosphere. After the reaction, the mixture was diluted with water (20 mL).

The separated aqueous phase was extracted with ethyl acetate (20 mL×3). The organic phases were combined, washed with saturated brine (20 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=1/1, volume ratio) to obtain the target product WX070. MS-ESI m/z: 470.9 [M+H]$^+$, 473.0 [M+H+2]$^+$. $^1$H NMR (400 MHz, CDCl$_3$) δ: 1.47 (t, J=6.9 Hz, 3H), 2.85 (s, 3H), 3.81 (dd, J=14.6, 4.52 Hz, 1H), 3.85 (s, 3H), 4.07-4.13 (m, 2H), 4.73 (dd, J=14.3, 10.3 Hz, 1H), 6.02 (dd, J=10.2, 4.4 Hz, 1H), 6.84 (d, J=8.5 Hz, 1H), 7.19 (dd, J=8.3, 2.0 Hz, 1H), 7.24 (d, J=2.0 Hz, 1H), 7.56 (d, J=2.0 Hz, 1H), 8.22 (d, J=2.0 Hz, 1H).

Embodiment 71: WX071

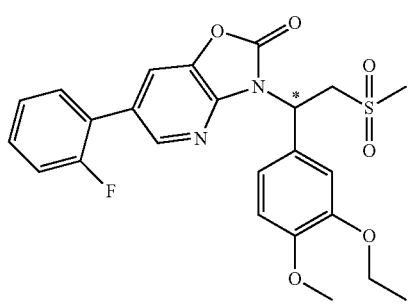 [SMILES: CCOc1cc(C(CS(C)(=O)=O)n2c(=O)oc3cc(-c4ccccc4F)cnc32)ccc1OC]

Synthetic Route:

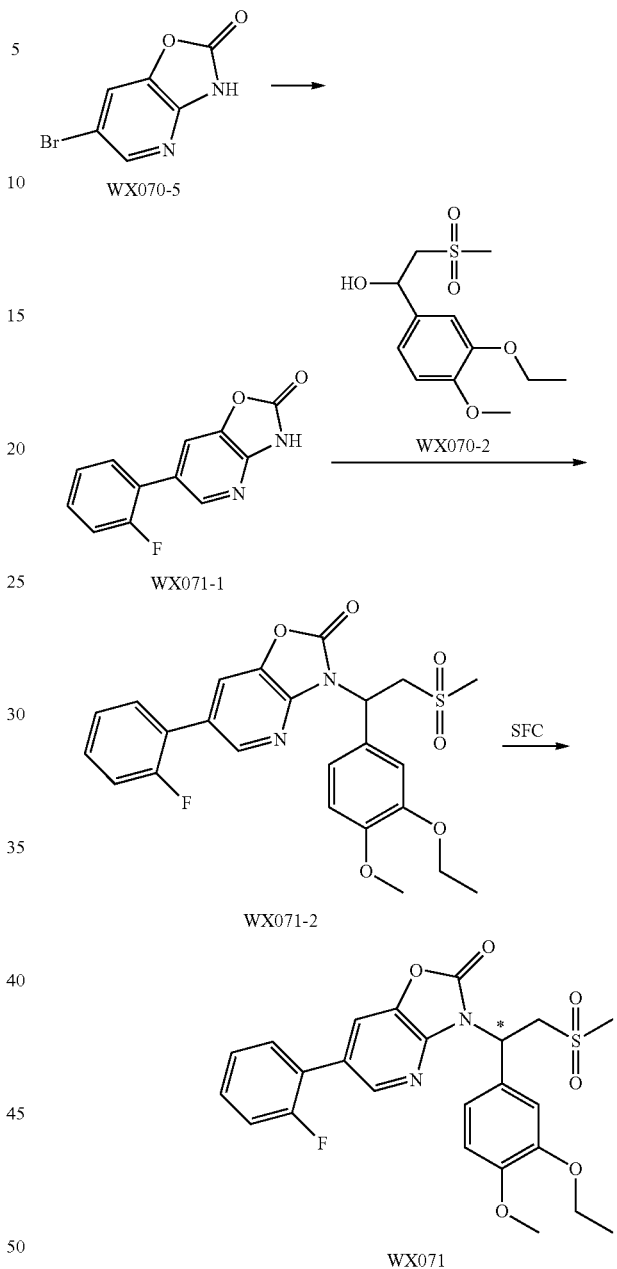

Step 1: Preparation of Compound WX071-1

Compound WX070-5 (1.80 g, 8.37 mmol), 2-fluorophenylboronic acid (1.41 g, 10.04 mmol) was dissolved in dioxane (30.00 mL) at room temperature, followed by the addition of [1,1'-bis(diphenylphosphino)ferrocene] palladium dichloride dichloromethane complex (341.76 mg, 418.50 μmol), potassium carbonate (4.68 g, 33.89 mmol) and water (10.00 mL). The reaction mixture was heated to 80° C. and stirred for 3 hours under nitrogen atmosphere. After the reaction, the mixture was cooled to room temperature, quenched with saturated brine (10 mL), diluted with water (30 mL) and extracted with ethyl acetate (10 mL×3). The organic phases were combined, washed with water (30 mL×2) and dried over anhydrous sodium sulfate, followed by filtration. The filtrate was concentrated under reduced pressure. The obtained residue was isolated by silica gel column chromatography (eluent: petroleum ether/ethyl acetate=3/1-1/1, volume ratio) to obtain the target product WX071-1. MS-ESI m/z: 231.0 [M+H]$^+$.

Step 2: Preparation of Compound WX071-2

Compound WX071-1 (800.00 mg, 3.48 mmol.), compound WX070-2 and triphenylphosphine (1.09 g, 4.17 mmol) were dissolved in tetrahydrofuran (5.00 mL) at room temperature. The reaction mixture was then cooled to 0° C., followed by the dropwise addition of diisopropyl azodicarboxylate (843.31 mg, 4.17 mmol, 810.88 μL). The reaction mixture was warmed to room temperature and stirred for 20 hours under nitrogen atmosphere. After the reaction, the mixture was concentrated under reduced pressure to remove the solvent. The residue obtained was isolated by silica gel chromatography (eluent: petroleum ether/ethyl acetate=1/1-1/2, volume ratio) to obtain the target product WX071-2. $^1$H NMR (400 MHz, CDCl$_3$) δ: 7.47-7.31 (m, 4H), 7.26-7.13 (m, 4H), 7.10 (dd, J=2.3, 8.3 Hz, 1H), 6.88 (d, J=8.3 Hz, 1H), 5.72 (dd, J=4.8, 9.3 Hz, 1H), 4.66 (dd, J=9.3, 14.8 Hz, 1H), 4.12 (q, J=7.0 Hz, 2H), 3.95-3.84 (m, 4H), 2.86 (s, 3H), 1.49 (t, J=6.9 Hz, 3H).

Step 3: Preparation of Compound WX071

Compound WX071-2 (550 mg) was isolated by supercritical fluid chromatography (conditions: column: Chiralpak AS-H 150×4.6 mm I.D., 5 μm; mobile phase: A: carbon dioxide, B: ethanol (0.05% diethylamine); about 40%; flow rate: 3 mL/min; column temperature: 40° C.; wavelength: 220 nm) and the sample with the retention time of 4.103 min was collected to obtain WX071 (ee %: 98.93%).

Embodiment 72: WX072

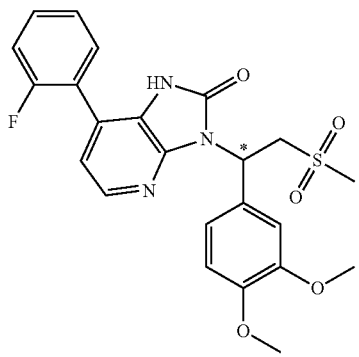 [SMILES: COc1ccc(C(CS(C)(=O)=O)n2c(=O)[nH]c3c(-c4ccccc4F)ccnc32)cc1OC]

Synthetic Route:

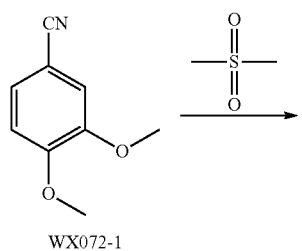

WX072-1

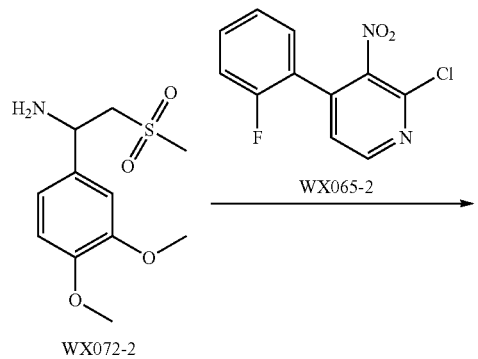

WX072-2

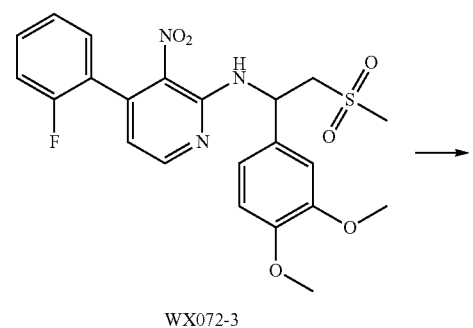

WX072-3

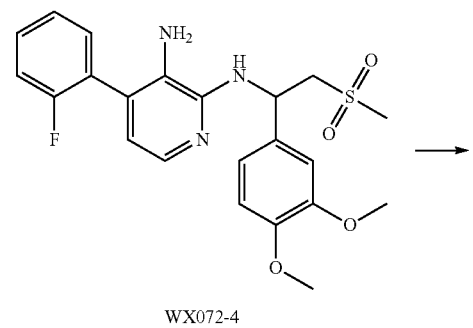

WX072-4

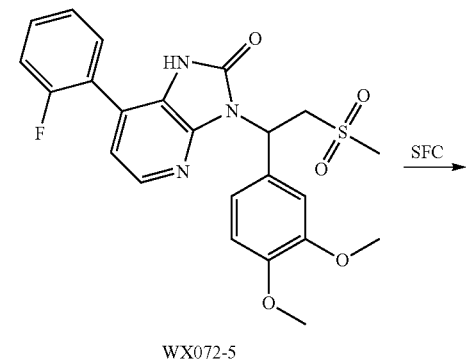

WX072-5

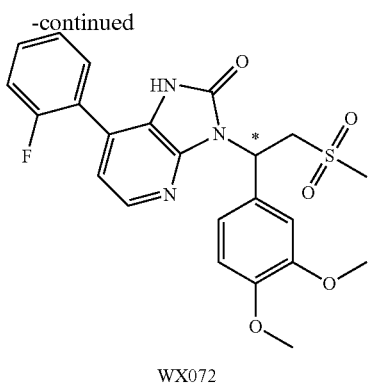

WX072

Step 1: Preparation of Compound WX072-2

Dimethyl sulfone (1.38 g, 14.71 mmol, 1.19 mL) was dissolved in tetrahydrofuran (15.00 mL) at room temperature. The reaction mixture was cooled to −5° C. under nitrogen atmosphere, followed by the dropwise addition of n-butyllithium (2.5 M, 5.39 mL). The reaction mixture was stirred at 0° C. for 1 hour, followed by the dropwise addition of the solution of compound WX072-1 (2.00 g, 12.26 mmol) in tetrahydrofuran (20.00 mL) at 0° C. The reaction mixture was stirred at 0° C. for 15 minutes and then warmed to room temperature and stirred for 1.5 hours. Subsequently, the mixture was cooled to 0° C., followed by the addition of sodium borohydride (602.93 mg, 15.94 mmol) with stirring for 10 minutes, acetic acid (3.39 g, 56.40 mmol, 3.23 mL) with stirring for 2 hours and aqueous sodium hydroxide solution (2.5 M, 16.18 mL) with stirring for 15 minutes. The reaction mixture was then slowly warmed to room temperature, heated to 60° C. and stirred with reflux for 12 hours. After the reaction, the mixture was cooled to room temperature, quenched with saturated brine (50 mL) and extracted with ethyl acetate (15 mL×3). The organic phases were combined, washed with water (50 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=5/1-1/1, volume ratio) to obtain the target product WX072-2. $^1$H NMR (400 MHz, CDCl$_3$) δ: 6.95-6.88 (m, 2H), 6.87-6.80 (m, 1H), 4.61 (dd, J=3.0, 9.5 Hz, 1H), 3.89 (s, 3H), 3.87 (s, 3H), 3.42-3.15 (m, 2H), 2.92 (s, 3H).

Step 2: Preparation of Compound WX072-3

Compound WX065-2 (369.85 mg, 1.46 mmol) and compound WX072-2 (316.00 mg, 1.22 mmol) were dissolved in N,N-dimethylformamide (3.00 mL) at room temperature, followed by the addition of diisopropylethylamine (315.35 mg, 2.44 mmol, 426.14 μL). The reaction mixture was heated to 65° C. and stirred for 24 hours. After the reaction, the mixture was cooled to room temperature, quenched with saturated brine (10 mL), diluted with water (10 mL) and extracted with ethyl acetate (10 mL×3). The organic phases were combined, washed with saturated brine (20 mL×2) and dried over anhydrous sodium sulfate, followed by filtration. The filtrate was concentrated under reduced pressure to remove the solvent. The obtained residue was isolated by silica gel column chromatography (eluent: petroleum ether/ ethyl acetate=2/1-1/1, volume ratio) to obtain the target product WX072-3. $^1$H NMR (400 MHz, CDCl$_3$) δ: 8.38 (d, J=4.8 Hz, 1H), 7.85 (d, J=6.8 Hz, 1H), 7.47-7.38 (m, 1H), 7.36-7.28 (m, 1H), 7.26-7.22 (m, 1H), 7.12 (t, J=9.2 Hz, 1H), 7.06 (dd, J=1.9, 8.2 Hz, 1H), 7.00 (d, J=2.0 Hz, 1H), 6.92 (d, J=8.3 Hz, 1H), 6.66 (d, J=4.8 Hz, 1H), 5.93 (q, J=6.5 Hz, 1H), 3.93 (s, 3H), 3.90 (s, 3H), 3.53 (dd, J=6.9, 14.7 Hz, 1H), 2.64 (s, 3H).

Step 3: Preparation of Compound WX072-4

Compound WX072-3 and ammonium chloride (151.87 mg, 2.84 mmol) were dissolved in methanol (3 mL) at room temperature, followed by the addition of zinc powder (92.83 mg, 1.42 mmol). The reaction mixture was stirred at room temperature 20 minutes under nitrogen atmosphere. After the reaction, the mixture was diluted with dichloromethane (5 mL) and filtered by diatomite. The filtrate was concentrated under reduced pressure and the residue was again added into dichloromethane (5 mL), filtered, concentrated to obtain the crude product WX072-4.

Step 4: Preparation of Compound WX072-5

Compound WX072-4 (35.00 mg, 303.70 μmol) and triethylamine (153.66 mg, 1.52 mmol, 210.49 μL) were dissolved in tetrahydrofuran (20.00 mL) at room temperature. The reaction mixture was then cooled to 0° C., followed by the addition of triphosgene (40.56 mg, 136.66 μmol). The reaction mixture was warmed to room temperature and stirred for 12 hours under nitrogen atmosphere. After the reaction, the insolubles was removed by filtration and the filtrate was concentrated under reduced pressure. The obtained residue was isolated by preparative HPLC to obtain the crude product WX072-5. $^1$H NMR (400 MHz, CDCl$_3$) δ: 9.49 (br s, 1H), 8.08 (d, J=5.3 Hz, 1H), 7.47-7.35 (m, 2H), 7.28 (br s, 1H), 7.26-7.12 (m, 3H), 7.02 (d, J=5.3 Hz, 1H), 6.73 (d, J=8.3 Hz, 1H), 6.16 (dd, J=4.4, 8.4 Hz, 1H), 4.80 (dd, J=9.7, 14.2 Hz, 1H), 3.87 (dd, J=4.0, 14.6 Hz, 1H), 3.77 (s, 6H), 2.67 (s, 3H).

Step 5: Preparation of Compound WX072

Compound WX072-5 (39.00 mg, 82.71 μmol) was isolated by supercritical fluid chromatography (conditions: column: Chiralpak AD 350×4.6 mm I.D., 3 um; mobile phase: A: carbon dioxide, B: ethanol (0.05% diethylamine); about 40%; column temperature: 40° C.; wavelength: 220 nm) and the sample with the retention time of 0.790 min was collected to obtain WX072 (ee %: 100%).

Embodiment 73: WX073

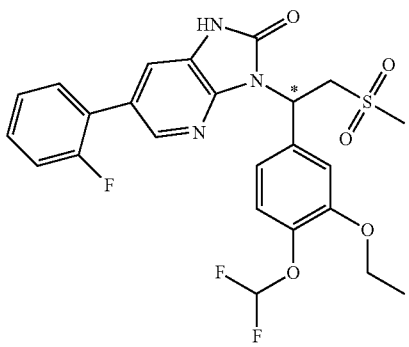 [SMILES: CCOc1cc(C(CS(C)(=O)=O)n2c(=O)[nH]c3cc(-c4ccccc4F)cnc32)ccc1OC(F)F]

Synthetic Route:

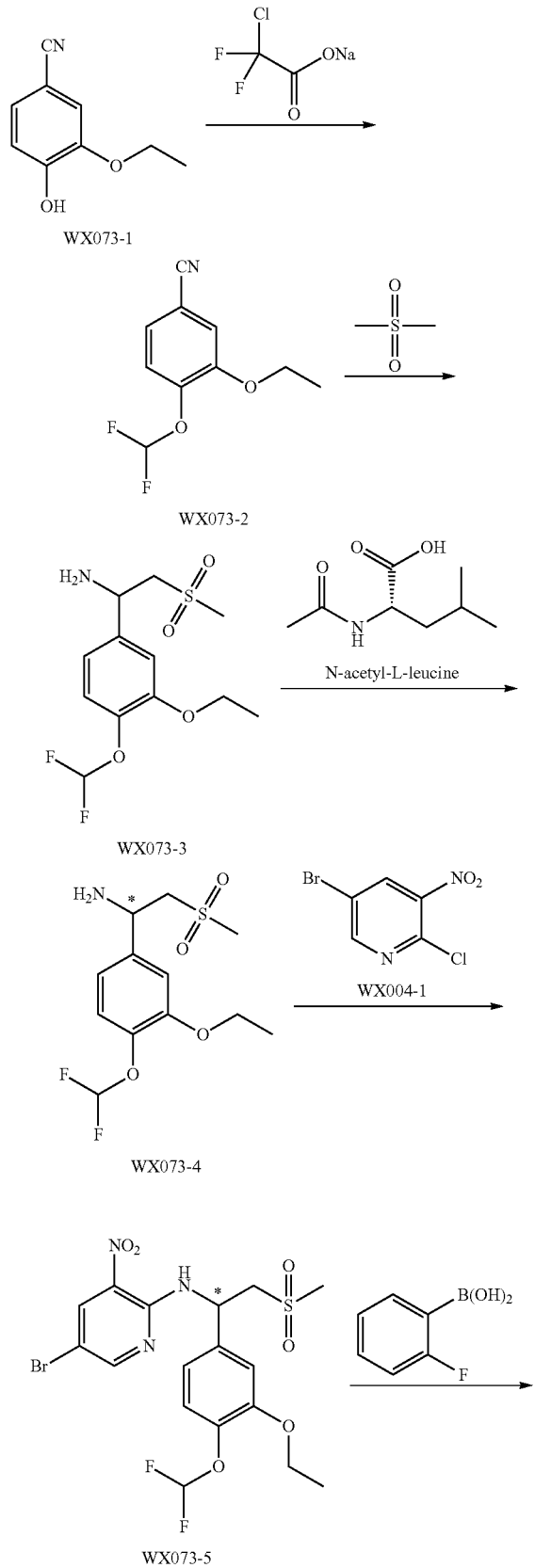

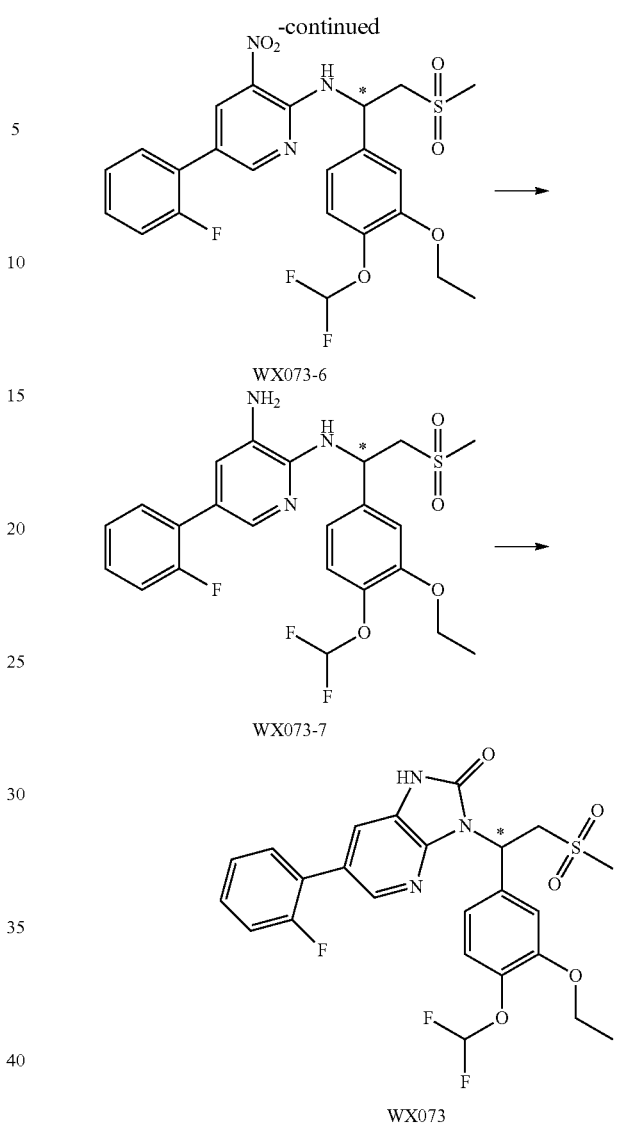

Step 1: Preparation of Compound WX073-2

Compound WX073-1 (29.00 g, 177.73 mmol), sodium 2-chloro-2,2-difluoroacetate (62.32 g, 408.78 mmol) and cesium carbonate (86.86 g, 266.60 mmol) were dissolved in N,N-dimethylformamide (600.00 mL) and water (150.00 mL) at room temperature. The reaction mixture was heated to 100° C. and stirred for 3 hours under nitrogen atmosphere. After the reaction, it was cooled to room temperature and diluted with ethyl acetate (1000 mL) and water (200 mL). The organic phases were separated, washed with saturated brine (200 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=10/1-3/1, volume ratio) to obtain the target product WX073-2. $^1$H NMR (400 MHz, CDCl$_3$) δ: 7.20-7.13 (m, 3H), 6.58 (t, J=74.4 Hz, 1H), 4.05 (q, J=6.8 Hz, 2H), 1.41 (t, J=6.8 Hz, 3H).

Step 2: Preparation of Compound WX073-3

Dimethyl sulfone (9.71 g, 103.20 mmol, 8.37 mL) was dissolved in tetrahydrofuran (300 mL) at room temperature. The reaction mixture was cooled to 0° C. under nitrogen atmosphere, followed by the dropwise addition of n-butyllithium (2.5 M, 41.28 mL). The reaction mixture was stirred at 0-5° C. for 1 hour, followed by the dropwise addition of the solution of compound WX073-2 (20.00 g, 93.82 mmol) in tetrahydrofuran (200.00 mL). The reaction mixture was stirred at 0-5° C. for further 30 minutes under nitrogen atmosphere and then warmed to room temperature with stirring for 1.5 hours, followed by the addition of sodium borohydride (4.61 g, 121.97 mmol) with stirring for further 30 minutes. The reaction mixture was then cooled to 0° C., followed by the addition of acetic acid (25.92 g, 431.57 mmol, 24.69 mL) with stirring at 0-5° C. for further 2 hours and aqueous sodium hydroxide solution (2.5 M, 123.84 mL) with stirring at 0-5° C. for further 30 minutes. The reaction mixture was heated to 60° C. and stirred with reflux for 12 hours. After the reaction, the mixture was cooled to room temperature and diluted with ethyl acetate (1000 mL) and water (200 mL). The organic phases were separated, washed with saturated brine (200 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=100/1-10/1, volume ratio) to obtain the target product WX073-3. $^1$H NMR (400 MHz, CDCl$_3$) δ: 7.08-6.84 (m, 3H), 6.50 (t, J=75.2 Hz, 1H), 4.58 (dd, J=2.8, 9.6 Hz, 1H), 4.04 (dd, J=6.8, 13.2 Hz, 2H), 3.27-3.12 (m, 2H), 2.90 (s, 3H), 1.38 (t, J=7.2 Hz, 3H).

Step 3: Preparation of Compound WX073-4

Compound WX073-3 (9.00 g, 29.10 mmol) and N-acetyl-L-leucine (3.02 g, 17.46 mmol) were dissolved in methanol (100.00 mL) at room temperature. The reaction mixture was heated to 80° C. and stirred for 2 hours under nitrogen atmosphere. Subsequently, the reaction mixture was cooled to room temperature with large amounts of solid precipitated, followed by filtration. The filter cake was dried in vacuum at 30-40° C. The obtained crude product was dissolved in methanol (100.00 mL), heated to 80° C. and stirred for 1 hour. The reaction mixture was cooled to room temperature with large amounts of solid precipitated, followed by filtration. The filter cake was washed with methanol (30.00 mL) and dried in vacuum at 30° C. The obtained white solid was dissolved in ethyl acetate (100 mL) and saturated sodium hydrogen sulfate solution (30 mL) and stirred at room temperature for 15 minutes. The organic phases were separated, washed with saturated brine (20 mL) and dried over anhydrous sodium sulfate, followed by filtration. The filtrate was concentrated under reduced pressure to remove the solvent to obtain the target product WX073-4. (retention time=2.853 min; Column: chiral pack AD_3 100×4.6 mm, 3 μm; Run Time: 10.0 Minutes).

Step 4: Preparation of Compound WX073-5

Compound WX073-4 (600.00 mg, 1.94 mmol) and compound WX004-1 (690.84 mg, 2.91 mmol) were dissolved in acetonitrile (6.00 mL) at room temperature, followed by the addition of potassium carbonate (402.19 mg, 2.91 mmol). The reaction mixture was heated to 85° C. and stirred for 5 hours under nitrogen atmosphere. After the reaction, the mixture was cooled to room temperature and diluted with dichloromethane (15 mL), followed by filtration. The filtrate was concentrated to remove the solvent. The obtained residue was isolated by silica gel column chromatography (eluent: petroleum ether/ethyl acetate=10/1-1/1, volume ratio) to obtain the crude product WX073-5. $^1$H NMR (400 MHz, CDCl$_3$) δ: 8.81 (d, J=7.3 Hz, 1H), 8.58 (d, J=2.3 Hz, 1H), 8.44 (s, 1H), 7.20 (d, J=8.3 Hz, 1H), 7.08-6.97 (m, 2H), 6.58 (t, J=75.0 Hz, 1H), 6.05-5.94 (m, 1H), 4.17-4.06 (m, 2H), 3.76 (dd, J=7.7, 14.7 Hz, 1H), 3.53 (dd, J=5.5, 14.6 Hz, 1H), 2.76 (s, 3H), 1.46 (t, J=7.2 Hz, 3H).

Step 5: Preparation of Compound WX073-6

Compound WX073-5 (250.00 mg, 489.90 μmol) and 2-fluorophenylboronic acid (102.82 mg, 734.85 μmol) were dissolved in dioxane (3 mL) and water (1 mL) at room temperature, followed by the addition of [1,1'-bis(diphenylphosphino)ferrocene] palladium dichloride dichloromethane complex (20.00 mg, 24.50 μmol) and potassium carbonate (101.56 mg, 734.85 μmol). The reaction mixture was heated to at 80° C. and stirred for 4 hours under nitrogen atmosphere. After the reaction, the mixture was cooled to room temperature, quenched with saturated brine (20 mL), diluted with water (20 mL) and extracted with ethyl acetate (10 mL×3). The organic phases were combined, washed with water (20 mL×2) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=10/1-2/1, volume ratio) to obtain the target product WX073-6. $^1$H NMR (400 MHz, CDCl$_3$) δ: 8.85 (d, J=7.3 Hz, 1H), 8.71-8.62 (m, 2H), 7.46-7.33 (m, 2H), 7.26-7.16 (m, 3H), 7.10 (d, J=2.0 Hz, 1H), 7.05 (dd, J=2.0, 8.0 Hz, 1H), 6.59 (t, J=75.2 Hz, 1H), 6.18-6.03 (m, 1H), 4.17-4.17 (m, 1H), 4.14 (q, J=7.0 Hz, 1H), 3.84 (dd, J=7.4, 14.9 Hz, 1H), 3.57 (dd, J=5.8, 14.6 Hz, 1H), 2.78 (s, 3H), 1.47 (t, J=7.0 Hz, 3H).

Step 6: Preparation of Compound WX073-7

Compound WX073-6 (191.00 mg, 363.46 μmol) and ammonium chloride (194.42 mg, 3.63 mmol, 127.07 μL) were dissolved in methanol (10 mL) at room temperature, followed by the addition of zinc powder (118.83 mg, 1.82 mmol). The reaction mixture was stirred at room temperature for 15 minutes under nitrogen atmosphere. After the reaction, the zinc powder was removed by filtration and the filtrate was concentrated under reduced pressure to remove the solvent. Dichloromethane (30 mL) was added to the obtained residue and stirred for 15 minutes, followed by filtration. The filtrate was concentrated under reduced pressure to remove the solvent to obtain the crude product WX073-7.

Step 7: Preparation of Compound WX073

Compound WX073-7 (120.00 mg, 242.17 μmol) and triethylamine (122.53 mg, 1.21 mmol, 167.85 μL) were dissolved in tetrahydrofuran (40.00 mL) at room temperature. The reaction mixture was cooled to 0° C., followed by the addition of triphosgene (40.56 mg, 136.66 μmol). The reaction mixture was stirred at 0° C. for 0.5 hour under nitrogen atmosphere and then warmed to room temperature and stirred for 12 hours. After the reaction, the mixture was quenched with saturated sodium bicarbonate solution (20 mL), diluted with water (20 mL) and extracted with ethyl acetate (15 mL×3). The organic phases were combined, washed with saturated brine (50 mL×2) and dried over anhydrous sodium sulfate, followed by filtration. The filtrate was concentrated under reduced pressure to remove the solvent. The obtained residue was isolated by preparative HPLC to obtain the target product WX073. MS-ESI m/z: 521.9 [M+H]$^+$. $^1$H NMR (400 MHz, CDCl$_3$) δ: 9.79 (br s, 1H), 8.24 (s, 1H), 7.55 (s, 1H), 7.46 (s, 1H), 7.45-7.35 (m, 2H), 7.28 (d, J=17.6 Hz, 2H), 7.24-7.12 (m, 2H), 6.54 (t, J=75.2 Hz, 1H), 6.31 (dd, J=3.0, 9.5 Hz, 1H), 5.04 (dd, J=10.3, 14.3 Hz, 1H), 4.17-4.05 (m, 2H), 3.86 (dd, J=3.1, 14.4 Hz, 1H), 2.86 (s, 3H), 1.42 (t, J=6.8 Hz, 3H).

Embodiment 74: WX074

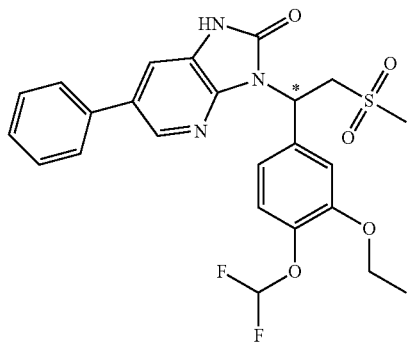 [SMILES: CCOc1cc(C(CS(C)(=O)=O)n2c(=O)[nH]c3cc(-c4ccccc4)cnc32)ccc1OC(F)F]

Synthetic Route:

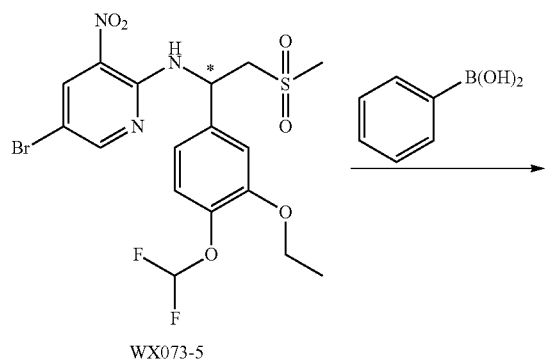

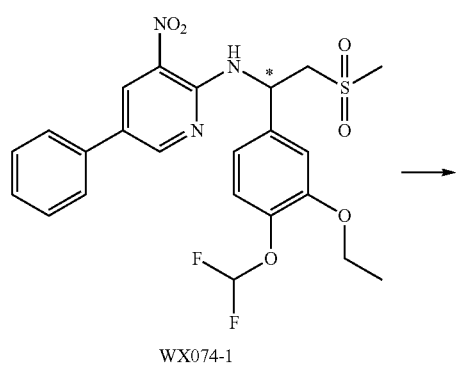

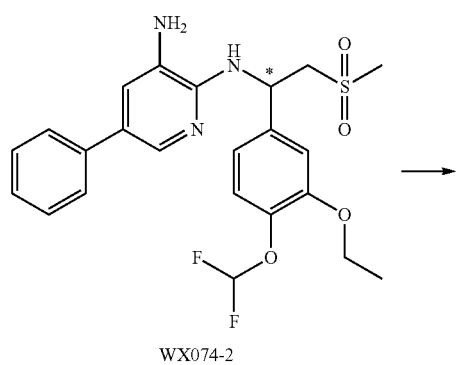

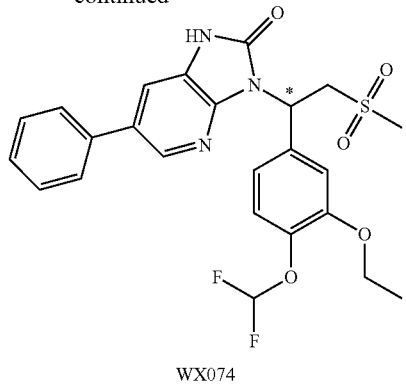

WX074

Step 1: Preparation of Compound WX074-1

Compound WX073-5 (250.00 mg, 489.90 μmol) and phenylboronic acid (89.60 mg, 734.85 μmol) were dissolved in dioxane (3.00 mL) and water (1.00 mL) at room temperature, followed by the addition of [1,1'-bis(diphenylphosphino)ferrocene] palladium dichloride dichloromethane complex (20.00 mg, 24.50 μmol) and potassium carbonate (101.56 mg, 734.85 μmol). The reaction mixture was heated to 80° C. and stirred for 4 hours under nitrogen atmosphere. After the reaction, the mixture was cooled to room temperature, quenched with saturated brine (20 mL), diluted with water (20 mL) and extracted with ethyl acetate (10 mL×3). The organic phases were combined, washed with water (20 mL×2) and dried over anhydrous sodium sulfate, followed by filtration. The filtrate was concentrated under reduced pressure to remove the solvent. The obtained residue was isolated by column chromatography (eluent: petroleum ether/ethyl acetate=10/1-2/1, volume ratio) to obtain the target product WX074-1. $^1$H NMR (400 MHz, CDCl$_3$) δ: 8.81 (d, J=7.3 Hz, 1H), 8.70 (d, J=2.5 Hz, 1H), 8.67 (d, J=2.3 Hz, 1H), 7.58-7.45 (m, 5H), 7.24-7.18 (m, 1H), 7.13-7.03 (m, 2H), 6.58 (t, J=75.2 Hz, 1H), 6.17-6.07 (m, 1H), 4.13 (q, J=7.0 Hz, 2H), 3.84 (dd, J=7.4, 14.7 Hz, 1H), 3.56 (dd, J=5.8, 14.6 Hz, 1H), 2.78 (s, 3H), 1.47 (t, J=6.9 Hz, 3H).

Step 2: Preparation of Compound WX074-2

Compound WX074-1 (140.00 mg, 275.86 μmol) and ammonium chloride (147.56 mg, 2.76 mmol) were dissolved in methanol (10 mL) at room temperature, followed by the addition of zinc powder (90.19 mg, 1.38 mmol). The reaction mixture was stirred at room temperature for 30 minutes under nitrogen atmosphere. After the reaction, the zinc powder was removed by filtration and the filtrate was concentrated under reduced pressure to remove the solvent. Dichloromethane (30 mL) was added to the obtained residue and stirred for 15 minutes, followed by filtration. The filtrate was concentrated under reduced pressure to remove the solvent to obtain the crude product WX074-2.

Step 7: Preparation of Compound WX074

Compound WX074-2 (100.00 mg, 209.42 μmol) and triethylamine (105.95 mg, 1.05 mmol, 145.14 μL) were dissolved in tetrahydrofuran (30.00 mL) at room temperature. The reaction mixture was cooled to 0° C., followed by the addition of triphosgene (24.86 mg, 83.77 μmol). The reaction mixture was stirred at 0° C. for 0.5 hour under nitrogen atmosphere and then warmed to room temperature and stirred for 12 hours. After the reaction, the mixture was quenched with saturated sodium bicarbonate solution (20 mL), diluted with water (20 mL) and extracted with ethyl acetate (15 mL×3). The organic phases were combined, washed with saturated brine (50 mL×2) and dried over anhydrous sodium sulfate, followed by filtration. The filtrate was concentrated under reduced pressure to remove the solvent. The obtained residue was isolated by preparative HPLC to obtain the target product WX074. MS-ESI m/z: 503.9 [M+H]⁺. ¹H NMR (400 MHz, CDCl₃) δ: 9.39 (br s, 1H), 8.29 (d, J=1.5 Hz, 1H), 7.56-7.51 (m, 3H), 7.51-7.44 (m, 3H), 7.44-7.38 (m, 1H), 7.30 (dd, J=1.9, 8.4 Hz, 1H), 7.14 (d, J=8.3 Hz, 1H), 6.55 (t, J=75.2 Hz, 1H), 6.33 (dd, J=4.0, 10.3 Hz, 1H), 5.05 (dd, J=10.3, 14.6 Hz, 1H), 4.11 (dquin, J=2.4, 6.9 Hz, 2H), 3.84 (dd, J=4.0, 14.6 Hz, 1H), 2.87 (s, 3H), 1.43 (t, J=7.0 Hz, 3H).

Embodiment 75: WX075

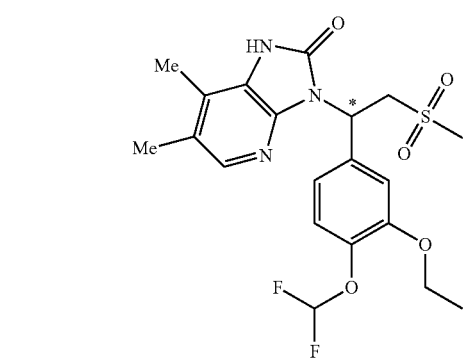 [SMILES: CCOc1cc(C(CS(C)(=O)=O)n2c(=O)[nH]c3c(C)c(C)cnc32)ccc1OC(F)F]

Synthetic Route:

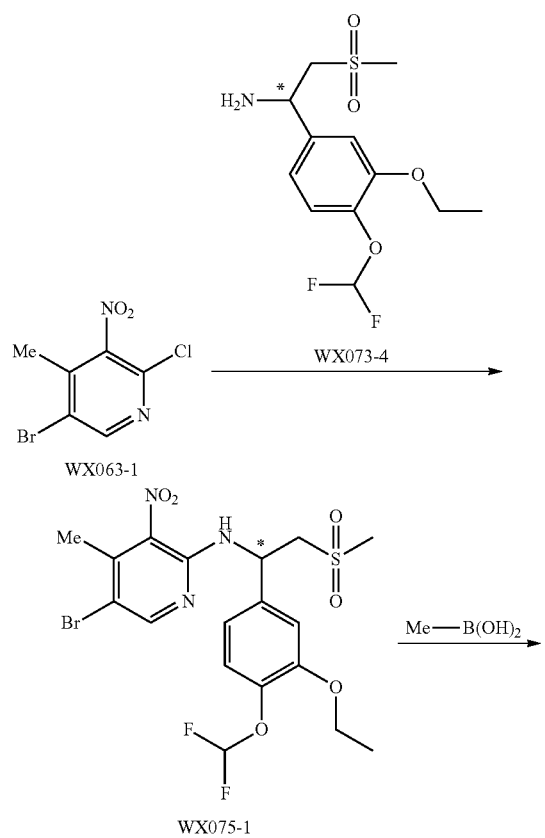

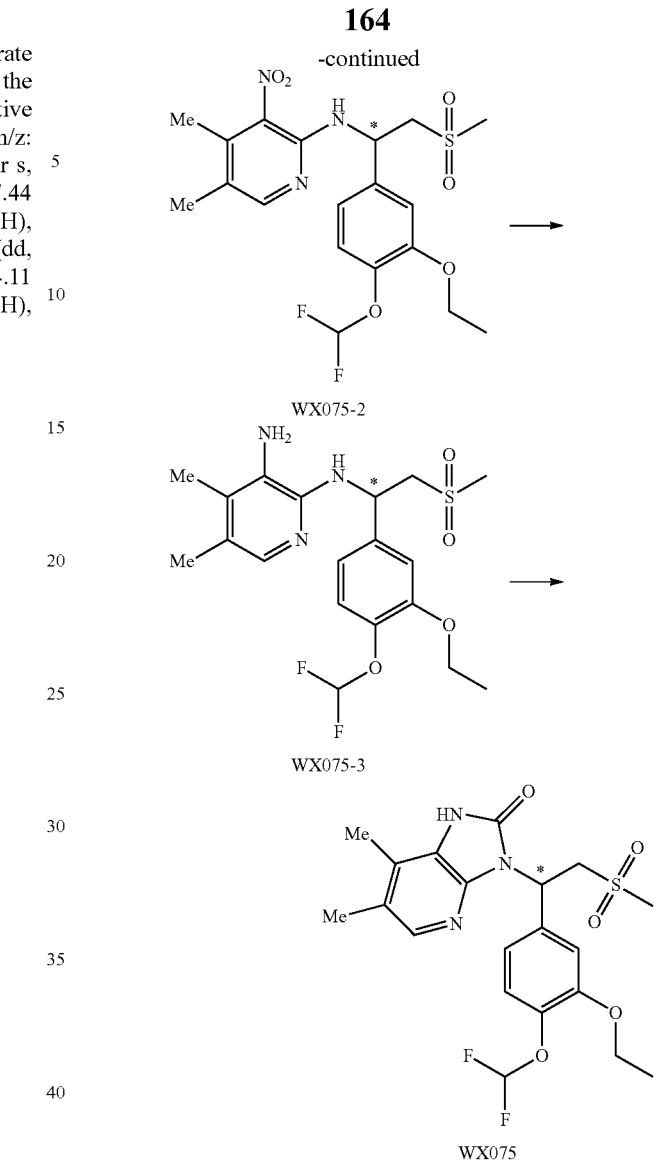

Step 1: Preparation of Compound WX075-1

Compound WX063-1 (1.00 g, 3.98 mmol) and compound WX073-4 (1.35 g, 4.38 mmol) were dissolved in N,N-dimethylformamide (15.00 mL) at room temperature, followed by the addition of diisopropylethylamine (1.54 g, 11.93 mmol, 2.08 mL). The reaction mixture was heated to 120° C. and stirred for 15 hours under nitrogen atmosphere. After the reaction, the mixture was diluted with water (100 mL) and extracted with ethyl acetate (50 mL×3). The organic phases were combined, washed with saturated brine (50 mL) and dried over anhydrous sodium sulfate, followed by filtration. The filtrate was concentrated under reduced pressure to remove the solvent. The obtained residue was isolated by silica gel column chromatography (eluent: petroleum ether/ethyl acetate=3/1, volume ratio) to obtain the target product WX075-1. ¹H NMR (400 MHz, CDCl₃) δ: 8.30 (s, 1H), 7.40 (d, J 8.0 Hz, 1H), 7.16 (d, J=8.5 Hz, 1H), 7.02 (d, J=2.0 Hz, 1H), 6.96 (dd, J=2.0, 8.5 Hz, 1H), 6.55 (t, J=76.0 Hz 1H), 5.85 (dt, J=5.3, 7.4 Hz, 1H), 4.22-4.00 (m, 2H), 3.73 (dd, J=7.8, 14.8 Hz, 1H), 3.46 (dd, J=5.3, 14.8 Hz, 1H), 2.75 (s, 3H), 2.54-2.46 (m, 3H), 1.50-1.39 (m, 3H).

Step 2: Preparation of Compound WX075-2

Compound WX075-1 (200.00 mg, 381.44 μmol), methylboronic acid (68.50 mg, 1.14 mmol) and potassium carbonate (158.16 mg, 1.14 mmol) were dissolved in dioxane (20.00 mL) and water (2.00 mL) at room temperature, followed by the addition of [1,1'-bis(diphenylphosphino)ferrocene] palladium dichloride dichloromethane complex (27.91 mg, 38.14 μmol). The reaction mixture was heated to 80° C. and stirred for 10 hours under nitrogen atmosphere. After the reaction, the mixture was cooled to room temperature and concentrated under reduced pressure to remove the solvent. The obtained residue was diluted with water (30 mL) and extracted with ethyl acetate (30 mL×3). The organic phases were combined, washed with saturated brine (50 mL) and dried over anhydrous sodium sulfate, followed by filtration. The filtrate was concentrated under reduced pressure to remove the solvent. The obtained residue was isolated by column chromatography (eluent: petroleum ether/ethyl acetate=3/1, volume ratio) to obtain the target product WX075-2. MS-ESI m/z: 460.1 [M+H]$^+$.

Step 3: Preparation of Compound WX075-3

Compound WX075-2 (90.00 mg, 195.88 μmol) was dissolved in methanol (15 mL) at room temperature. The reaction mixture was then cooled to 0° C., followed by the addition of zinc powder (128.09 mg, 1.96 mmol) and ammonium chloride (31.43 mg, 587.64 μmol). The reaction mixture was warmed to room temperature and stirred for 2 hours under nitrogen atmosphere. After the reaction, the insolubles was removed by filtration and the filtrate was concentrated under reduced pressure to remove the solvent. The obtained residue was diluted with water (20 mL) and extracted with ethyl acetate (20 mL×3). The organic phase was combined, washed with saturated brine (20 mL) and dried over anhydrous sodium sulfate, followed by filtration. The filtrate was concentrated under reduced pressure to remove the solvent to obtain the crude product WX075-3. MS-ESI m/z: 430.1 [M+H]$^+$.

Step 4: Preparation of Compound WX075

Compound WX075-3 (70.00 mg, 162.99 μmol) and triethylamine (105.95 mg, 1.05 mmol, 145.14 μL) were dissolved in tetrahydrofuran (30.00 mL) at room temperature. The reaction mixture was then cooled to 0° C., followed by the addition of triphosgene (24.86 mg, 83.77 μmol). The reaction mixture was stirred at 0° C. for 0.5 hour under nitrogen atmosphere and then warmed to room temperature and stirred for 12 hours. After the reaction, the mixture was quenched with saturated sodium bicarbonate solution (20 mL), diluted with water (20 mL) and extracted with ethyl acetate (15 mL×3). The organic phases were combined, washed with saturated brine (10 mL) and dried over anhydrous sodium sulfate, followed by filtration.

The filtrate was concentrated under reduced pressure to remove the solvent. The obtained residue was isolated by preparative HPLC to obtain the target product WX075. MS-ESI m/z: 456.0 [M+H]$^+$. $^1$H NMR (400 MHz, CDCl$_3$) δ: 10.59 (s, 1H), 7.81 (s, 1H), 7.49 (s, 1H), 7.30-7.12 (m, 1H), 7.04 (d, J=8.5 Hz, 1H), 6.65-6.28 (m, 2H), 4.97 (t, J=11.0 Hz, 1H), 4.03 (d, J=6.0 Hz, 2H), 3.68 (d, J=13.1 Hz, 1H), 2.86 (br s, 3H), 2.25 (m, 6H), 1.35 (t, J=6.5 Hz, 3H).

Embodiment 76: WX076

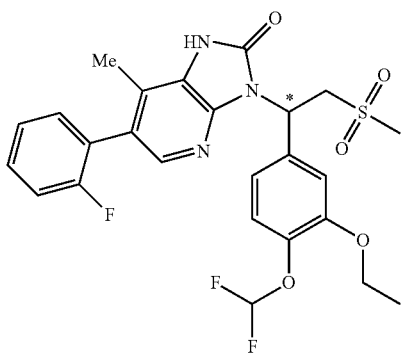 [SMILES: CCOc1cc(C(CS(C)(=O)=O)n2c(=O)[nH]c3c(C)c(-c4ccccc4F)cnc32)ccc1OC(F)F]

Synthetic Route:

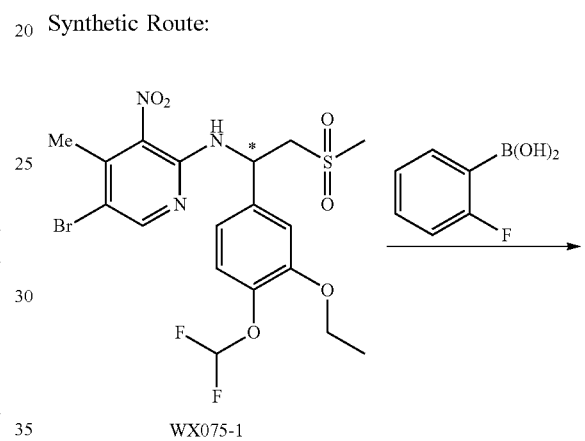

WX075-1

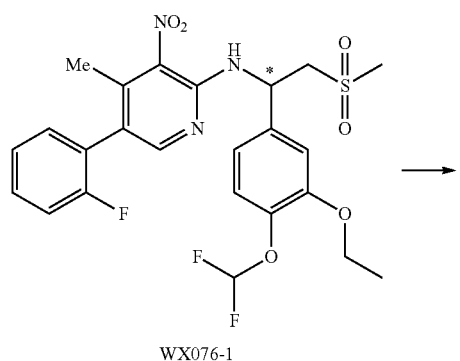

WX076-1

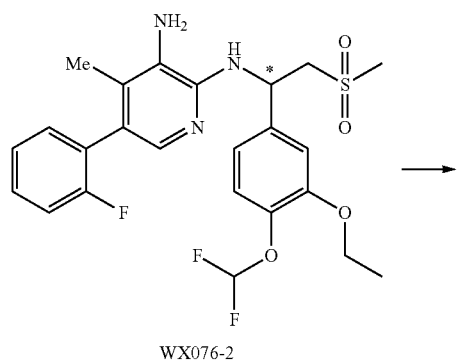

WX076-2

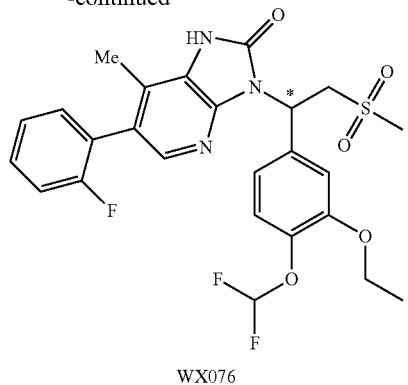

WX076

Step 1: Preparation of Compound WX076-1

Compound WX075-1 (200.00 mg, 381.44 μmol), 2-fluorobenzeneboronic acid (58.71 mg, 419.58 μmol) and potassium carbonate (105.44 mg, 762.88 μmol) were dissolved in dioxane (20.00 mL) and water (1.00 mL) at room temperature, followed by the addition of [1,1′-bis(diphenylphosphino)ferrocene] palladium dichloride dichloromethane complex (27.91 mg, 38.14 μmol). The reaction mixture was heated to 80° C. and stirred for 10 hours under nitrogen atmosphere. After the reaction, the mixture was cooled to room temperature and concentrated to remove the solvent. The residue was diluted with water (30 mL) and extracted with ethyl acetate (30 mL×3). The organic phases were combined, washed with saturated brine (50 mL) and dried over anhydrous sodium sulfate, followed by filtration. The filtrate was concentrated under reduced pressure to remove the solvent. The obtained residue was isolated by column chromatography (eluent: petroleum ether/ethyl acetate=3/1, volume ratio) to obtain the target product WX076-1. MS-ESI m/z: 540.1 [M+H]+.

Step 2: Preparation of Compound WX076-2

Compound WX076-1 (160.00 mg, 296.56 μmol) was dissolved in methanol (15 mL) at room temperature. The reaction mixture was then cooled to 0° C., followed by the addition of zinc powder (193.92 mg, 2.97 mmol, 10.00 eq) and ammonium chloride (47.59 mg, 889.68 μmol). The reaction mixture was warmed to room temperature and stirred for 2 hours under nitrogen atmosphere. After the reaction, the insolubles was removed by filtration and the filtrate was concentrated under reduced pressure to remove the solvent. The obtained residue was diluted with water (20 mL) and extracted with ethyl acetate (20 mL×3). The organic phase was combined, washed with saturated brine (20 mL) and dried over anhydrous sodium sulfate, followed by filtration. The filtrate was concentrated under reduced pressure to remove the solvent to obtain the crude product WX076-2. MS-ESI m/z: 510.5 [M+H]+.

Step 3: Preparation of Compound WX076

Compound WX076-2 (100.00 mg, 196.26 μmol) and triethylamine (119.16 mg, 1.18 mmol, 163.23 μL) were dissolved in tetrahydrofuran (10.00 mL) at room temperature. The reaction mixture was then cooled to 0° C., followed by the addition of triphosgene (34.94 mg, 117.76 μmol). The reaction mixture was stirred at 5° C. for 2 hours under nitrogen atmosphere. After the reaction, the mixture was concentrated to remove the solvent, diluted with water (10 mL) and extracted with ethyl acetate (10 mL×3). The organic phases were combined, washed with saturated brine (10 mL) and dried over anhydrous sodium sulfate, followed by filtration. The filtrate was concentrated under reduced pressure to remove the solvent. The obtained residue was isolated by preparative HPLC to obtain the target product WX076. MS-ESI m/z: 535.9 [M+H]+. 1H NMR (400 MHz, CDCl3) δ: 9.73 (br s, 1H), 7.97 (s, 1H), 7.53 (s, 1H), 7.45 (dd, J=3.5, 8.5 Hz, 1H), 7.34-7.28 (m, 2H), 7.27-7.25 (m, 1H), 7.24-7.05 (m, 2H), 6.54 (t, J=76.0 Hz 1H), 6.45-6.41 (m, 1H), 5.04 (dd, J=10.5, 14.6 Hz, 1H), 4.26-4.01 (m, 2H), 3.90-3.71 (m, 1H), 2.93 (s, 3H), 2.25 (s, 3H), 1.42 (t, J=7.0 Hz, 3H).

Embodiment 77: WX077

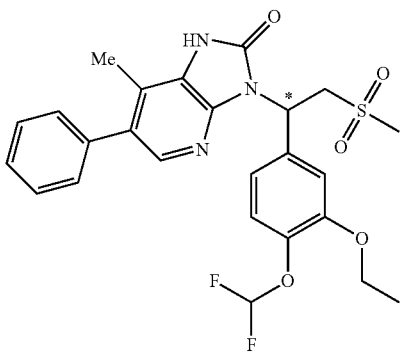 [SMILES: CCOc1cc(C(CS(C)(=O)=O)n2c(=O)[nH]c3c(C)c(-c4ccccc4)cnc32)ccc1OC(F)F]

Synthetic Route:

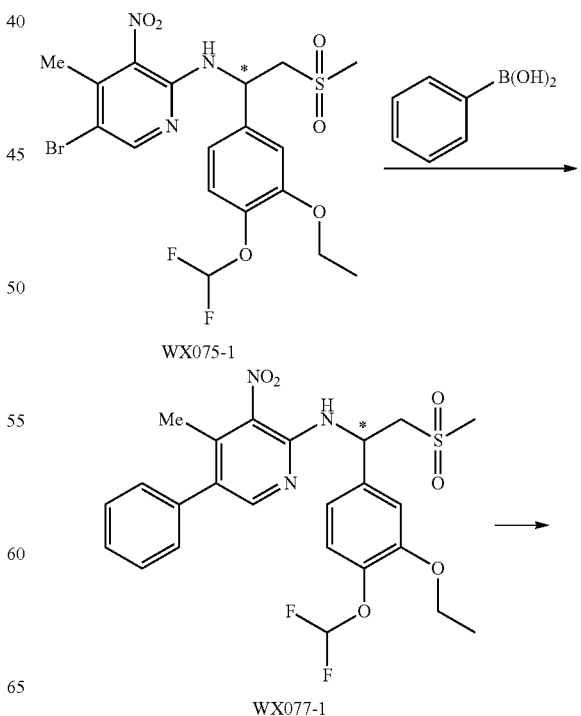

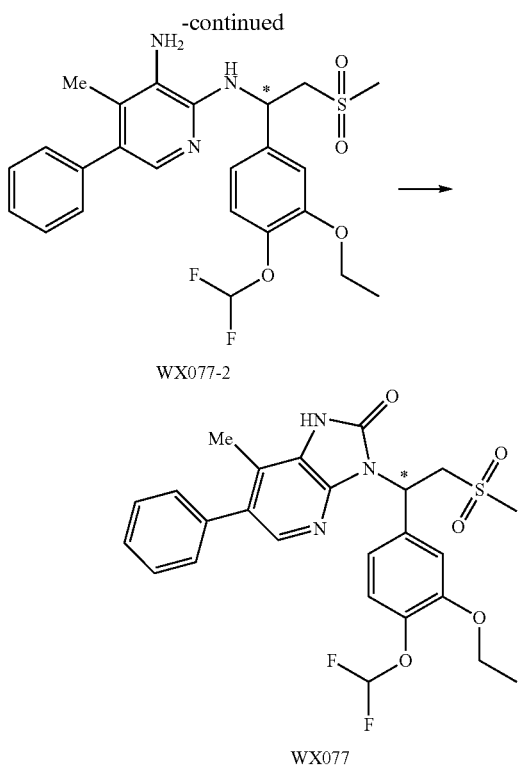

Step 3: Preparation of Compound WX077

Compound WX077-2 (110.00 mg, 223.78 μmol) were dissolved in tetrahydrofuran (10.00 mL) at room temperature. The reaction mixture was then cooled to 0° C., followed by the addition of triphosgene (34.94 mg, 117.76 μmol) and triethylamine (135.87 mg, 1.34 mmol, 186.12 μL). The reaction mixture was stirred at 5° C. for 2 hours under nitrogen atmosphere. After the reaction, the mixture was concentrated under reduced pressure to remove the solvent, diluted with water (10 mL) and extracted with ethyl acetate (10 mL×3). The organic phases were combined, washed with saturated brine (10 mL) and dried over anhydrous sodium sulfate, followed by filtration. The filtrate was concentrated under reduced pressure to remove the solvent. The obtained residue was isolated by preparative HPLC to obtain the target product WX077. MS-ESI m/z: 517.9 [M+H]$^+$. $^1$H NMR (400 MHz, CDCl$_3$) δ: 10.47 (br s, 1H), 7.90 (s, 1H), 7.43-7.30 (m, 4H), 7.23 (d, J=7.0 Hz, 2H), 7.20-7.16 (m, 1H), 7.04 (d, J=8.0 Hz, 1H), 6.46 (t, J=76.0 Hz 1H), 6.25-6.17 (m, 1H), 4.99 (dd, J=10.5, 14.6 Hz, 1H), 4.06-3.95 (m, 2H), 3.76 (dd, J=4.0, 14.6 Hz, 1H), 2.77 (s, 3H), 2.23 (s, 3H), 1.33 (t, J=7.0 Hz, 3H).

Embodiment 78: WX078

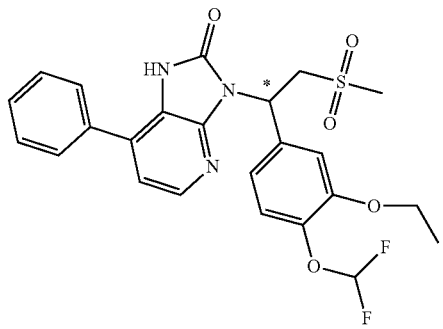 [SMILES: CCOc1cc(C(CS(C)(=O)=O)n2c(=O)[nH]c3c(-c4ccccc4)ccnc32)ccc1OC(F)F]

Synthetic Route:

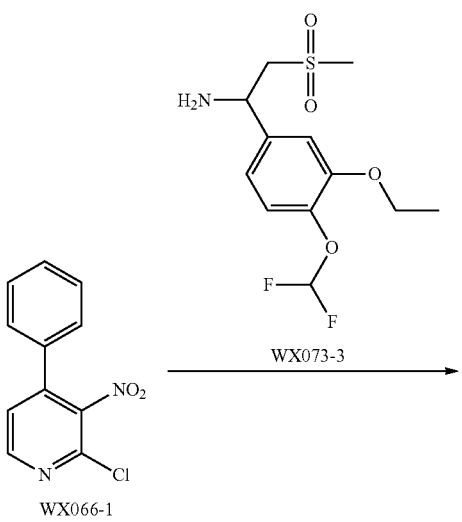

Step 1: Preparation of Compound WX077-1

Compound WX075-1 (200.00 mg, 381.44 μmol), phenylboronic acid (55.81 mg, 457.73 μmol) and potassium carbonate (52.72 mg, 381.44 μmol) were dissolved in dioxane (20.00 mL) and water (2.00 mL) at room temperature, followed by the addition of [1,1'-bis(diphenylphosphino)ferrocene] palladium dichloride dichloromethane complex (279.1 mg, 381.44 μmol). The reaction mixture was heated to 80° C. and stirred for 10 hours under nitrogen atmosphere. After the reaction, the mixture was cooled to room temperature and concentrated under reduced pressure to remove solvent. The residue was diluted with water (30 mL) and extracted with ethyl acetate (30 mL×3). The organic phases were combined, washed with saturated brine (50 mL) and dried over anhydrous sodium sulfate, followed by filtration. The filtrate was concentrated under reduced pressure to remove the solvent. The obtained residue was isolated by column chromatography (eluent: petroleum ether/ethyl acetate=3/1, volume ratio) to obtain the target product WX077-1. MS-ESI m/z: 522.4 [M+H]$^+$.

Step 2: Preparation of Compound WX077-2

Compound WX077-1 (180.00 mg, 345.14 μmol) was dissolved in methanol (15 mL) at room temperature. The reaction mixture was then cooled to 0° C., followed by the addition of zinc powder (225.69 mg, 3.45 mmol) and ammonium chloride (55.38 mg, 1.04 mmol). The reaction mixture was warmed to room temperature and stirred for 2 hours under nitrogen atmosphere. After the reaction, the insolubles was removed by filtration and the filtrate was concentrated under reduced pressure to remove the solvent. The obtained residue was diluted with water (20 mL) and extracted with ethyl acetate (20 mL×3). The organic phase was combined, washed with saturated brine (20 mL) and dried over anhydrous sodium sulfate, followed by filtration. The filtrate was concentrated under reduced pressure to remove the solvent to obtain the crude product WX077-2. MS-ESI m/z: 492.5 [M+H]$^+$.

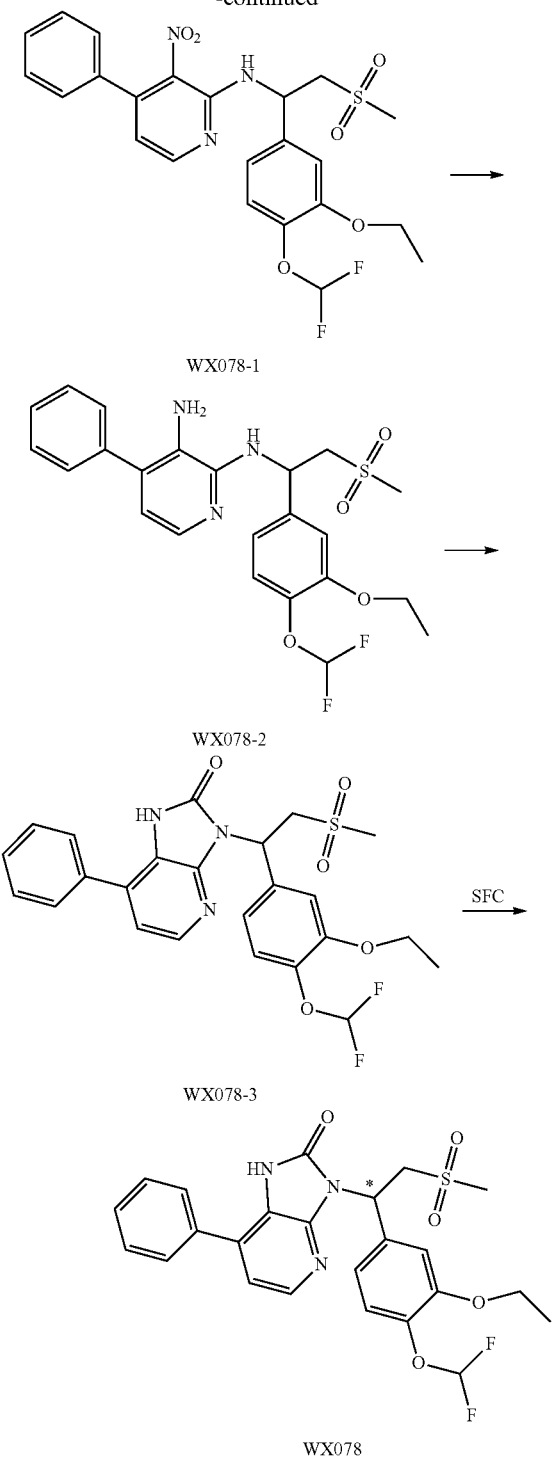

WX078-1

WX078-2

WX078-3

WX078

Step 1: Preparation of Compound WX078-1

Compound WX066-1 (5.00 g, 21.31 mmol), compound WX073-3 (6.59 g, 21.31 mmol) and cesium fluoride (6.47 g, 42.62 mmol) were dissolved in dimethyl sulfoxide (200.00 mL) at room temperature. The reaction mixture was heated to 50° C. and stirred for 12 hours under nitrogen atmosphere. After the reaction, the reaction mixture was cooled to room temperature and diluted with ethyl acetate (800 mL) and water (200 mL), partioned. The organic phase was separated and washed with saturated brine (100 mL×2) and dried over anhydrous sodium sulfate, followed by filtration. The filtrate was concentrated under reduced pressure to remove the solvent. The obtained residue was isolated by column chromatography (eluent: petroleum ether) to obtain the crude product WX078-1. MS-ESI m/z: 508.2 [M+H]$^+$.

Step 2: Preparation of Compound WX078-2

Compound WX078-1 (7.00 g, 13.79 mmol), zinc powder (9.02 g, 137.90 mmol) and ammonium chloride (7.38 g, 137.90 mmol, 4.82 mL) were dissolved in methanol (200.00 mL) at room temperature. The reaction mixture was stirred at room temperature for 5 hours under nitrogen atmosphere. After the reaction, the mixture was filtered by diatomite and the filtrate was concentrated under reduced pressure to remove the solvent. Dichloromethane (100 mL) and water (20 mL) were added to the obtained residue, partioned. The organic phase was separated and washed with saturated brine (20 mL×2) and dried over anhydrous sodium sulfate, followed by filtration. The filtrate was concentrated under reduced pressure to obtain the target product WX078-2. MS-ESI m/z: 478.1 [M+H]$^+$. $^1$H NMR (400 MHz, CDCl$_3$) δ: 7.60-7.54 (m, 1H), 7.44-7.37 (m, 2H), 7.37-7.29 (m, 3H), 7.11-7.05 (m, 2H), 7.00-6.94 (m, 1H), 6.58 (t, J=76 Hz, 1H), 5.68 (q, J=6.4 Hz, 1H), 4.07-3.98 (m, 2H), 3.81 (br dd, J=7.2, 14.7 Hz, 1H), 3.47 (br dd, J=5.4, 14.7 Hz, 2H), 2.78 (s, 3H), 1.36 (t, J=6.9 Hz, 3H).

Step 3: Preparation of Compound WX078-3

Compound WX078-2 (5.00 g, 10.47 mmol), triphosgene (1.86 g, 6.28 mmol) and triethylamine (6.36 g, 62.82 mmol, 8.71 mL) were dissolved in tetrahydrofuran (150.00 mL) at room temperature. The reaction mixture was cooled to 0-5° C. and stirred for 3 hours under nitrogen atmosphere. After the reaction, the mixture was diluted with ethyl acetate (300 mL) and water (100 mL), partioned. The organic phase was separated and washed with saturated brine (100 mL×2) and dried over anhydrous sodium sulfate, followed by filtration. The filtrate was concentrated under reduced pressure. The obtained crude product was purified by column chromatography (eluent: petroleum ether/ethyl acetate=5/1-1/2, volume ratio) to obtain the target product WX078-3. MS-ESI m/z: 504.1 [M+H]$^+$. $^1$H NMR (400 MHz, CDCl$_3$) δ: 9.91 (br s, 1H), 8.07 (d, J=5.5 Hz, 1H), 7.56-7.45 (m, 4H), 7.44-7.37 (m, 1H), 7.33 (d, J=1.8 Hz, 1H), 7.13 (dd, J=1.8, 8.3 Hz, 1H), 7.07-6.99 (m, 2H), 6.45 (t, J=76.0 Hz, 1H), 6.18 (dd, J=4.4, 9.9 Hz, 1H), 4.89 (dd, J=9.9, 14.7 Hz, 1H), 3.99-3.91 (m, 2H), 3.78 (dd, J=4.4, 14.7 Hz, 1H), 2.70 (s, 3H), 1.32 (t, J=6.9 Hz, 3H).

Step 4: Preparation of Compound WX078

Compound WX078-3 (2.50 g, 4.92 mmol) was isolated by supercritical fluid chromatography (conditions: column: Chiralpak AD_3 100×4.6 mm, 3 μm; mobile phase: A: carbon dioxide, B: ethanol (0.05% diethylamine); about 40%; flow rate: 2.8 mL/min; column temperature: 40° C.; wavelength: 220 nm) and the sample with the retention time of 4.842 min was collected to obtain WX078.

Experimental Embodiment 1: Evaluation of the Inhibitory Effect on the Enzyme In Vitro Inhibitory activity of the compounds against PDE 4B The enzyme activity was indicated by measuring the AMP/GMP expression and tracing AMP/GMP antibody binding based on fluorescence polarization in the biological assay.

Reagents:

Experimental Buffer Solution:

10 mM Tris-HCl (pH 7.5), 5 mM MgCl$_2$, 0.01% Brij 35, 1 mM DTT and 1% DMSO.

Enzyme:

Recombinant human PDE4B (Gen accession number: NM_002600; amino acid 305 end) was expressed by baculovirus in Sf9 insect cells using an N-terminal GST tag. MW=78 kDa.

Enzyme Substrate:

1 µM cAMP

Detection:

Transcreener® AMP2/GMP2 antibody and AMP2/GMP2 AlexaFluor633 tracer

Operation Procedures:

i) Recombinant human PDE4B and the enzyme substrate (1 µM cAMP) were dissolved in the newly-prepared buffer solution, respectively.

ii) The PDE4B buffer solution defined as above was transferred into the reaction wells.

iii) The compound which was dissolved in 100% DMSO was added to the reaction wells of the PDE4B buffer solution by ultrasonic oscillator (echo 550; nanoliter range) and incubated at room temperature for 10 minutes.

iv) The enzymatic buffer solution was then added to the reaction wells defined as above to initiate the reaction.

v) The reaction was incubated at room temperature for 1 hour.

vi) The reaction was terminated by adding detecting mixture (Transcreener® AMP2/GMP2 antibody and AMP2/GMP2 AlexaFluor633 tracer) and incubated for 90 minutes with slowly mixing. The measurement range of fluorescence polarization is Ex/Em=620/688.

Data Analysis:

The fluorescence polarization signal was converted into nM according to the AMP/GMP standard curve and the percent enzyme activity relative to DMSO calculated by Excel. GraphPad Prism was used to plot the curves (Drawing Medicine Icon).

TABLE 7

Testing results of inhibitory activity of the compound of the present invention against PDE 4B In vitro

| Compound | $IC_{50}$(nM) |
| --- | --- |
| WX001 | 9.48 |
| WX002 | 5.66 |
| WX003 | 10.6 |
| WX004 | 7.09 |
| WX005 | 5.03 |
| WX006 | 1.80 |
| WX007 | 2.81 |
| WX008 | 4.89 |
| WX009 | 0.860 |
| WX010 | 2.60 |
| WX011 | 3.40 |
| WX012 | 3.90 |
| WX013 | 0.994 |
| WX014 | <0.5 |
| WX015 | 1.04 |
| WX016 | <0.5 |
| WX017 | 0.641 |
| WX018 | 0.391 |
| WX019 | 3.38 |
| WX020 | 65.8 |
| WX021 | 26.1 |
| WX022 | 26.5 |
| WX023 | 68.1 |
| WX024 | 2.70 |
| WX025 | 9.53 |
| WX026 | 4.51 |
| WX027 | 19.1 |
| WX028 | 9.70 |
| WX029 | 14.8 |
| WX030 | 0.515 |

TABLE 7-continued

Testing results of inhibitory activity of the compound of the present invention against PDE 4B In vitro

| Compound | $IC_{50}$(nM) |
| --- | --- |
| WX031 | 0.861 |
| WX032 | 0.234 |
| WX033 | 0.671 |
| WX034 | 5.18 |
| WX035 | 15.5 |
| WX036 | 6.27 |
| WX037 | 10.2 |
| WX038 | 14.5 |
| WX039 | 21.7 |
| WX040 | 10.4 |
| WX041 | 16.4 |
| WX042 | 5.42 |
| WX043 | 2.53 |
| WX044 | 26.6 |
| WX045 | 6.50 |
| WX046 | 7.79 |
| WX047 | 41.6 |
| WX048 | 19.8 |
| WX049 | 90.7 |
| WX050 | 11.0 |
| WX051 | 9.10 |
| WX052 | 8.20 |
| WX053 | 1.49 |
| WX054 | 6.90 |
| WX055 | 6.99 |
| WX056 | 3.40 |
| WX057 | 1.25 |
| WX058 | 1.99 |
| WX059 | 2.02 |
| WX060 | 3.48 |
| WX061 | 0.989 |
| WX062 | 3.50 |
| WX063 | 0.685 |
| WX064 | 2.23 |
| WX065 | 1.87 |
| WX066 | 2.48 |
| WX067 | 18.5 |
| WX068 | 2.24 |
| WX069 | 47.8 |
| WX070 | 73.8 |
| WX071 | 0.740 |
| WX072 | 24.6 |
| WX073 | <0.5 |
| WX074 | 1.03 |
| WX075 | 5.39 |
| WX076 | <0.5 |
| WX077 | 1.01 |
| WX078 | <0.5 |

Conclusion: The compounds of the present invention all exhibit excellent inhibitory activity against PDE4B in vitro.

Experimental Embodiment 2: Evaluation of the Inhibitory Effect Against TNFα in hPBMC In Vitro Inhibitory activity of the compounds against the LPS-induced TNFα from the peripheral monocytes of human.

Experimental Procedure:

1. Whole blood in normal human was collected and EDTA-K2 was used as anticoagulant.

2. PBMC was isolated by Ficoll density gradient centrifugation. The concentration of the cells was adjusted to $2 \times 10^6$/mL.

3. $2 \times 10^5$ of cells were seed in per well of the 96-well U-bottom plate, followed by the addition of 200 µL/well of LPS with 1 ng/mL and 200 µL/per well of the compound with different concentration: 100 µM, 10 µM, 1 µM, 100 µM, 10 µM, 1 pM, 100 pM and 10 pM, with two duplicates of each concentration.

4. The reaction was incubated for 24 hours and the supernatant was collected.

5. ELISA was used to detect the level of TNFα in the supernatant and Graphpad Prism software was used to plot the inhibition curve and calculate the value of $IC_{50}$.

TABLE 8

| Compound | $IC_{50}$ (nM) |
|---|---|
| Apremilast | 16.5 (n = 3) |
| WX057 | 3.4 |
| WX063 | 0.56 (n = 2) |
| WX065 | 8.8 (n = 3) |
| WX066 | 3.8 |
| WX067 | 6.4 |

Conclusion: The compounds of the present invention all exhibit excellent inhibitory activity against TNFα in hPBMC in vitro, which is superior to Apremilast.

Experimental Embodiment 3: In Vivo CIA Model

Experimental Objective:

The collagen-induced mouse arthritis model is an animal model for evaluating the therapeutic effect of drug treatment for psoriatic arthritis, of which pathogenesis and symptoms are obviously related to psoriatic arthritis. The model activated the reactivity of B cells and T cells to collagen by the injection of type II collagen. The activated B cells and T cells were attracted to the joints to cause the inflammation, thereby triggering a series of symptoms related to human psoriatic arthritis, such as redness and swelling of the joints, articular cartilage, joint capsule damage and other symptoms. Collagen-induced mouse arthritis is often used to evaluate the therapeutic effect during preclinical evaluation of candidate compounds for the medication for treating psoriatic arthritis.

The purpose of the experiment was to examine the therapeutic effect of the compound WX063 of embodiment 63 on collagen-induced arthritis in mice, thereby providing the preclinical pharmacodynamics information for subsequent clinical studies.

Experimental Procedure:

1. Immunization of the Type II Collagen and Complete Freund's Adjuvant

Preparation of the acetic acid: The acetic acid was diluted to 100 mM, filtered by 0.22 μm filter membrane and reserved at 4° C.

Preparation of the bovine type II collagen solution: Bovine type II collagen was dissolved in the acetic acid solution and reserved at 4° C.

Preparation of the emulsion: The overnight stored CII solution was mixed with an equal volume of complete Freund's adjuvant and homogenized by high-speed homogenizer to form a stable emulsion.

Preparation of lipopolysaccharide (LPS): weigh the LPS, add normal saline, mix until a stable solution is formed, the concentration of which is 0.3 mg/kg.

2. Induction of Arthritis

Mice were randomly divided into different treatment groups. The first immunization day is recorded as Day 0, and the following days were recorded in order.

After the DBA/1 mice were anesthetized with isoflurane, the prepared collagen emulsion was subcutaneously injected into the tail.

On Day 23, 100 μL of LPS solution was administered intraperitoneally.

Mice in the normal group need no immunization.

3. Administration and Dose

On day 27, as the mean clinical score reached about 1 point, 60 mice with moderate disease were selected and re-randomized according to body weight and score, with 10 mice per group.

Dexamethasone as a positive control drug was administered at a dose of 0.3 mg/kg, which was common in the CIA model. In addition, the relevant dose design of the test compound Example WX063 and the control compound Apremilast was determined based on the results of previous pre-experiments. Group 1 was normal mice without any treatment; Group 2 was treated with vehicle; Group 3 was administered with dexamethasone at a dose of 0.3 mg/kg; Group 4 was administered with Apremilast at a dose of 5 mg/kg; Group 5, Group 6, and Group 7 was administered with the compound WX063 of embodiment 63 at a dose of 0.3, 1 and 3 mg/kg, respectively. It was administered once a day for a total of 11 days. The volume of the intragastric administration was 10 mL/kg.

TABLE 9

| Group and dose | | | | | |
|---|---|---|---|---|---|
| Group | Test compound | Amount | Route of administration | Concentration mg/mL | Dose mg/kg | Dosing frequency |
| 1 | Normal group | 5 | N/A. | N/A | N/A | N/A |
| 2 | Vehicle | 10 | Intragastric administration | N/A | N/A | Once a day, 11 days |
| 3 | Dexamethasone | 10 | Intragastric administration | 0.03 | 0.3 | Once a day, 11 days |
| 4 | Apremilast | 10 | Intragastric administration | 0.5 | 5 | Once a day, 11 days |
| 5 | WX063 of embodiment 63 | 10 | Intragastric administration | 0.03 | 0.3 | Once a day, 11 days |
| 6 | WX063 of embodiment 63 | 10 | Intragastric administration | 0.1 | 1 | Once a day, 11 days |
| 7 | WX063 of embodiment 63 | 10 | Intragastric administration | 0.3 | 3 | Once a day, 11 days |

4. Determination of Arthritis Incidence Index

Clinical observation: From Day 7 before immunization to Day 23 after immunization, the basic health status and the body weight changes of the DBA/1 mice were observed daily (recorded once a week). After Day 23, the health status, the arthritis incidence and the body weight changes of the mice were observed daily (recorded at least three times a week) until the end of the experiment.

Clinical score: After LPS injection, the arthritis incidence of mice was observed daily. As the clinical symptoms of arthritis occurred, the degree of disease was scored according to the standards of 0-4 (redness, joint deformation) at least three times a week, wherein the highest score for each limb was 4 points, and the highest score for each animal was 16 points. The scoring standards were as shown in Table 10. Scored at least three times a week.

TABLE 10

Clinical scoring standard of arthritis

| Score | Clinical symptoms |
|---|---|
| 0 | No erythema and swelling |
| 1 | Mild erythema and swelling near the tarsal, ankle or metatarsus; swelling on one toe |
| 2 | Slight erythema and swelling of the ankle and metatarsus; swelling on more than two toes |
| 3 | Moderate erythema and swelling on the ankle, wrist and metatarsus |
| 4 | Severe erythema and swelling on the ankel, wrist, metatarsus and toes |

Pathology: On day 38, the mice were euthanized. The hind limbs of the mice were taken, soaked in the 10% formalin solution, decalcified with formic acid solution, embedded in paraffin, sectioned, and stained with hematoxylin-eosin and photographed by microscopy. The degree of joint damage was evaluated from four aspects: inflammatory cell infiltration, formation of vasospasm, cartilage damage and bone resorption, and scored according to the standards of 0-4. The various scoring standards were shown in Table 11.

TABLE 11

Pathological scoring standard of arthritis

| Pathological changes | Characteristics of pathological changes | Score |
|---|---|---|
| Inflammatory cell infiltration | No inflammatory cell | 0 |
| | Subserosal cell fibrosis with little cell infiltration | 1 |
| | Synovial cell hyperplasia with a small amount of mononuclear cell infiltration | 2 |
| | Synovial cell hyperplasia with a large amount of monocytes, plasma cells and lymphocytes infiltration | 3 |
| | Inflammation of the inflammatory cells around the joints, tissue fibrosis and thickening of the synovium | 4 |
| Formation of vasospasm | No formation of vasospasm | 0 |
| | Very few vasospasm formation on the edge of the cartilage | 1 |
| | Interstitial fibrous tissue hyperplasia, a small amount of vasospasm formation on the edge of the joint | 2 |
| | Formation of vasospasm on 50% of articular cartilage | 3 |
| | Formation of vasospasm on the whole articular cartilage | 4 |
| Cartilage damage | No cartilage damage | 0 |
| | Articular chondrocyte proliferation | 1 |
| | Chondrocyte matrix lost, a small amount of chondrocytes destroyed | 2 |
| | Fibroplasia around the joints, a large amount of chondrocytes destroyed | 3 |
| | A large amount of fibrous tissue hyperplasia between articular cartilage, cartilage erosion | 4 |
| Bone resorption | No bone resorption | 0 |
| | Little bone resorption at the edge of the synovial membrane | 1 |
| | A small amount of osteoclasts in small-scale bone tissue | 2 |
| | Bone resorption on partial articular cartilage bone tissue | 3 |
| | Bone resorption on a large range of bone tissue with cartilage erosion | 4 |

5. Statistical Processing

The experimental data were expressed as mean value±standard error of mean (Mean±SEM). The body weight and the clinical scores were analyzed by double factor variance (two-way ANOVA). Pathological scores and AUC were tested by T test. $p<0.05$ was considered as significant difference.

Experimental Results:

1. Clinical Score

On Day 25 after the first immunization (Day 2 after the second immunization), the mice began to develop the clinical symptoms of arthritis. Administration was started on Day 27. The mean clinical score of the vehicle control group gradually increased to 8.3 points on Day 36, indicating the successful establishment of a collagen-induced arthritis model.

Compared with the vehicle control group, the compound WX063 of embodiment 63 at a dose of 0.3, 1 and 3 mg/kg significantly reduced the clinical score of arthritic mice at the end of the experiment (Day 37) and the mean clinical score of three doses decreased to 3.6 ($p<0.0001$), 4.3 ($p<0.001$) and 3.5 ($p<0.0001$), respectively. Therefore, the compound WX063 of embodiment 63 effectively relieves the collagen-induced arthritis at a dose as low as 0.3 mg/kg. Dexamethasone at a dose of 0.3 mg/kg significantly inhibited the increase of the clinical score of the collagen-induced arthritis. The clinical score was 0 on Day 30 and maintained to the end of the trial, which was significantly different from the vehicle control group ($p<0.0001$). The group of Apremilast at a dose of 5 mg/kg also inhibited the increase of the clinical score and exhibited significant difference from the vehicle control group from Day 33 to the end of the trial. On Day 37, the mean clinical score was 4.2, which was 3.7 points lower ($p<0.001$) compared with the vehicle control group.

The area under curve (AUC) was calculated by analyzing the clinical score curve of each animal in each group, and the percentage inhibition of each administration group relative to the vehicle control group was calculated by the mean area under the curve between the groups. Compared with the vehicle control group, the clinical scores of arthritis animals were significantly reduced in the dexamethasone group and the Apremilast group, and the percentage inhibition was 96.4% ($p<0.0001$) and 41.3% ($p<0.05$), respectively. The compound WX063 of embodiment 63 at a dose of 0.3, 1 and 3 mg/kg significantly reduced the area under the clinical scoring curve of arthritis animals. The inhibition rate was 43.9% ($p<0.05$), 39.4% ($p<0.05$) and 51.7% ($p<0.01$), respectively. The percentage inhibition of 1 mg/kg WX063 group was comparable to the one of 5 mg/kg Apremilast group ($p<0.05$ for both groups), while the percentage inhibition of 3 mg/kg WX063 group was superior to the one of 5 mg/kg Apremilast group ($p<0.01$ and $<0.05$, respectively).

2. Histopathological Score

The hind limbs of each group of mice were taken for HE staining, taking the two hind limbs as total score. The total pathological score of the arthritic mice in the vehicle control group was 20.20±1.15. Compared with the vehicle control group, the pathological score of arthritic mice in the control 5 mg/kg Apremilast group was also significantly reduced to 13.90±1.89 (p<0.05). The compound WX063 of embodiment 63 at a dose of 1 and 3 mg/kg significantly reduced the pathological scores of arthritis mice to 14.00±2.43 (p<0.05) and 9.20±1.83 (p<0.0001). The arthritis pathological score of 1 mg/kg WX063 group was comparable to the one of 5 mg/kg Apremilast group (p<0.05), while the arthritis pathological score of 3 mg/kg WX063 group was superior to the one of 5 mg/kg Apremilast group (p<0.0001 and <0.05, respectively).

3. Conclusion

1) The compound WX063 of embodiment 63 has a significant improvement in the treatment of collagen-induced arthritis and in the pathological changes of arthritis at the doses of 0.3, 1 and 3 mg/kg. The three dose groups exhibited a significant dose-effect relationship in the arthritis pathological score.

2) The therapeutic effect of WX063 at a dose of 3 mg/kg (clinical score and arthritis pathology score) is better than the one of Apremilast at a dose of 5 mg/kg.

What is claimed is:

1. A compound as shown in formula (I) or a pharmaceutically acceptable salt thereof,

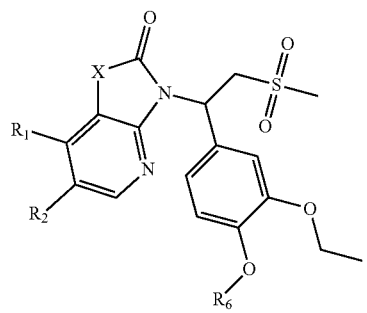

(I)

wherein,

X is selected from the group consisting of O, N($R_3$), and —CH($R_3$)—;

$R_3$ is selected from the group consisting of H, F, Cl, Br, I, OH, CN, $NH_2$, COOH, and $R_4$-$L_1$-, or selected from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, each of which is optionally substituted by 1, 2 or 3 R;

$R_4$ is selected from the group consisting of $C_{3-6}$ cycloalkyl, 3-6 membered heterocycloalkyl, phenyl and 5-6 membered heteroaryl, each of which is optionally substituted by 1, 2 or 3 R;

$L_1$ is selected from the group consisting of —$CH_2$—, —$CH_2CH_2$—, O, S, NH, and —C(=O)—;

$R_1$ and $R_2$ are each independently selected from the group consisting of H, F, Cl, Br, I, OH, CN, $NH_2$, and $R_5$-$L_2$-, or selected from the group consisting of $C_{1-6}$ alkyl, $C_{1-6}$ alkoxy, $C_{1-6}$ alkylthio, $C_{1-6}$ alkylamino, $C_{2-6}$ alkenyl, $C_{3-6}$ cycloalkenyl, 3-6 membered heterocycloalkenyl, $C_{3-6}$ cycloalkyl, 3-6 membered heterocycloalkyl, phenyl and 5-6 membered heteroaryl, each of which is optionally substituted by 1, 2 or 3 R;

$R_5$ is selected from the group consisting of $C_{3-6}$ cycloalkyl, 3-6 membered heterocycloalkyl, 3-6 membered heterocycloalkenyl, phenyl and 5-6 membered heteroaryl, each of which is optionally substituted by 1, 2 or 3 R;

$L_2$ is selected from the group consisting of —$CH_2$—, —$CH_2CH_2$—, O, S, and NH;

$R_6$ is $C_{1-3}$ alkyl, which is optionally substituted by 1, 2 or 3 R;

R is selected from the group consisting of H, halogen, OH, $NH_2$, and CN, or selected from the group consisting of $C_{1-6}$ alkyl and $C_{1-6}$ heteroalkyl, each of which is optionally substituted by 1, 2 or 3 R';

R' is selected from the group consisting of H, F, Cl, Br, I, OH, $NH_2$, Me, Et, $CF_3$, $CHF_2$, $CH_2F$, $NHCH_3$, and $N(CH_3)_2$;

the "hetero" in the $C_{1-6}$ heteroalkyl, 3-6 membered heterocycloalkyl, 5-6 membered heteroaryl and 3-6 membered heterocycloalkenyl is selected from the group consisting of —C(=O)NH—, —NH—, —C(=NH)—, —S(=O)$_2$NH—, —S(=O)NH—, —O—, —S—, =O, =S, —O—N=, —C(=O)O—, —C(=O)—, —C(=S)—, —S(=O)—, —S(=O)$_2$— and —NHC(=O)NH—;

the "hetero" represents a heteroatom or a heteroatom group;

in any of the above cases, the number of the heteroatom or the heteroatom group is independently selected from the group consisting of 1, 2, and 3.

2. The compound or the pharmaceutically acceptable salt thereof according to claim 1, wherein R is selected from the group consisting of H, F, Cl, Br, I, OH, $NH_2$, and CN, or selected from the group consisting of $C_{1-3}$ alkyl, $C_{1-3}$ alkoxy, $C_{1-3}$ alkylthio, $C_{1-3}$ alkylamino, $C_{1-4}$-alkyl-OC(=O)— and N,N'-di($C_{1-3}$ alkyl)amino, each of which is optionally substituted by 1, 2 or 3 R'.

3. The compound or the pharmaceutically acceptable salt thereof according to claim 1, wherein $R_4$ is selected from the group consisting of phenyl, pyridyl, pyrimidinyl, pyrazinyl, thienyl, imidazolyl, pyrazolyl, oxazolyl, thiazolyl, isoxazolyl and isothiazolyl, each of which is optionally substituted by 1, 2 or 3 R.

4. The compound or the pharmaceutically acceptable salt thereof according to claim 1 wherein $R_4$-$L_1$- is selected from the group consisting of

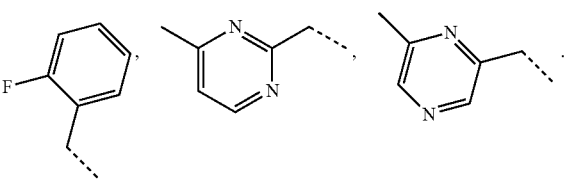

5. The compound or the pharmaceutically acceptable salt thereof according to claim 1, wherein $R_3$ is selected from the group consisting of H, F, Cl, Br, I, OH, $NH_2$, and $R_4$-$L_1$-, or selected from the group consisting of $C_{1-3}$ alkyl, $C_{3-6}$ cycloalkyl, —$C_{1-3}$-alkyl-C(=O)O—$C_{1-3}$ alkyl-, $C_{1-3}$-alkyl-S(=O)$_2$—$C_{1-3}$ alkyl-, phenyl, pyridyl, pyrimidinyl and pyrazinyl, each of which is optionally substituted by 1, 2 or 3 R.

6. The compound or the pharmaceutically acceptable salt thereof according to claim 1, wherein X is selected from the group consisting of

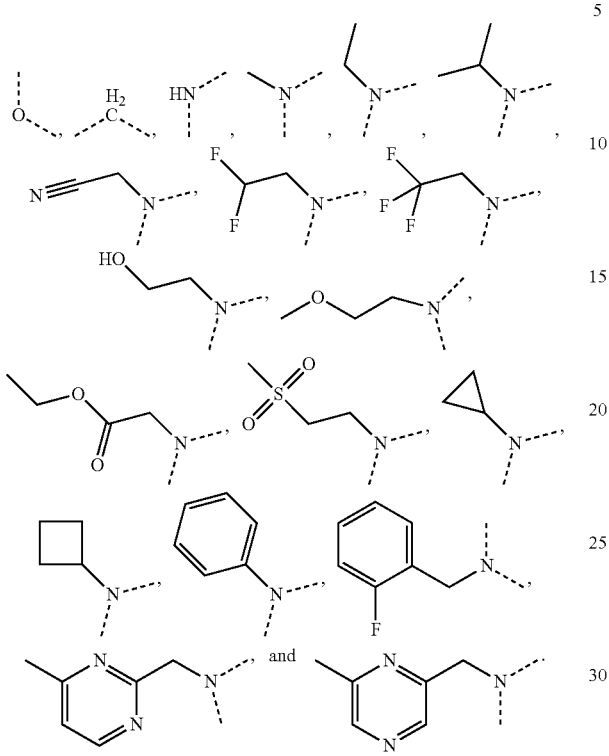

7. The compound or the pharmaceutically acceptable salt thereof according to claim 1, wherein R₅ is selected from the group consisting of phenyl, pyridyl, pyrimidinyl, pyrazinyl, pyridazinyl, thienyl, imidazolyl, pyrazolyl, oxazolyl, thiazolyl, isoxazolyl and isothiazolyl, each of which is optionally substituted by 1, 2 or 3 R.

8. The compound or the pharmaceutically acceptable salt thereof according to claim 1, wherein R₅-L₂- is selected from the group consisting of

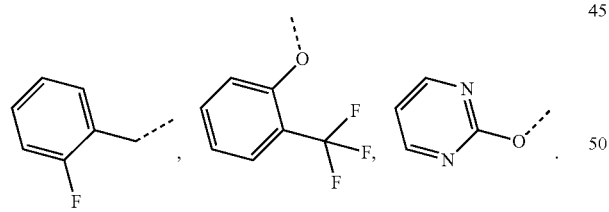

9. The compound or the pharmaceutically acceptable salt thereof according to claim 1, wherein R₁ and R₂ are each independently selected from the group consisting of H, F, Cl, Br, I, OH, NH₂, CN, and R₅-L₂-, or selected from the group consisting of C₁₋₃ alkyl, C₁₋₃ alkoxy, C₁₋₃ alkylthio, C₁₋₃ alkylamino, C₂₋₄ alkenyl, 1,2,3,6-tetrahydropyridyl, pyridin-2(1H)-one-yl, phenyl, pyridyl, pyrimidinyl, pyrazinyl, pyridazinyl, pyrazolyl, imidazolyl, thiazolyl, isothiazolyl and thienyl, each of which is optionally substituted by 1, 2 or 3 R.

10. The compound or the pharmaceutically acceptable salt thereof according to claim 1, wherein R₆ is selected from the group consisting of Me and Et, each of which is optionally substituted by 1, 2 or 3 R.

11. The compound or the pharmaceutically acceptable salt thereof according to claim 1, which is selected from the group consisting of

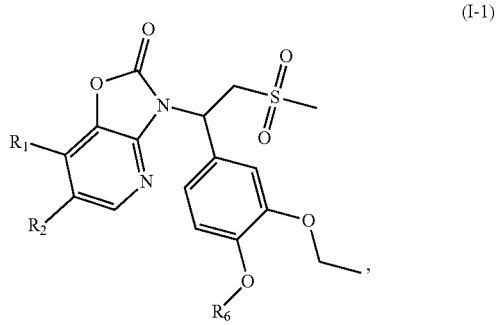

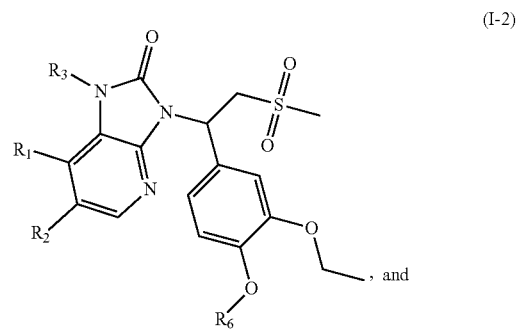

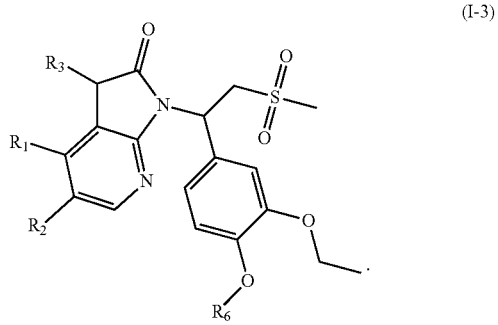

12. The compound or the pharmaceutically acceptable salt thereof according to claim 11, which is selected from the group consisting of

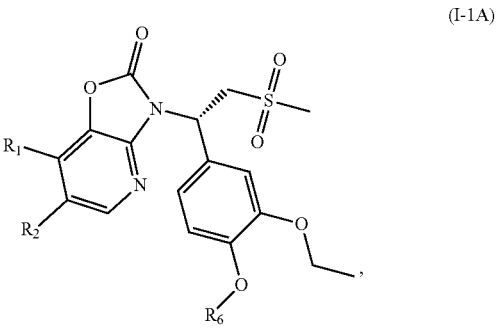

-continued (I-1B) 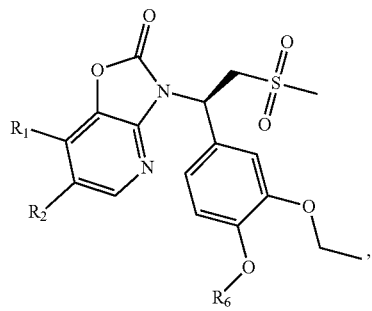, (I-2A) 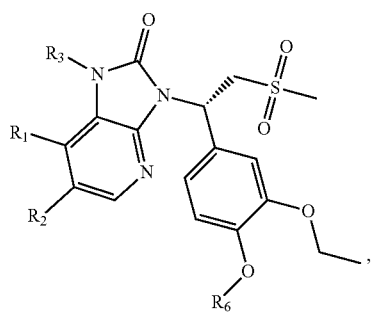, (I-2B) 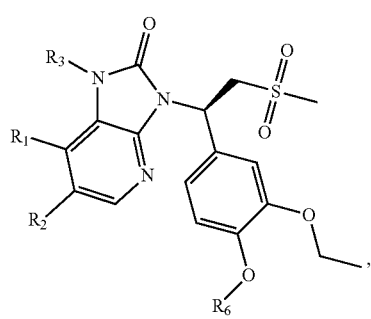, (I-3A) 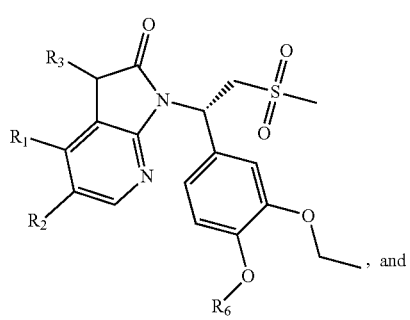, and (I-3B) 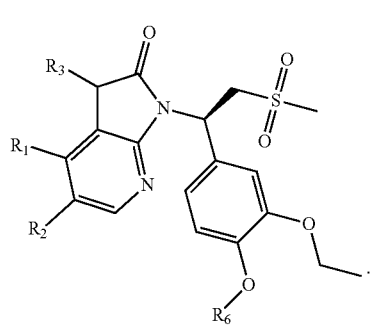.

13. The compound or the pharmaceutically acceptable salt thereof according to claim 1, wherein $R_4$ is selected from the group consisting of

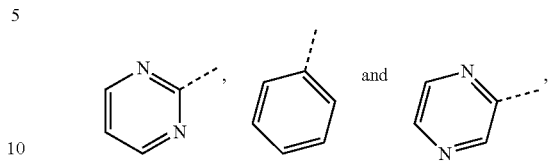

each of which is optionally substituted by 1, 2 or 3 R.

14. The compound or the pharmaceutically acceptable salt thereof according to claim 1, wherein $R_4$ is selected from the group consisting of

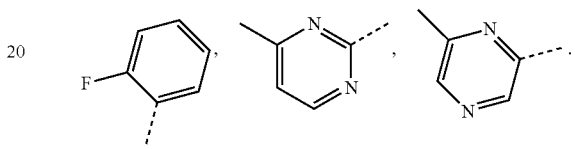

15. The compound or the pharmaceutically acceptable salt thereof according to claim 1, wherein $R_3$ is selected from the group consisting of H, F, Cl, Br, I, OH, $NH_2$ and $R_4$-$L_1$-, or selected from the group consisting of Me, Et,

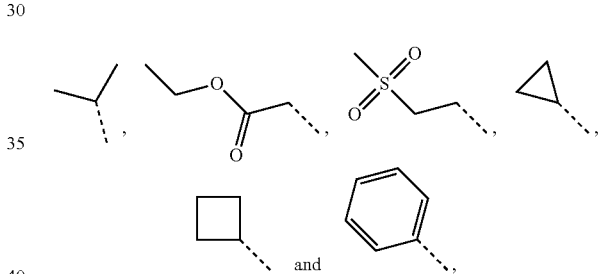

each of which is optionally substituted by 1, 2 or 3 R.

16. The compound or the pharmaceutically acceptable salt thereof according to claim 1, wherein $R_3$ is selected from the group consisting of H, F, Cl, Br, I, OH, $NH_2$, Me, Et,

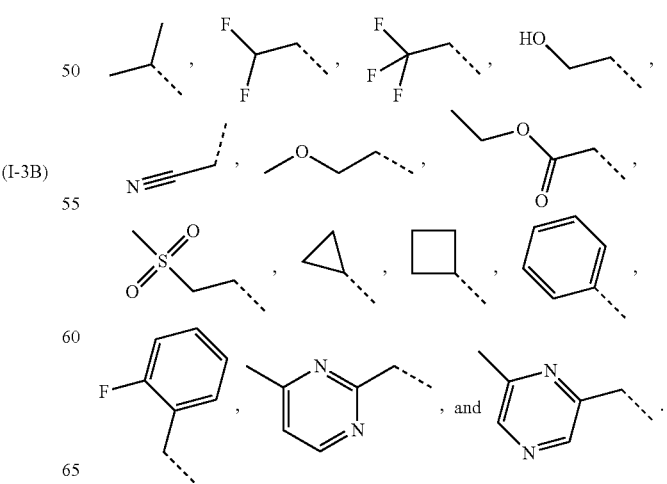

17. The compound or the pharmaceutically acceptable salt thereof according to claim 1, wherein $R_5$ is selected from the group consisting of

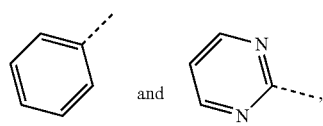

each of which is optionally substituted by 1, 2 or 3 R.

18. The compound or the pharmaceutically acceptable salt thereof according to claim 1, wherein $R_5$ is selected from the group consisting of

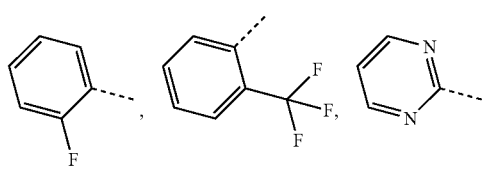

19. The compound or the pharmaceutically acceptable salt thereof according to claim 1, wherein $R_1$ and $R_2$ are each independently selected from the group consisting of H, F, Cl, Br, I, OH, $NH_2$, CN and $R_5$-$L_2$-, or selected from the group consisting of

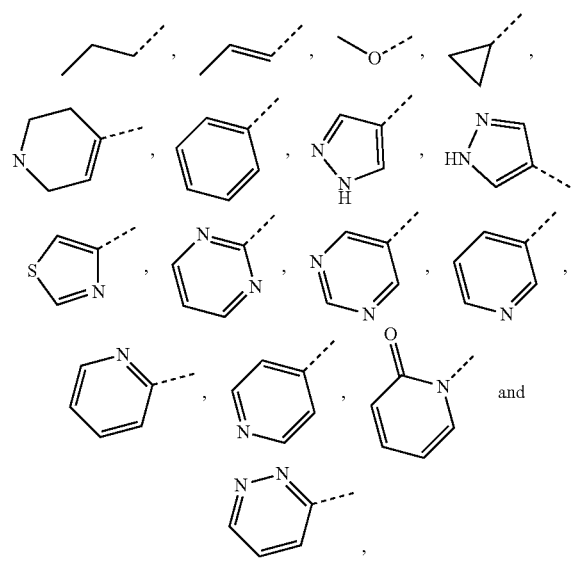

each of which is optionally substituted by 1, 2 or 3 R.

20. The compound or the pharmaceutically acceptable salt thereof according to claim 1, wherein $R_1$ and $R_2$ are each independently selected from the group consisting of H, F, Cl, Br, I, OH, $NH_2$, CN, Me,

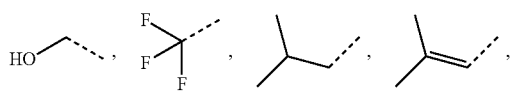

-continued

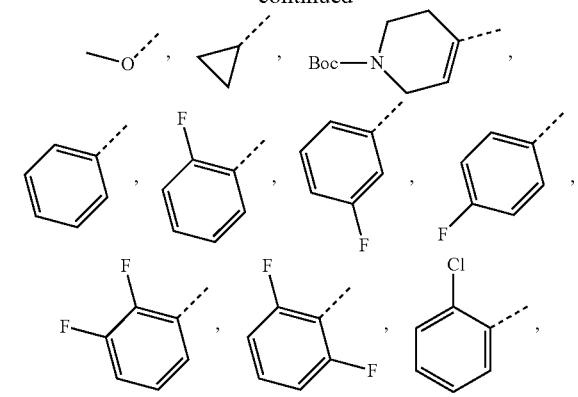

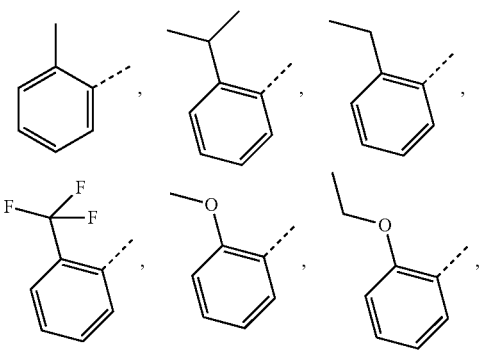

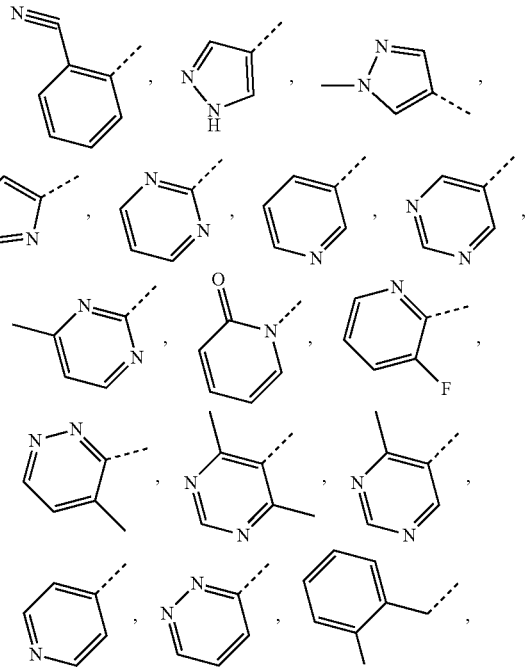

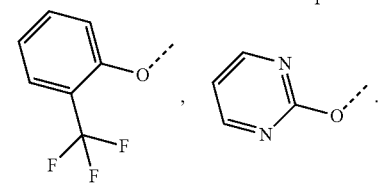

21. The compound or the pharmaceutically acceptable salt thereof according to claim 1, wherein $R_6$ is selected from the group consisting of Me, $CH_2F$ and $CHF_2$.

22. A pharmaceutical composition comprising a therapeutically effective amount of the compound or the pharmaceutically acceptable salt thereof according to claim 1 as the active ingredient and a pharmaceutically acceptable carrier.

23. A method for inhibiting PDE4 in a subject in need thereof, comprising: administering an effective amount of the compound or the pharmaceutically acceptable salt thereof according to claim 1 to the subject.

24. A process for treating PDE4 related diseases in a subject in need thereof, comprising: administering an effective amount of the compound or the pharmaceutically acceptable salt thereof according to claim 1 to the subject, wherein the disease related to PDE4 refers to psoriasis, psoriatic arthritis, chronic obstructive pneumonia, ankylosing spondylitis, inflammatory bowel disease.

25. A compound as shown in formula (I) or a pharmaceutically acceptable salt thereof,

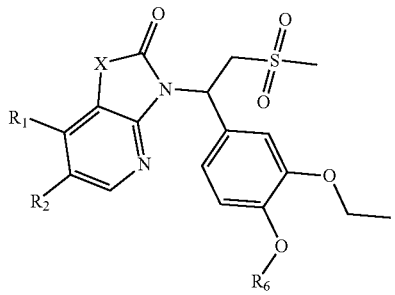

(I)

wherein,

X is selected from the group consisting of O, N(R₃) and —CH(R₃)—;

R₃ is selected from the group consisting of H, F, Cl, Br, I, OH, CN, NH₂, COOH and R₄-L₁-, or selected from the group consisting of $C_{1-6}$ alkyl, $C_{1-6}$ heteroalkyl, $C_{3-6}$ cycloalkyl, 3-6 membered heterocycloalkyl, phenyl and 5-6 membered heteroaryl, each of which is optionally substituted by 1, 2 or 3 R;

R₄ is selected from the group consisting of $C_{3-6}$ cycloalkyl, 3-6 membered heterocycloalkyl, phenyl and 5-6 membered heteroaryl, each of which is optionally substituted by 1, 2 or 3 R;

L₁ is selected from the group consisting of —CH₂—, —CH₂CH₂—, O, S, NH and —C(=O)—;

R₁ and R₂ are each independently selected from the group consisting of H, F, Cl, Br, I, OH, CN, NH₂ and R₅-L₂-, or selected from the group consisting of $C_{1-6}$ alkyl, $C_{1-6}$ alkoxy, $C_{1-6}$ alkylthio, $C_{1-6}$ alkylamino, $C_{2-6}$ alkenyl, $C_{3-6}$ cycloalkenyl, 3-6 membered heterocycloalkenyl, $C_{3-6}$ cycloalkyl, 3-6 membered heterocycloalkyl, phenyl and 5-6 membered heteroaryl, each of which is optionally substituted by 1, 2 or 3 R;

R₅ is selected from the group consisting of $C_{3-6}$ cycloalkyl, 3-6 membered heterocycloalkyl, 3-6 membered heterocycloalkenyl, phenyl and 5-6 membered heteroaryl, each of which is optionally substituted by 1, 2 or 3 R;

L₂ is selected from the group consisting of —CH₂—, —CH₂CH₂—, O, S and NH;

R₆ is $C_{1-3}$ alkyl, which is optionally substituted by 1, 2 or 3 R;

R is selected from the group consisting of H, F, Cl, Br, I, OH, NH₂, CN, Me, CF₃, CHF₂, CH₂F, Et,

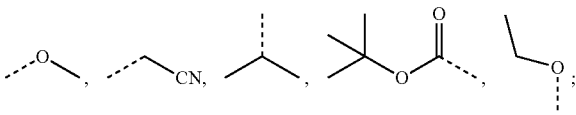

the "hetero" in the $C_{1-6}$ heteroalkyl, 3-6 membered heterocycloalkyl, 5-6 membered heteroaryl and 3-6 membered heterocycloalkenyl is selected from the group consisting of —C(=O)NH—, —NH—, —C(=NH)—, —S(=O)₂NH—, —S(=O)NH—, —O—, —S—, =O, =S, —O—N=, —C(=O)O—, —C(=O)—, —C(=S)—, —S(=O)—, —S(=O)₂— and —NHC(=O)NH—;

the "hetero" represents a heteroatom or a heteroatom group;

in any of the above cases, the number of the heteroatom or the heteroatom group is independently selected from the group consisting of 1, 2 and 3.

26. A compound or a pharmaceutically acceptable salt thereof, which is selected from the group consisting of

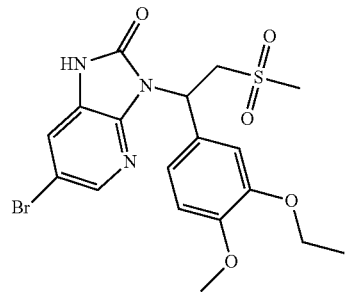

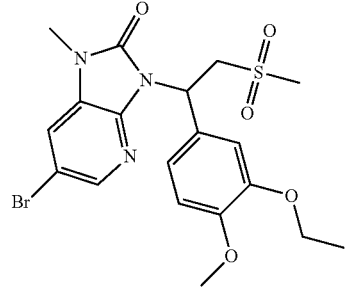

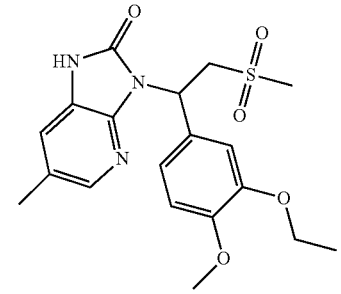

-continued
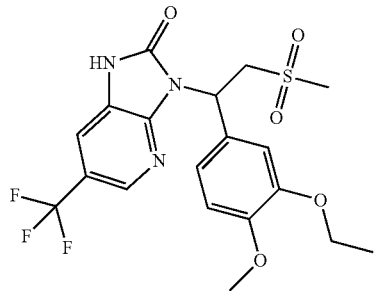
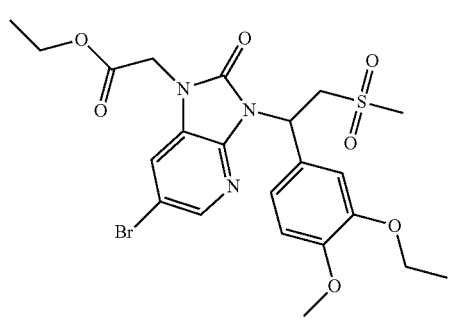
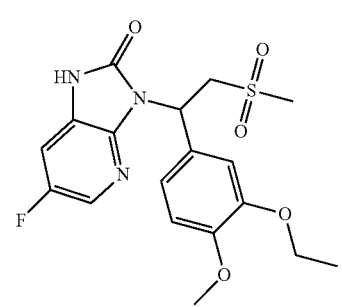
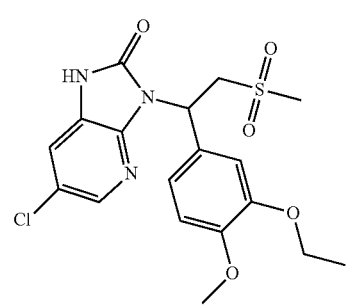
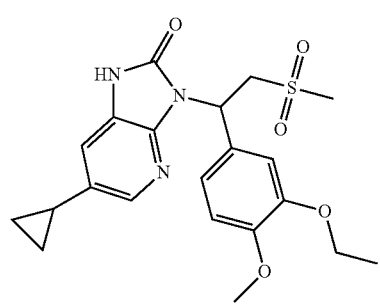
-continued
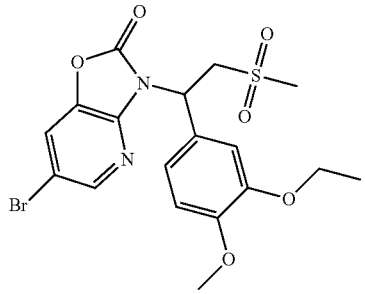
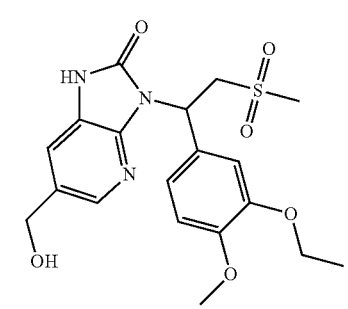
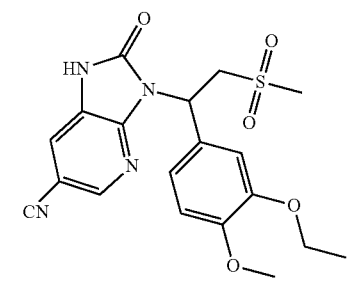
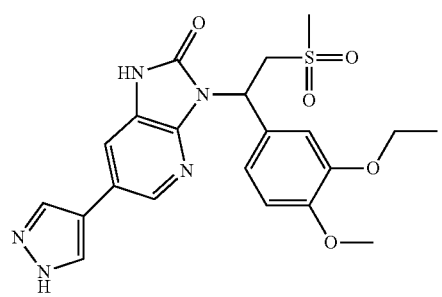
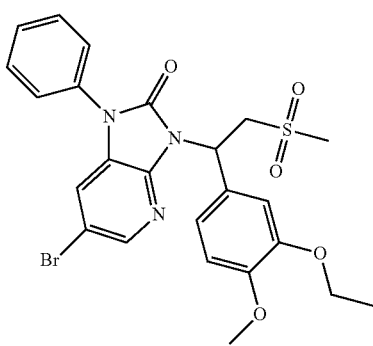

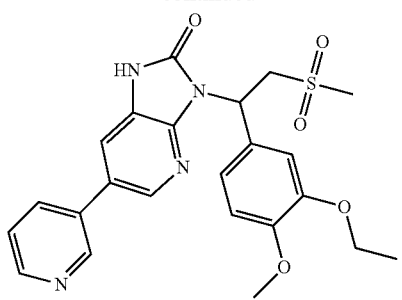
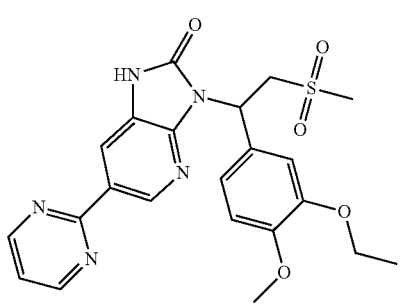
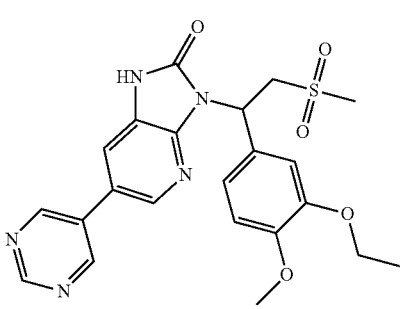
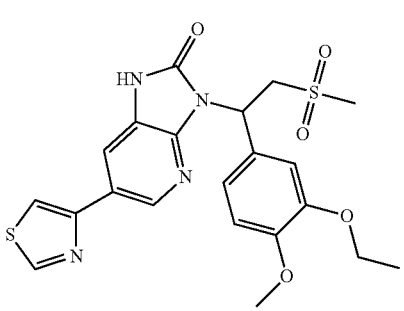
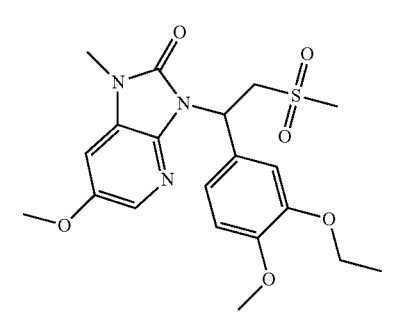
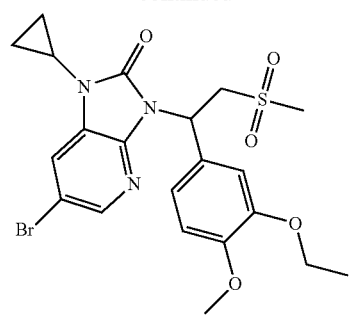
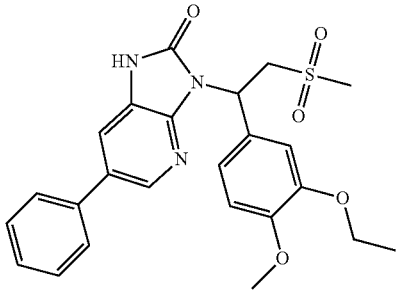
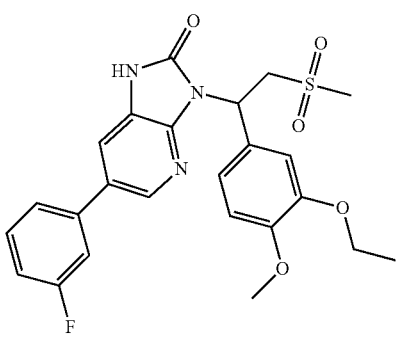
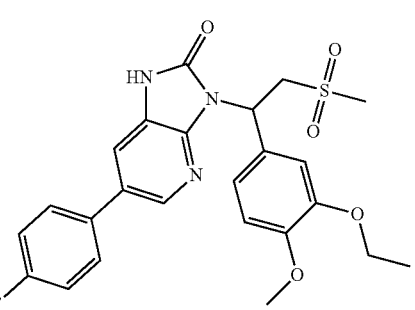
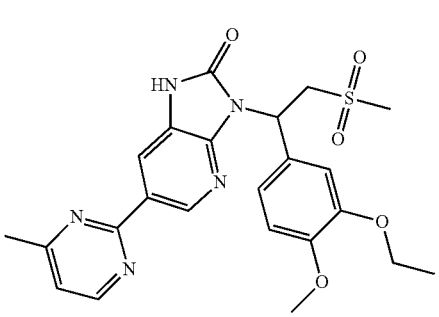

193
-continued
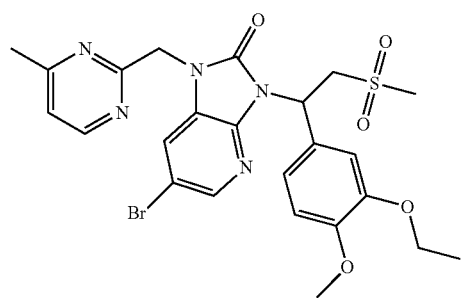
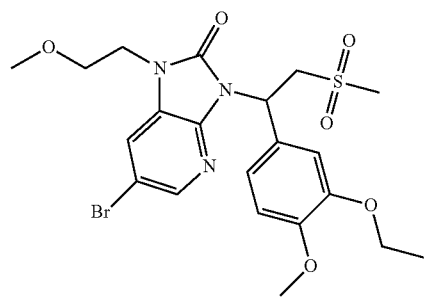
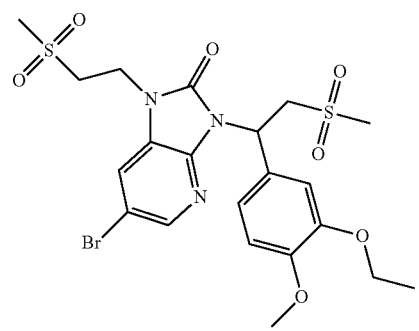
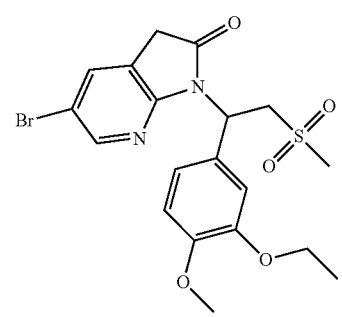
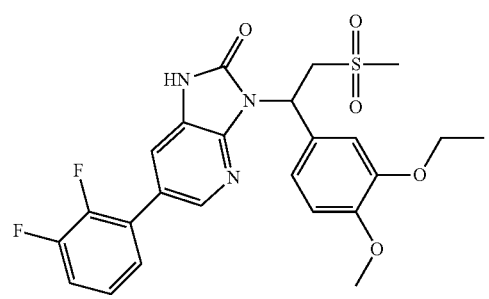
194
-continued
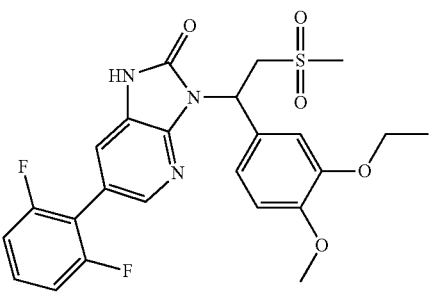
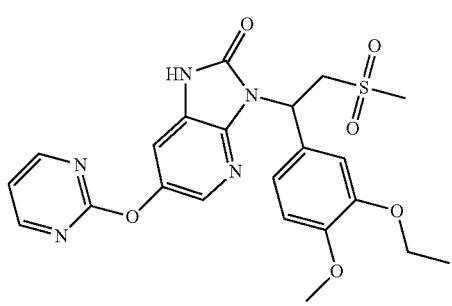
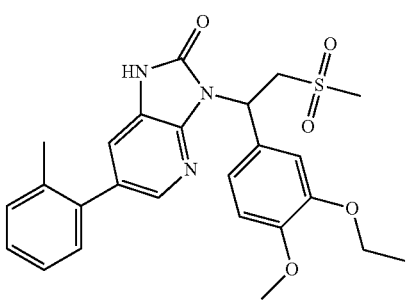
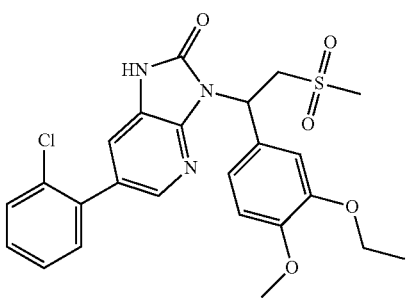
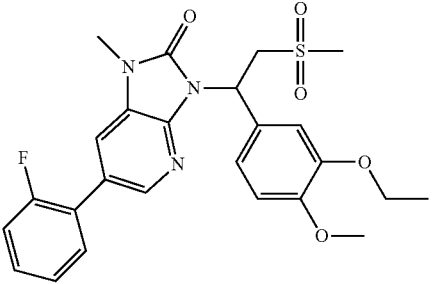

195
-continued
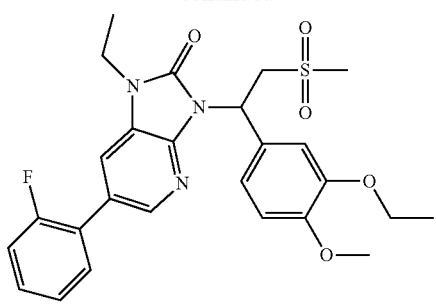
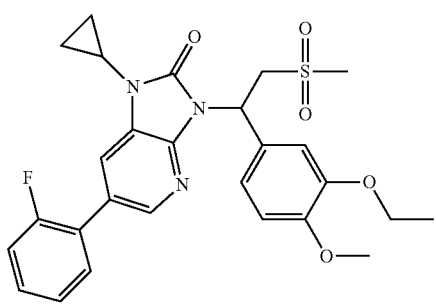
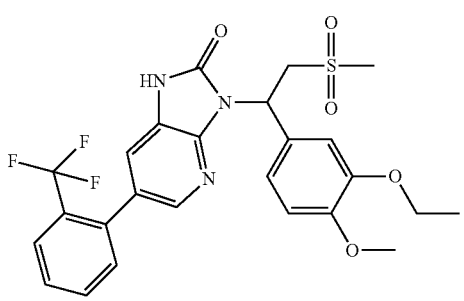
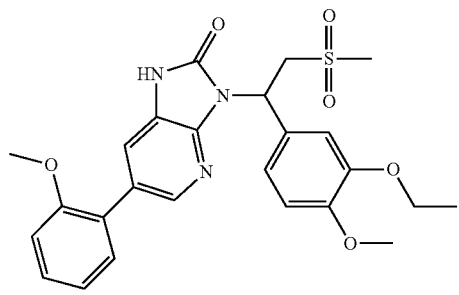
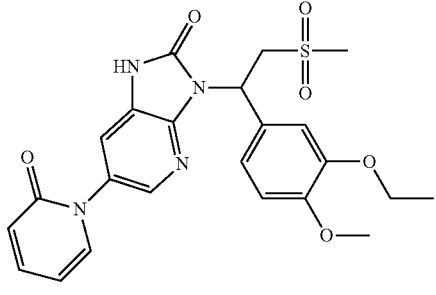
196
-continued
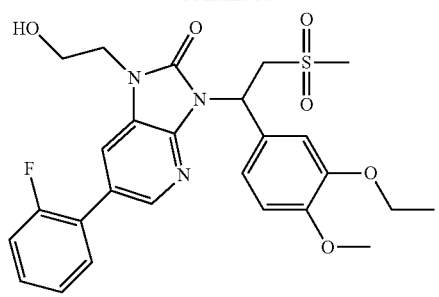
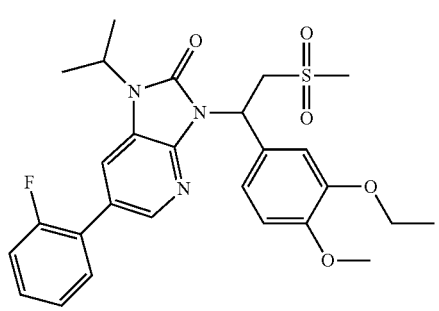
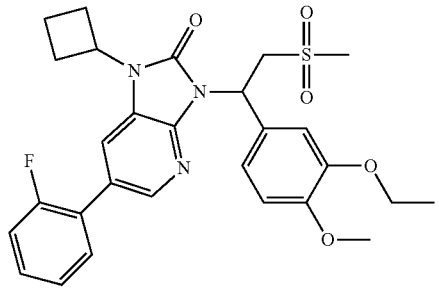
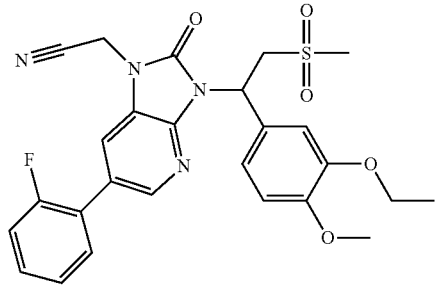
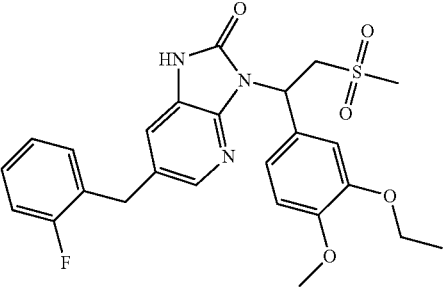

197
-continued
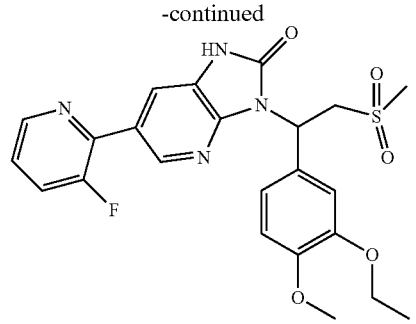
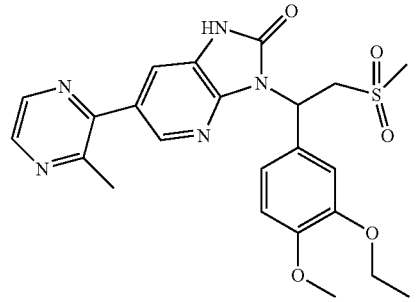
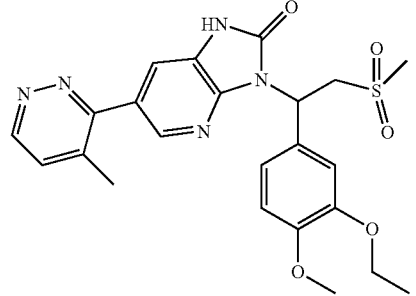
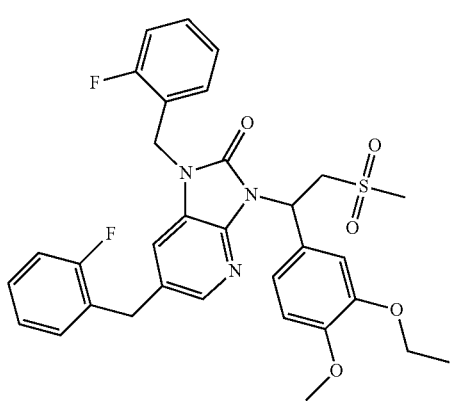
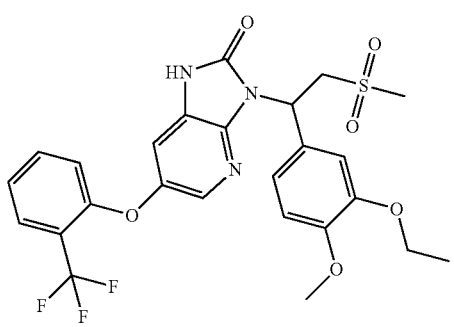
198
-continued
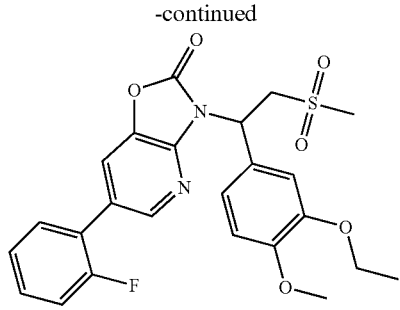
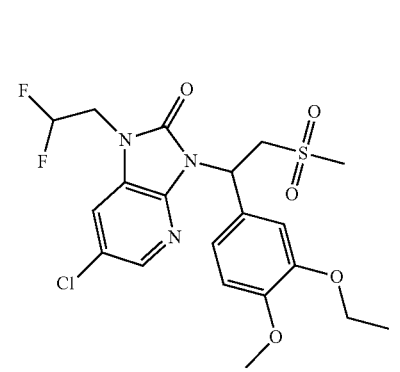
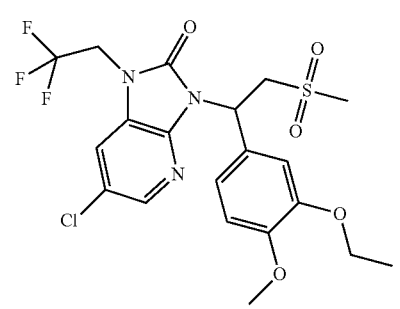
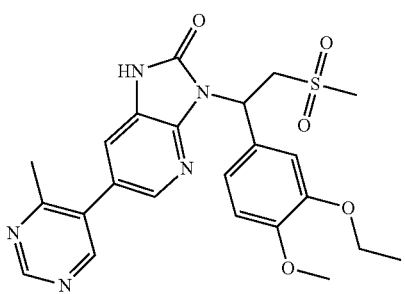
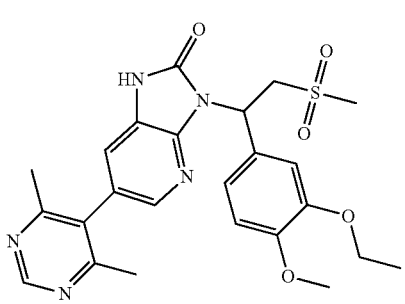

199
-continued
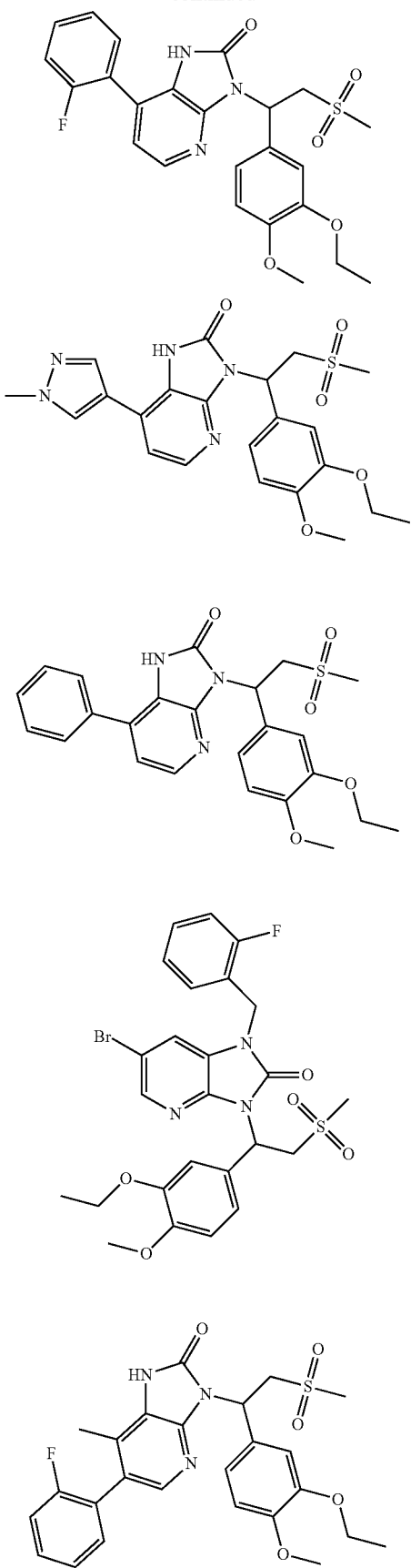
200
-continued
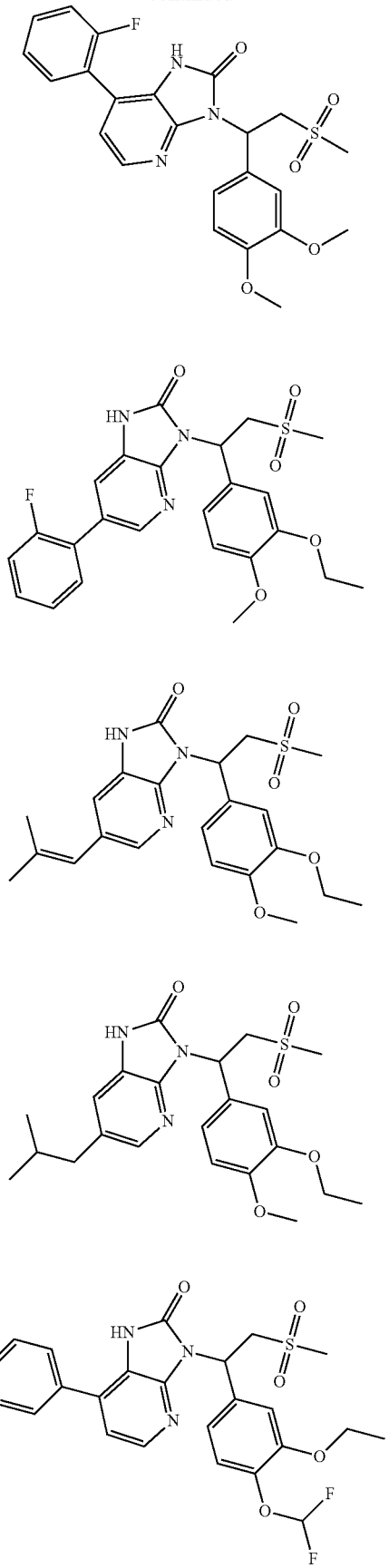

201
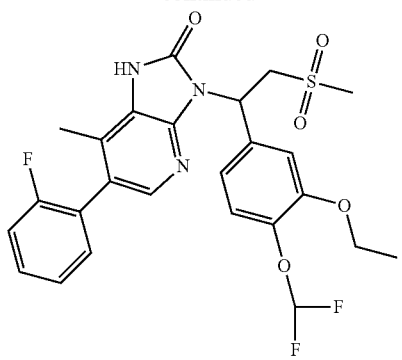
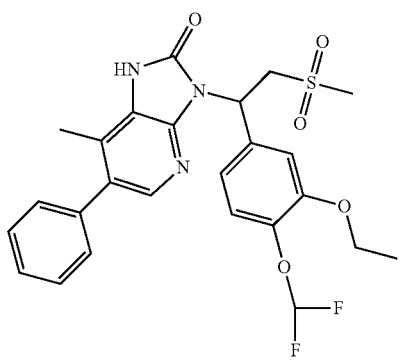
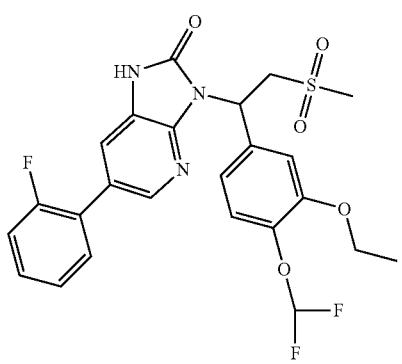
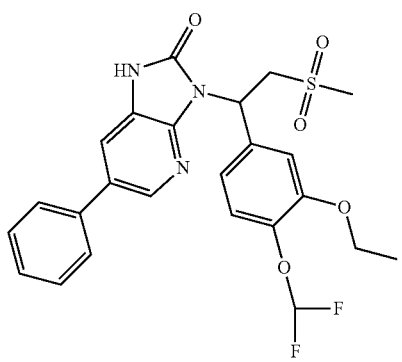
202
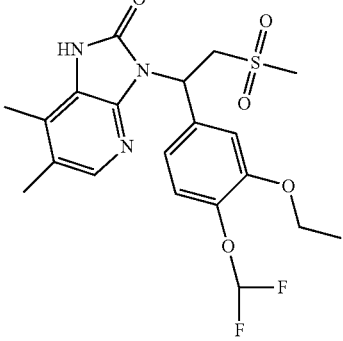
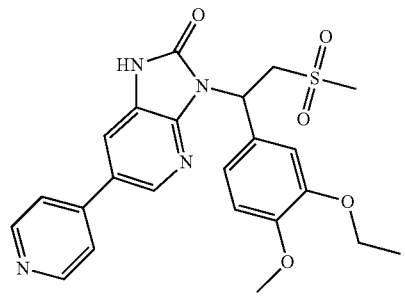
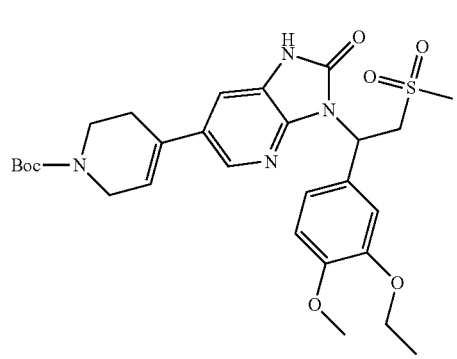
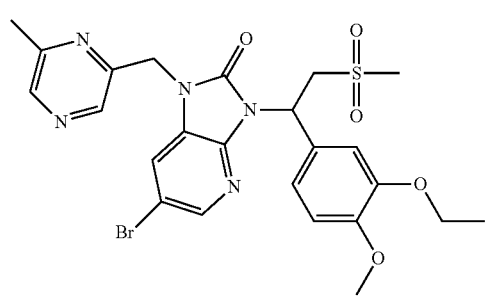
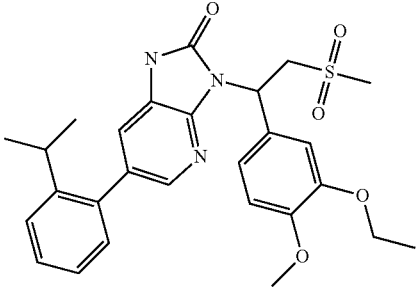

27. The compound or the pharmaceutically acceptable salt thereof according to claim 26, which is selected from the group consisting of -continued
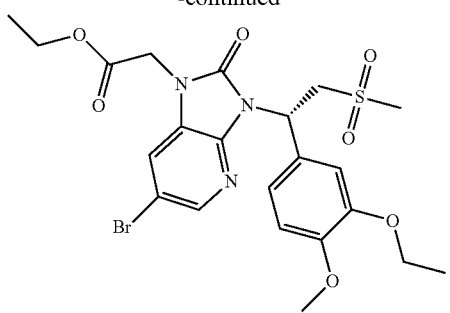
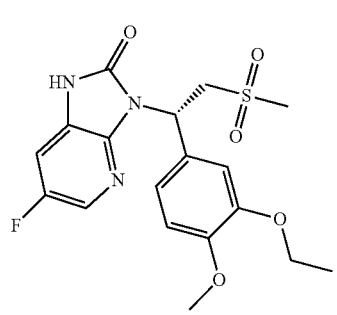
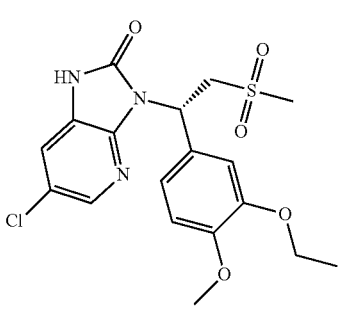
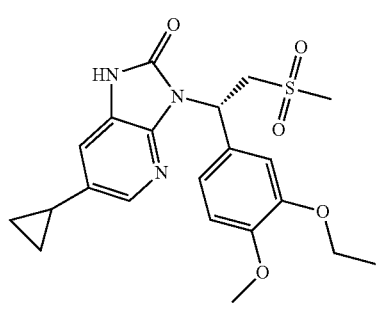
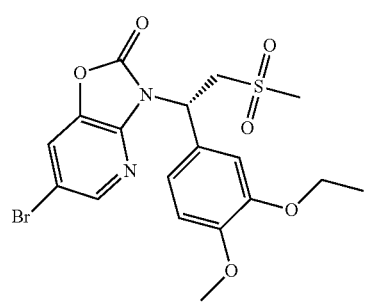
-continued
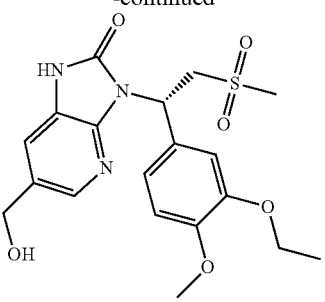
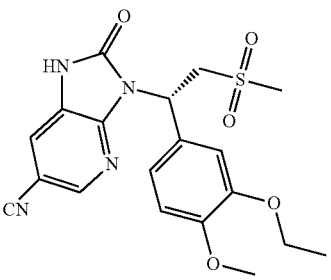
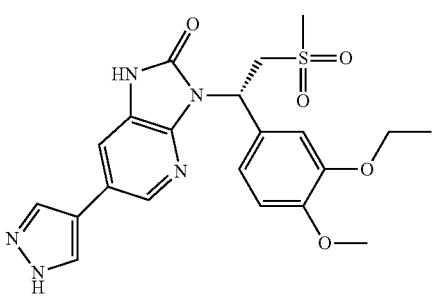
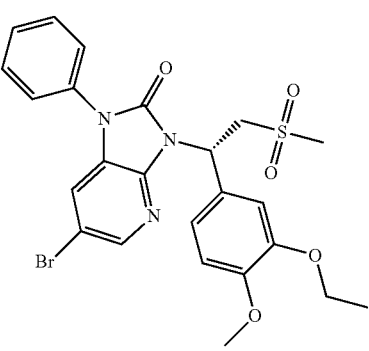
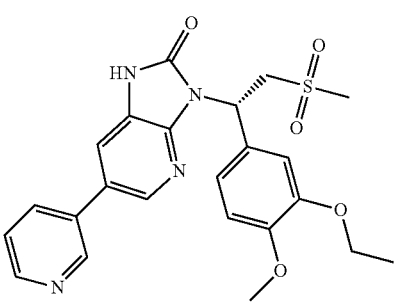

207
-continued
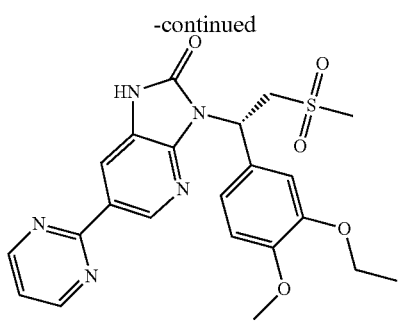
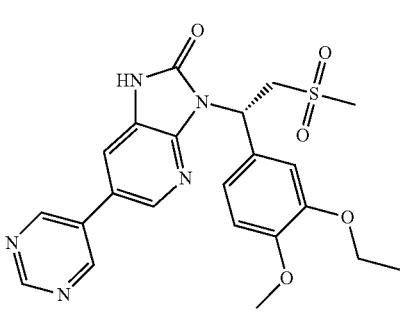
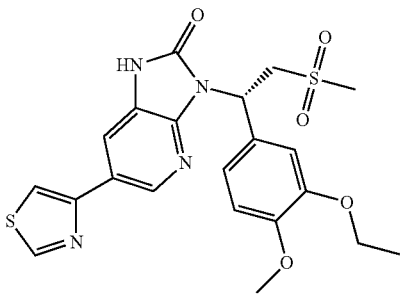
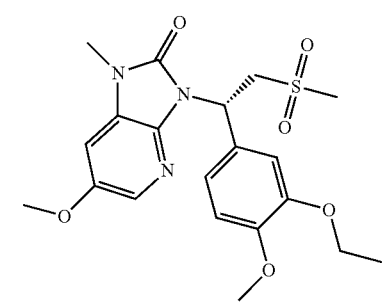
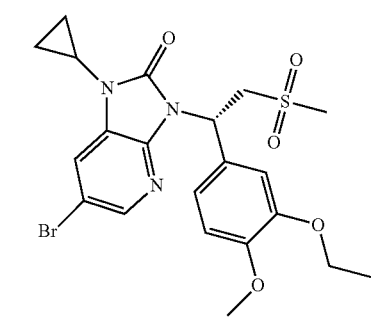
208
-continued
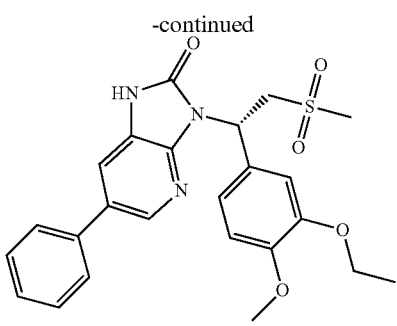
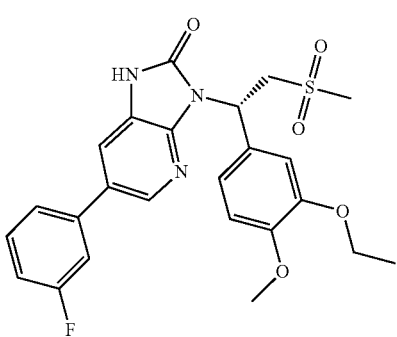
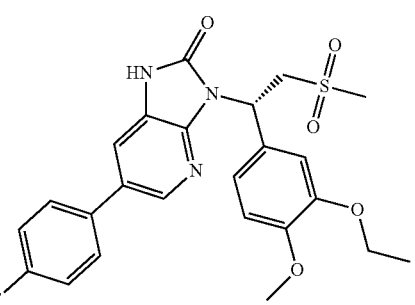
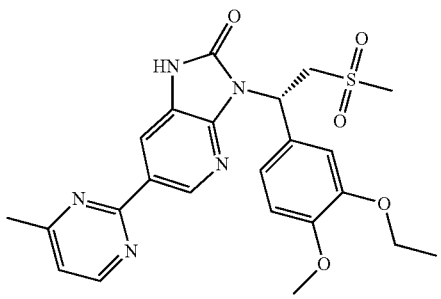
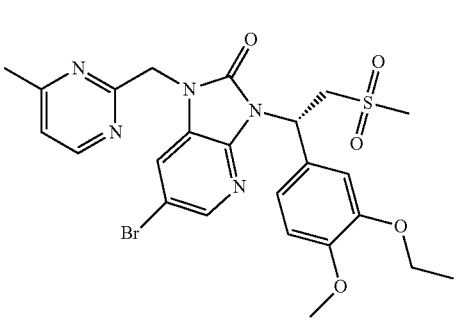

209
-continued
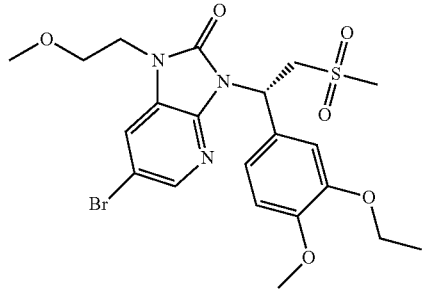
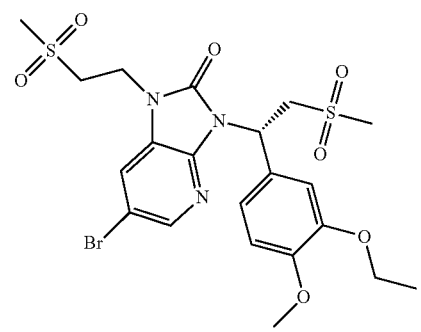
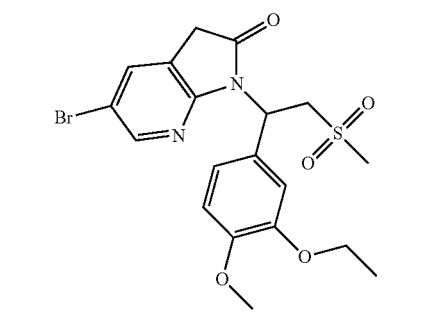
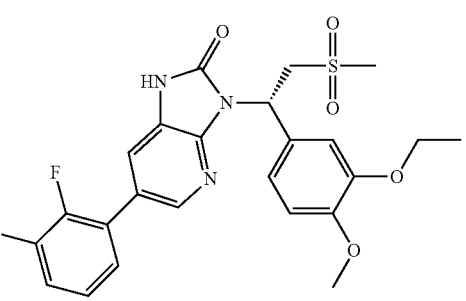
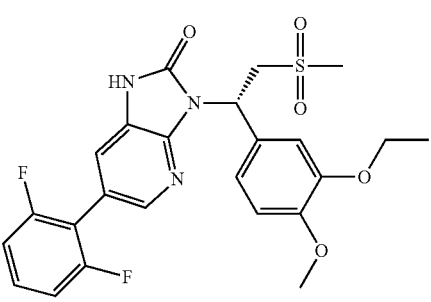
210
-continued
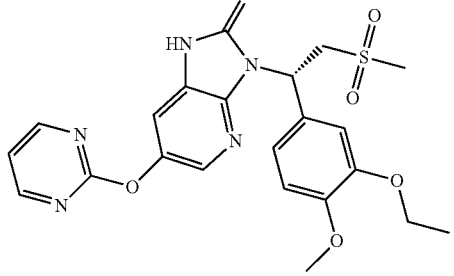
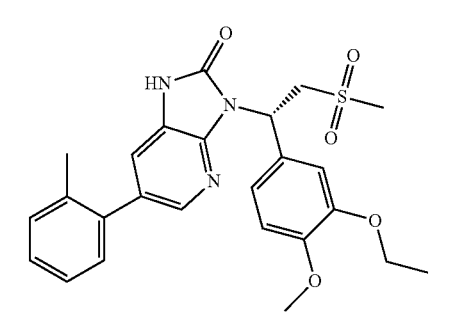
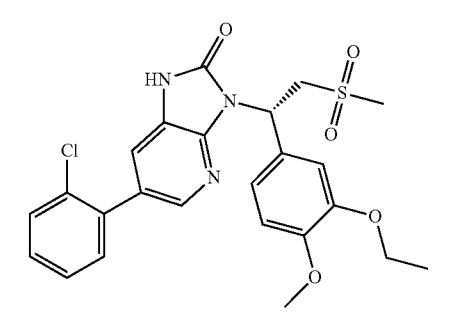
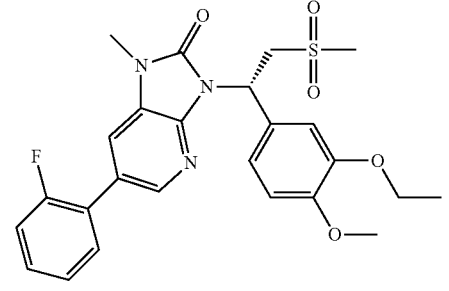
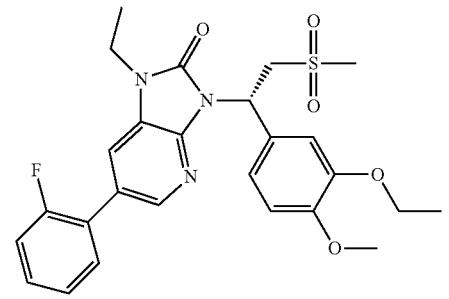

211
-continued
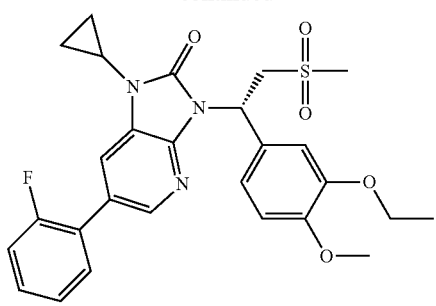
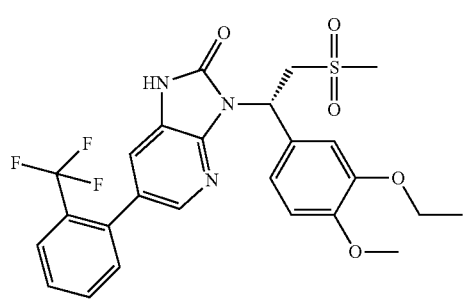
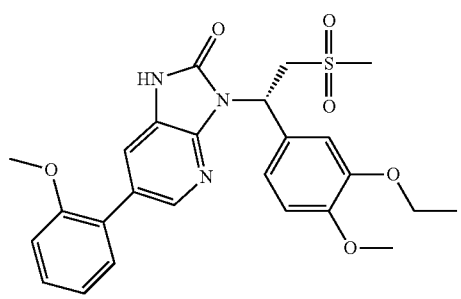
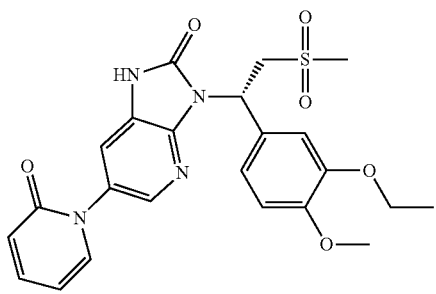
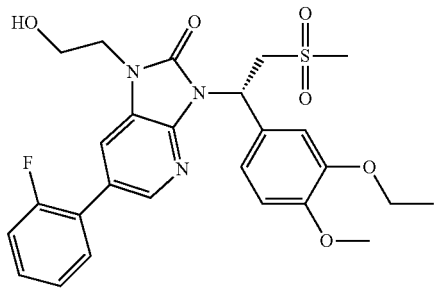
212
-continued
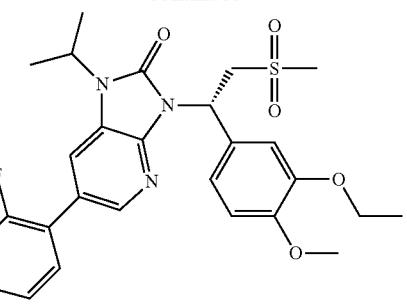
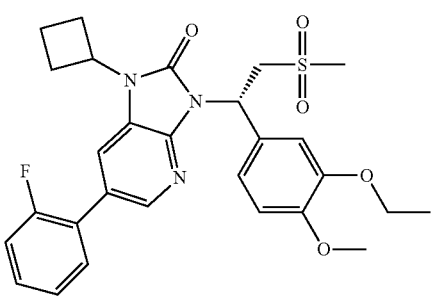
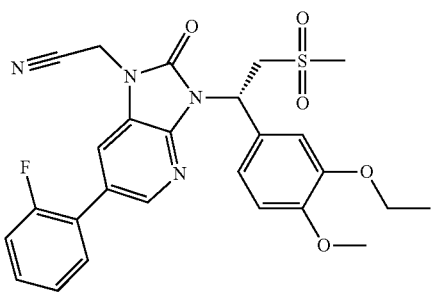
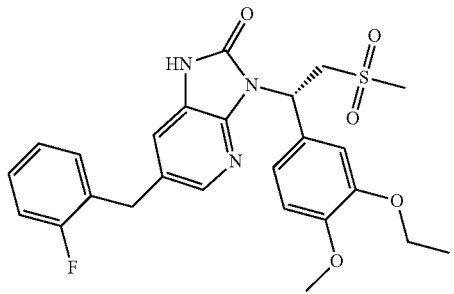
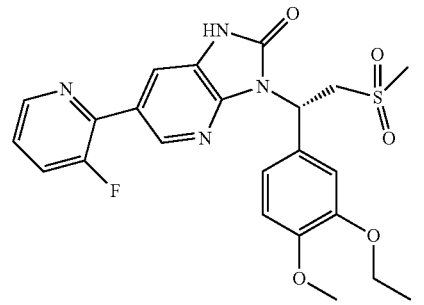

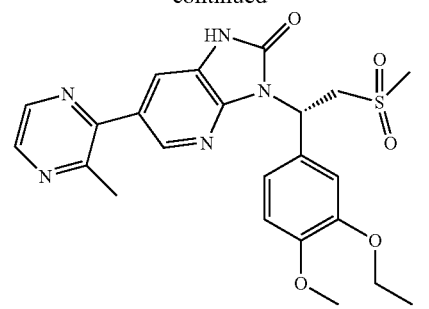
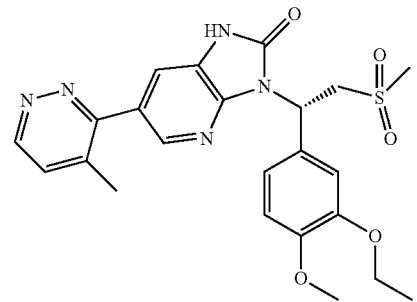
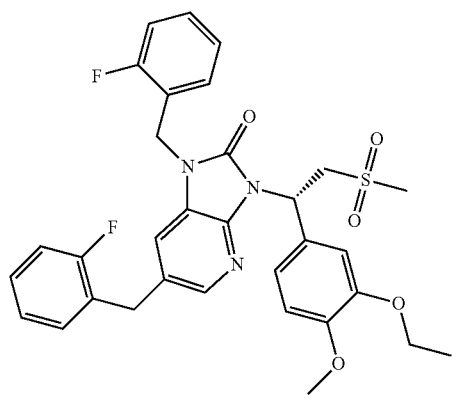
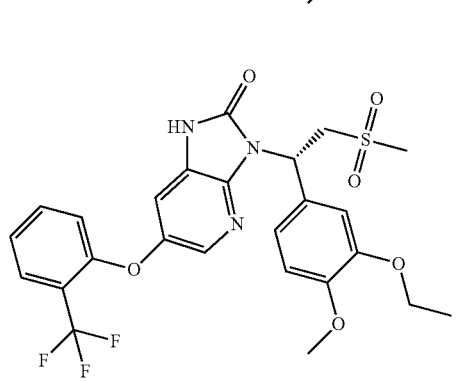
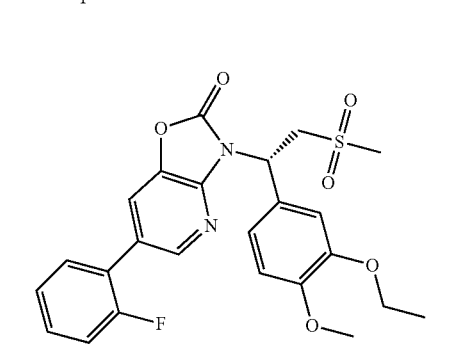
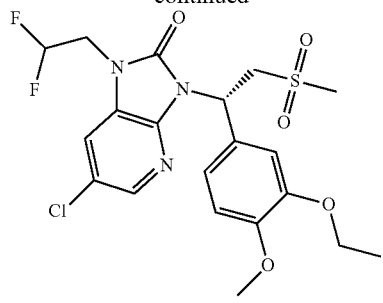
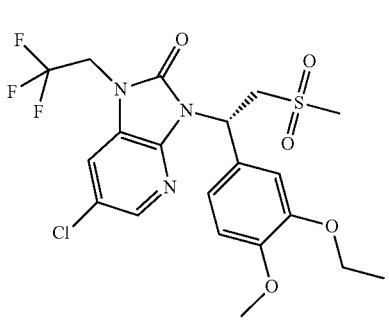
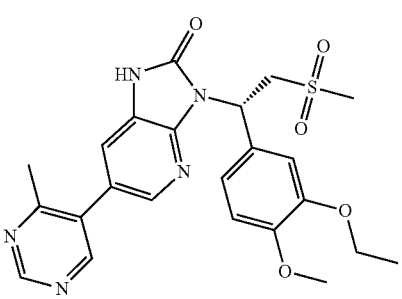
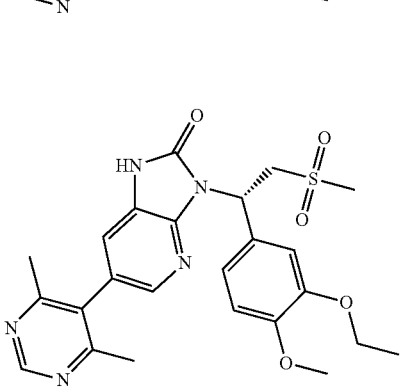
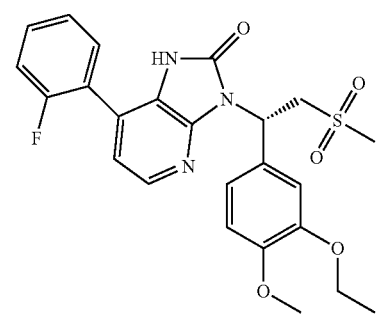

215
-continued
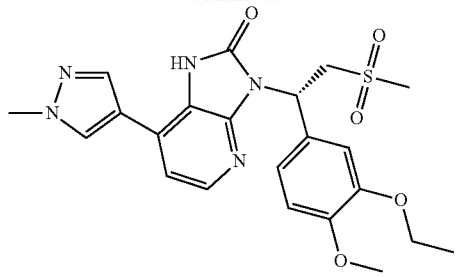
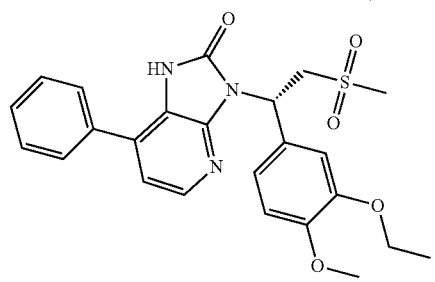
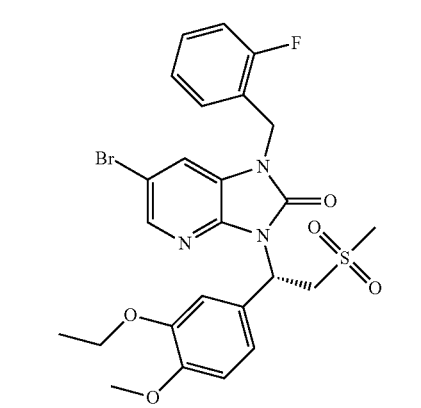
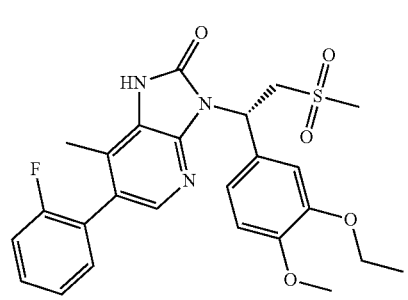
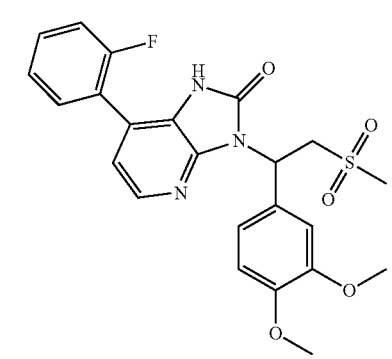
216
-continued
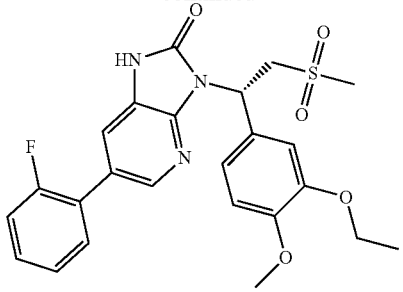
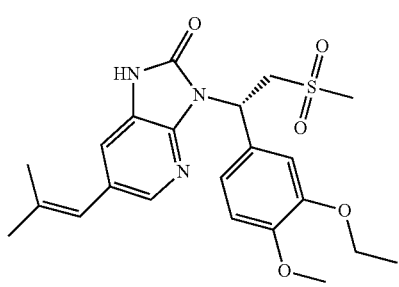
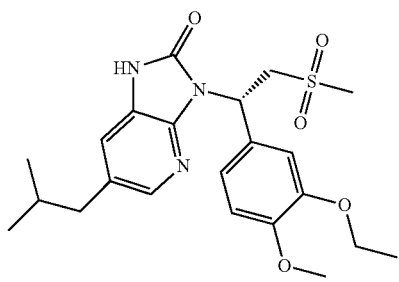
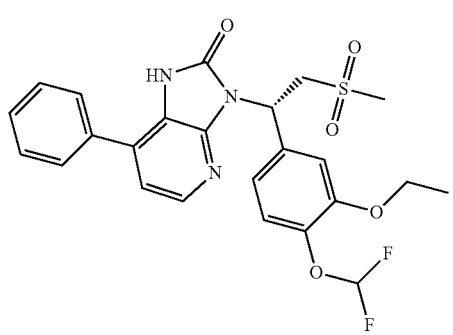
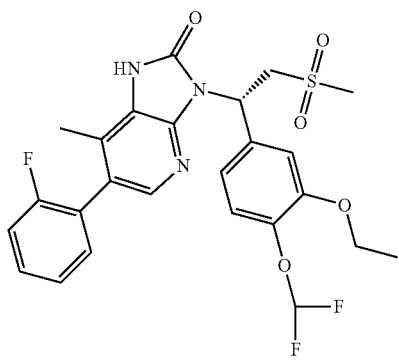

-continued
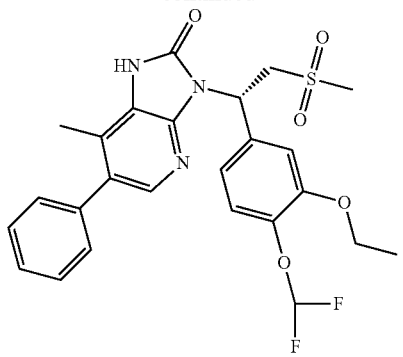
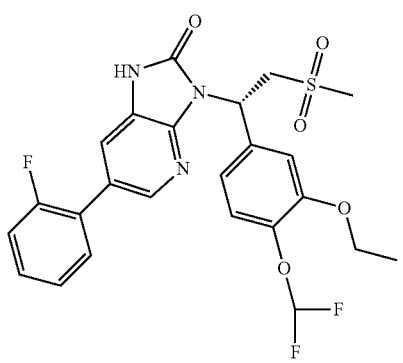
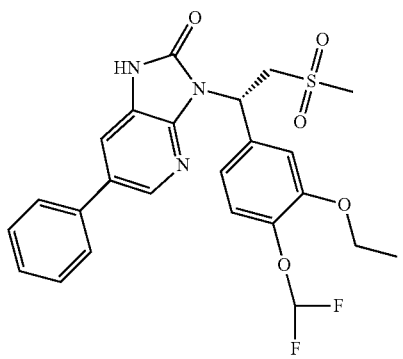
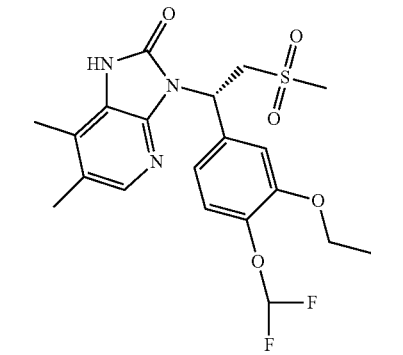
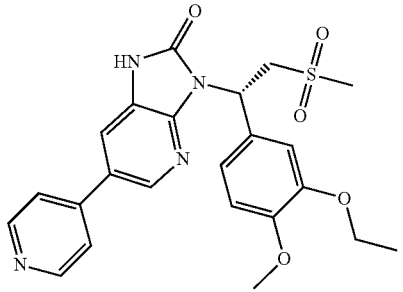
-continued
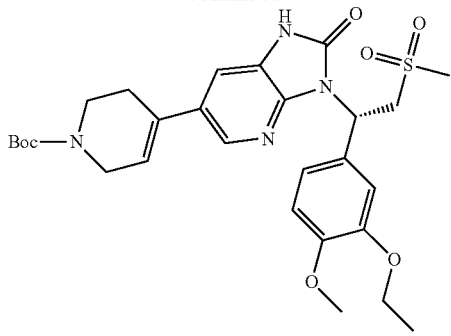
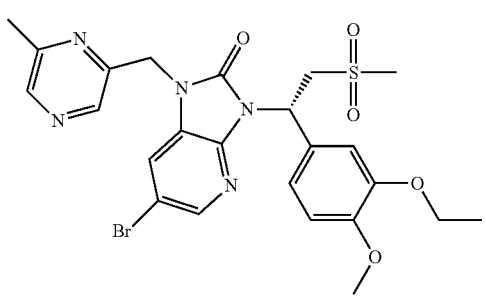
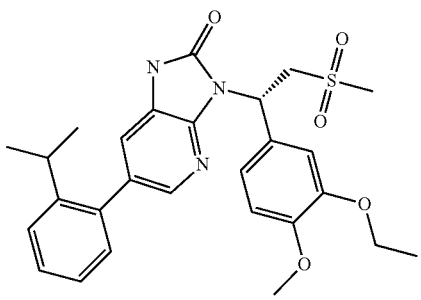
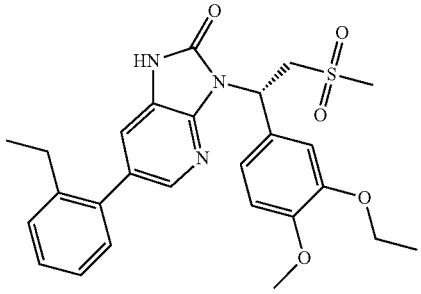
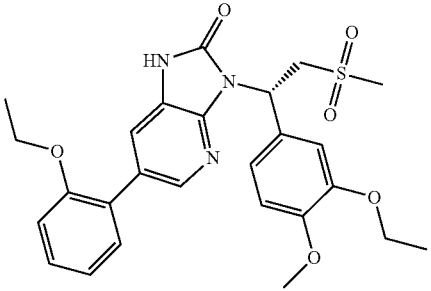

-continued
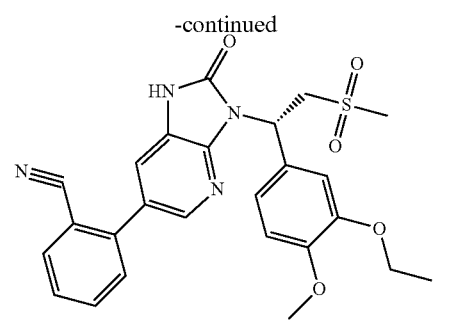
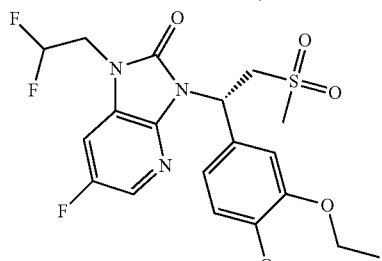
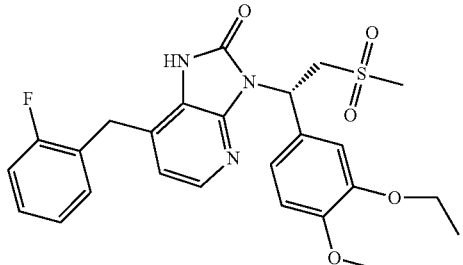
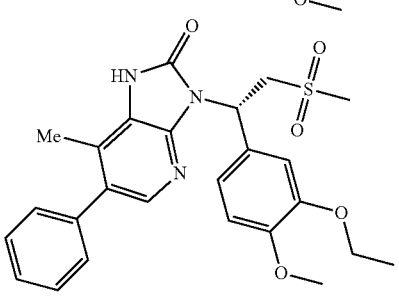
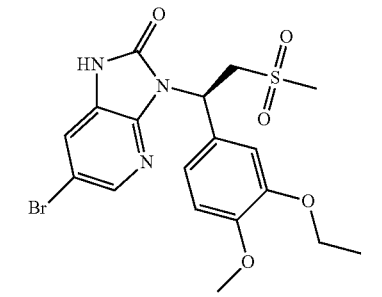
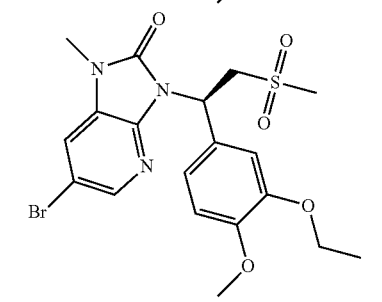
-continued
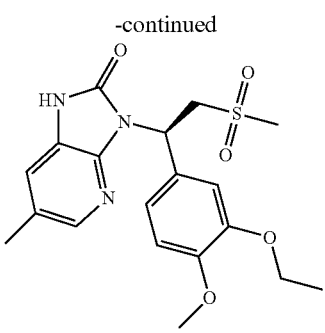
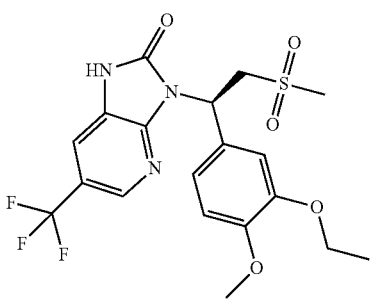
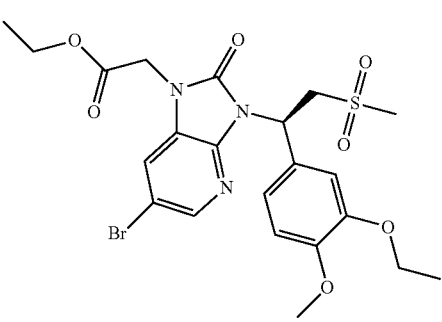
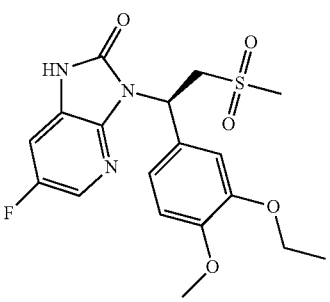
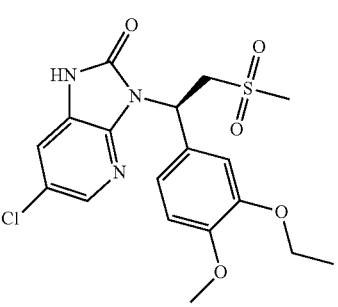

221
-continued
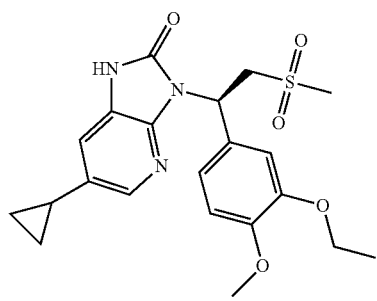
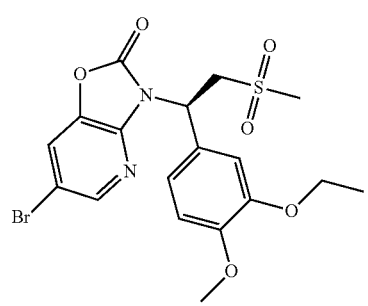
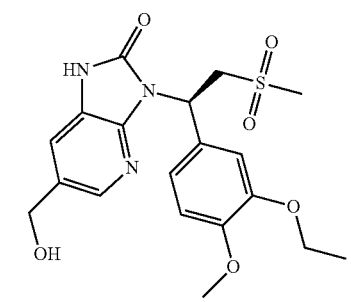
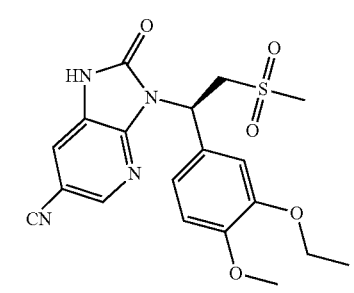
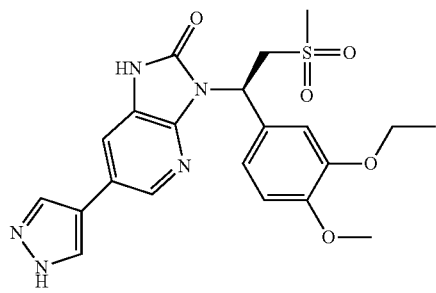
222
-continued
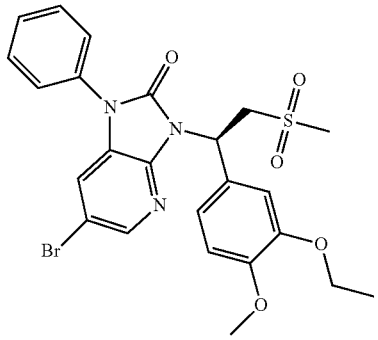
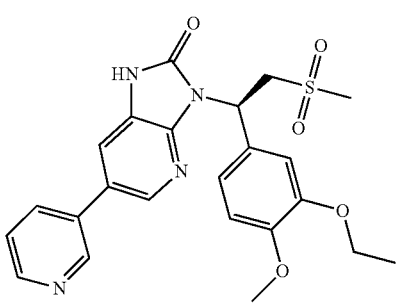
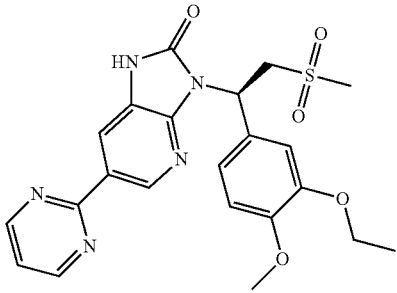
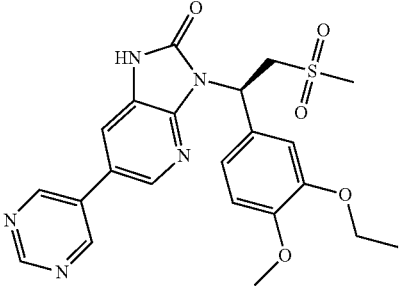
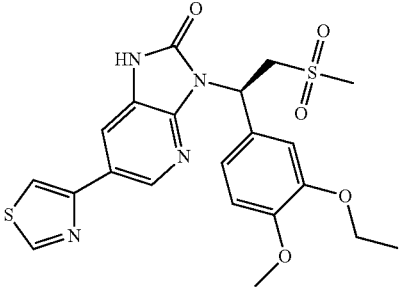

223
-continued
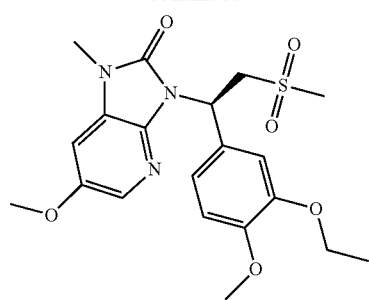
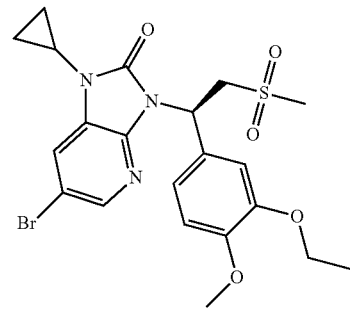
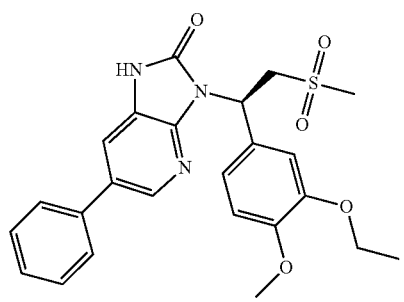
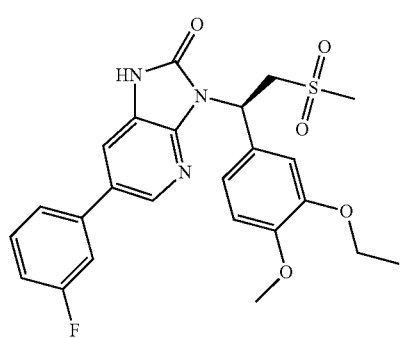
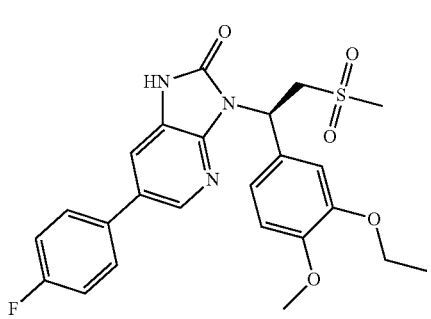
224
-continued
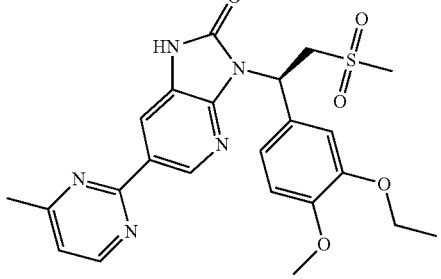
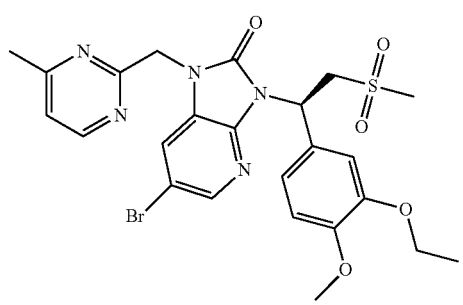
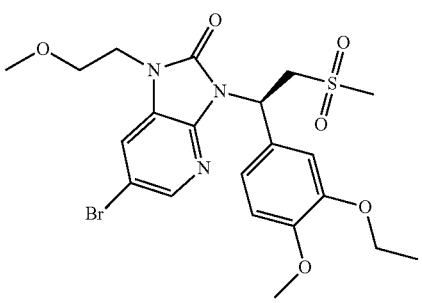
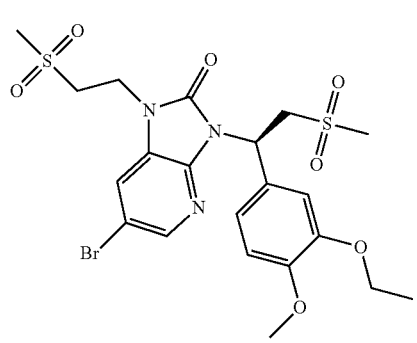
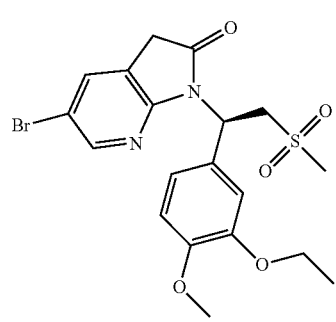

225
-continued
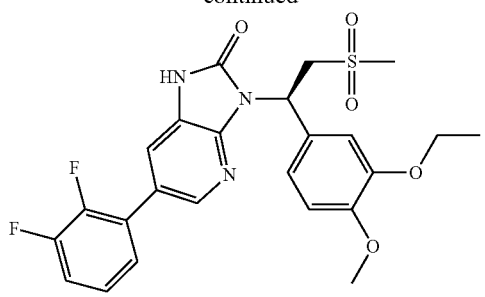
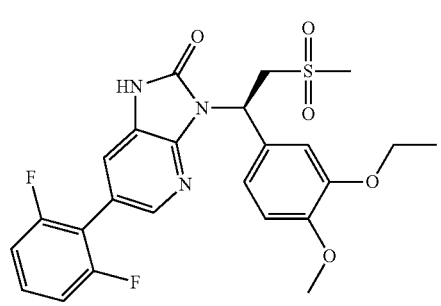
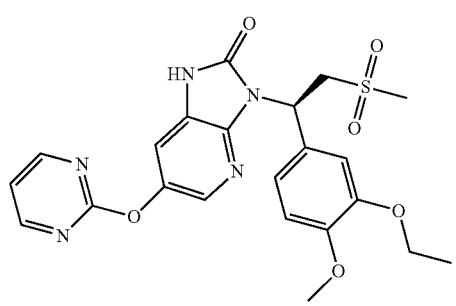
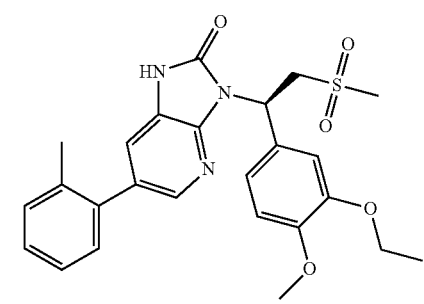
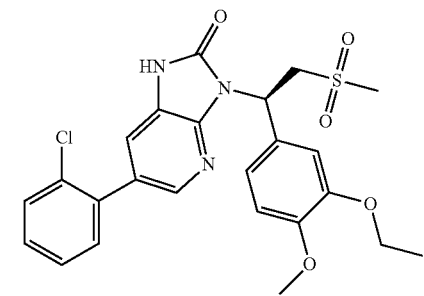
226
-continued
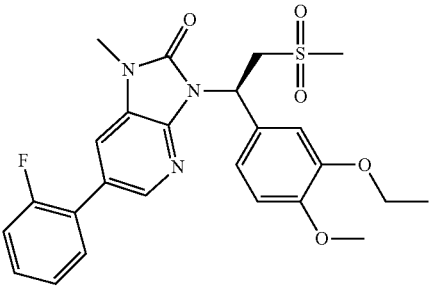
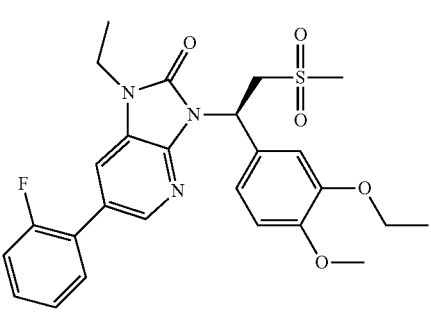
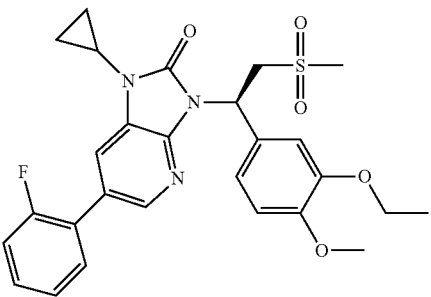
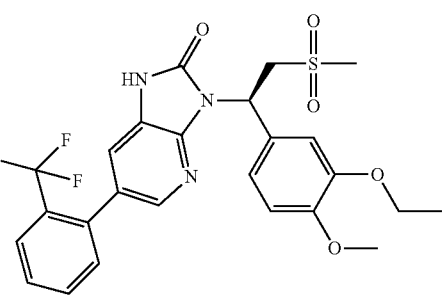
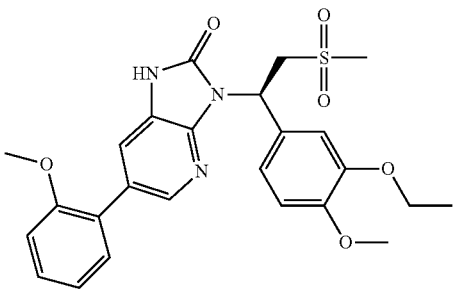

227
-continued
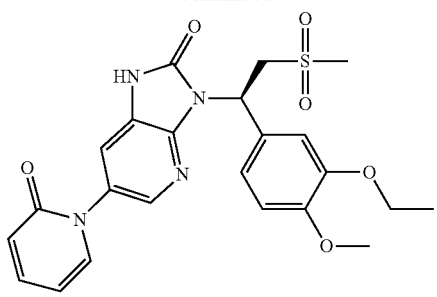
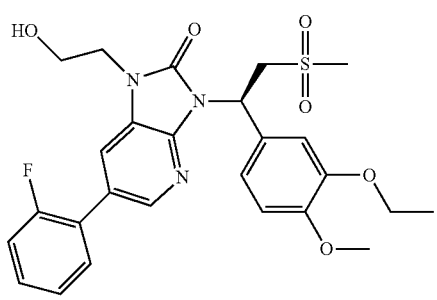
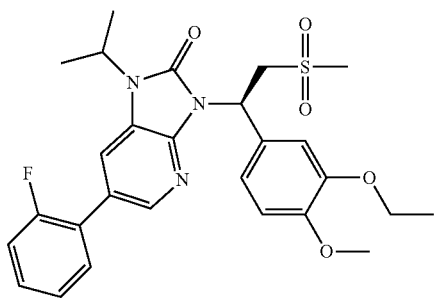
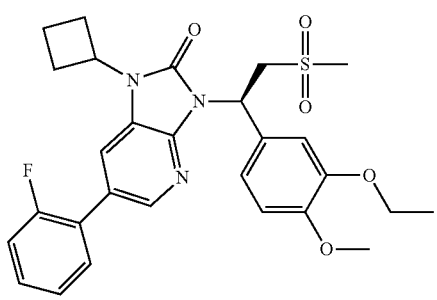
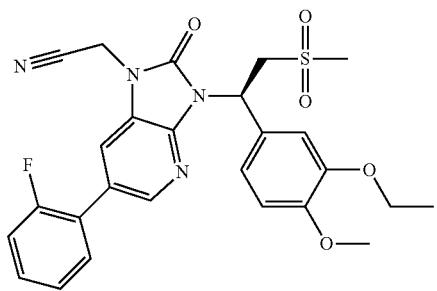
228
-continued
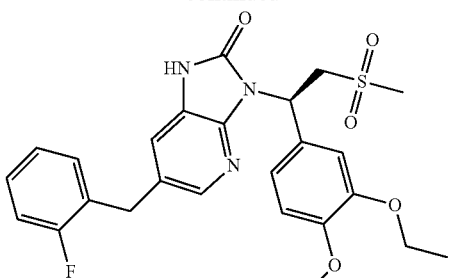
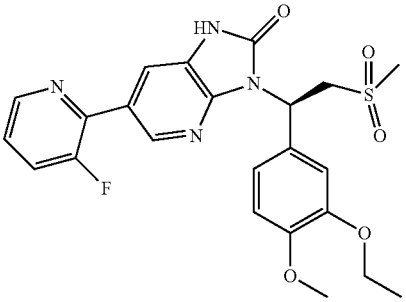
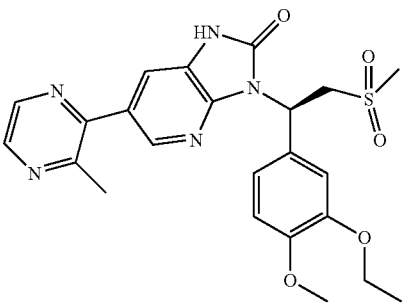
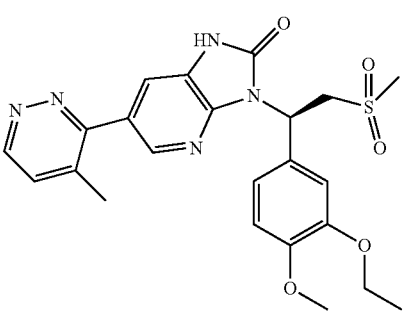
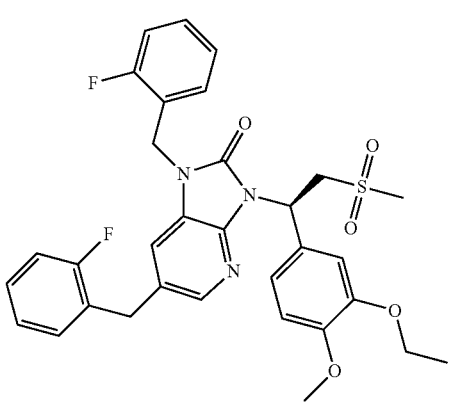

229
-continued
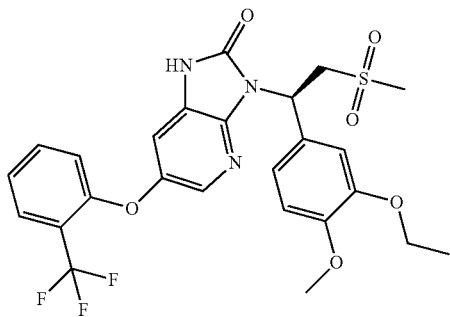
230
-continued
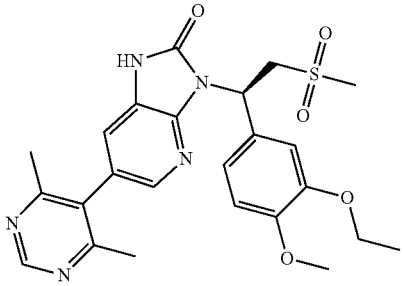
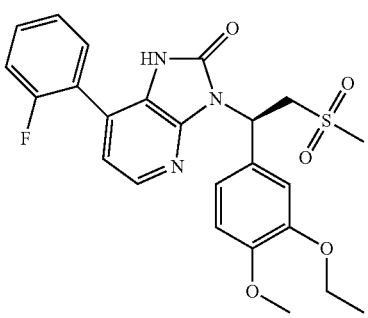
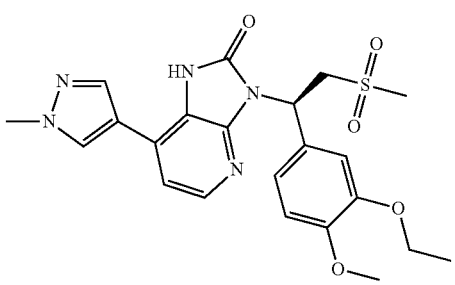
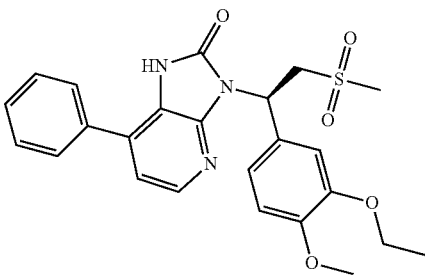
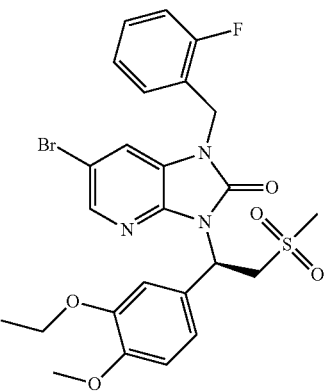

231
-continued
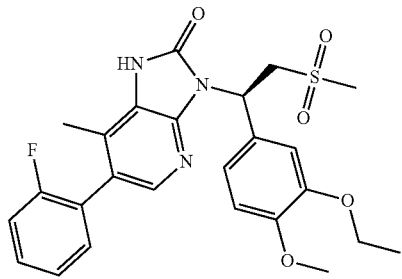
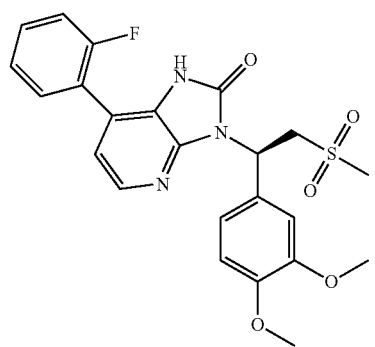
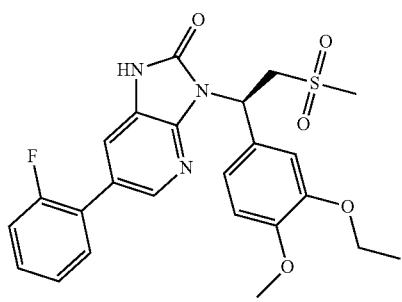
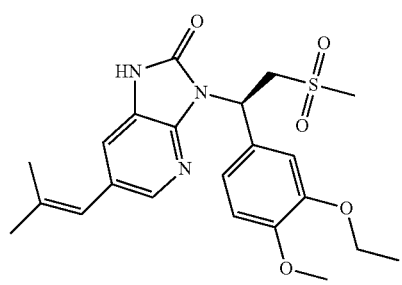
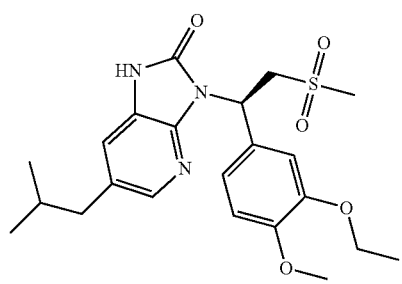
232
-continued
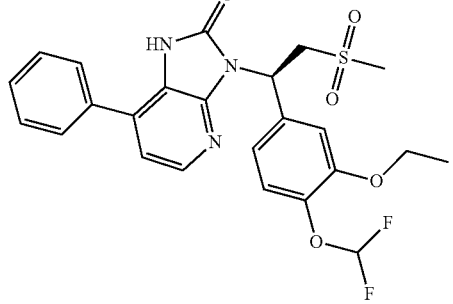
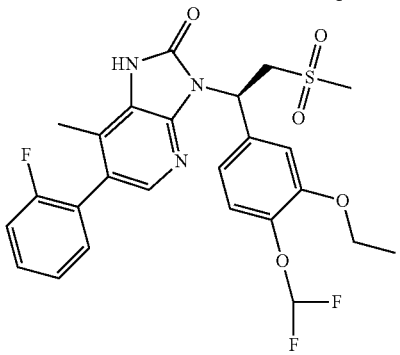
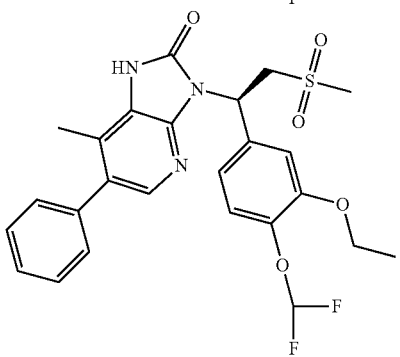
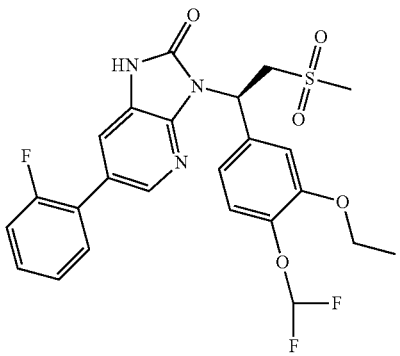
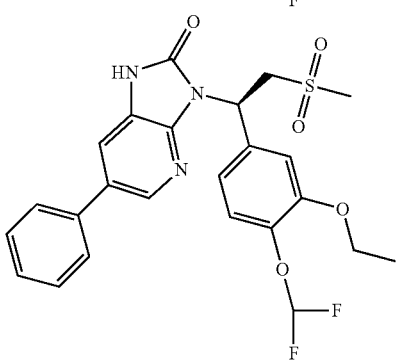

233
-continued
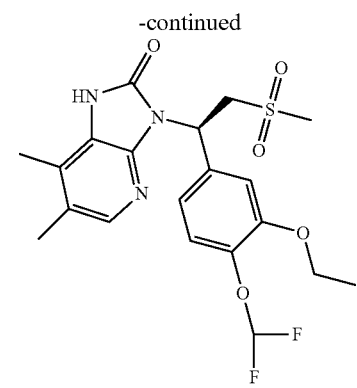
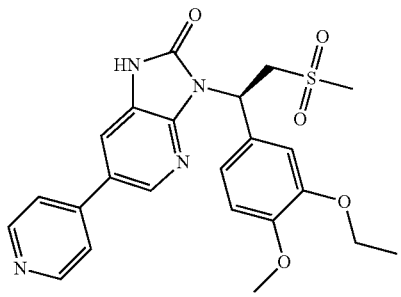
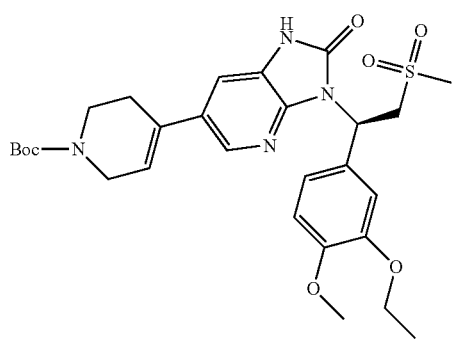
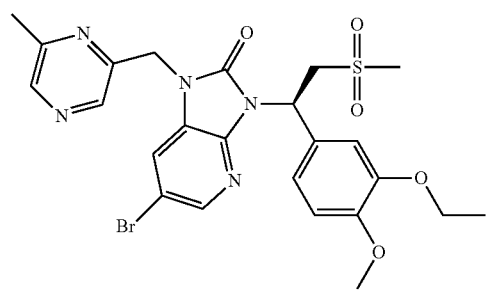
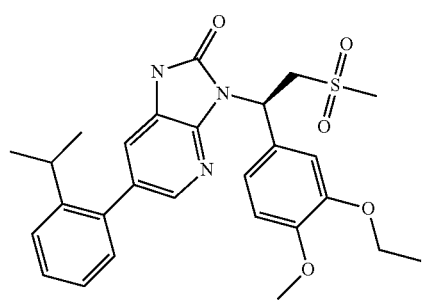
234
-continued
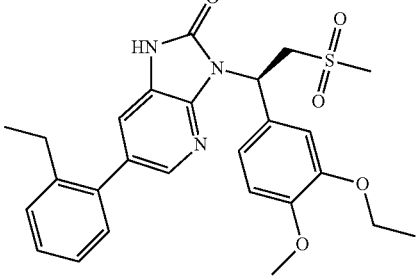
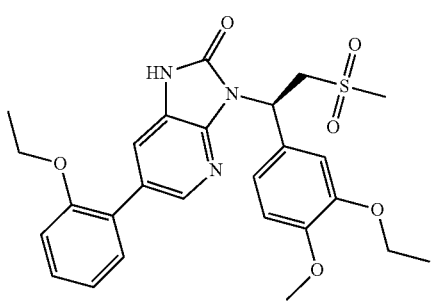
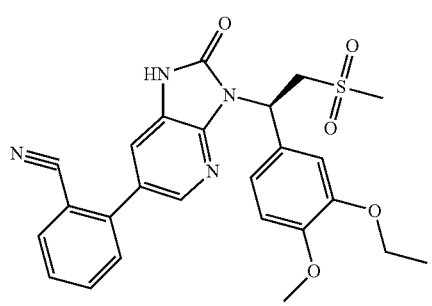
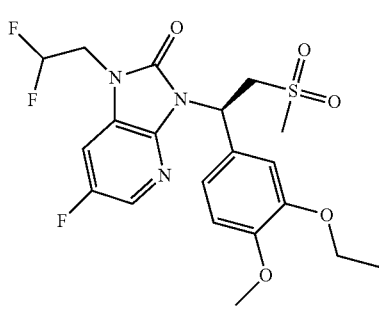
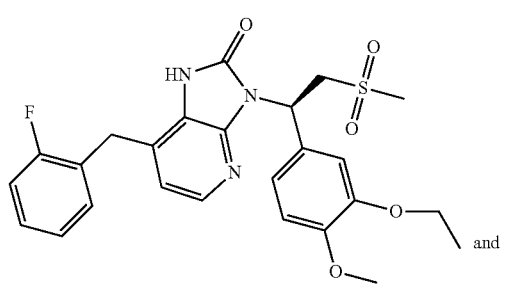
and -continued

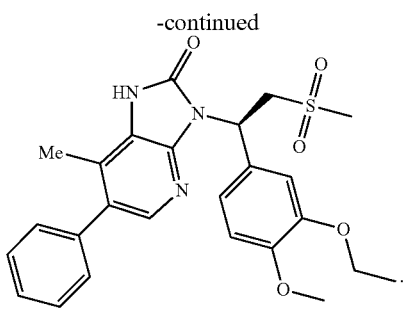

28. A pharmaceutical composition comprising a therapeutically effective amount of the compound or the pharmaceutically acceptable salt thereof according to claim 26 as the active ingredient and a pharmaceutically acceptable carrier.

29. A pharmaceutical composition comprising a therapeutically effective amount of the compound or the pharmaceutically acceptable salt thereof according to claim 27 as the active ingredient and a pharmaceutically acceptable carrier.

30. A process for treating PDE4 related diseases in a subject in need thereof, comprising: administering an effective amount of the compound or the pharmaceutically acceptable salt thereof according to claim 26 to the subject, wherein the disease related to PDE4 refers to psoriasis, psoriatic arthritis, chronic obstructive pneumonia, ankylosing spondylitis, inflammatory bowel disease.

31. A method for inhibiting PDE4 in a subject in need thereof, comprising: administering an effective amount of the compound or the pharmaceutically acceptable salt thereof according to claim 26 to the subject.

* * * * *